(12) United States Patent
Hwang et al.

(10) Patent No.: US 9,627,629 B2
(45) Date of Patent: Apr. 18, 2017

(54) COMPOUND FOR ORGANIC OPTOELECTRONIC DEVICE, ORGANIC LIGHT EMITTING DIODE INCLUDING THE SAME, AND DISPLAY INCLUDING THE ORGANIC LIGHT EMITTING DIODE

(71) Applicants: SAMSUNG ELECTRONICS CO., LTD., Suwon-si, Gyeonggi-do (KR); CHEIL INDUSTRIES INC., Gumi-si, Gyeongsangbuk-do (KR)

(72) Inventors: Kyu Young Hwang, Ansan-si (KR); Sang Mo Kim, Hwaseong-si (KR); Young Kwon Kim, Euiwang-si (KR); Joo Hee Seo, Euwang-si (KR); Jhun Mo Son, Yongin-si (KR); Yong Sik Jung, Seoul (KR); Seok-Hwan Hong, Seoul (KR)

(73) Assignee: SAMSUNG ELECTRONICS CO., LTD., Gyeongsangbuk-Do (KR)

( * ) Notice: Subject to any disclaimer, the term of this patent is extended or adjusted under 35 U.S.C. 154(b) by 485 days.

(21) Appl. No.: 14/176,287

(22) Filed: Feb. 10, 2014

(65) Prior Publication Data
US 2014/0225088 A1    Aug. 14, 2014

(30) Foreign Application Priority Data
Feb. 12, 2013 (KR) .................. 10-2013-0015049

(51) Int. Cl.
*H01L 51/00* (2006.01)
*C07D 471/04* (2006.01)
(Continued)

(52) U.S. Cl.
CPC ........ *H01L 51/0072* (2013.01); *C07D 471/04* (2013.01); *C07D 471/14* (2013.01);
(Continued)

(58) Field of Classification Search
None
See application file for complete search history.

(56) References Cited

U.S. PATENT DOCUMENTS

| 2012/0235123 A1* | 9/2012 | Lee ..................... H01L 51/0072 257/40 |
| 2013/0112950 A1* | 5/2013 | Yokoyama ........... C07D 209/86 257/40 |

FOREIGN PATENT DOCUMENTS

| KR | 1020110015836 A | 2/2011 |
| KR | 1020120021203 A | 3/2012 |

(Continued)

*Primary Examiner* — Nathan T Leong
(74) *Attorney, Agent, or Firm* — Cantor Colburn LLP

(57) ABSTRACT

A compound for an organic optoelectronic device represented by Chemical Formula 1

Chemical Formula 1

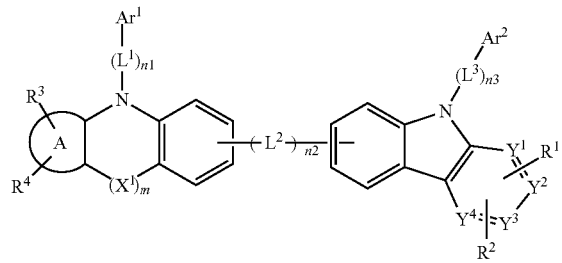

wherein, in Chemical Formula 1, variables A, $Y^1$ to $Y^4$, $X^1$, m, $R^1$ to $R^4$, $L^1$ to $L^3$, n1 to n3, $Ar^1$ and $Ar^2$ are described in the specification.

22 Claims, 3 Drawing Sheets

(51) Int. Cl.
*C07D 471/14* (2006.01)
*H01L 51/50* (2006.01)

(52) U.S. Cl.
CPC ...... *H01L 51/0067* (2013.01); *H01L 51/5012* (2013.01); *H01L 51/5056* (2013.01); *H01L 51/5072* (2013.01); *Y02E 10/549* (2013.01)

(56) References Cited

FOREIGN PATENT DOCUMENTS

| KR | 1020120038056 A | 4/2012 |
| KR | 1020120050557 A | 5/2012 |
| WO | WO2011019156 A1 | 2/2011 |
| WO | 2012001986 A1 | 1/2012 |

\* cited by examiner

COMPOUND FOR ORGANIC OPTOELECTRONIC DEVICE, ORGANIC LIGHT EMITTING DIODE INCLUDING THE SAME, AND DISPLAY INCLUDING THE ORGANIC LIGHT EMITTING DIODE

CROSS-REFERENCE TO RELATED APPLICATION

This application claims priority to Korean Patent Application No. 10-2013-0015049 filed in the Korean Intellectual Property Office on Feb. 12, 2013, and all the benefits accruing therefrom under 35 U.S.C. §119, the entire contents of which are incorporated herein by reference.

BACKGROUND

1. Field

A compound for an organic optoelectronic device being capable of providing an organic optoelectronic device having improved life-span, efficiency, electrochemical stability, and thermal stability, an organic light emitting diode, and a display device including the organic light emitting diode are disclosed.

2. Description of the Related Art

An organic photoelectric device is a device requiring a charge exchange between an electrode and an organic material by using holes or electrons.

An organic optoelectronic device may be classified in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of the organic optoelectronic device includes an organic light emitting diode, an organic solar cell, an organic photoconductor drum, an organic transistor, and the like, which require a hole injecting or transport material, an electron injecting or transport material, or a light emitting material.

Particularly, an organic light emitting diode (OLED) has recently drawn attention due to an increasing demand for flat panel displays. In general, organic light emission refers to a process of conversion of electrical energy into photo-energy.

Such an organic light emitting diode converts electrical energy into light by applying a current to an organic light emitting material. The diode has a structure in which a functional organic material layer is interposed between an anode and a cathode. The organic material layer includes a multi-layer including different materials, for example a hole injection layer (HIL), a hole transport layer (HTL), an emission layer, an electron transport layer (ETL), and an electron injection layer (EIL), in order to improve efficiency and stability of an organic light emitting diode.

In such an organic light emitting diode, when a voltage is applied to an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material may be used for a light emitting material of an organic light emitting diode in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to implement improved performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming a material for an organic light emitting diode has thus far not been satisfactory and thus there is a need for a novel material. This material development is also required for other organic optoelectronic devices.

A low molecular organic light emitting diode is manufactured as a thin film by a vacuum deposition method, and can have good efficiency and life-span performance. A polymer organic light emitting diode manufactured by an Inkjet or spin coating method has an advantage of having low initial cost and being large-sized.

Both low molecular organic light emitting and polymer organic light emitting diodes have an advantage of self-light emitting, high speed response, wide viewing angle, ultra-thinness, high image quality, durability, large driving temperature range, and the like. In particular, the diodes have good visibility due to the self-light emitting characteristic compared with a conventional LCD (liquid crystal display), and have an advantage of decreasing thickness and weight of an LCD by up to a third, because the diodes do not need a backlight.

In addition, since the diodes have a response speed of a microsecond unit, which is 1,000 times faster than an LCD, they can realize a perfect motion picture without an after-image. Based on these advantages, the diodes have been remarkably developed to have 80 times the efficiency and more than 100 times the life-span since they first came out in the late 1980s. Recently, the diodes have rapidly increased in size, such that a 40-inch organic light emitting diode panel is now possible.

The diodes are simultaneously required to have improved luminous efficiency and life-span in order to be larger.

Herein, their luminous efficiency requires smooth combination between holes and electrons in an emission layer. However, since an organic material in general has slower electron mobility than hole mobility, it has a drawback of inefficient combination between holes and electrons. Accordingly, increasing electron injection and mobility from a cathode and simultaneously preventing movement of holes is required.

In order to improve the life-span of the organic light emitting diode, it is desired to prevent material crystallization caused by Joule heat generated during device operation. Accordingly, there has been a strong need for an organic compound having improved electron injection and mobility, and high electrochemical stability.

SUMMARY

A compound for an organic optoelectronic device that may act as a hole injection and/or transport material or electron injection and/or transport material, and that may also act as a light emitting host along with an appropriate dopant, is provided.

An organic light emitting diode having improved life-span, efficiency, driving voltage, electrochemical stability, and thermal stability, and a display device including the same, are provided.

In an embodiment, a compound for an organic optoelectronic device represented by the following Chemical Formula 1 is provided.

Chemical Formula 1

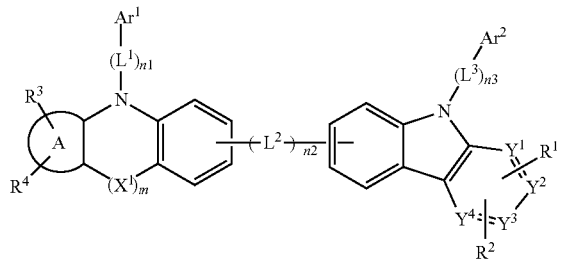

In Chemical Formula 1,

A is a C6 to C40 aryl group including 1 to 4 aromatic rings, wherein the 1 to 4 aromatic rings include at least one nitrogen, $Y^1$ to $Y^4$ are each independently CR' or N, $X^1$ is —CR'R"—, —SiR'R"—, —O—, —NR'—, —S—, —$SO_2$—, —C(O)—, or —P(O)—, m is an integer ranging from 0 to 2, $R^1$ to $R^4$, R', and R" are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

The compound for an organic optoelectronic device may be represented by the following Chemical Formula 2.

Chemical Formula 2

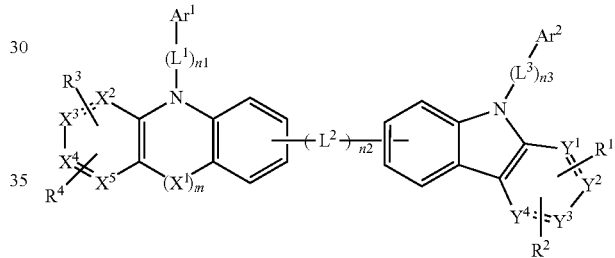

In Chemical Formula 2, $X^1$ is —CR'R"—, —SiR'R"—, —O—, —NR'—, —S—, —$SO_2$—, —C(O)—, or —P(O)—, m is an integer ranging from 0 to 2, $Y^1$ to $Y^4$ are each independently CR' or N, $X^2$ to $X^5$ are each independently CR' or N, provided that at least one of $X^2$ to $X^5$ is N, $R^1$ to $R^4$, R', and R" are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

The compound for an organic optoelectronic device may be represented by the following Chemical Formula 3.

Chemical Formula 3

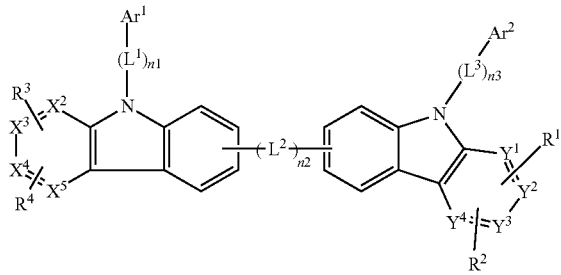

In Chemical Formula 3, $X^2$ to $X^5$ are each independently CR' or N, provided that at least one of $X^2$ to $X^5$ is N, $Y^1$ to $Y^4$ are each independently CR' or N, $R^1$ to $R^4$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

The compound for an organic optoelectronic device may be represented by the following Chemical Formula 4.

Chemical Formula 4

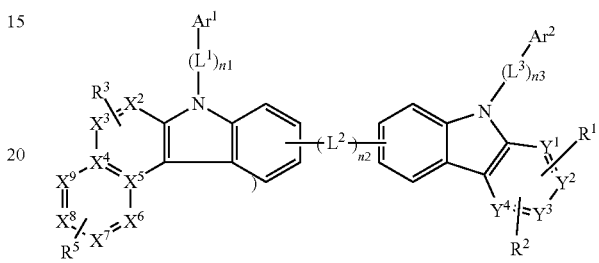

In Chemical Formula 4, $X^2$, $X^3$, and $X^6$ to $X^9$ are each independently CR', or N, and $X^4$ and $X^5$ are C, provided that at least one of $X^2$, $X^3$, and $X^6$ to $X^9$ is N, $Y^1$ to $Y^4$ are each independently CR' or N, $R^1$ to $R^5$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

The compound for an organic optoelectronic device may be represented by the following Chemical Formula 5.

Chemical Formula 5

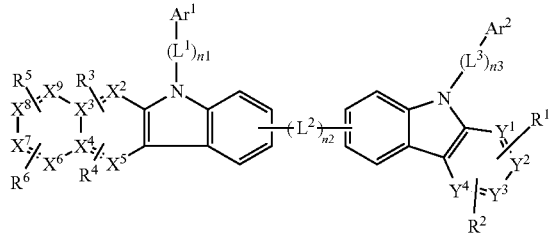

In Chemical Formula 5, $X^2$ and $X^5$ to $X^9$ are each independently CR', or N, and $X^3$ and $X^4$ are C, provided that at least one of $X^2$, $X^5$, and $X^6$ to $X^9$ is N, $Y^1$ to $Y^4$ are each independently CR' or N, $R^1$ to $R^6$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

The compound for an organic optoelectronic device may be represented by the following Chemical Formula 6.

Chemical Formula 6

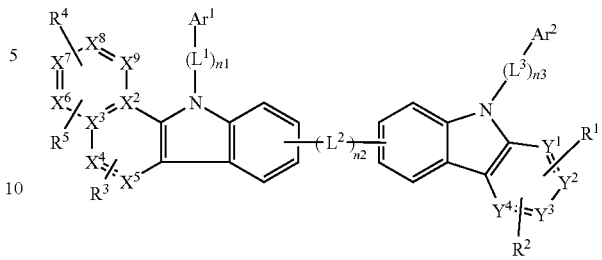

In Chemical Formula 6, $X^4$ to $X^9$ are each independently CR', or N, and $X^2$ and $X^3$ are C, provided that at least one of $X^4$, $X^5$, and $X^6$ to $X^9$ is N, $Y^1$ to $Y^4$ are each independently CR' or N, $R^1$ to $R^5$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

$Ar^1$ may be a substituted or unsubstituted C6 to C30 aryl group.

n2 may be 0.

In Chemical Formulae 2 or 3, $X^2$ may be N, and $X^3$ to $X^5$ may be CR'.

$X^3$ may be N, and $X^2$, $X^4$, and $X^5$ may be CR'.

$X^4$ may be N, and $X^2$, $X^3$, and $X^5$ may be CR'.

$X^5$ may be N, and $X^2$, $X^3$, and $X^4$ may be CR'.

$X^2$ and $X^4$ may be N, and $X^3$ and $X^5$ may be CR'.

$Ar^1$ and $Ar^2$ may be independently selected from Chemical Formulae W-1 to W-8.

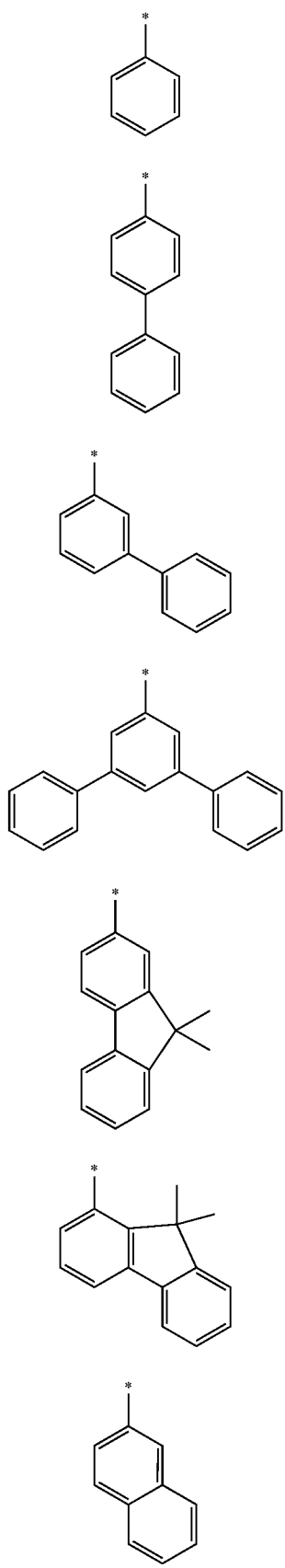
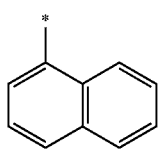
The substituted or unsubstituted C2 to C30 heteroaryl group having electron characteristics may be one of Chemical Formulae X-1 to X-22.
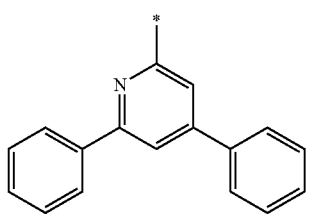
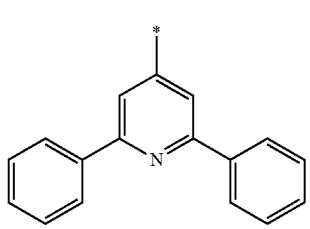
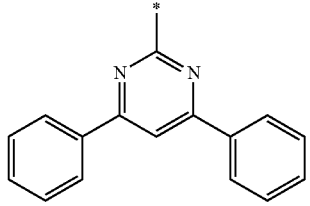
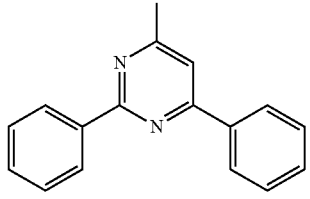
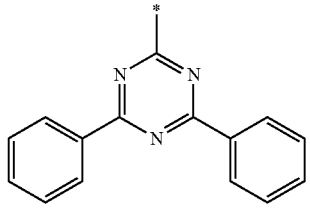
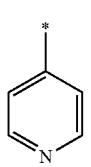

-continued
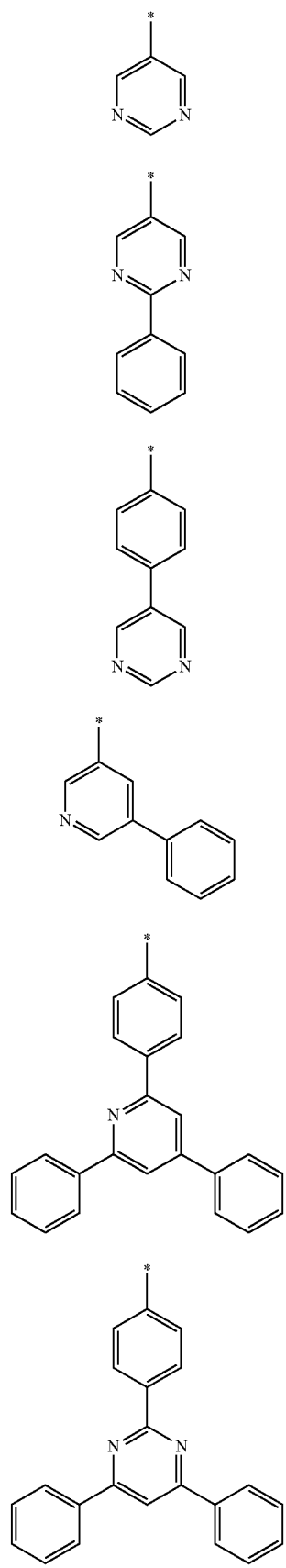
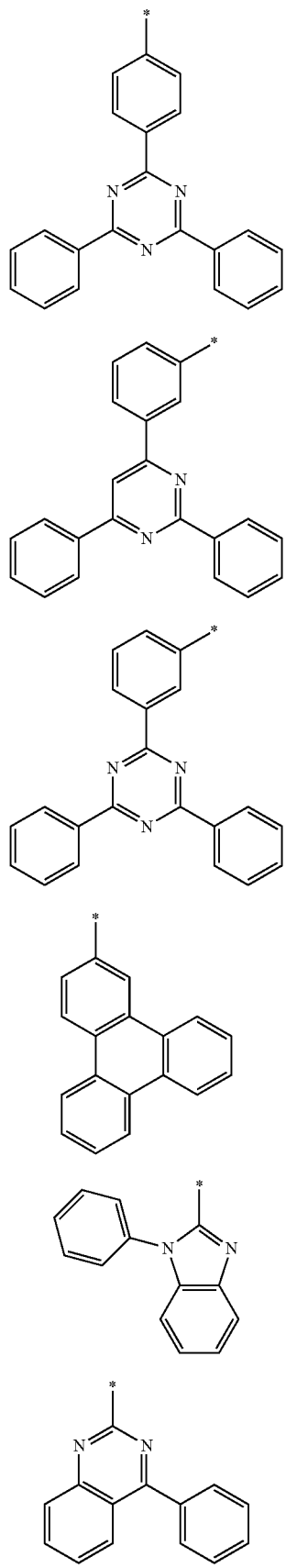

X-19
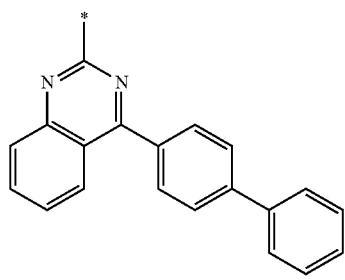
X-20
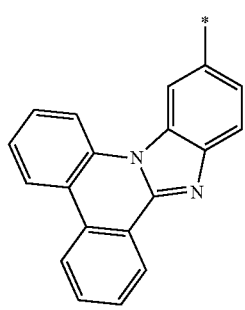
X-21
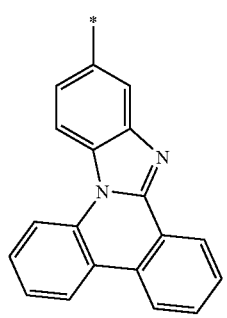
X-22
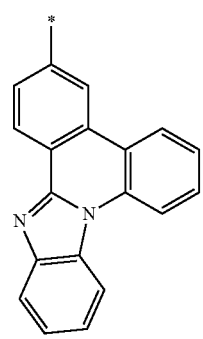
The compound for an organic optoelectronic device may be represented by one of the following Chemical Formulae A-1 to A-168.
A-1
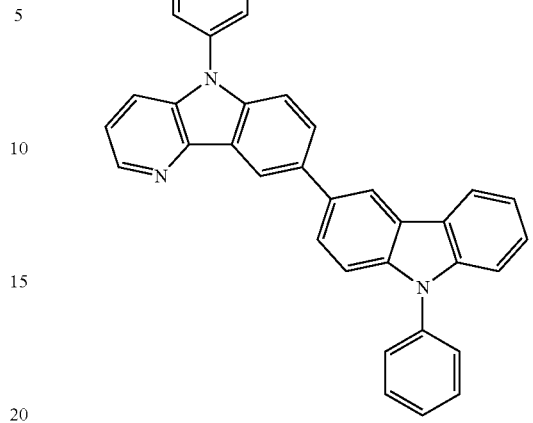
A-2
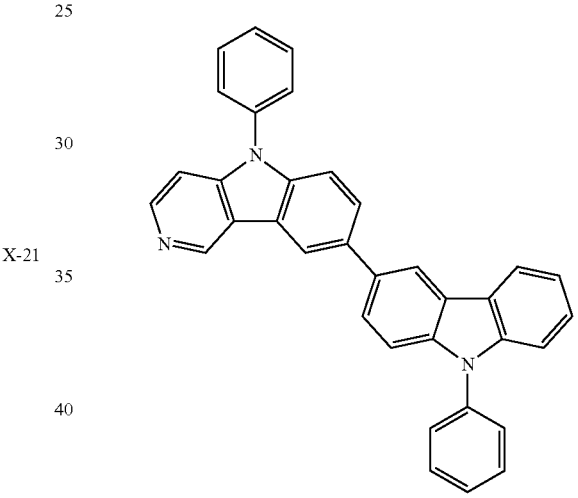
A-3
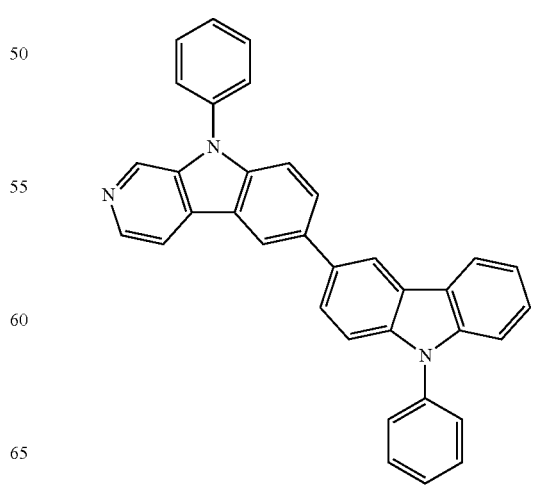

-continued
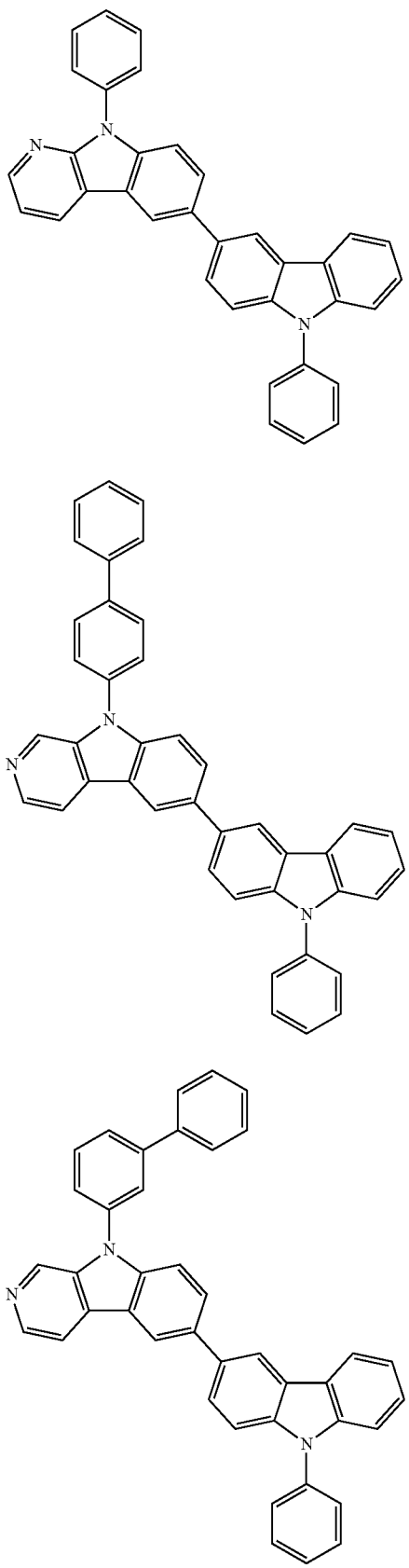
A-4
A-5
A-6
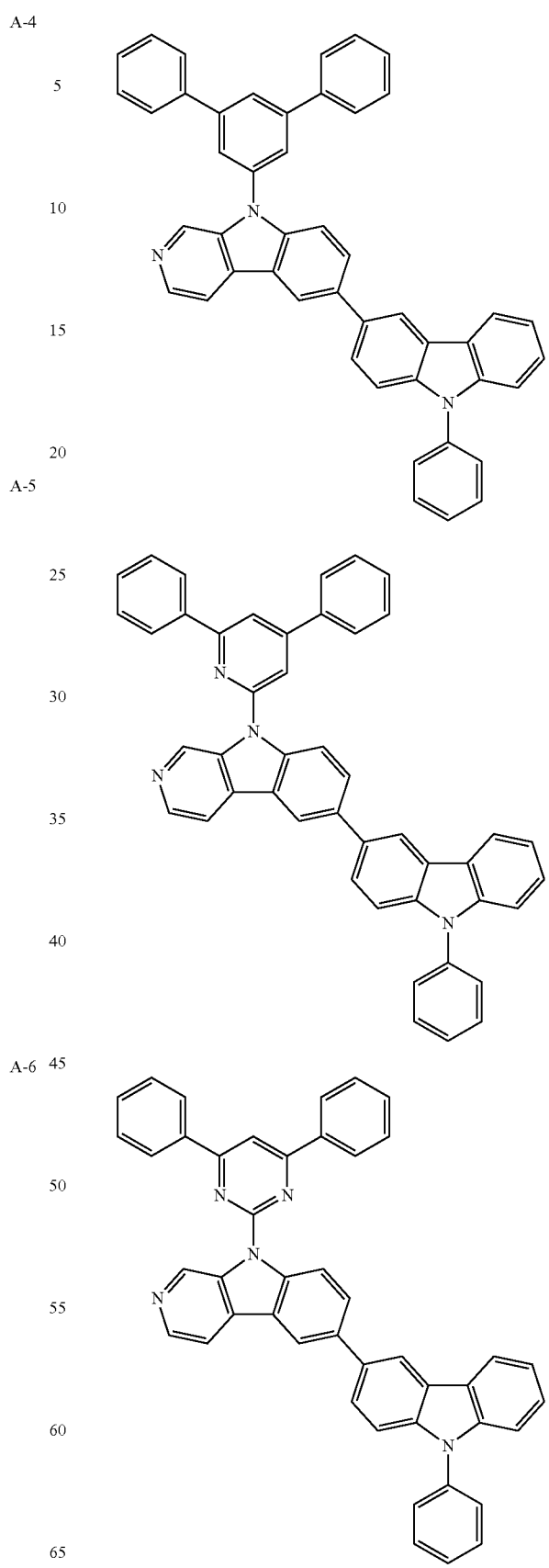
A-7
A-8
A-9

A-10
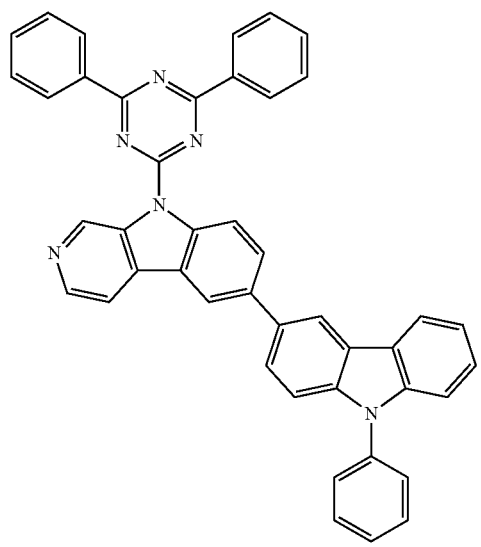
A-11
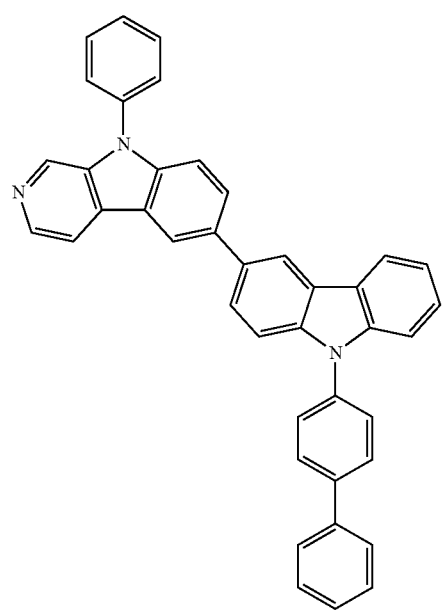
A-12
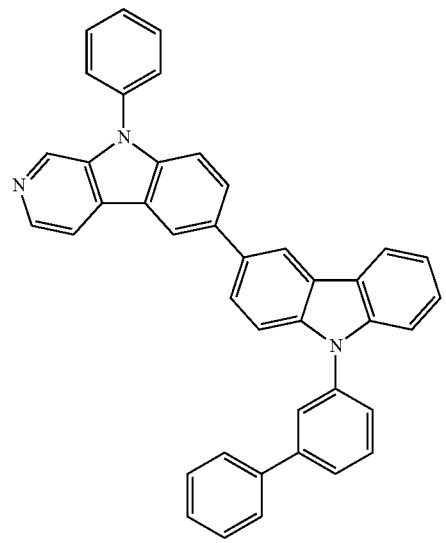
A-13
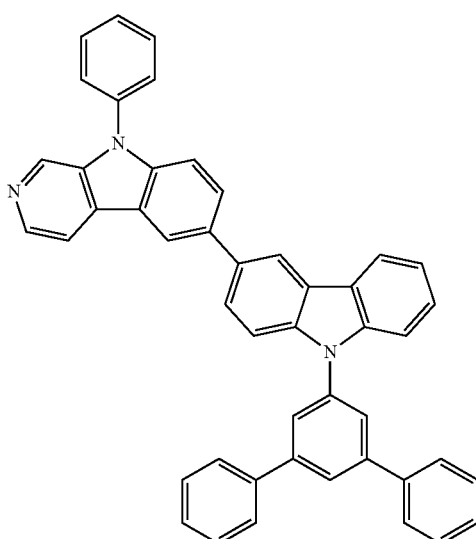
A-14
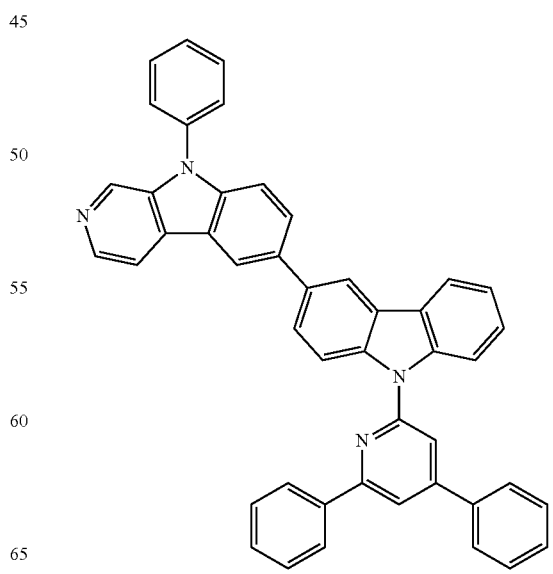

A-15
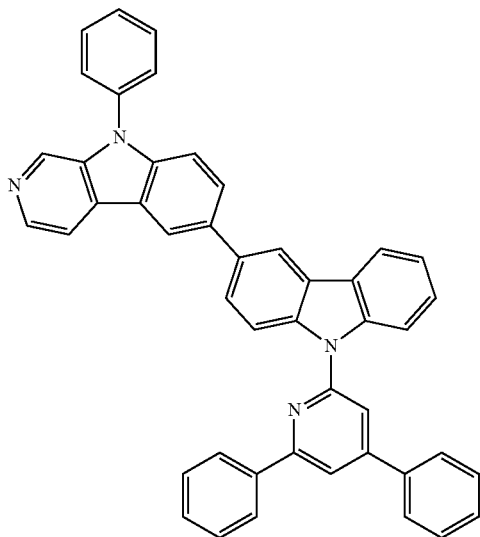
A-18
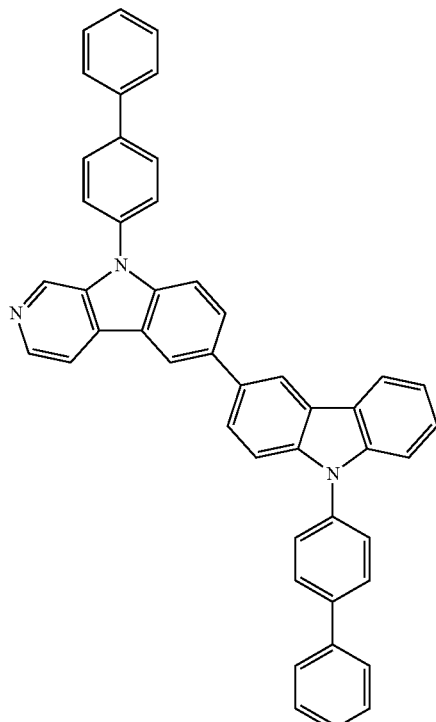
A-16
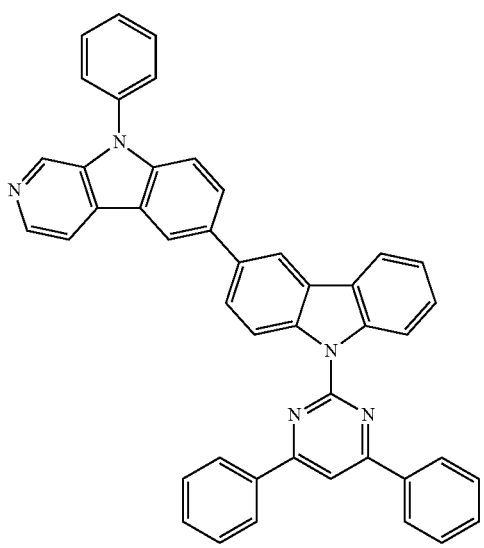
A-17
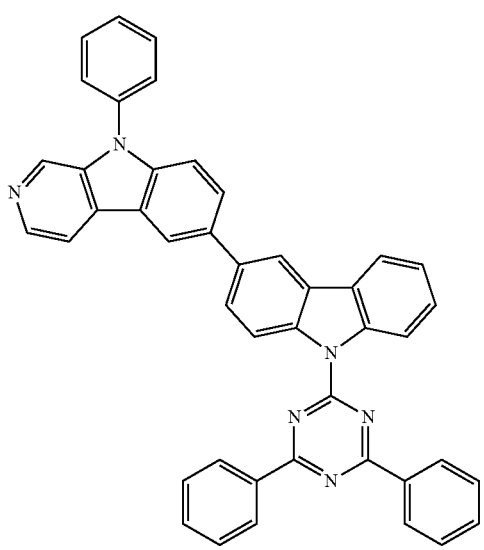
A-19
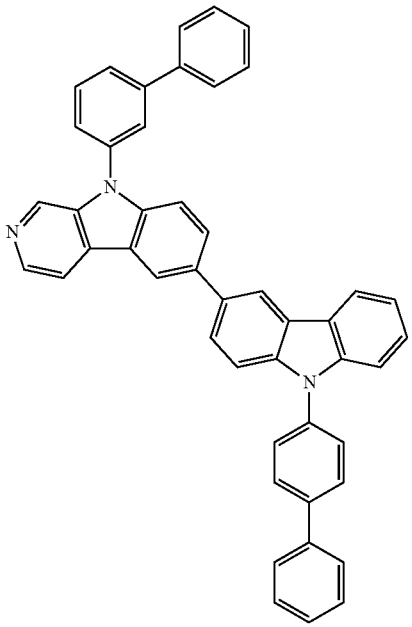

A-20
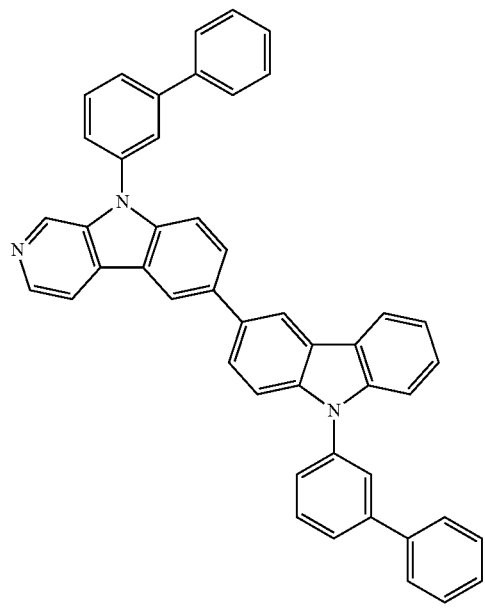
A-21
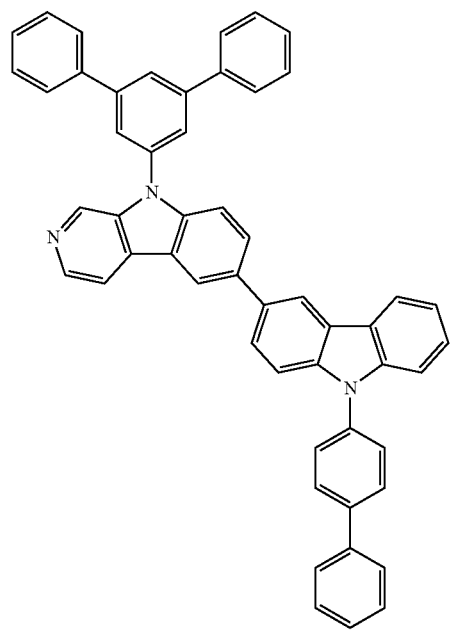
A-22
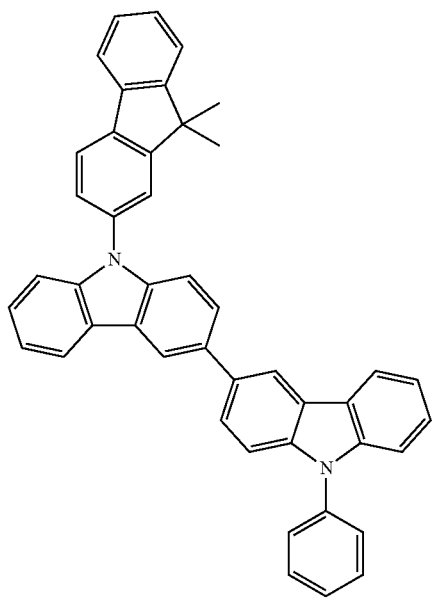
A-23
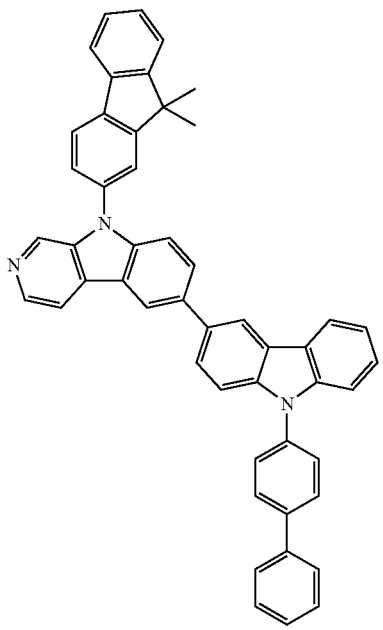

A-24
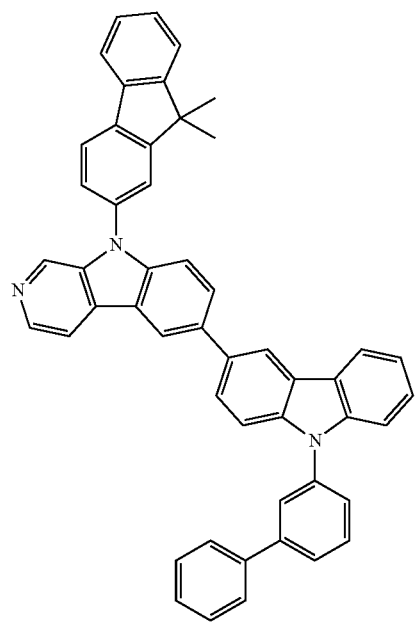
A-25
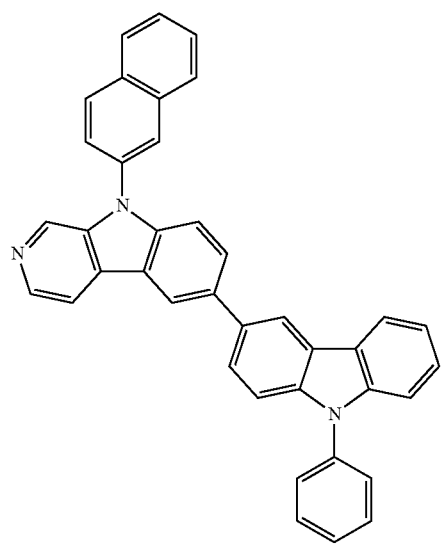
A-26
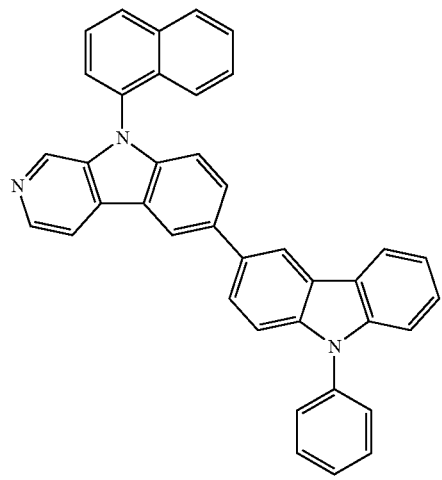
A-27
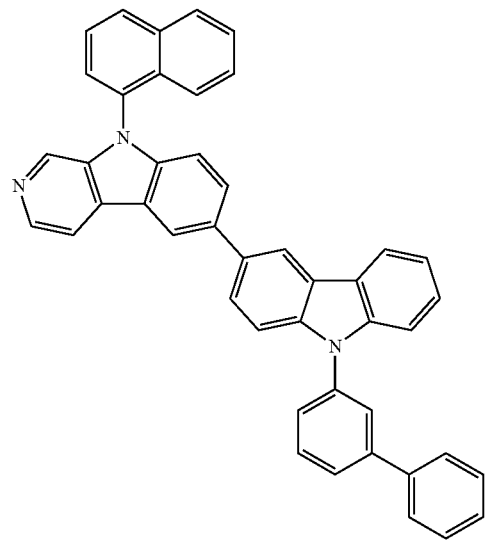
A-28
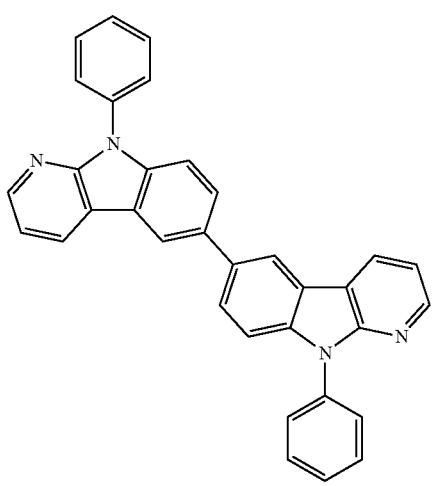
A-29
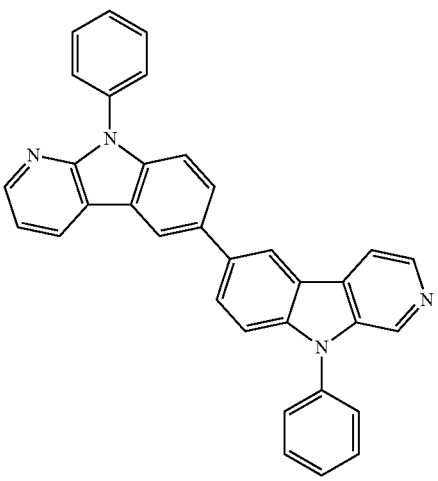

A-30
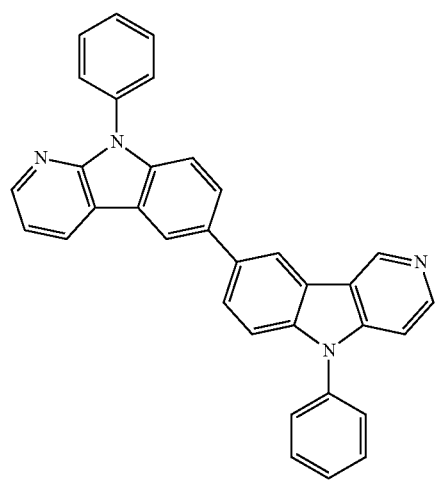
A-33
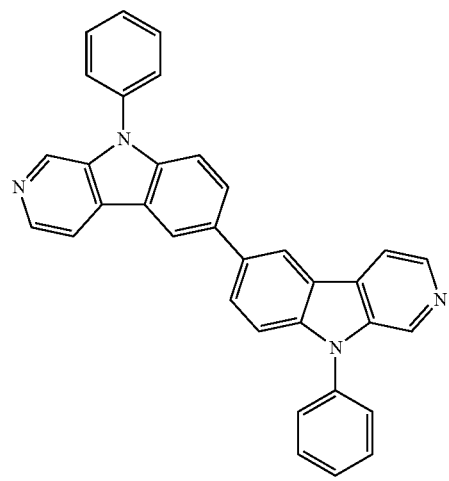
A-31
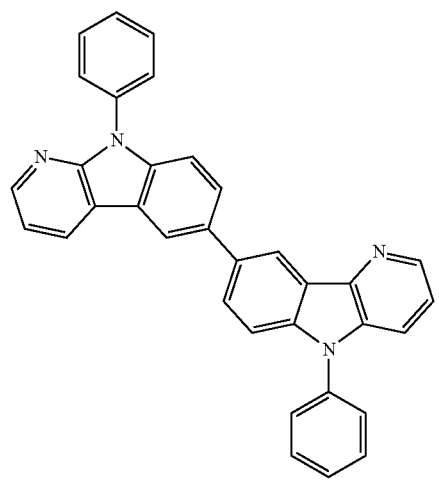
A-34
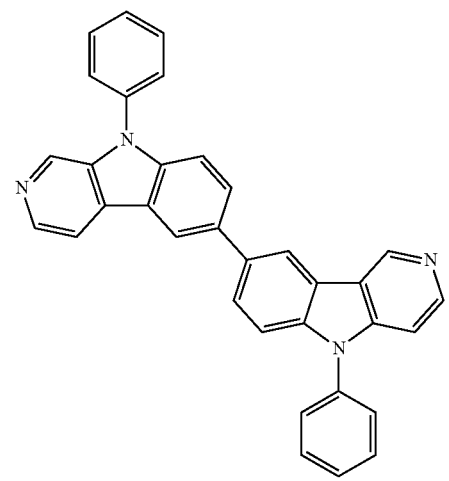
A-32
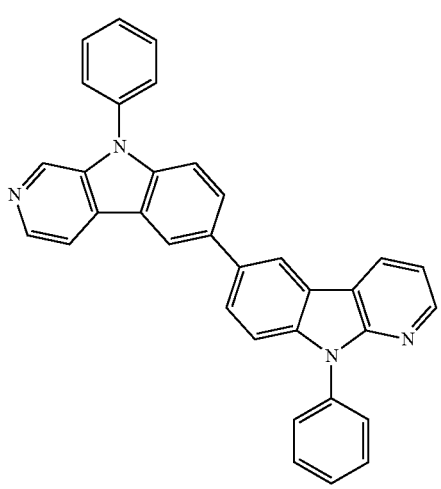
A-35
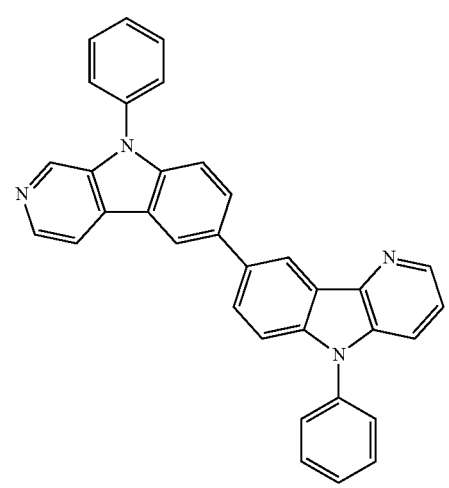

A-36
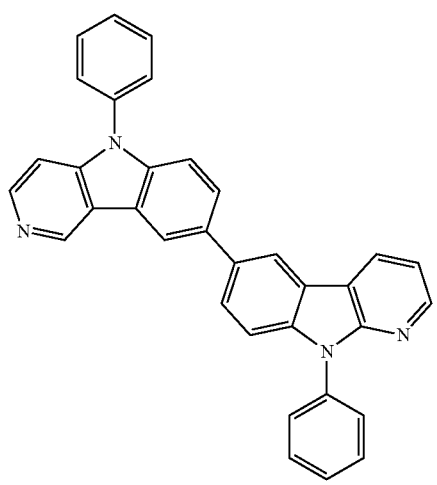
A-37
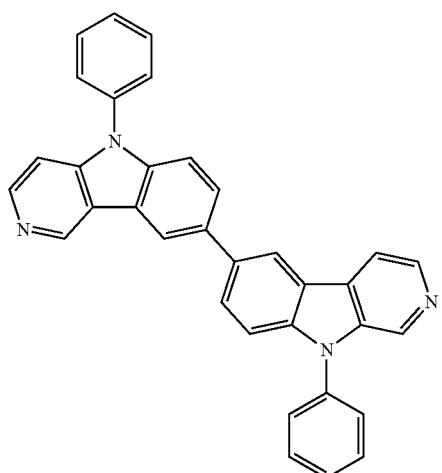
A-38
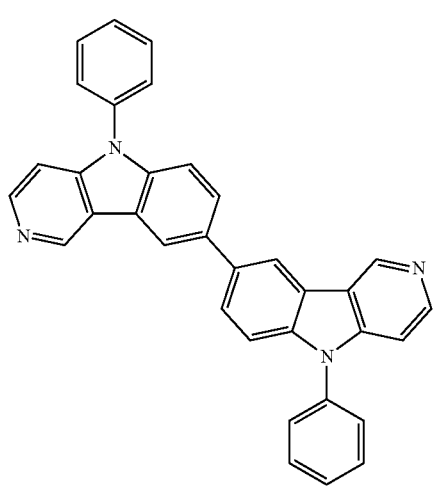
A-39
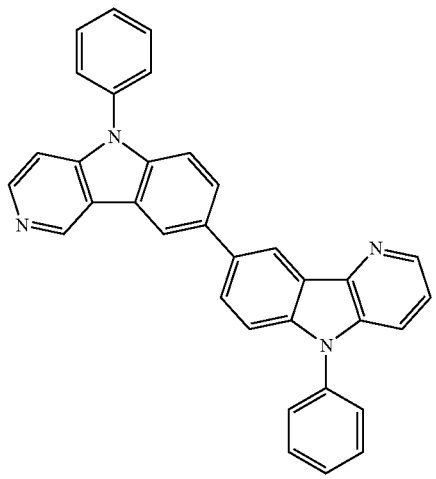
A-40
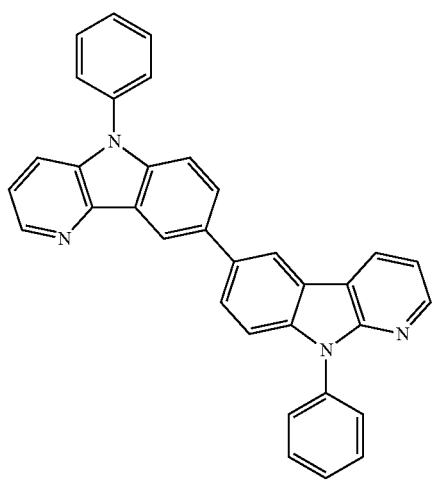
A-41
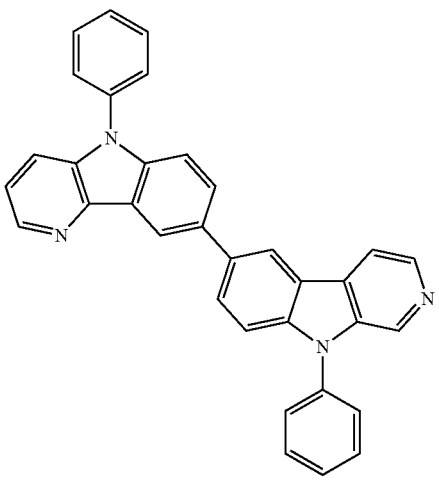

A-42
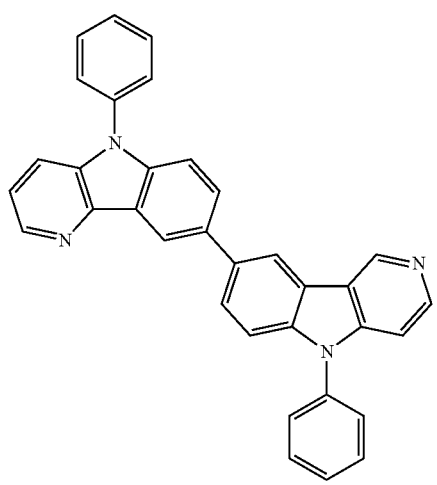
A-43
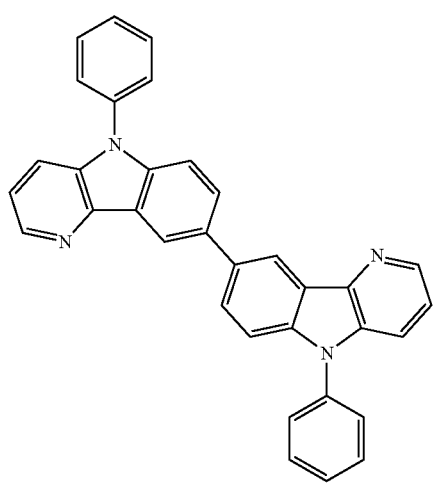
A-44
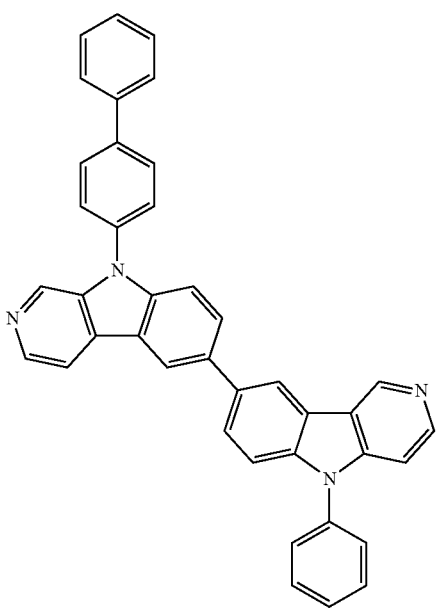
A-45
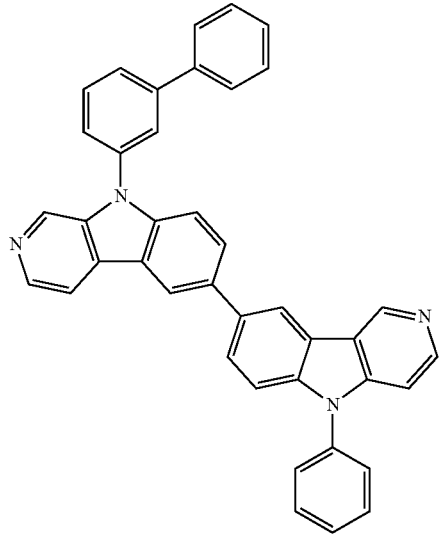
A-46
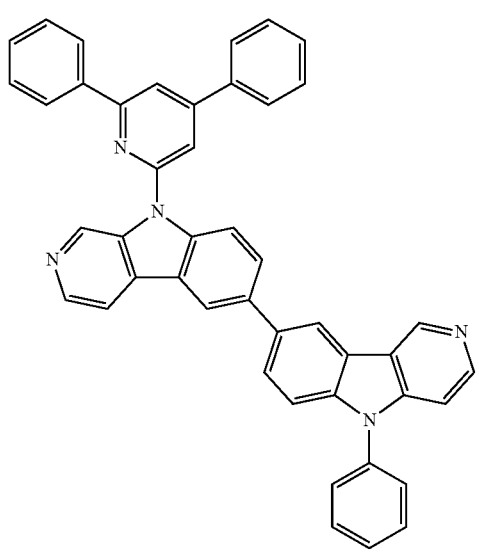
A-47
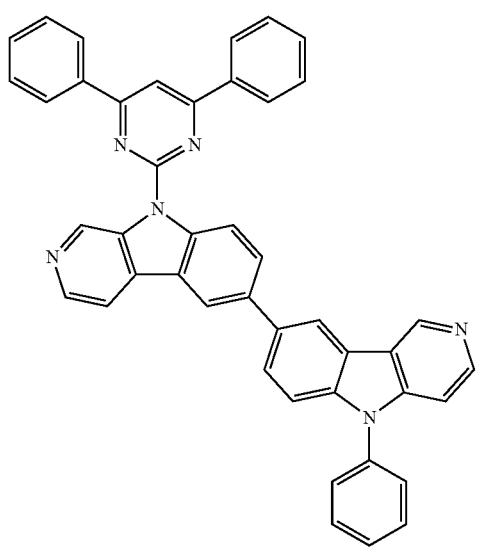

A-48
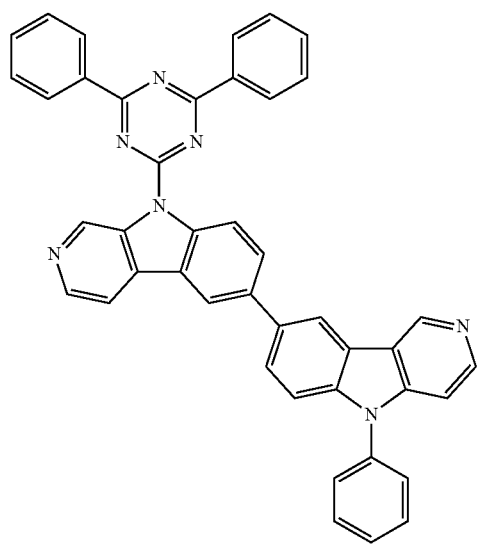
A-49
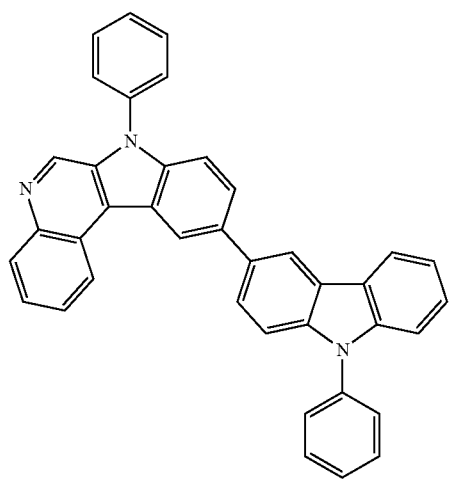
A-50
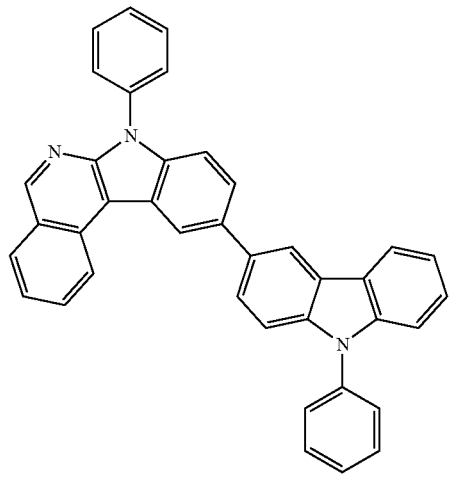
A-51
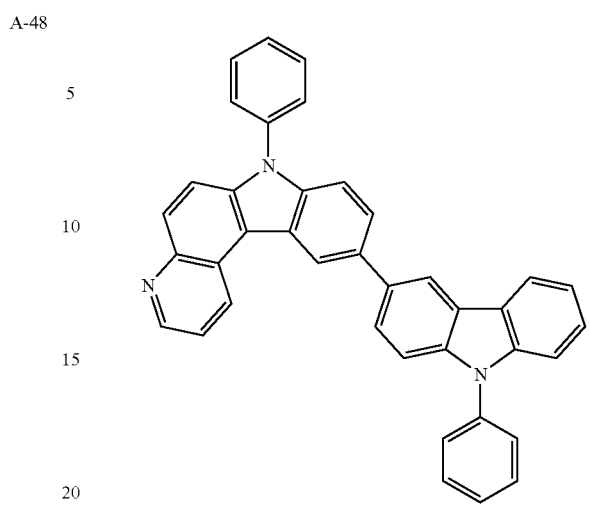
A-52
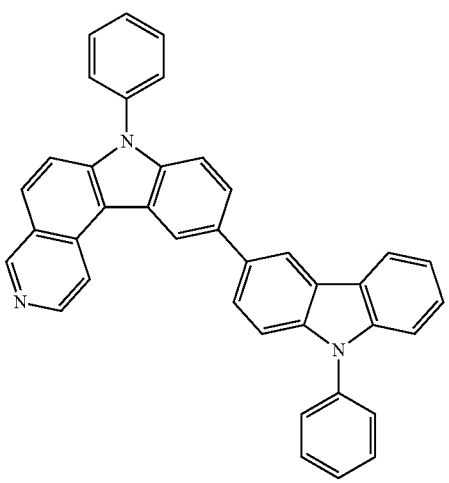
A-53
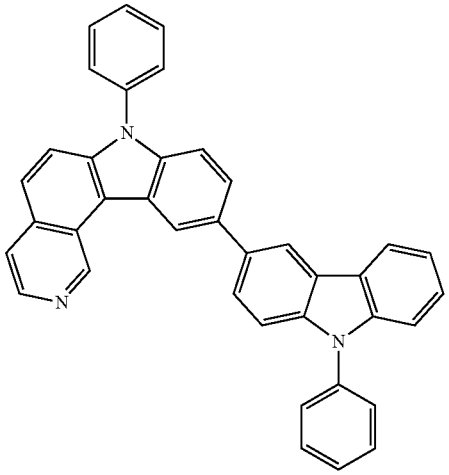

-continued
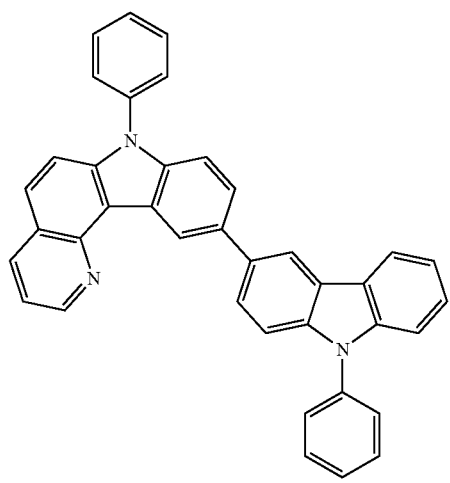
A-54
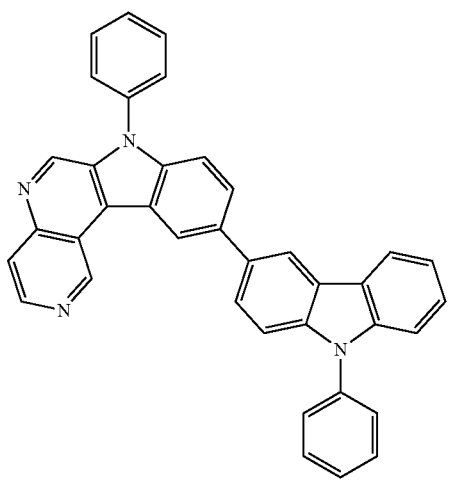
A-57
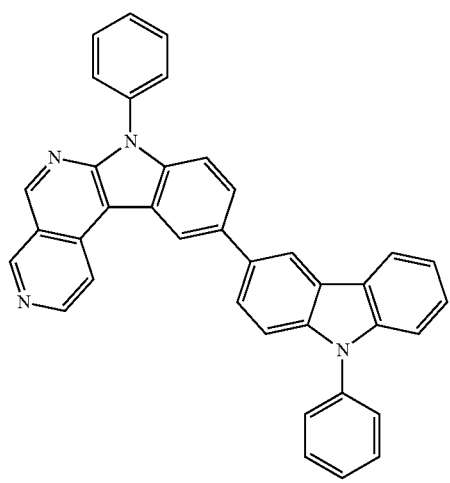
A-55
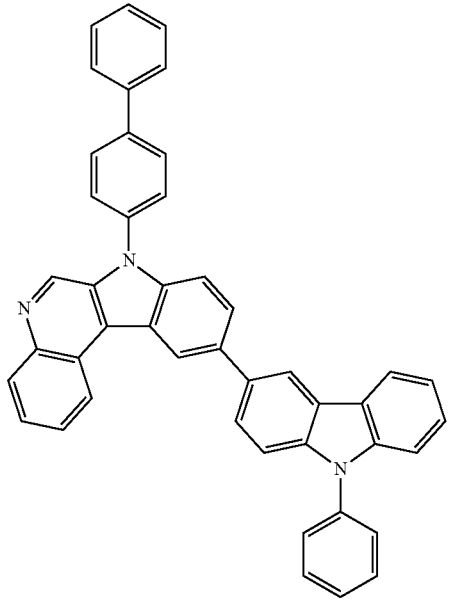
A-58
A-56

A-59
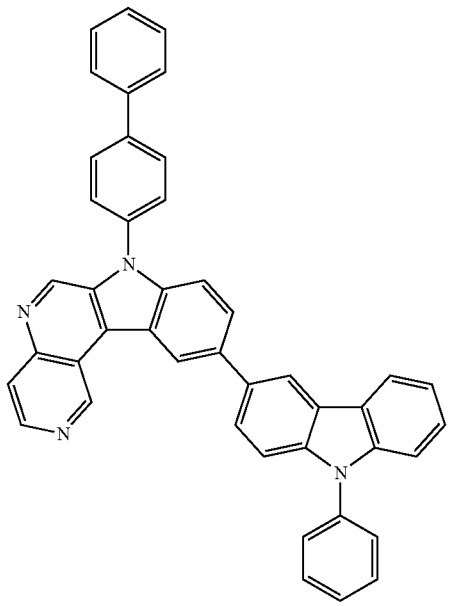
A-60
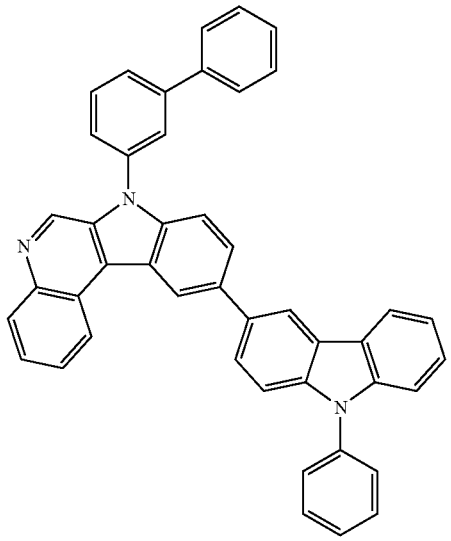
A-61
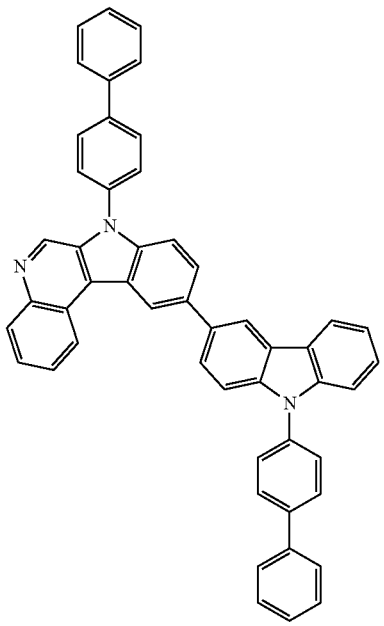
A-62
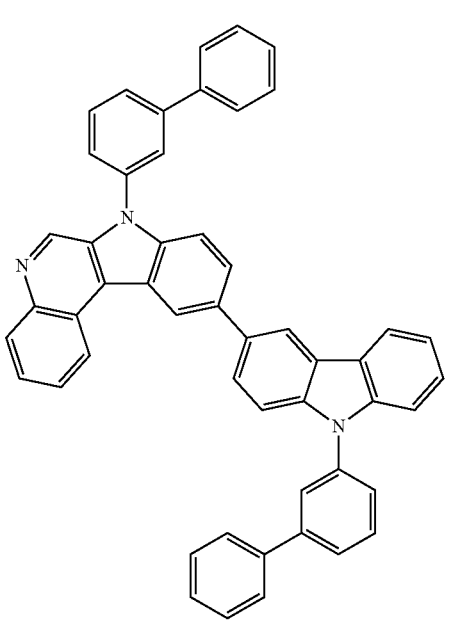

-continued
A-63
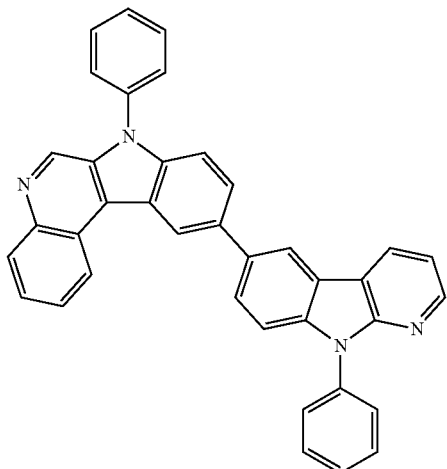
A-64
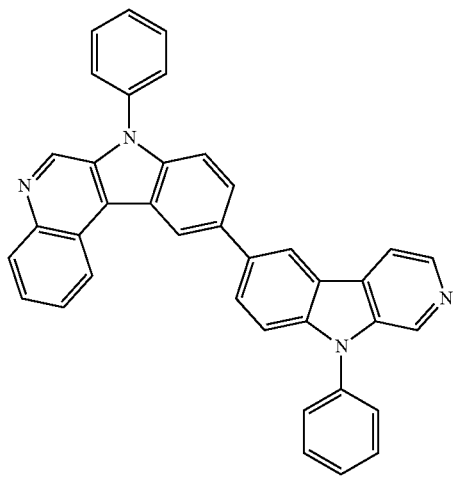
A-65
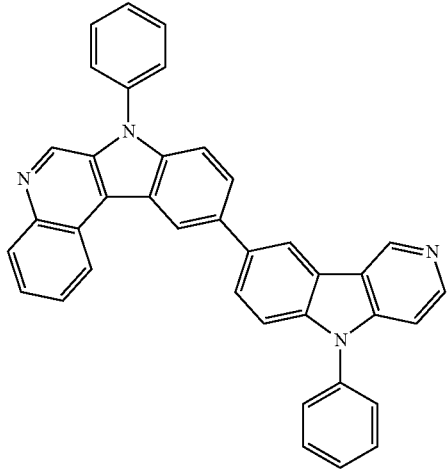
-continued
A-66
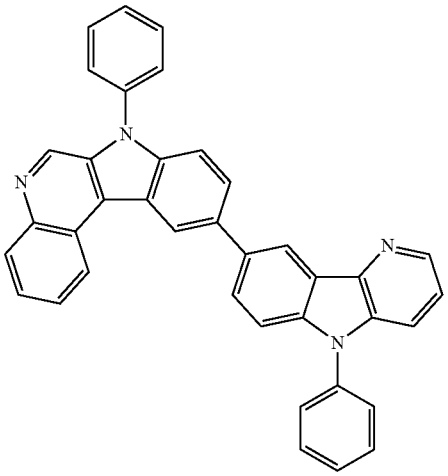
A-67
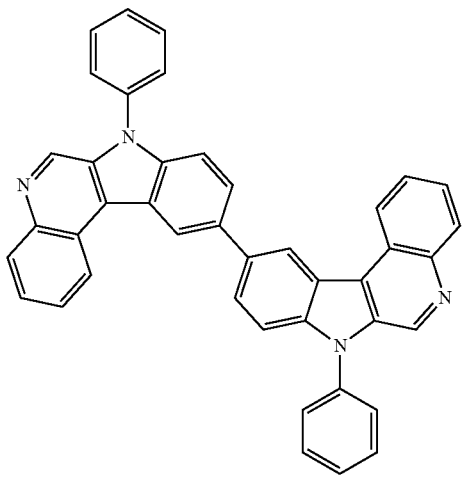
A-68
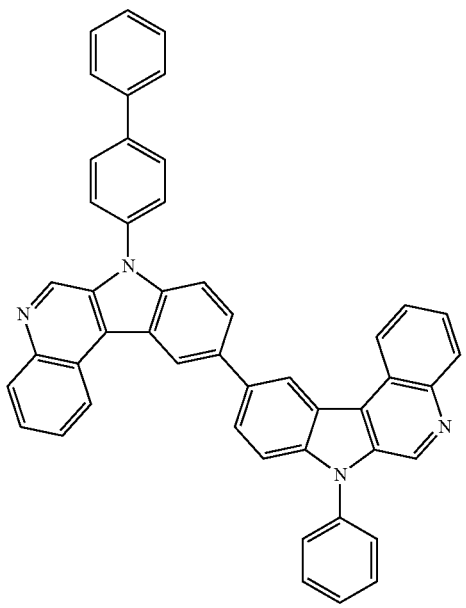

A-69
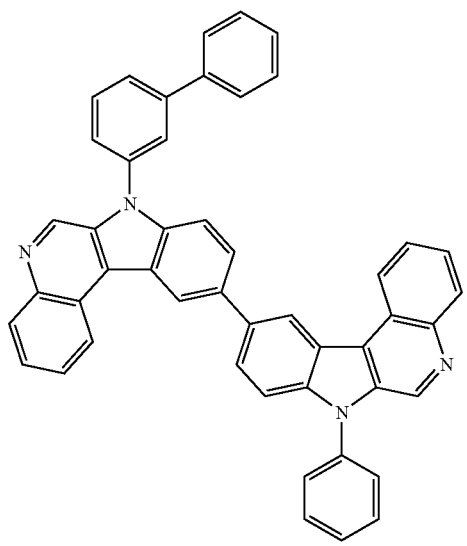
A-70
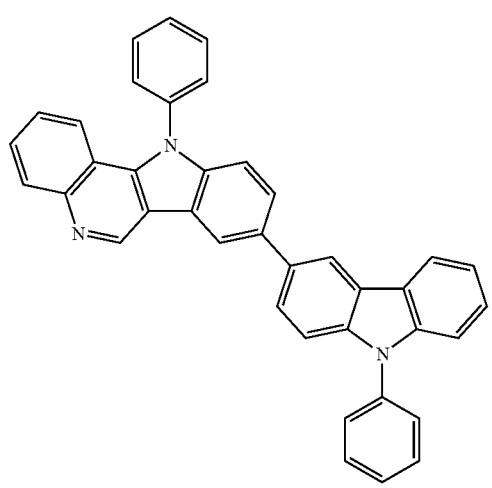
A-71
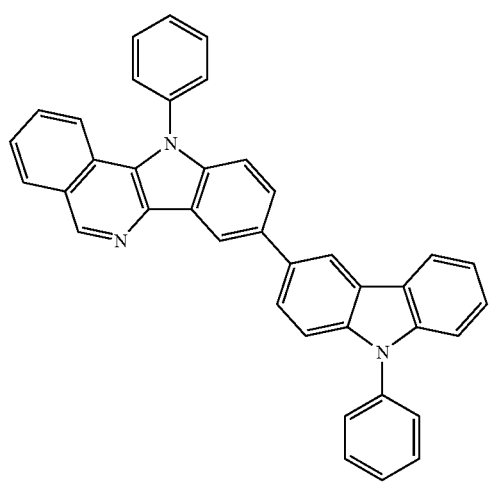
A-72
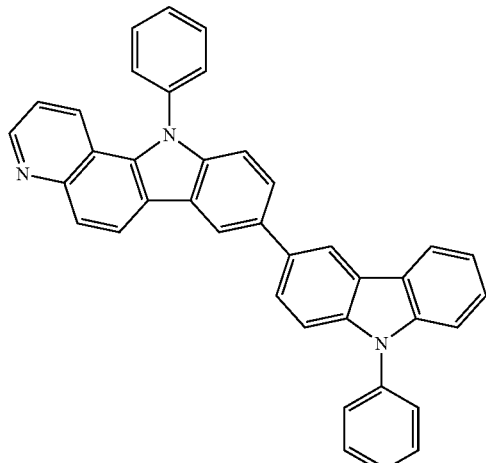
A-73
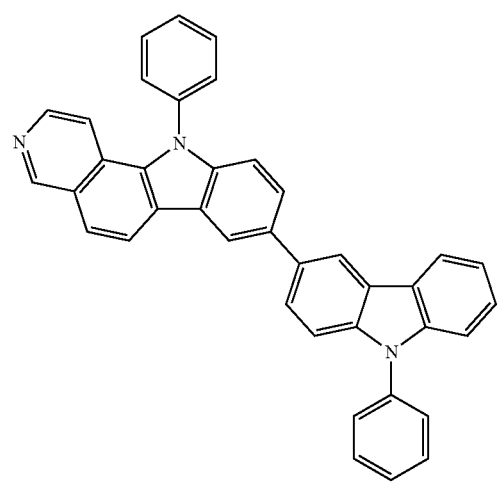
A-74
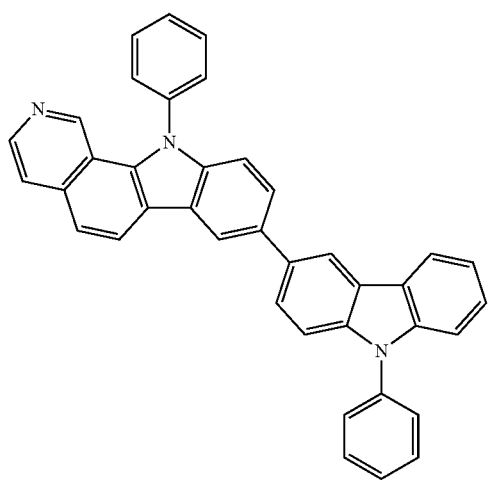

A-75
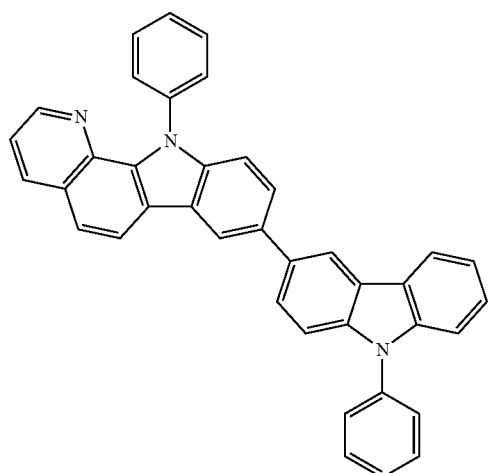
A-76
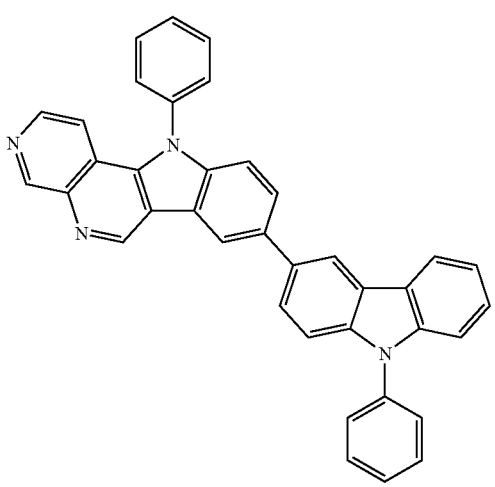
A-77
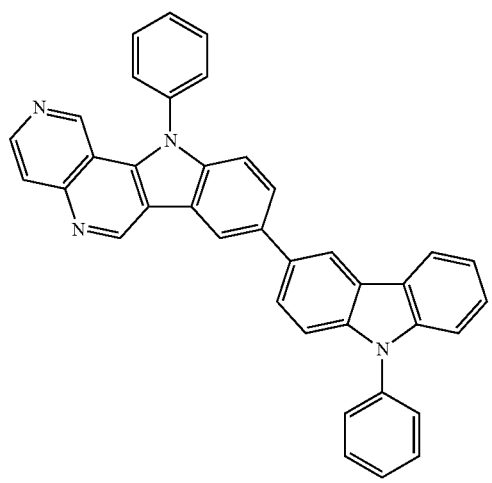
A-78
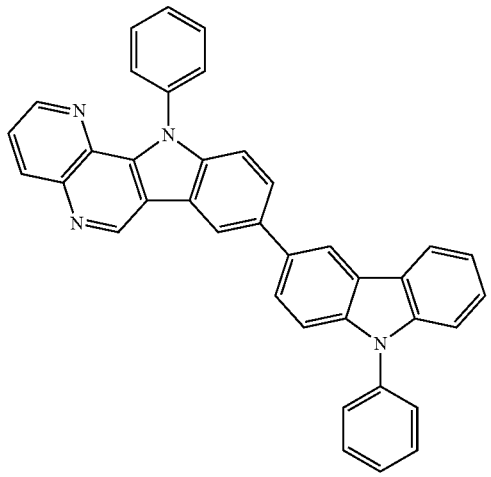
A-79

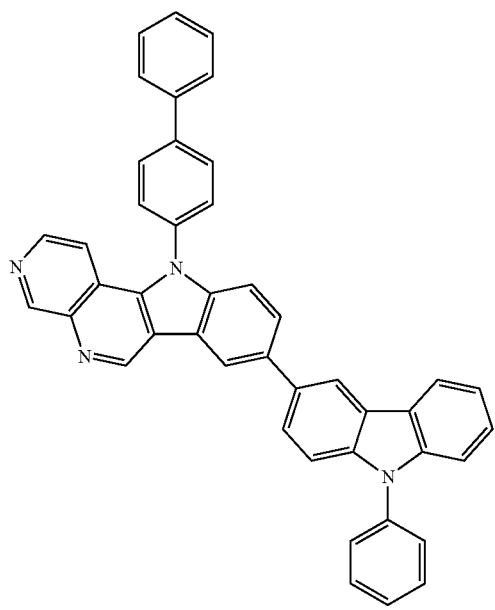
A-80
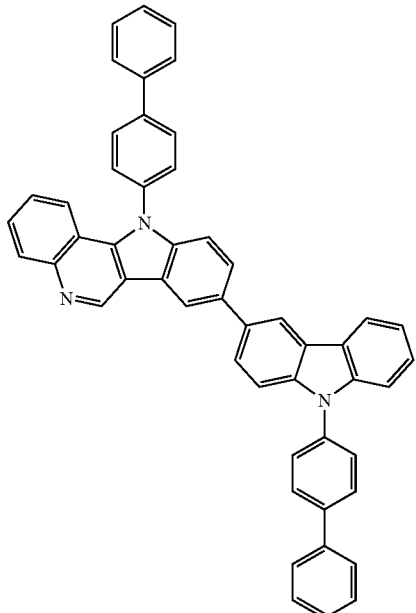
A-82
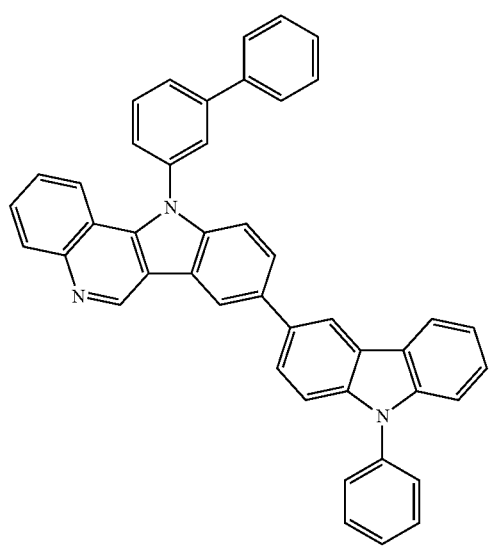
A-81
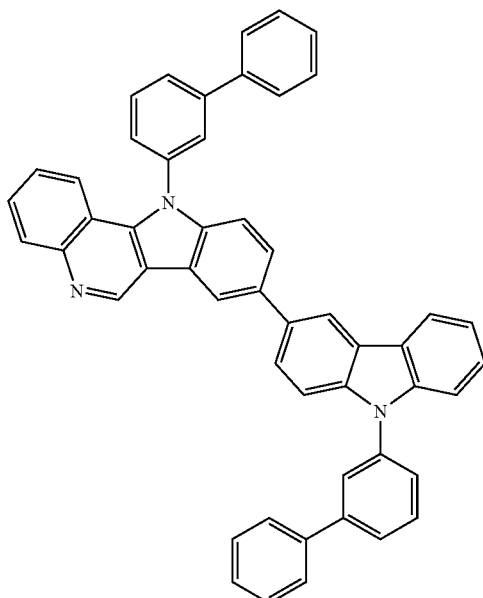
A-83

A-84
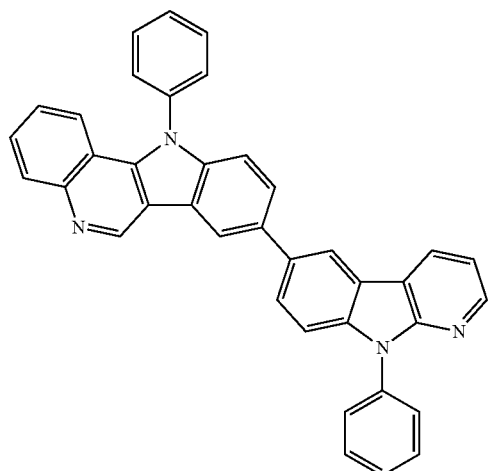
A-85
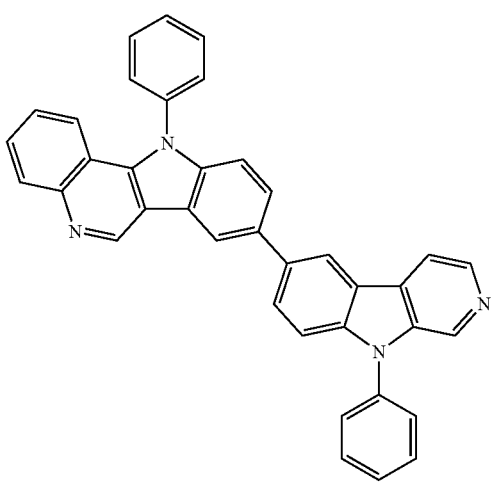
A-86
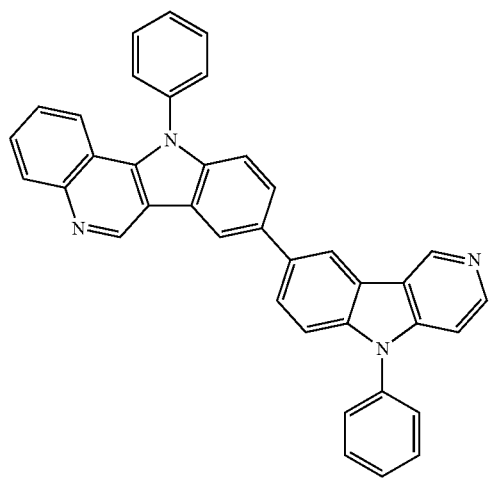
A-87
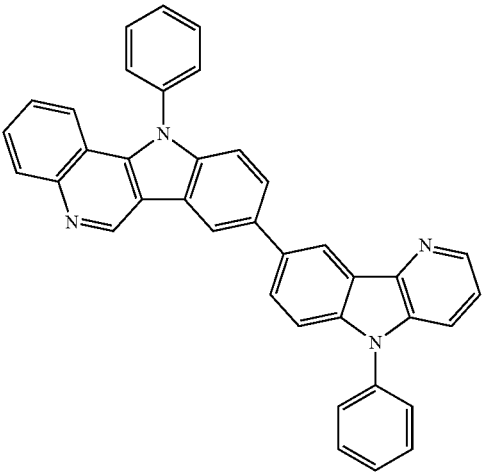
A-88
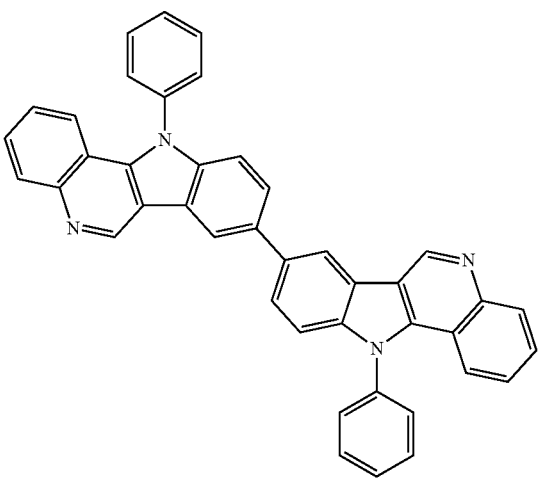
A-89

-continued
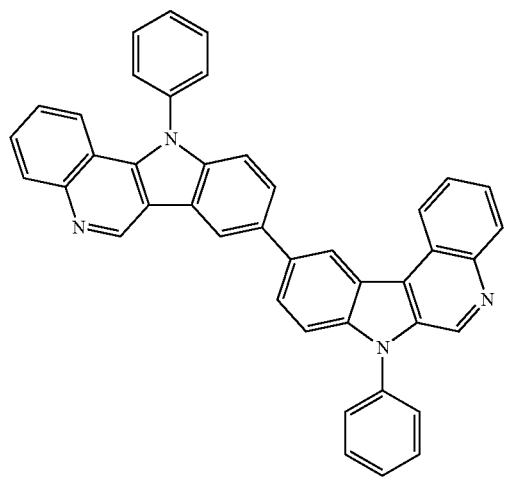
A-90
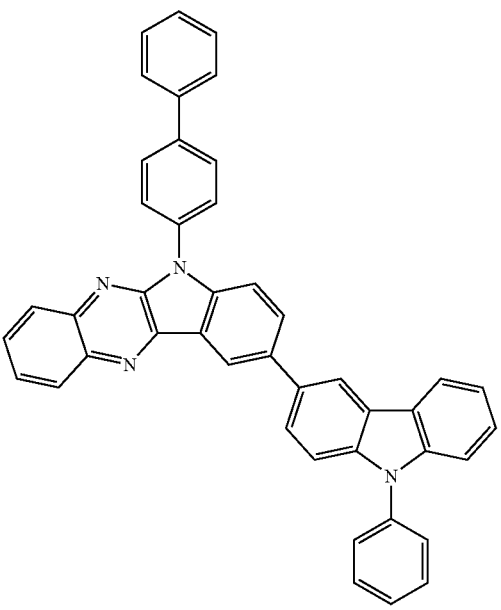
A-93
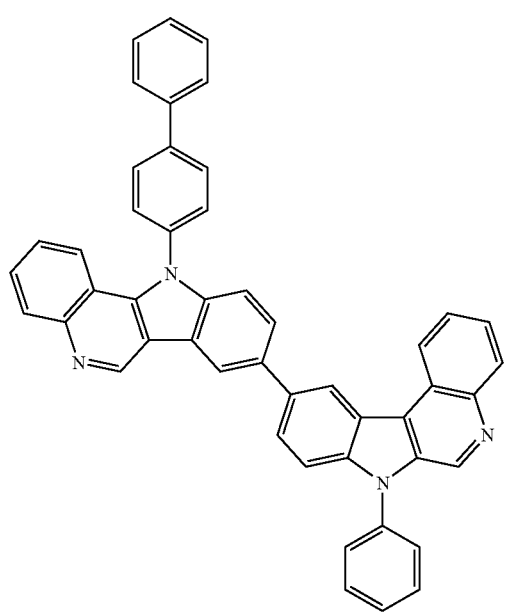
A-91
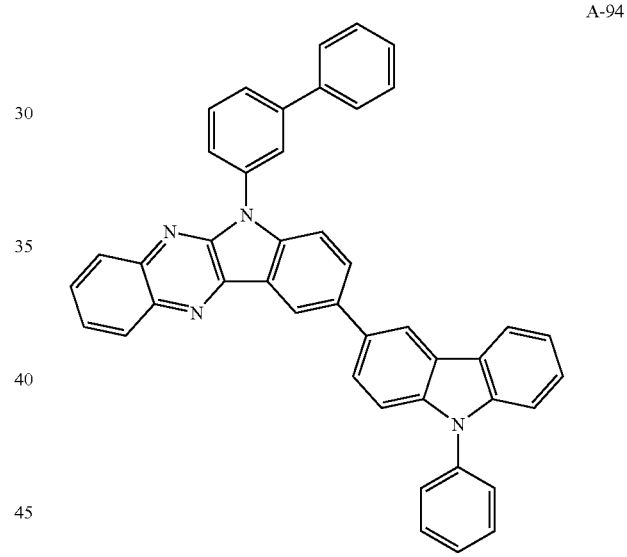
A-94
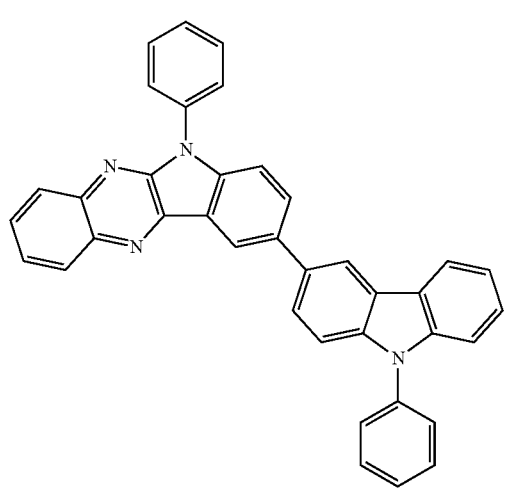
A-92
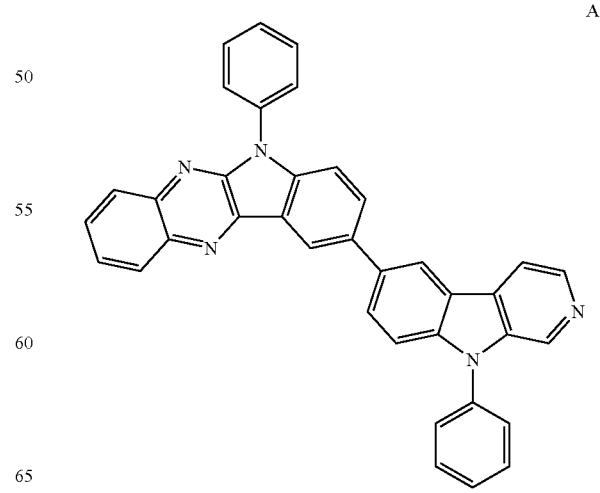
A-95

A-96
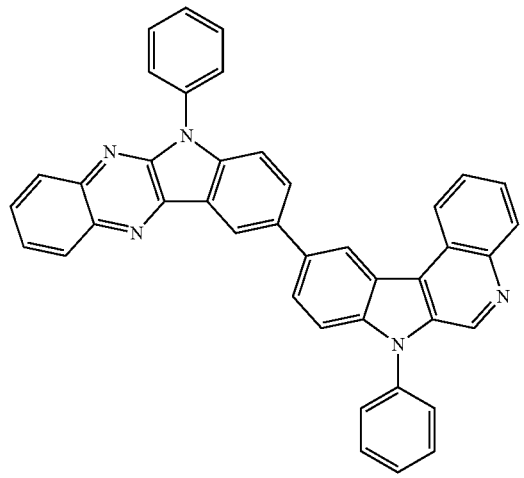
A-97
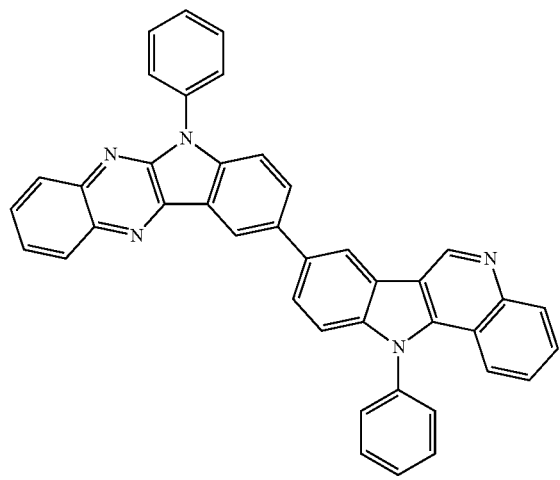
A-98
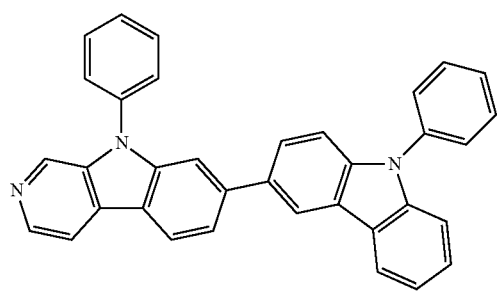
A-99
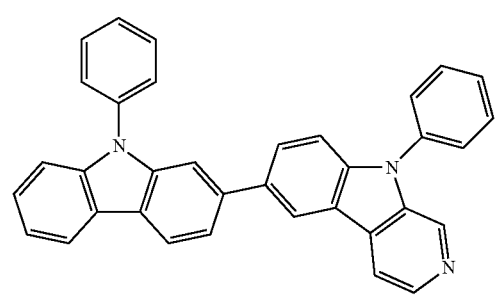
A-100
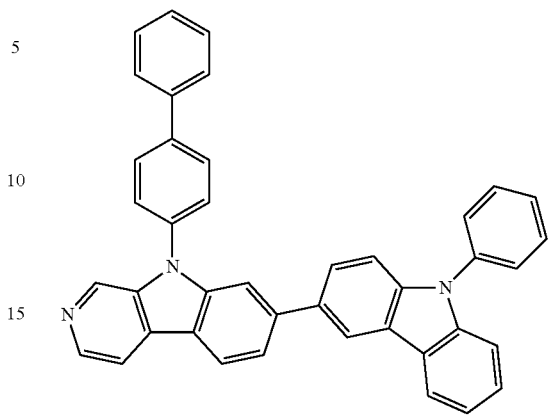
A-101
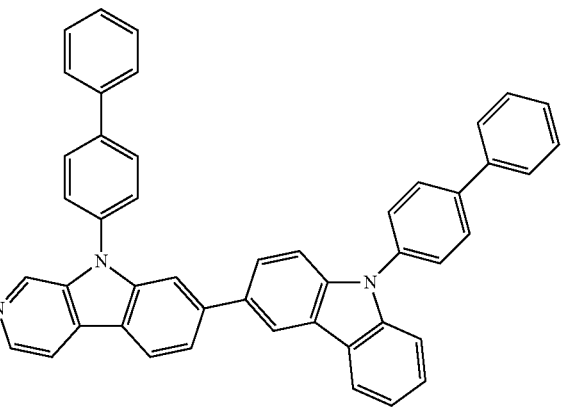
A-102
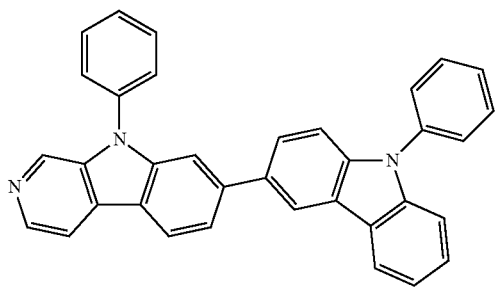
A-103

A-104
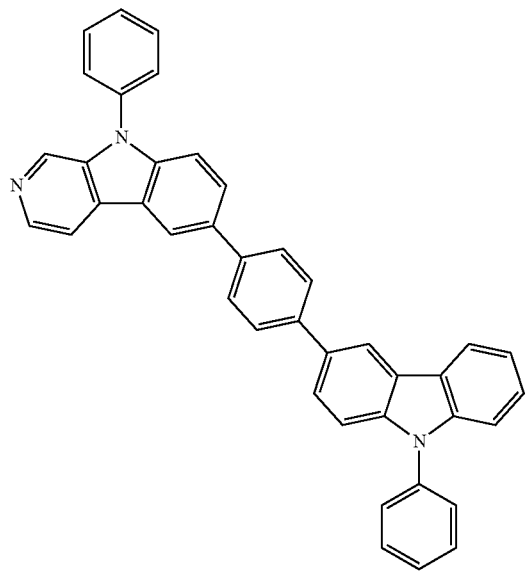
A-105
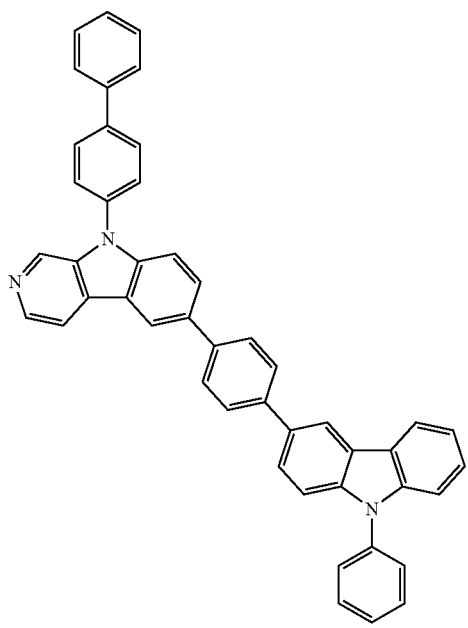
A-106
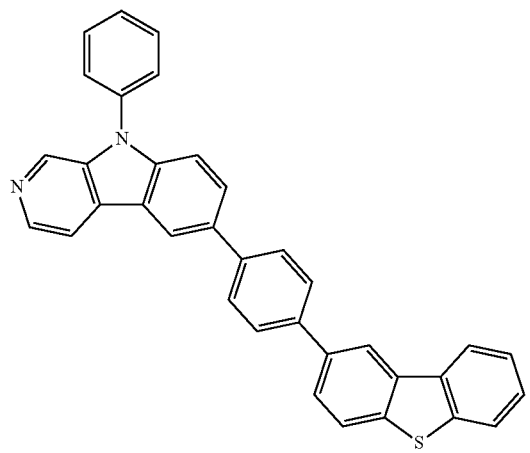
A-107
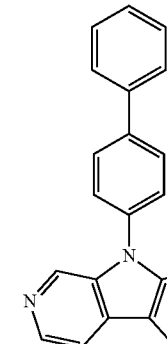
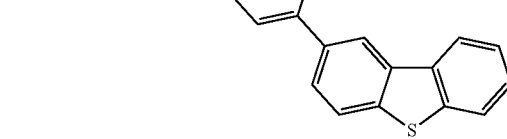
A-108
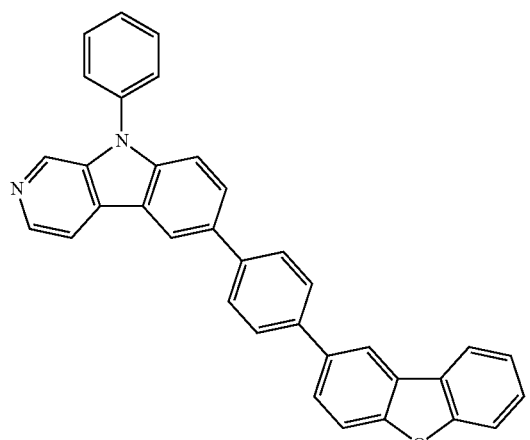

A-109
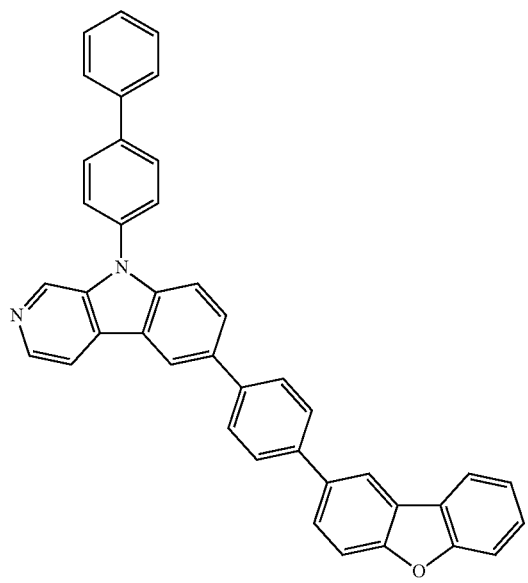
A-110
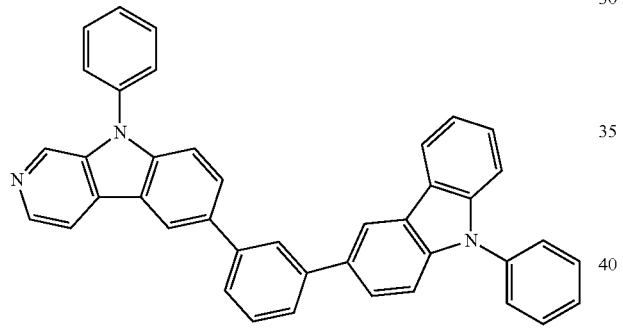
A-111
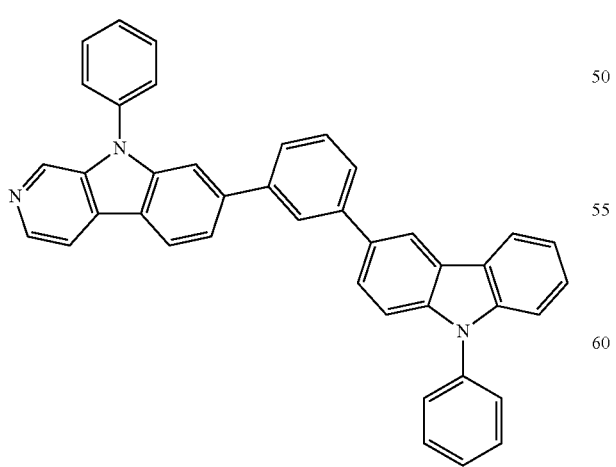
A-112
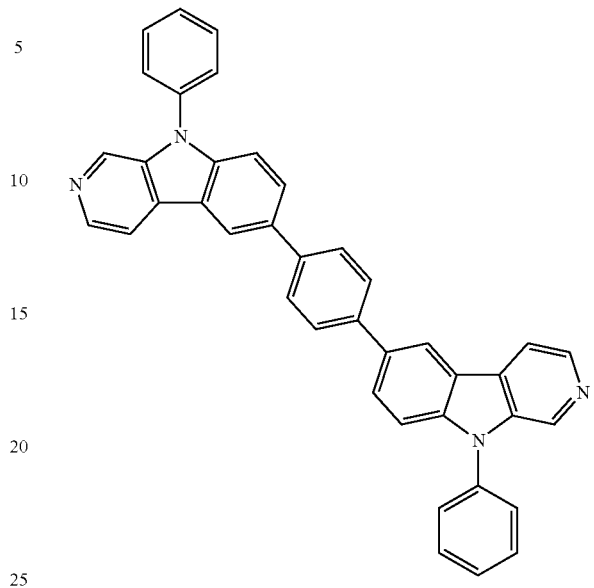
A-113
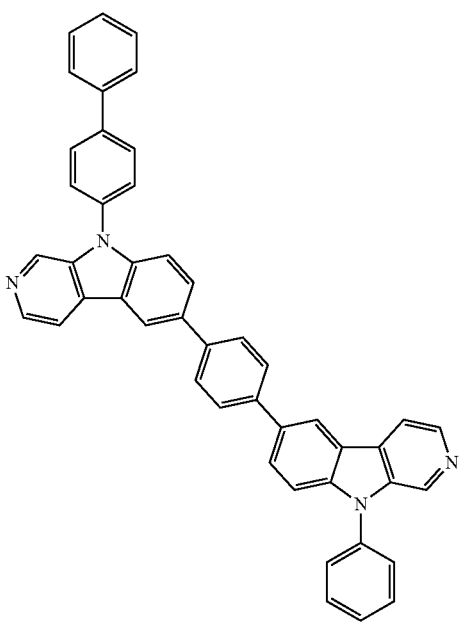

A-114
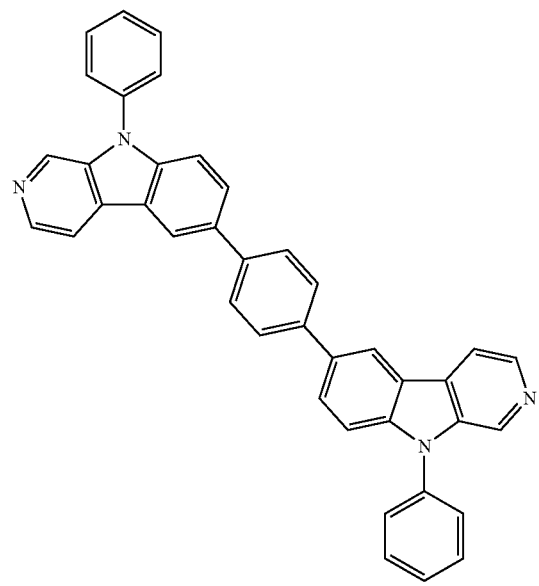
A-115
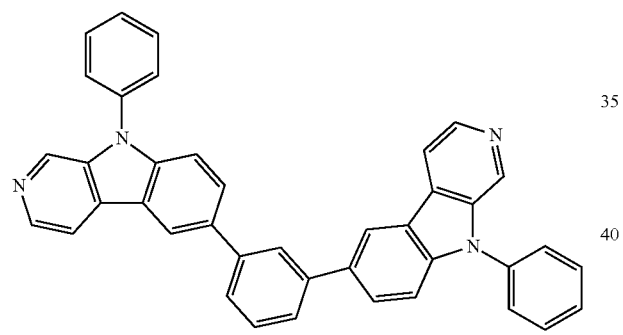
A-116
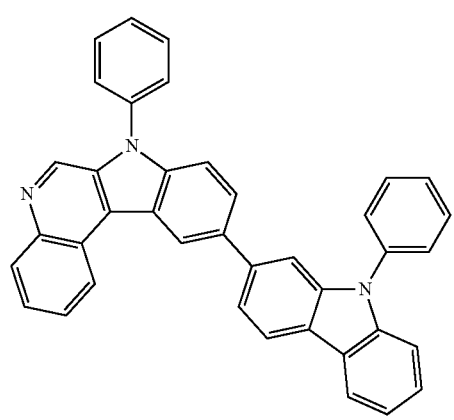
A-117
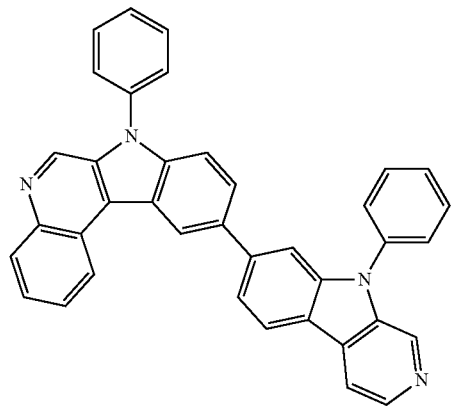
A-118
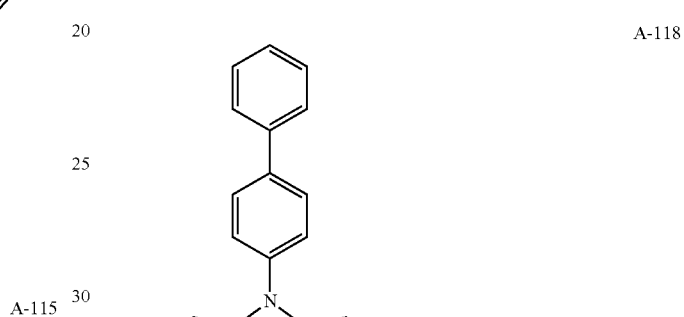
A-119
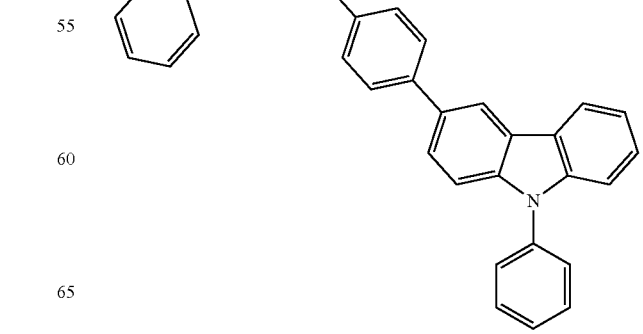

A-120
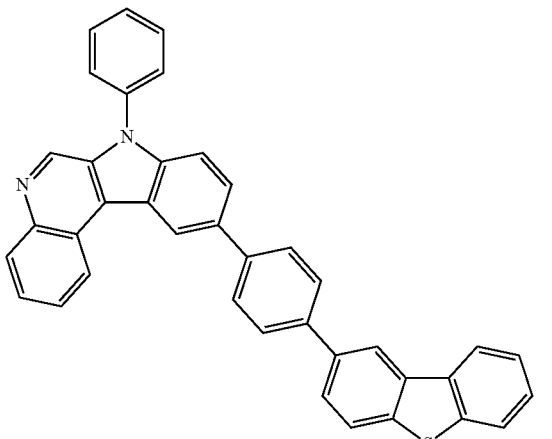
A-124
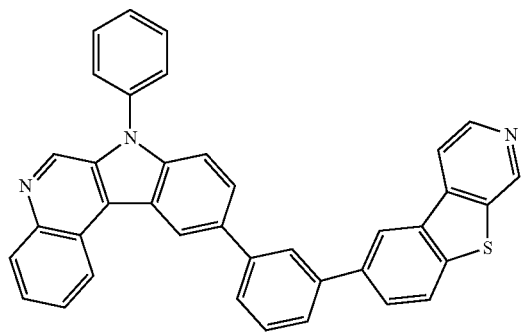
A-121
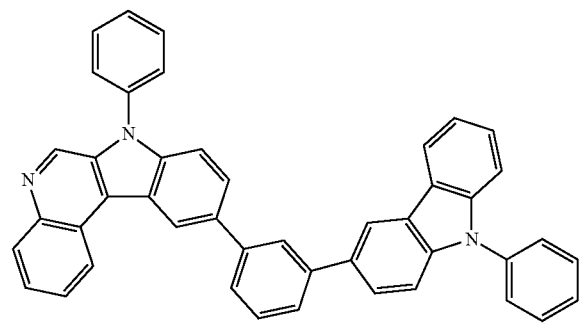
A-125
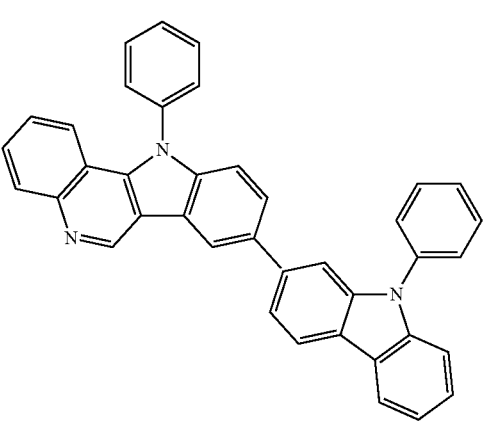
A-122
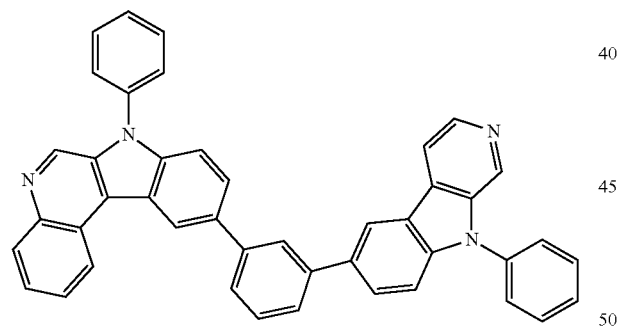
A-126
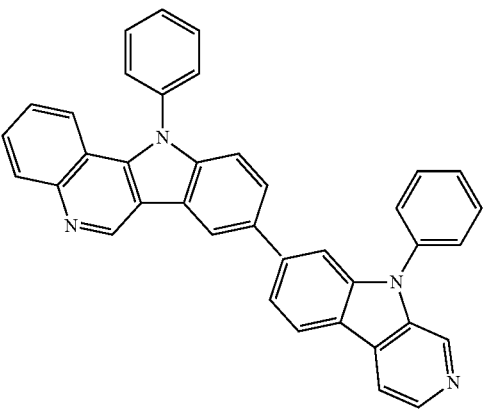
A-123
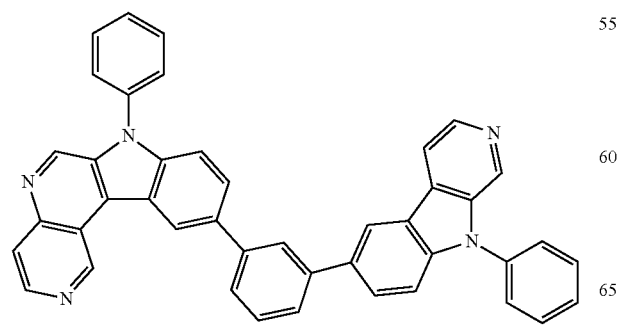

A-127
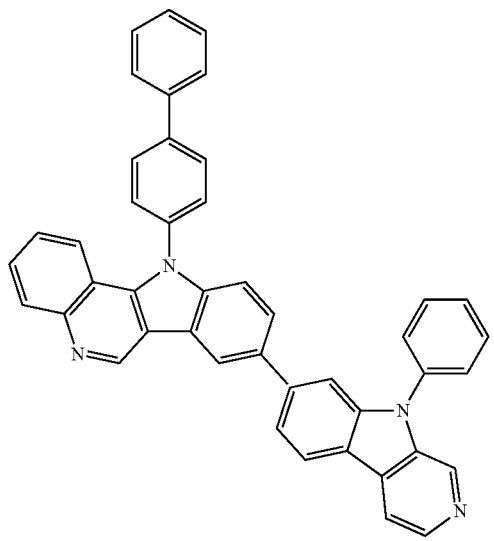
A-130
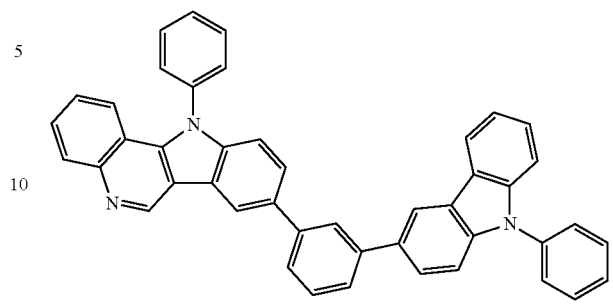
A-128
A-131
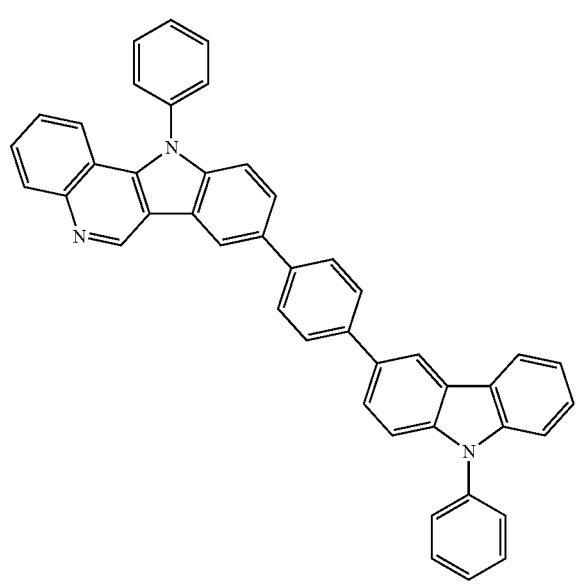
A-132
A-129
A-133
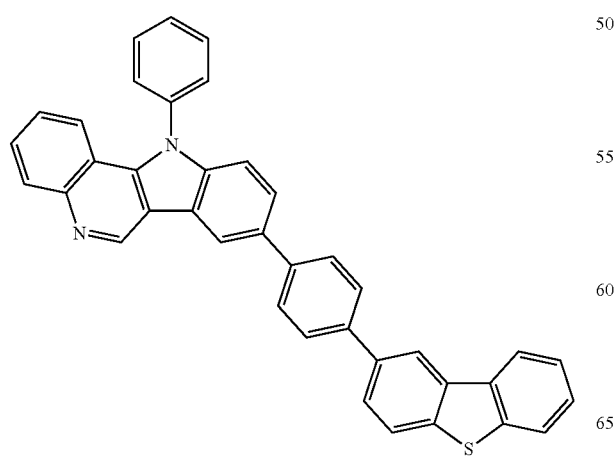

A-134
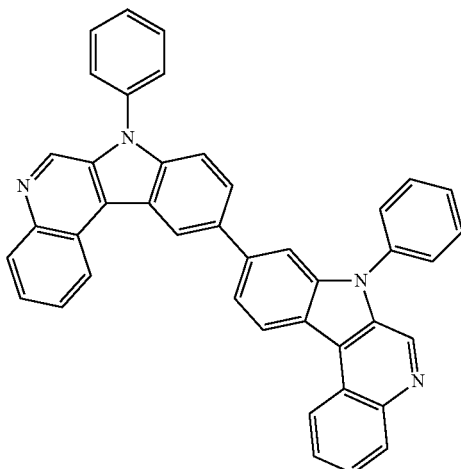
A-137
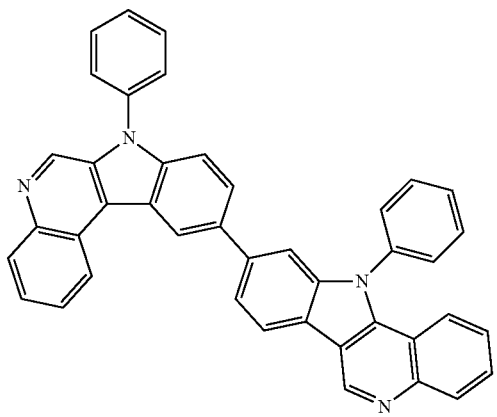
A-135
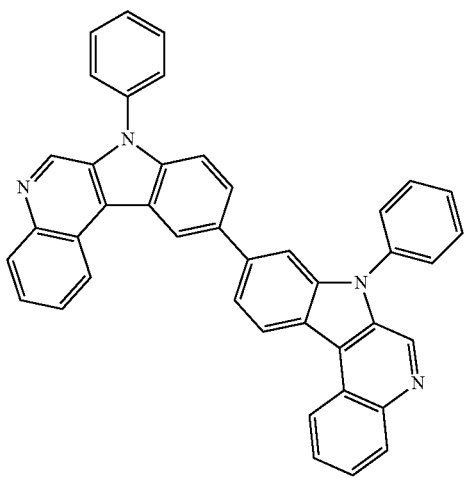
A-138
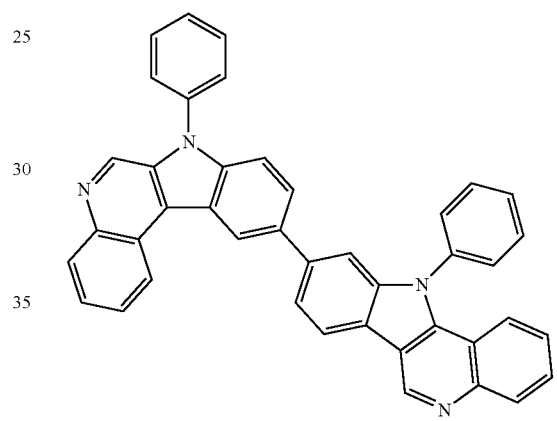
A-136
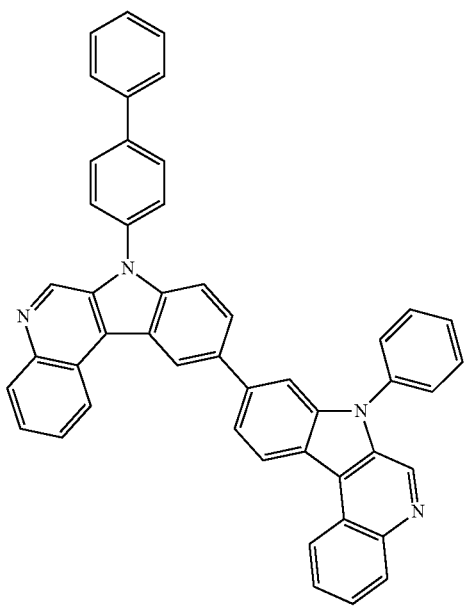
A-139
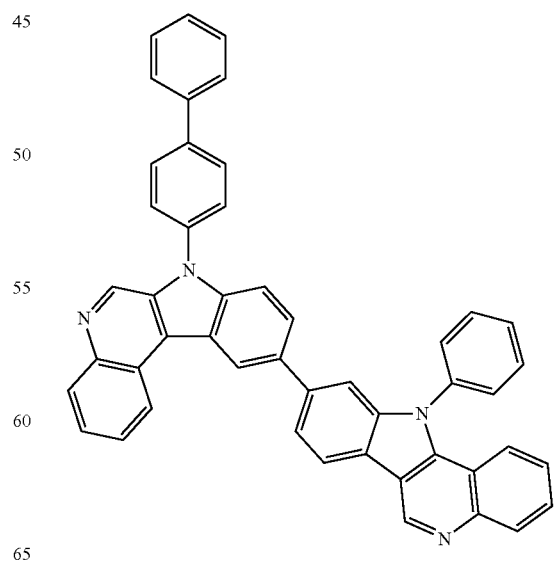

-continued
A-140
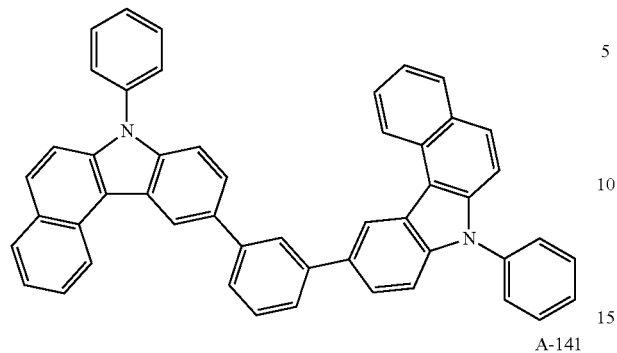
A-141
A-142
A-143
-continued
A-144
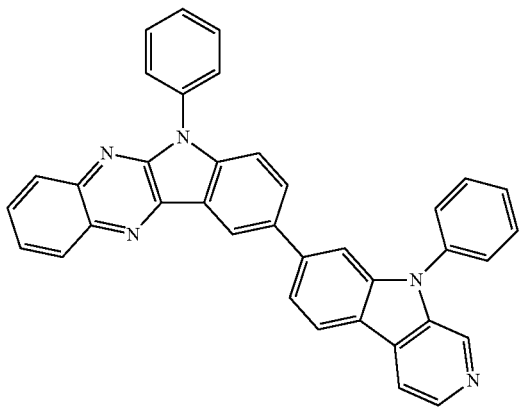
A-145
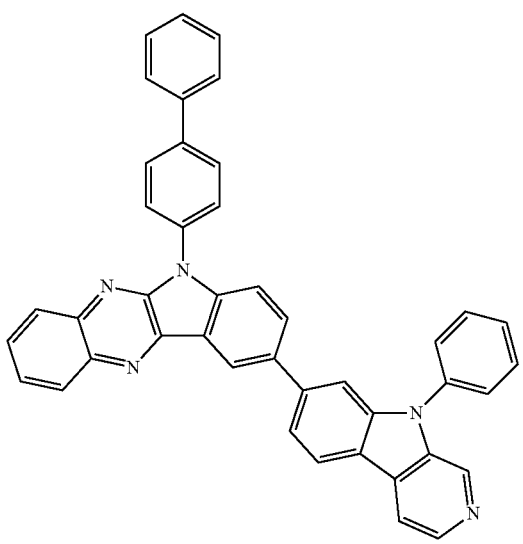
A-146
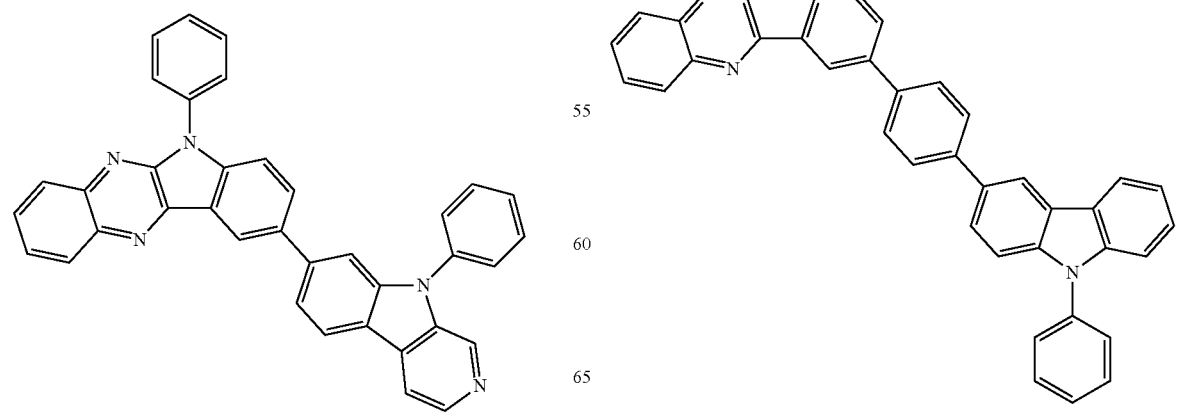

A-147
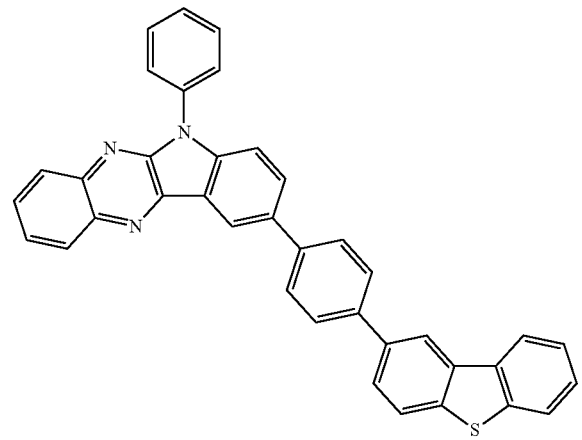
A-148
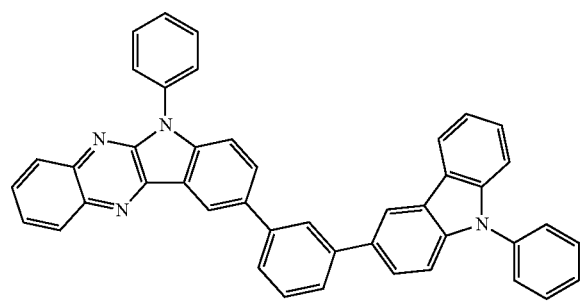
A-149
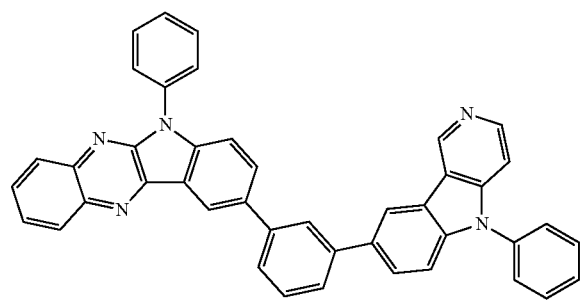
A-150
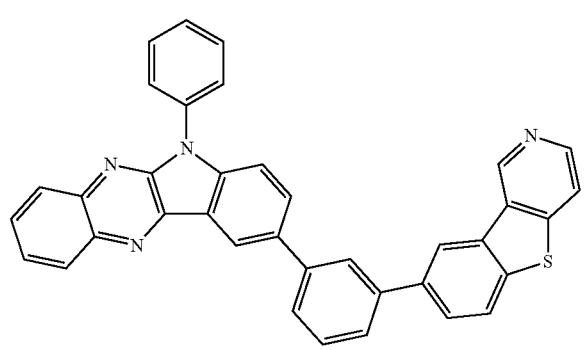
A-151
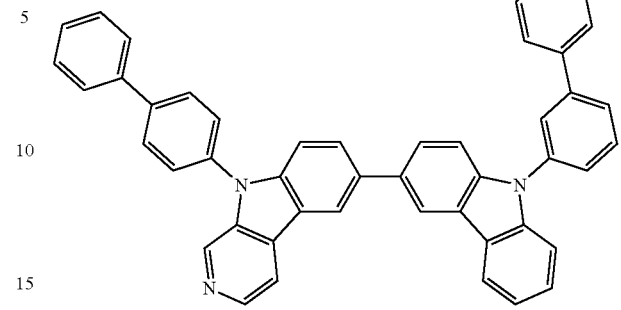
A-152
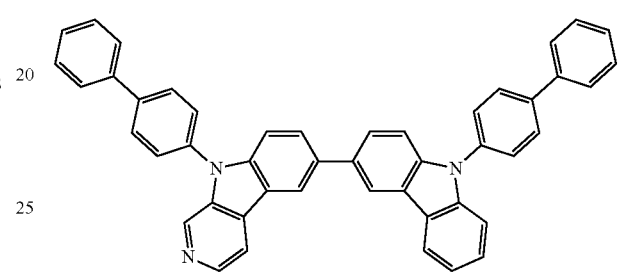
A-153
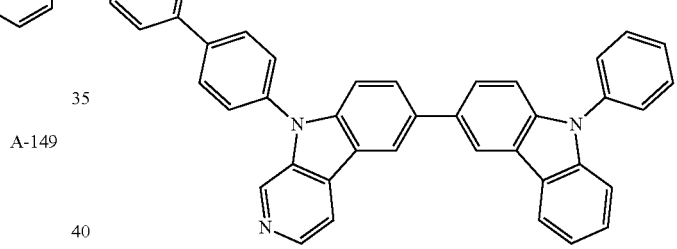
A-154
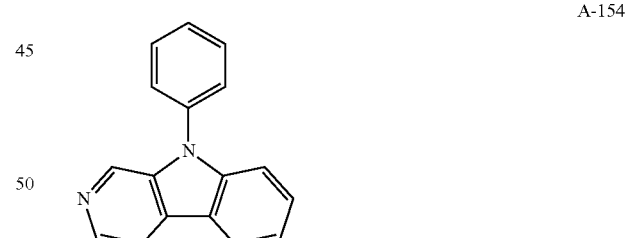
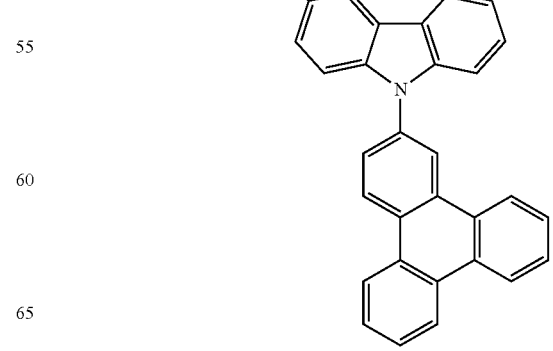

A-155
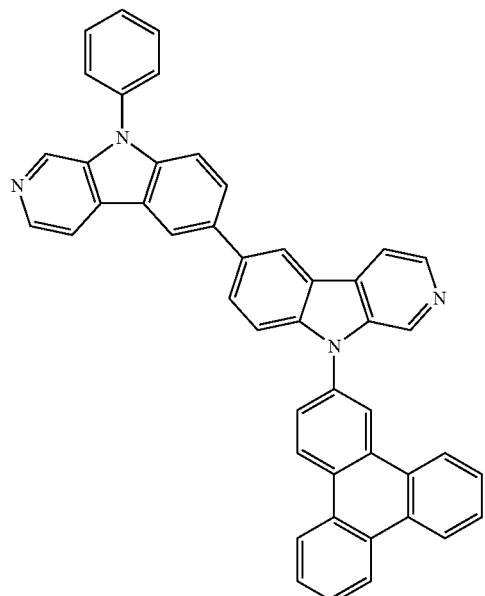
A-156
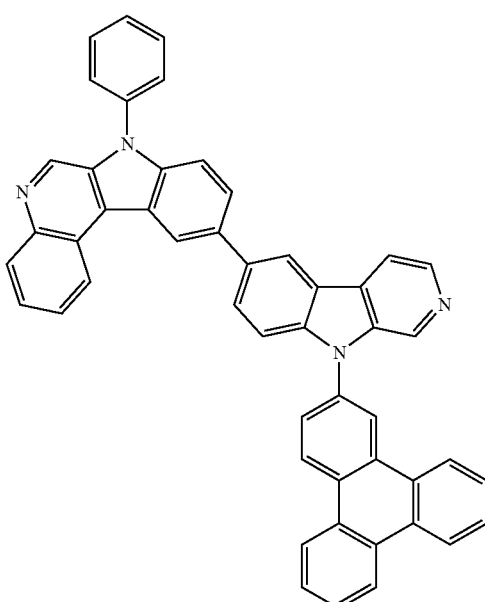
A-157
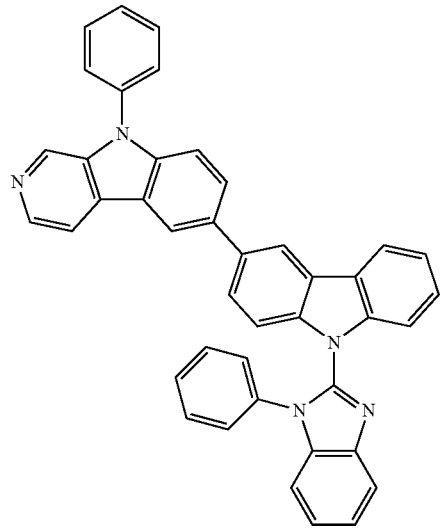
A-158
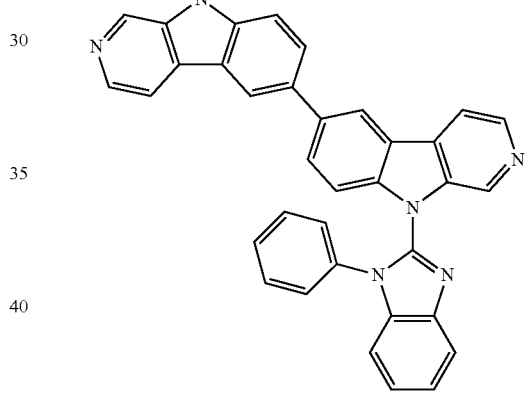
A-159
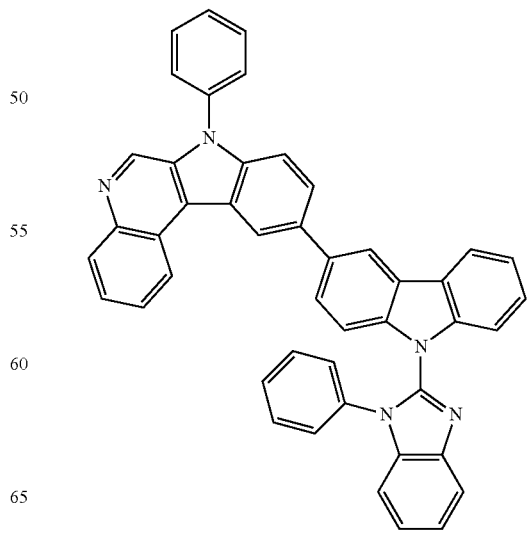

A-160
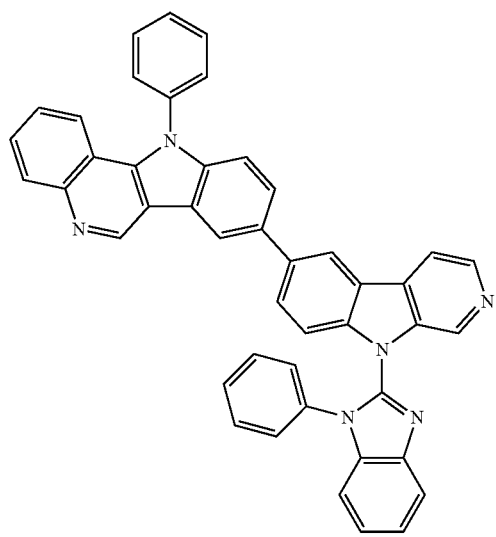
A-161
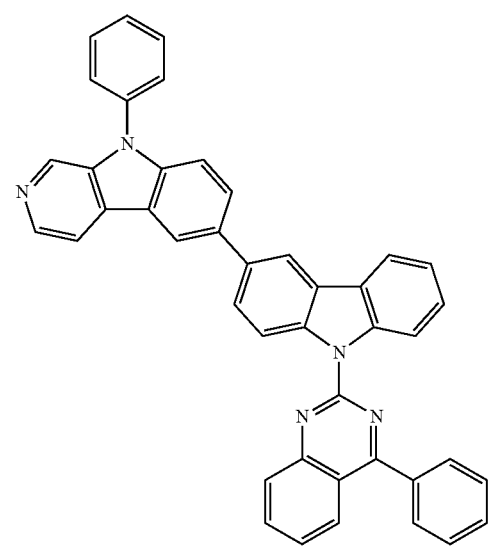
A-162
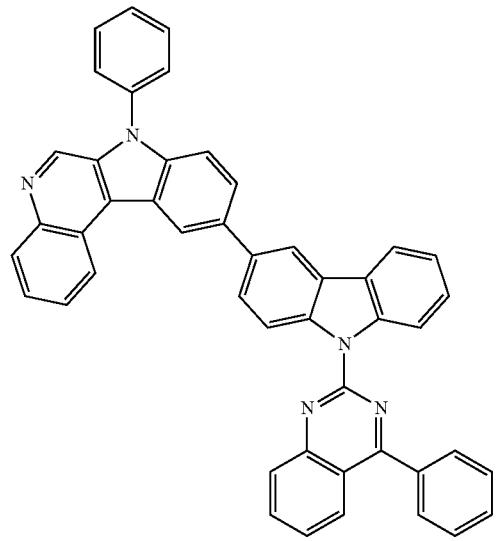
A-163
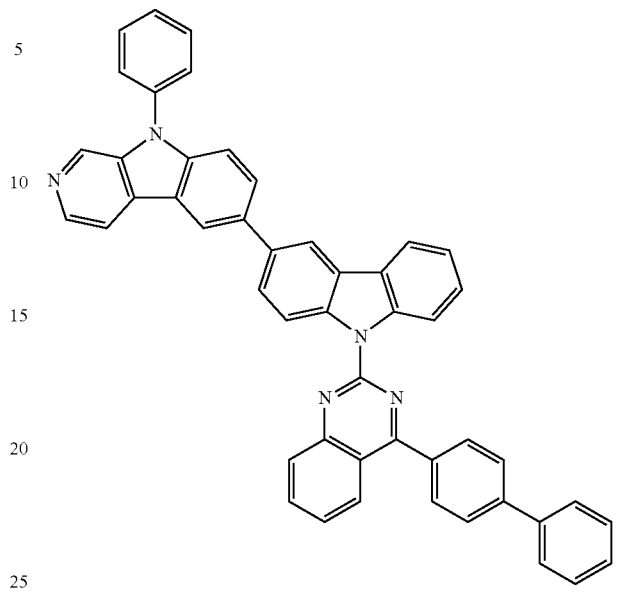
A-164
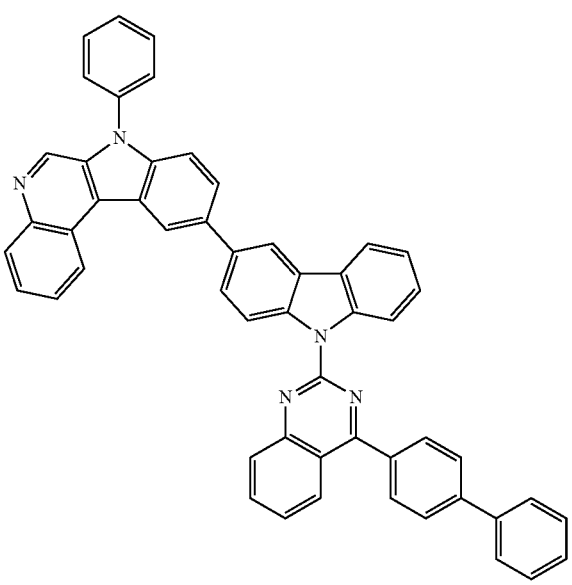

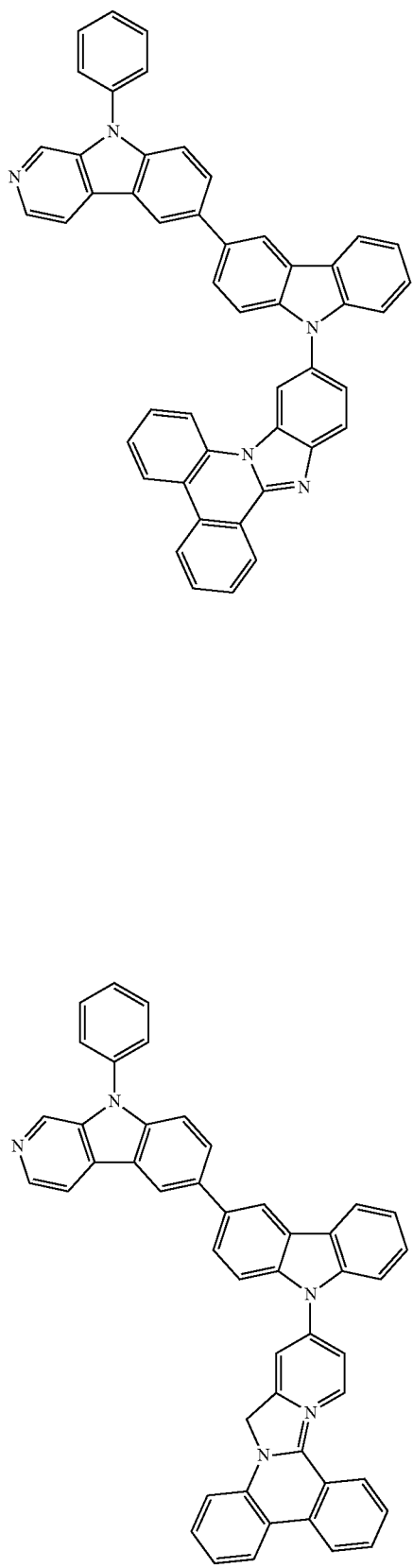

A-165

A-166

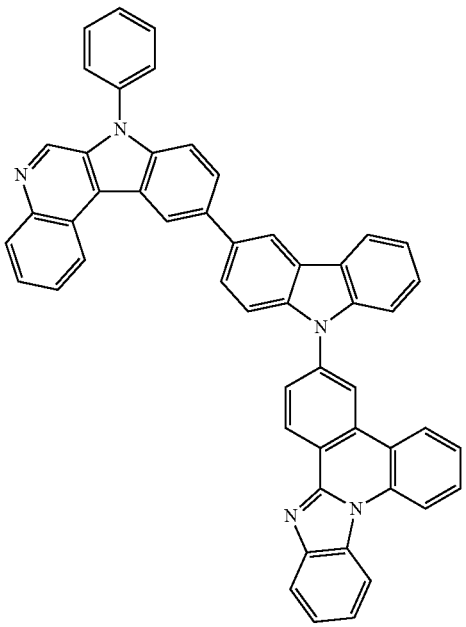

A-167

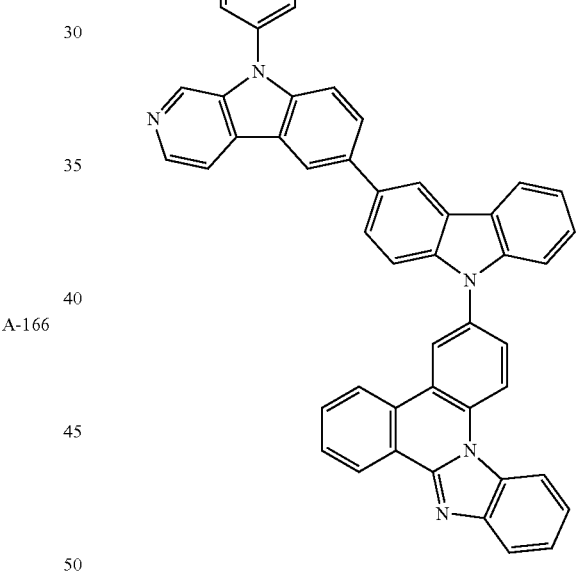

A-168

The organic optoelectronic device may be selected from an organic photoelectric device, an organic light emitting diode, an organic solar cell, an organic transistor, an organic photoconductor drum, and an organic memory device.

In another embodiment, an organic light emitting diode including an anode, a cathode, and at least one organic thin layer disposed between the anode and the cathode is provided. At least one organic thin layer includes the compound for an organic optoelectronic device described above.

The organic thin layer may be selected from an emission layer, a hole transport layer, a hole injection layer, an electron transport layer, an electron injection layer, a hole blocking layer, and a combination thereof.

The compound for an organic optoelectronic device may be included in an emission layer.

The compound for an organic photoelectric device may be used as a phosphorescent or fluorescent host material in an emission layer.

In yet another embodiment, a display device including the organic light emitting diode is provided.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
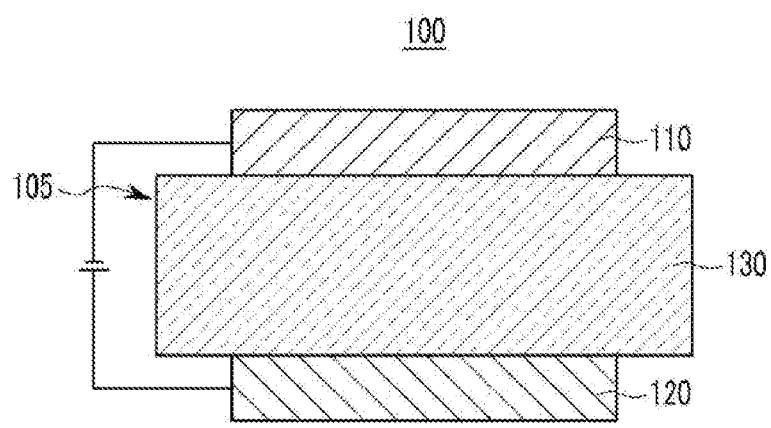
FIGS. 1 to 5 are cross-sectional views showing organic light emitting diodes according to various embodiments, including a compound for an organic optoelectronic device according to an embodiment.

Exemplary embodiments will hereinafter be described in detail. However, these embodiments are only exemplary, and the present disclosure is not limited thereto but rather is defined by the scope of the appended claims.

Accordingly, the embodiments are merely described below, by referring to the figures, to explain aspects of the present description. As used herein, the term "and/or" includes any and all combinations of one or more of the associated listed items. The term "or" means "and/or." Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Additional aspects will be set forth in part in the description which follows and, in part, will be apparent from the description.

As used herein, when specific definition is not otherwise provided, the term "substituted" refers to a group substituted with deuterium, a halogen, a hydroxy group (—OH), an amino group (—NH$_2$), a carboxyl group (—CO$_2$H), a substituted or unsubstituted C1 to C30 amine group, a nitro group (—NO$_2$), a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group (—F), a C1 to C10 trifluoroalkyl group such as a trifluoromethyl group (—CF$_3$), and the like, or a cyano group (—CN) instead of at least one hydrogen of a substituting group or compound.

Two adjacent substituents selected from a hydroxy group, an amino group, a substituted or unsubstituted C1 to C20 amine group, a nitro group (—NO$_2$), a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a trifluoroalkyl group such as a trifluoromethyl group (—CF$_3$), or a cyano group (—CN) may be fused to each other to provide a ring.

As used herein, when specific definition is not otherwise provided, the term "hetero" refers to a group wherein one or more carbons are replaced with 1 to 3 hetero atoms selected from nitrogen (N), oxygen (O), sulfur (S), and phosphorus (P).

As used herein, when a definition is not otherwise provided, the term "combination thereof" refers to at least two substituents bound to each other by a linker, or at least two substituents fused to each other.

In the specification, when a definition is not otherwise provided, the term "alkyl group" may refer to an aliphatic hydrocarbon group. The alkyl group may be a saturated group without any double bond or triple bond.

The alkyl group may be branched, linear, or cyclic.

As used herein, when a definition is not otherwise provided, the term "alkenyl group" may refer to a substituent including at least one carbon-carbon double bond, and the "alkynyl group" may refer to a substituent including at least one carbon-carbon triple bond.

The alkyl group may be a C1 to C20 alkyl group. For example, the alkyl group may be a C1 to C10 alkyl group or a C1 to C6 alkyl group.

For example, the C1 to C4 alkyl group may have 1 to 4 carbon atoms, and may be selected from methyl, ethyl, propyl, iso-propyl, n-butyl, iso-butyl, sec-butyl, and t-butyl.

Examples of the alkyl group may include a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, when a definition is not otherwise provided, the term "alkoxy group" may refer to "alkyl-O—" wherein the alkyl is the same as described above and having the specified number of carbon atoms. Non-limiting examples of the alkoxy group include methoxy, ethoxy, propoxy, 2-propoxy, butoxy, t-butoxy, pentyloxy, hexyloxy, cyclopropoxy, and cyclohexyloxy.

As used herein, when a definition is not otherwise provided, the term "aromatic group" may refer to a substituent including all elements of the cycle having p-orbitals which form conjugation. Examples may include an aryl group and a heteroaryl group.

As used herein, when a definition is not otherwise provided, the term "aryl group" may refer to a monocyclic or fused ring polycyclic (i.e., wherein the rings share adjacent pairs of carbon atoms) group.

As used herein, when a definition is not otherwise provided, the term "aryloxy group" may refer to "—O-aryl" having the specified number of carbon atoms. A non-limiting example of the aryloxy group is phenoxy.

As used herein, when a definition is not otherwise provided, the term "silyl group" may refer to a monovalent or higher valency group derived from a completely saturated, branched or unbranched (or a straight or linear) silane, and having the specified number of carbon atoms. A non-limiting example of silyl group is trimethylsilyl (($CH_3$)$_3$Si—).

As used herein, when a definition is not otherwise provided, the term "silyloxy group" may refer to "—O-silyl" having the specified number of carbon atoms. A non-limiting example of silyloxy group is trimethylsilyloxy (($CH_3$)$_3$SiO—).

As used herein, when a definition is not otherwise provided, the term "acyl group" may refer to "—C(=O)-alkyl" wherein the alkyl is the same as described above and having the specified number of carbon atoms. A non-limiting example of the acyl group is acetyl ($CH_3$C(=O)—).

As used herein, when a definition is not otherwise provided, the term "alkoxycarbonyl group" may refer to "—C(=O)—O-alkyl" wherein the alkyl is the same as described above and having the specified number of carbon atoms.

A non-limiting example of the alkoxycarbonyl group is methoxycarbonyl ($CH_3$OC(=O)—).

As used herein, when a definition is not otherwise provided, the term "acyloxy group" may refer to "—O-acyl" wherein the acyl is the same as described above and having the specified number of carbon atoms. A non-limiting example of the acyloxy group is acetyloxy ($CH_3$C(=O)O—).

As used herein, when a definition is not otherwise provided, the term "acylamino group" may refer to "—NH-acyl" wherein the acyl is the same as described above and having the specified number of carbon atoms. A non-limiting example of the acylamino group is acetylamino ($CH_3$C(=O)NH—).

As used herein, when a definition is not otherwise provided, the term "alkoxycarbonylamino group" may refer to "—NH—C(=O)—O-alkyl" wherein the alkyl is the same as described above and having the specified number of carbon atoms. A non-limiting example of the alkoxycarbonylamino group is methoxycarbonylamino ($CH_3$C(=O)NH—).

As used herein, when a definition is not otherwise provided, the term "aryloxycarbonylamino group" may refer to "—NH—C(=O)—O-aryl" wherein the aryl is the same as described above and having the specified number of carbon atoms. A non-limiting example of the aryloxycarbonylamino group is phenoxycarbonylamino (PhOC(=O)NH—).

As used herein, when a definition is not otherwise provided, the term "sulfamoylamino group" may refer to $H_2$NS($O_2$)NH—, alkyl-NHS($O_2$)NH—, (alkyl)$_2$NS($O_2$)NH—, aryl-NHS($O_2$)NH—, (aryl)$_2$NS(O)$_2$NH—, heteroaryl-NHS($O_2$)—NH—, or (heteroaryl)$_2$NHS($O_2$)—NH—, wherein alkyl, aryl, and heteroaryl are the same as described above and having the specified number of carbon atoms.

As used herein, when a definition is not otherwise provided, the term "sulfonyl group" may refer to alkyl-S($O_2$)—, aryl-S($O_2$)—, or heteroaryl-S($O_2$)—, wherein alkyl, aryl, and heteroaryl are the same as described above and having the specified number of carbon atoms.

As used herein, when a definition is not otherwise provided, the term "alkylthio group" may refer to "alkyl-S—" wherein the alkyl is the same as described above and having the specified number of carbon atoms. Non-limiting example of the alkylthio group include methylthio.

As used herein, when a definition is not otherwise provided, the term "arylthio group" may refer to "aryl-S—" wherein the aryl is the same as described above and having the specified number of carbon atoms. Non-limiting example of the arylthio group include phenylthio.

As used herein, when a definition is not otherwise provided, the term "heterocyclothio group" may refer to "heterocyclo-S—", wherein the heterocyclo is a saturated hydrocarbon ring group, including at least one heteroatom selected from nitrogen (N), oxygen (O), phosphorous (P), and sulfur (S), wherein the rest of the cyclic atoms are carbon, and having the specified number of carbon atoms. A non-limiting example of a heterocycloalkyl group includes tetrahydro-2H-pyran-2-yl-thio-(OC$_5$H$_9$—S—).

As used herein, when a definition is not otherwise provided, the term "ureide group" may refer to $H_2$NC(O)NH—, alkyl-NHC(O)NH—, (alkyl)$_2$NC(O)NH—, aryl-NHC(O)NH—, (aryl)$_2$NC(O)NH—, heteroaryl-NHC(O)—NH—, or (heteroaryl)$_2$NHC(O)NH—, wherein alkyl, aryl, and heteroaryl are the same as described above and having the specified number of carbon atoms.

As used herein, when a definition is not otherwise provided, the term "halogen" may refer to —F, —Cl, —Br, or —I.

As used herein, when a definition is not otherwise provided, the term "ferrocenyl group" may refer to a monovalent or higher valency group derived from ferrocene (bis (η5-cyclopentadienyl)iron) by a removal of one or more hydrogen atoms.

As used herein, when a definition is not otherwise provided, the term "heteroaryl group" may refer to an aryl group including 1 to 3 hetero atoms selected from nitrogen (N), oxygen (O), sulfur (S), and phosphorus (P), and remaining carbons in one functional group. The heteroaryl group may be a fused ring cyclic group where each cycle may include the 1 to 3 heteroatoms.

Non-limiting examples of a monocyclic heteroaryl group include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol- 4-yl, 1,2,3-triazol-5-yl, tetrazolyl, pyrid-2-yl, pyrid-3-yl, 2-pyrazin-2-yl, pyrazin-4-yl, pyrazin-5-yl, 2-pyrimidin-2-yl, 4-pyrimidin-2-yl, and 5-pyrimidin-2-yl.

Non-limiting examples of a bicyclic heteroaryl group include indolyl, isoindolyl, indazolyl, indolizinyl, purinyl, quinolizinyl, quinolinyl, isoquinolinyl, cinnolinyl, phthalazinyl, naphthyridinyl, quinazolinyl, quinoxalinyl, phenanthridinyl, phenathrolinyl, phenazinyl, phenothiazinyl, phenoxazinyl, benzisoqinolinyl, thieno[2,3-b]furanyl, furo[3,2-b]pyranyl, 5H-pyrido[2,3-d]-o-oxazinyl, 1H-pyrazolo[4,3-d]oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridyl, pyrrolo[3,2-c]pyridyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridyl, pyrazolo[3,4-d]pyridyl, pyrazolo[3,4-b]pyridyl, imidazo[1,2-a]pyridyl, pyrazolo[1,5-a]pyridyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

As used herein, the terms "alkenylene", "alkynylene", "arylene", and "heteroarylene" indicate divalent groups respectively derived from "alkenyl", "alkynyl", "aryl", and "heteroaryl" groups.

In this specification, when a definition is not otherwise provided, the term "hole characteristics" may refer to a characteristic that a hole formed in the anode is readily injected into the emission layer and transported in the emission layer due to a conductive characteristic according to HOMO level. For example, the hole characteristics are similar to electron-repelling characteristics.

In this specification, when a definition is not otherwise provided, the term "electron characteristics" may refer to a characteristic that an electron formed in the cathode is readily injected into the emission layer and transported in the emission layer due to a conductive characteristic according to LUMO level. For example, the hole characteristics are similar to electron-withdrawing characteristics.

A compound for an organic optoelectronic device according to an embodiment may include, for example, a core structure where a mono or fused azacarbazole group and a carbazole group are linked to each other. If the compound includes a fused azacarbazolyl group as a core, the azacarbazolyl group may be substituted with a carbazole group when a nitrogen atom is separately present in a fused ring.

For example, the compound according to an embodiment may have a core structure including an aromatic group including at least one nitrogen in a fused ring or a carbazole group, and a separate carbazole group. The structure may selectively include various substituents.

The core structure may be used as a light emitting material, a hole injection material, or a hole transport material of an organic optoelectronic device. Particularly, it may be adapted for an electron injection material or an electron transport material.

The compound for an organic optoelectronic device includes a core part and various substituents for substituting the core part, and thus may have various energy band gaps.

The compound may have an appropriate energy level depending on the substituents, and thus may fortify electron transporting capability and hole transport capability of an organic optoelectronic device and bring about improved effects in terms of efficiency and driving voltage, and may also have improved electrochemical and thermal stability and thus improve life-span characteristics during the operation of the organic optoelectronic device.

According to an embodiment, a compound for an organic optoelectronic device represented by the following Chemical Formula 1 is provided.

Chemical Formula 1

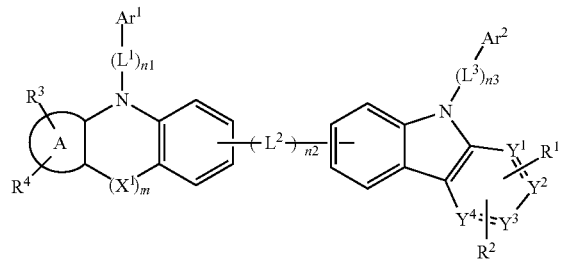

In Chemical Formula 1,

A is a C6 to C40 aryl group including 1 to 4 aromatic rings, wherein the 1 to 4 aromatic rings include at least one nitrogen, $Y^1$ to $Y^4$ are each independently CR' or N, $X^1$ is —CR'R"—, —SiR'R"—, —O—, —NR'—, —S—, —SO$_2$—, —C(O)—, or —P(O)—, m is an integer ranging from 0 to 2, $R^1$ to $R^4$, R', and R" are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and Ar² is a substituted or unsubstituted C6 to C30 aryl group.

The compound may have an improved characteristic of transporting electrons and holes due to the core structure of an A-containing moiety having electron characteristics and a separate carbazole group bonded with the A-containing moiety, and improved thermal stability.

The electron characteristics of the compound may be reinforced by selectively positioning a substituted or unsubstituted C2 to C30 heteroaryl group having electron characteristics in a place of Ar¹.

In an embodiment, the Ar¹ and Ar² may both be substituted or unsubstituted C6 to C30 aryl groups. The substituted or unsubstituted C6 to C30 aryl groups in the Ar¹ and Ar² may improve the thermal decomposition temperature of the compound and thus remarkably improve processability.

For example, the Ar¹ and Ar² are each independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triperylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof, but are not limited thereto.

For example, the Ar¹ and Ar² may be one of the following Chemical Formulae W-1 to W-8, but are not limited thereto.

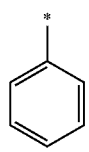

W-1

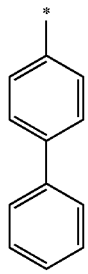

W-2

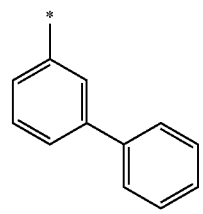

W-3

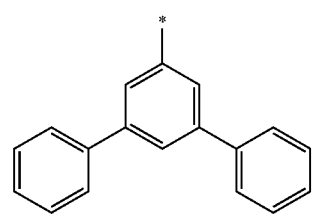

W-4

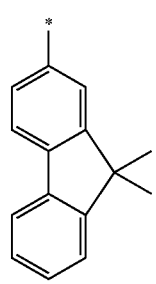

W-5

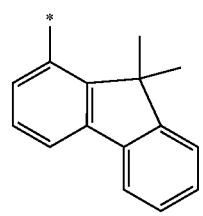

W-6

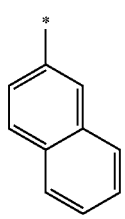

W-7

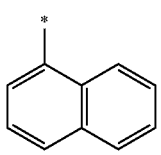

W-8

A total conjugation length of the compound may be controlled by selecting $L^1$ to $L^3$ appropriately, and thereby bandgap of triplet energy may be adjusted. Thereby, a material required for an organic optoelectronic device may be obtained. In addition, ortho, para, or meta binding positions may adjust the triplet energy bandgap.

Examples of the $L^1$ to $L^3$ may be a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluorenylene group, a substituted or unsubstituted p-terphenyl group, a substituted or unsubstituted m-terphenyl group, a substituted or unsubstituted pyrenylene group, and the like.

For example, the $L^2$ may be a phenylene group. When the $L^2$ is a phenylene group, core moieties at both sides may be linked at an ortho, meta, or para position relative to the phenylene group.

When the position is para, charge movement in the moieties of the compound may be improved, resultantly improving device efficiency. For example, when the position is meta, thermal stability may be improved and crystallinity may be reduced.

As an example, the compound represented by the Chemical Formula 1 may be represented by the following Chemical Formula 2.

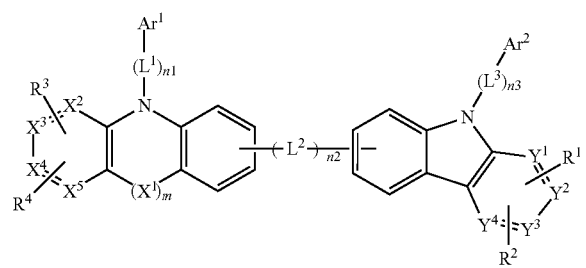

Chemical Formula 2

In Chemical Formula 2, $X^1$ is —CR'R"—, —SiR'R"—, —O—, —NR'—, —S—, —$SO_2$—, —C(O)—, or —P(O)—, m is an integer ranging from 0 to 2, $Y^1$ to $Y^4$ are each independently CR' or N, $X^2$ to $X^5$ are each independently CR' or N, provided that at least one of $X^2$ to $X^5$ is N, $R^1$ to $R^4$, R', and R" are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

As another example, the compound represented by the Chemical Formula 1 may be represented by the following Chemical Formula 3.

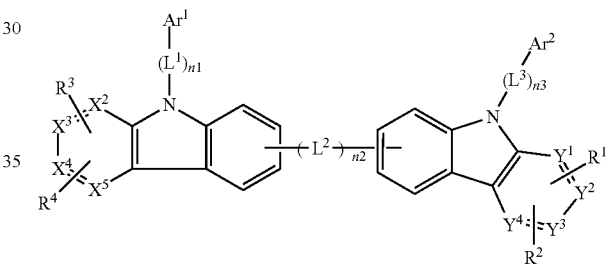

Chemical Formula 3

In Chemical Formula 3, $X^2$ to $X^5$ are each independently CR' or N, provided that at least one of $X^2$ to $X^5$ is N, $Y^1$ to $Y^4$ are each independently CR' or N, $R^1$ to $R^4$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

As in Chemical Formula 3, when the cores at both sides all have a carbazole moiety, the entire compound has a carbazole structure having high thermal and/or electrical stability and improved thermal stability.

As another example, the compound represented by the Chemical Formula 1 may be represented by the following Chemical Formula 4.

$L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

As in Chemical Formula 4, when the compound includes an additionally fused azacarbazole moiety in the core of the molecule, the triplet energy state (T1) of the compound may be adjusted and easily applied to a device. In addition, since the glass transition temperature of the compound is increased, the compound may secure device stability. Furthermore, the compound may have improved thermal stability.

As another example, the compound represented by the Chemical Formula 1 may be represented by the following Chemical Formula 5.

Chemical Formula 4

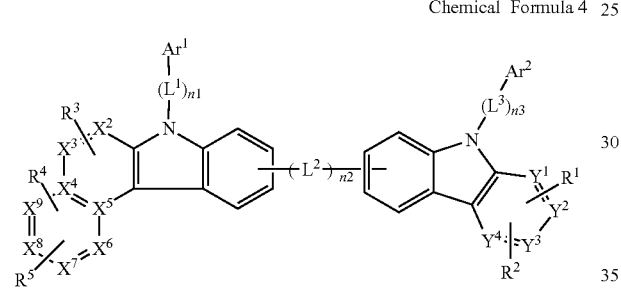

Chemical Formula 5

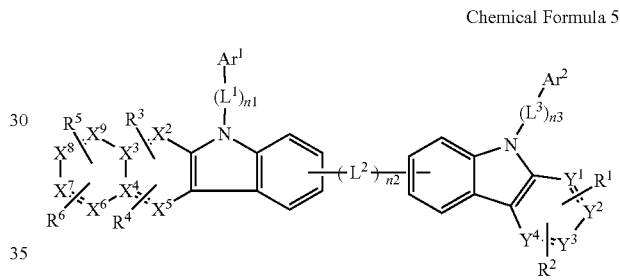

In Chemical Formula 4, $X^2$, $X^3$, and $X^6$ to $X^9$ are each independently CH, CR', or N, and $X^4$ and $X^5$ are C, provided that at least one of $X^2$, $X^3$, and $X^6$ to $X^9$ is N, $Y^1$ to $Y^4$ are each independently, CR' or N, $R^1$ to $R^5$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, In Chemical Formula 5, $X^2$ and $X^5$ to $X^9$ are each independently CR' or N, and $X^3$ and $X^4$ are C, provided that at least one of $X^2$, $X^5$, and $X^6$ to $X^9$ is N, $Y^1$ to $Y^4$ are each independently, CR' or N, $R^1$ to $R^6$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

In Chemical Formula 5, the position of an additionally fused ring is changed, but the embodiment is not limited thereto.

As another example, the compound represented by the Chemical Formula 1 may be represented by the following Chemical Formula 6.

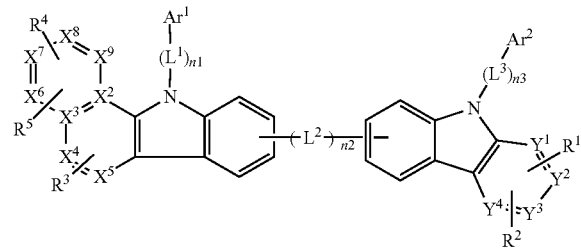

Chemical Formula 6

In Chemical Formula 6, $X^4$ to $X^9$ are each independently CR', or N, and $X^2$ and $X^3$ are C, provided that at least one of $X^4$, $X^5$, and $X^6$ to $X^9$ is N, $Y^1$ to $Y^4$ are each independently, CR' or N, $R^1$ to $R^5$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

In Chemical Formula 6, the position of an additionally fused ring is changed, but the embodiment is not limited thereto.

In an embodiment, n2 may be 0. In other words, when a separate linking group is not present in the core, the compound may have a lower sublimation temperature due to a relatively low molecular weight, which may improve processability. In addition, the compound may be structurally compact, and thus, it may form a uniform device film.

For specific azacarbazole moieties, $X^2$ may be N, and $X^3$ to $X^5$ may be CR'. $X^3$ may be N, and $X^2$, $X^4$, and $X^5$ may be CR'. $X^4$ may be N, and $X^2$, $X^3$, and $X^5$ may be CR'. $X^5$ may be N, and $X^2$, $X^3$, and $X^4$ may be CR'. $X^2$ and $X^4$ may be N, and $X^3$ and $X^5$ may be CR'. However, the moieties may be selectively adjusted depending on characteristics of a desired compound, without limitation.

The $Ar^1$ and $Ar^2$ may be independently one selected from the following Chemical Formulae W-1 to W-8, but are not limited thereto.

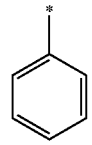

W-1

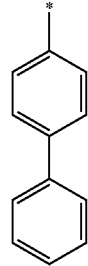

W-2

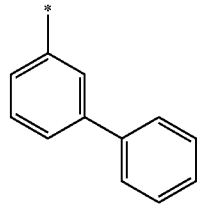

W-3

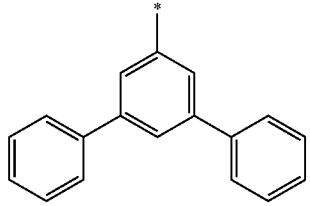

W-4

W-5
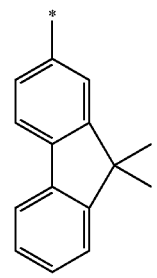
W-6
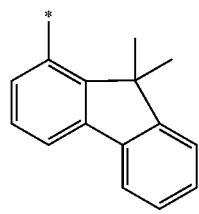
W-7
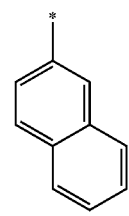
W-8
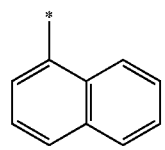
For example, the substituted or unsubstituted C2 to C30 heteroaryl group having electron characteristics may be one of the following Chemical Formulae X-1 to X-22, but are not limited thereto.
X-1
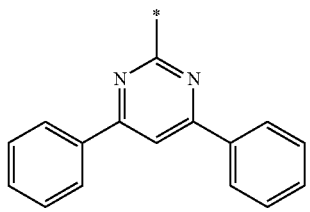
X-3
X-2
X-4
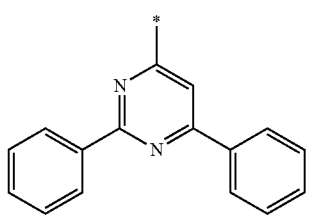
X-5
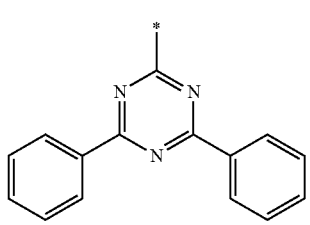
X-6
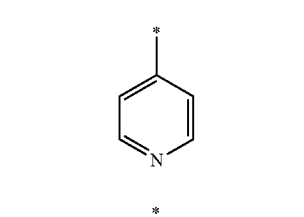
X-7
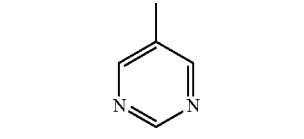
X-8
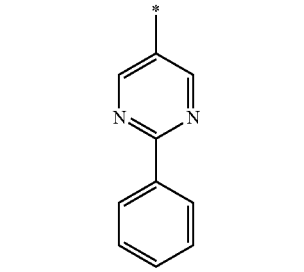
X-9
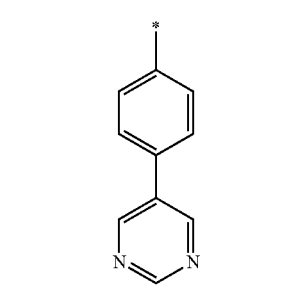

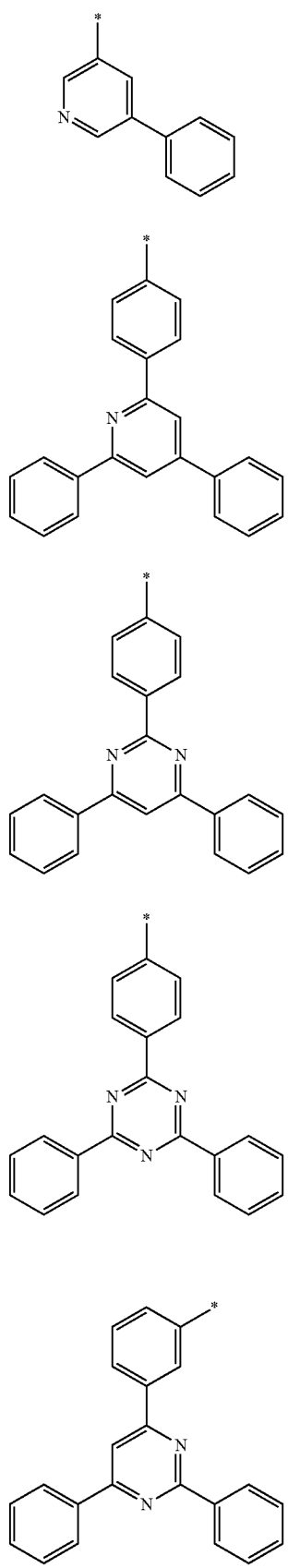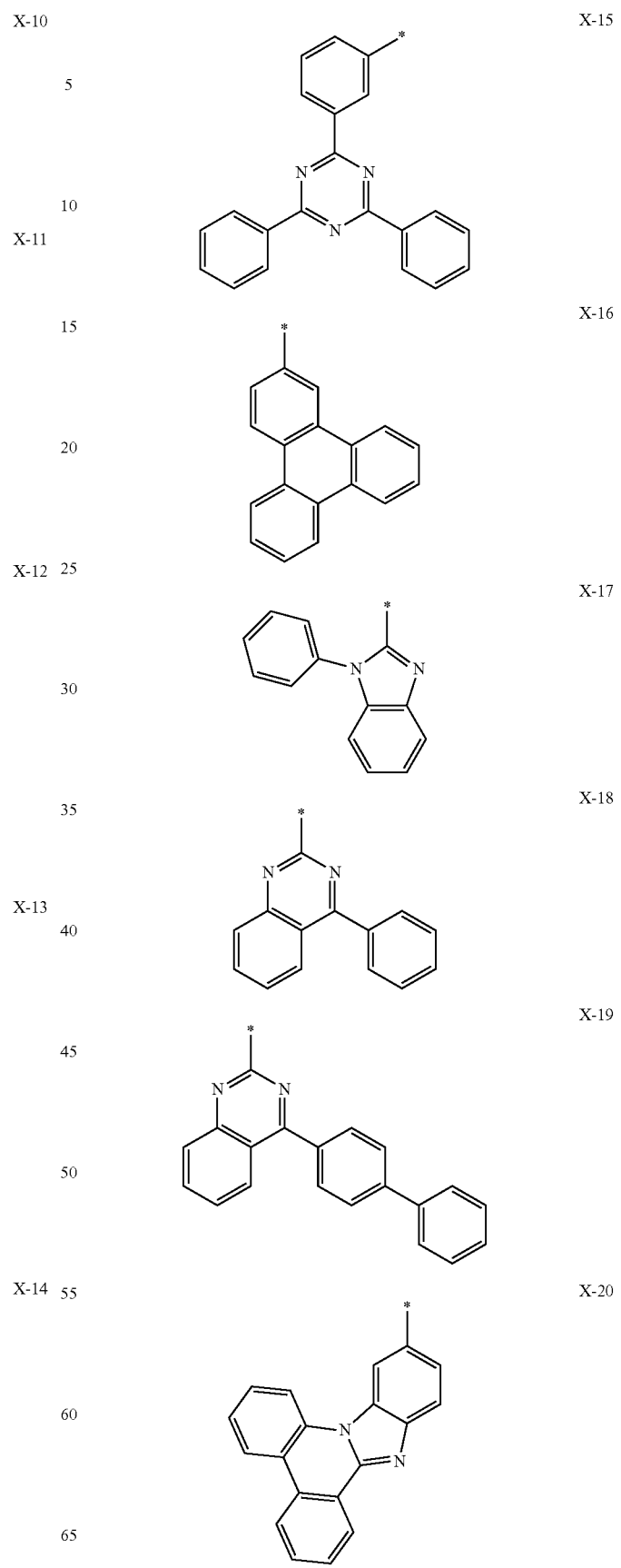

X-21
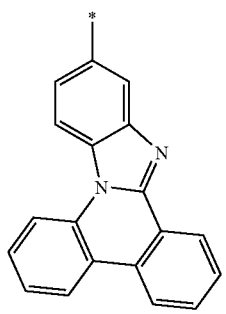
X-22
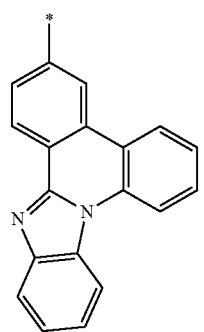
Specific examples of the compound for an organic optoelectronic device may be represented by one of the following Chemical Formulae A-1 to A-168, but are not limited thereto.
A-1
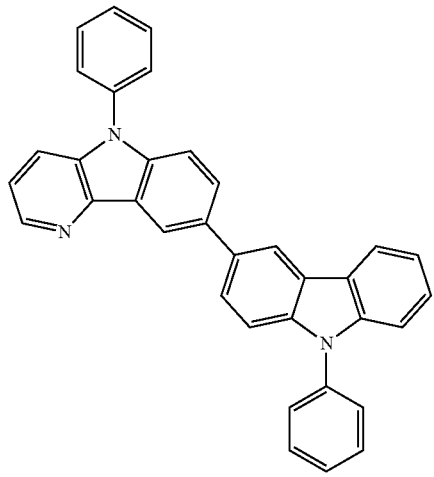
A-2
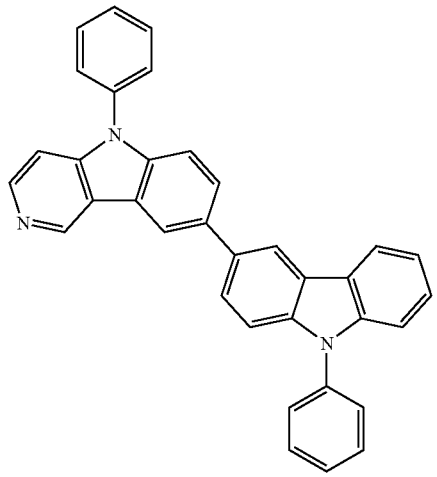
A-3
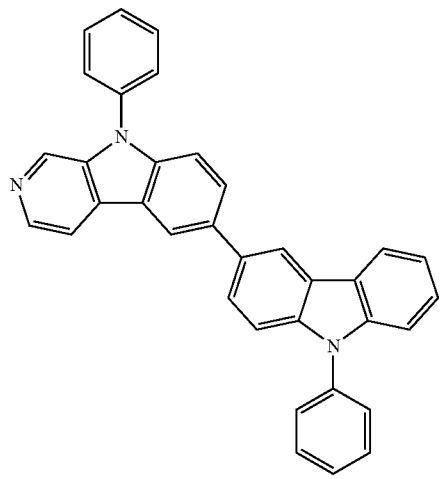
A-4
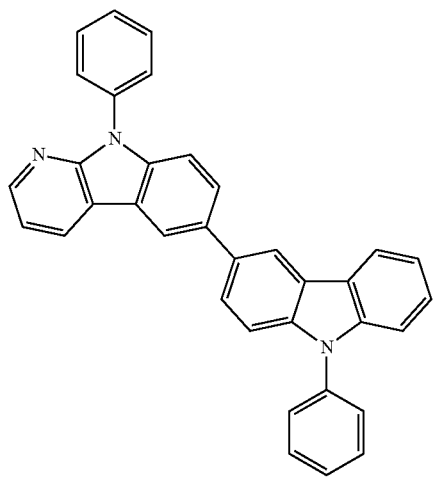

A-5
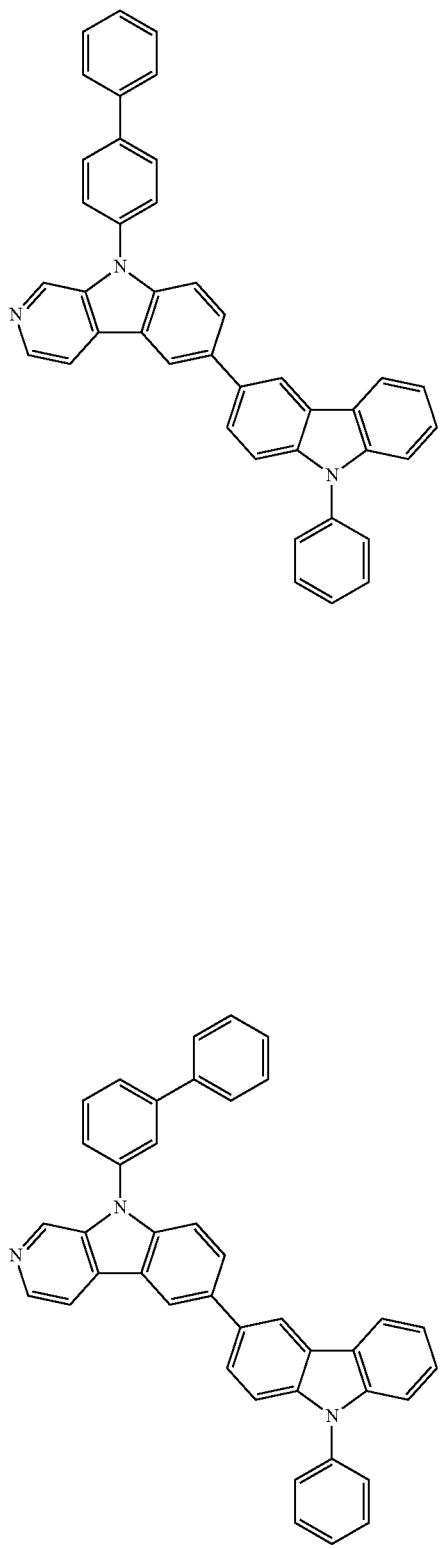
A-6
A-7
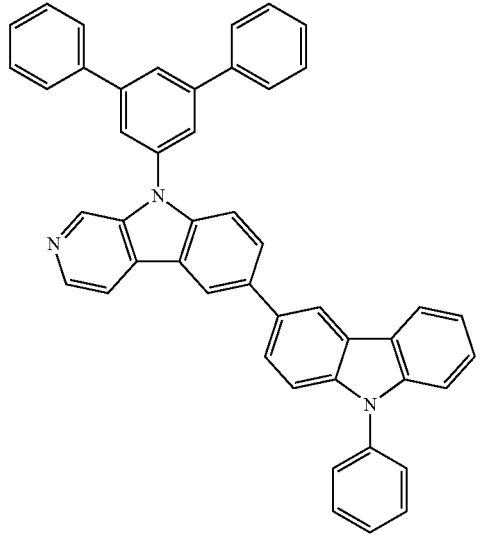
A-8
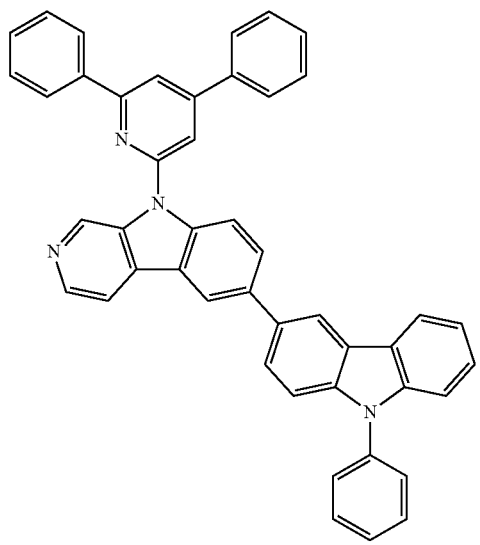
A-9
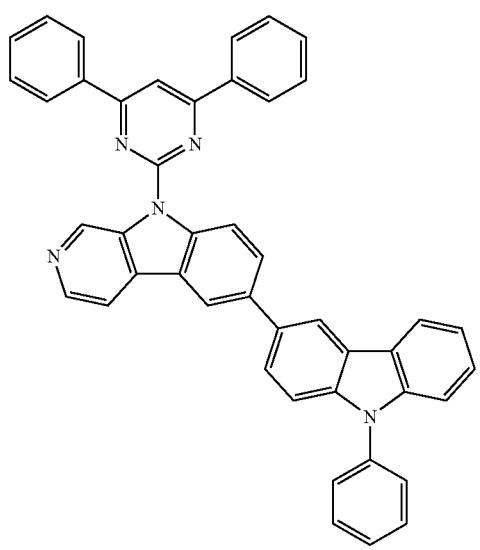

A-10
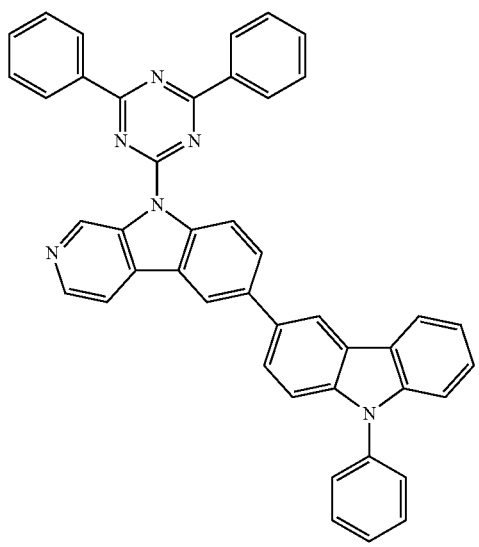
A-11
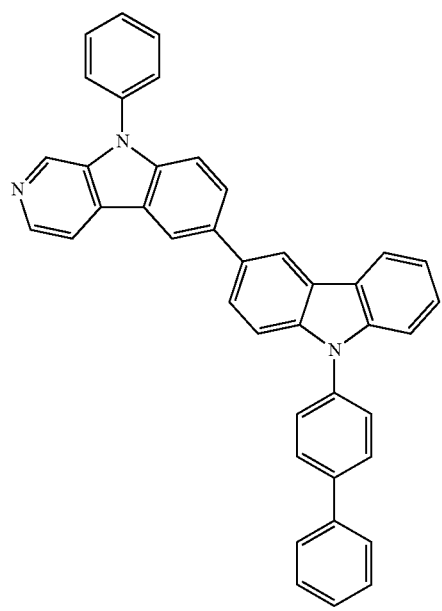
A-12
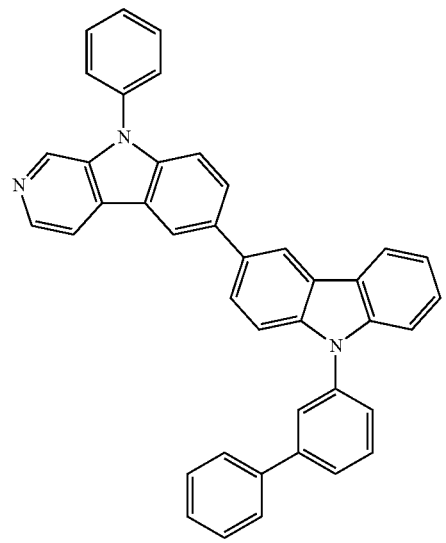
A-13
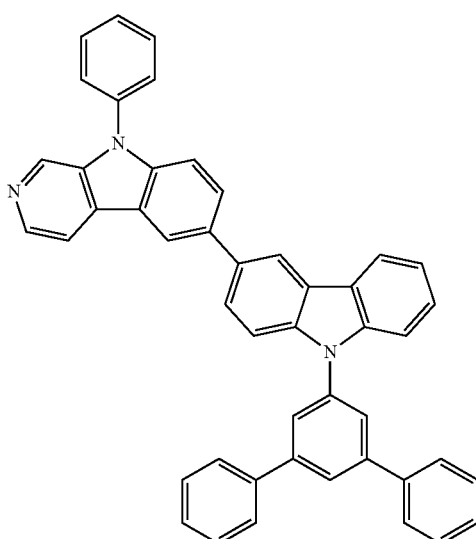
A-14
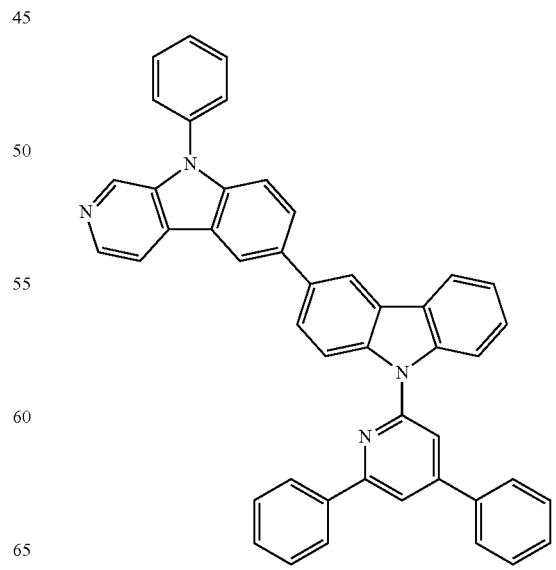

A-15
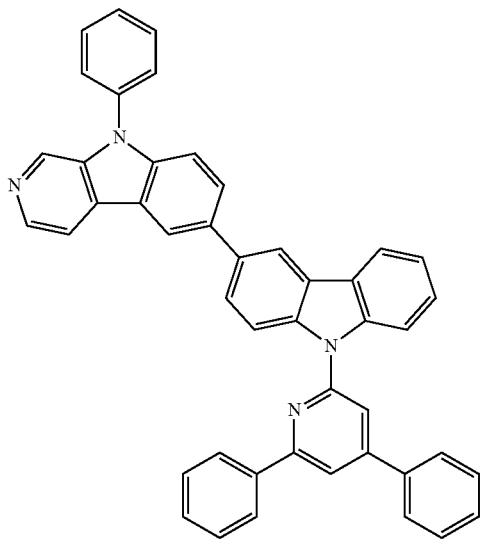
A-16
A-17
A-18
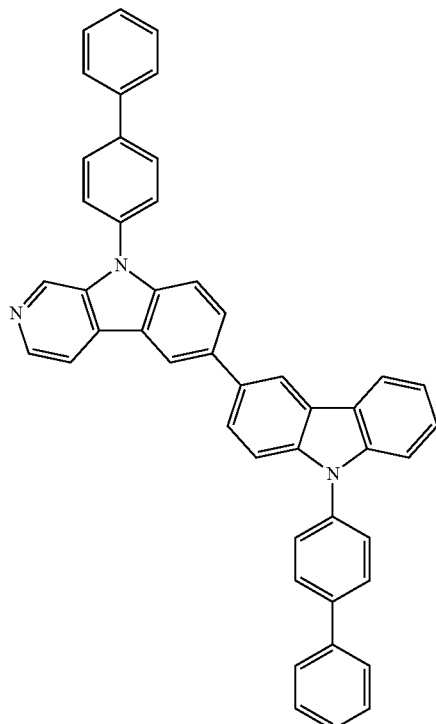
A-19
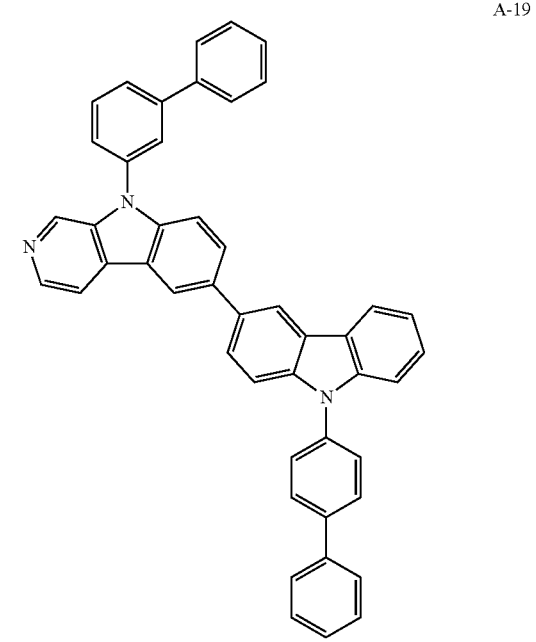

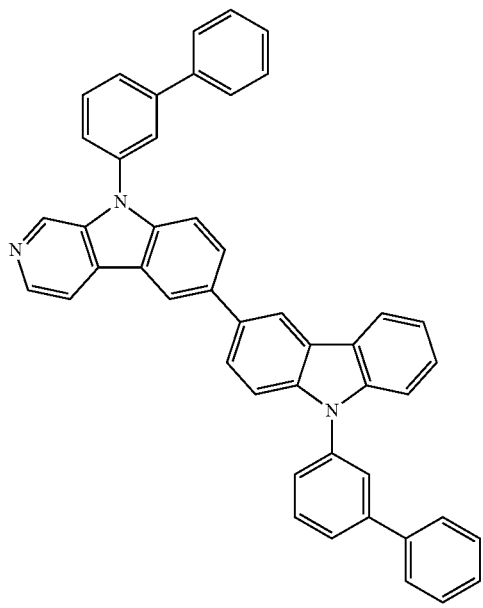
A-20
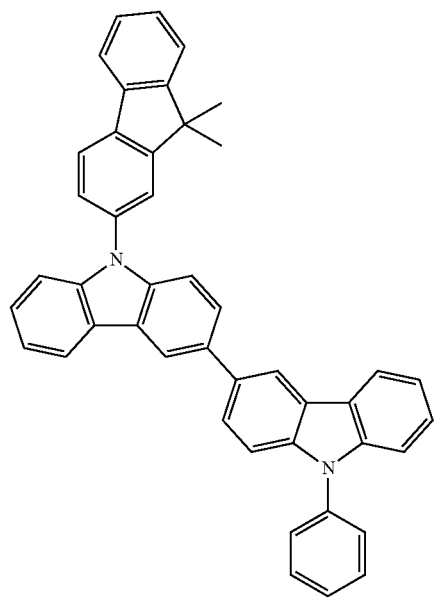
A-22
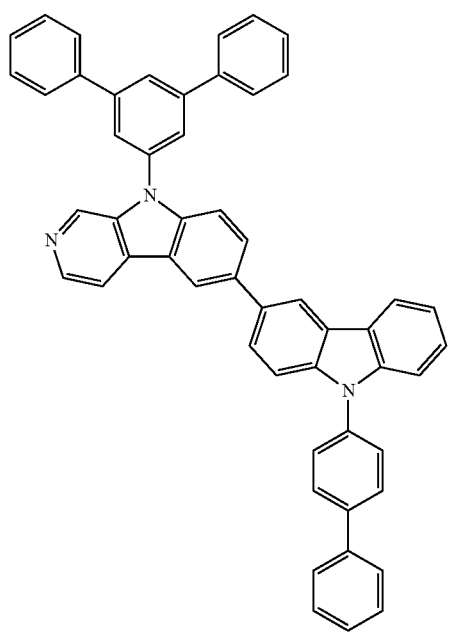
A-21
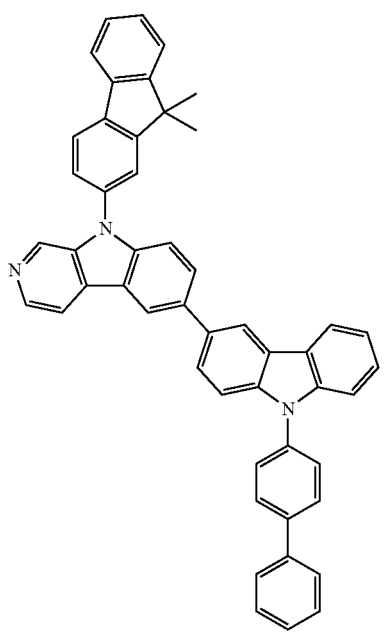
A-23

A-24
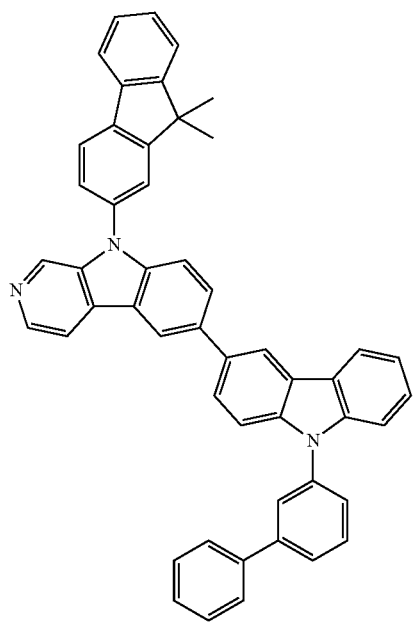
A-25
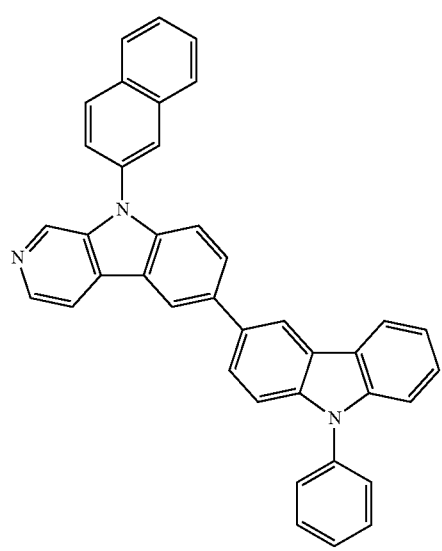
A-26
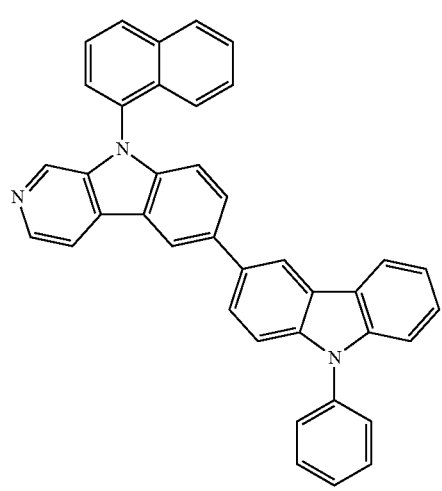
A-27
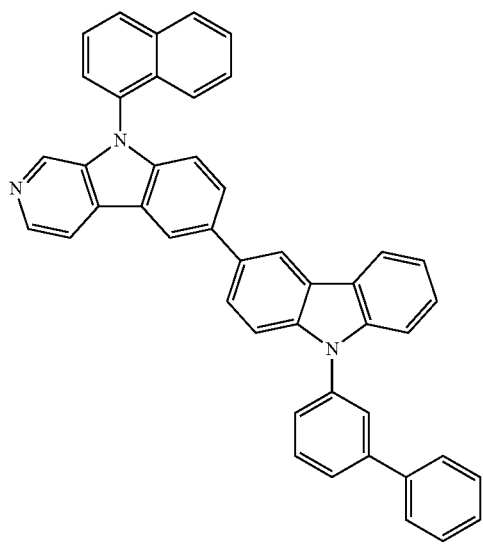
A-28
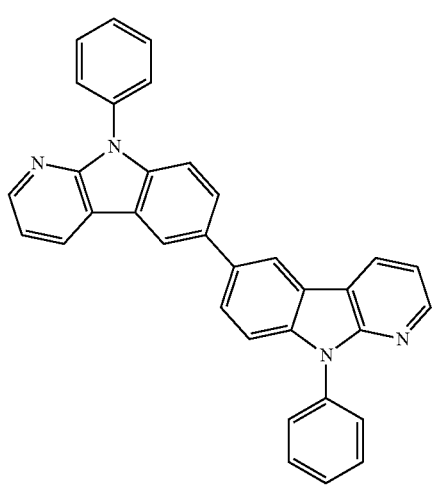
A-29
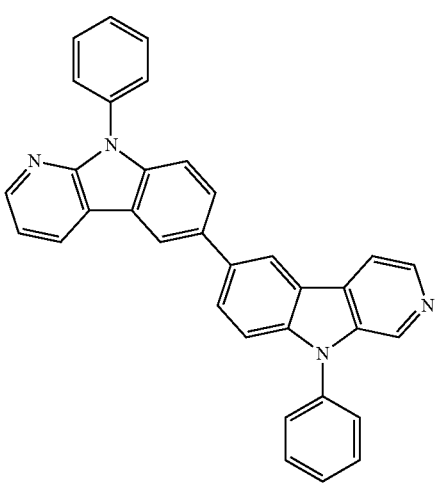

A-30
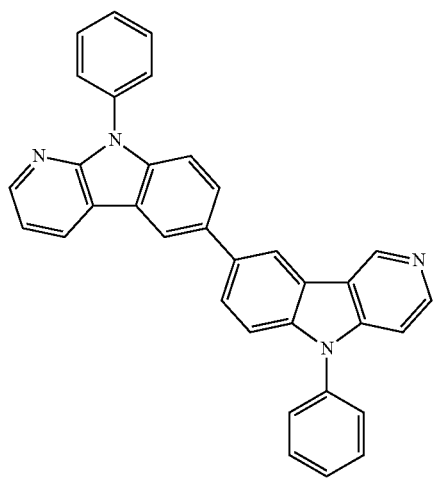
A-31
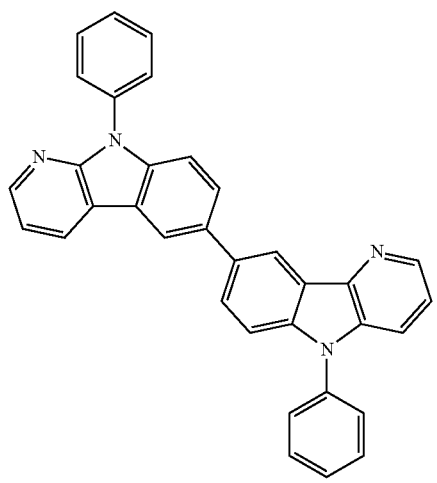
A-32
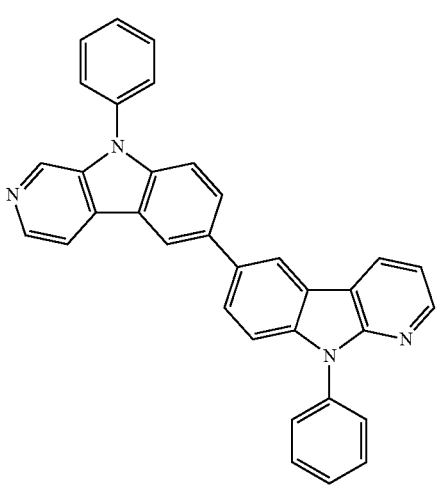
A-33
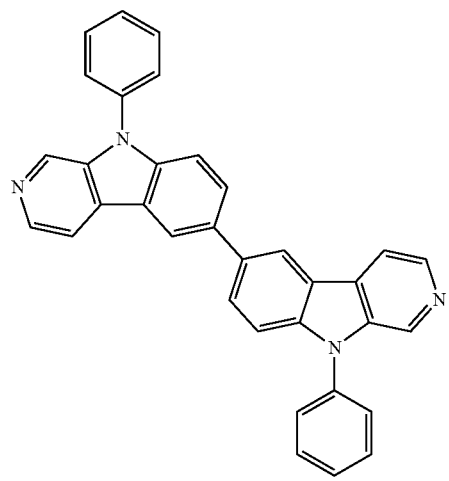
A-34
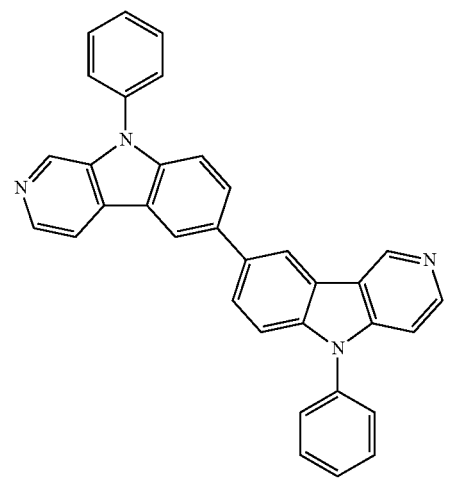
A-35
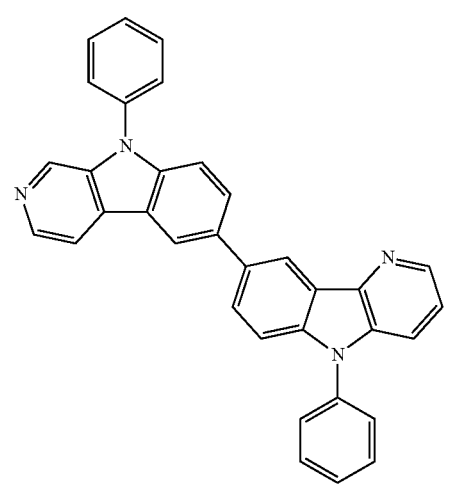

A-36
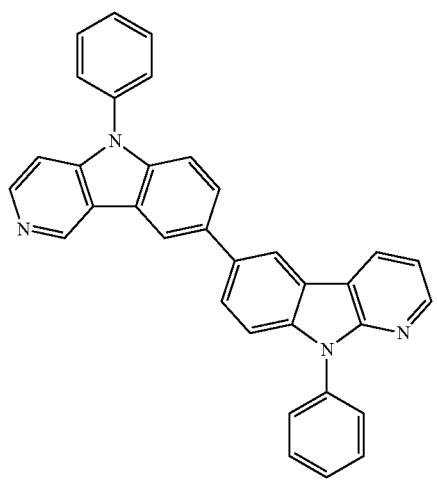
A-37
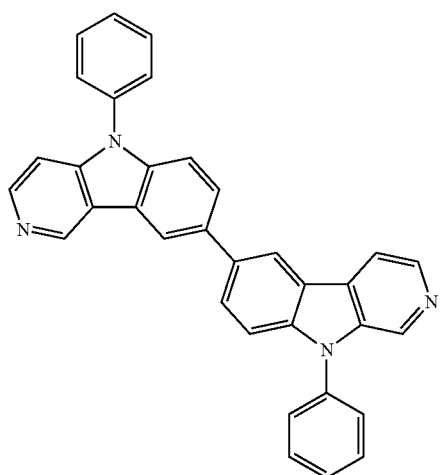
A-38
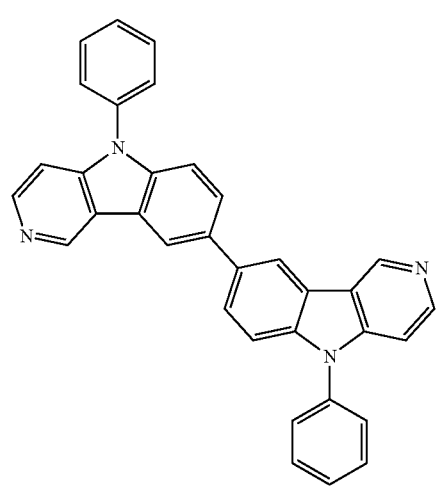
A-39
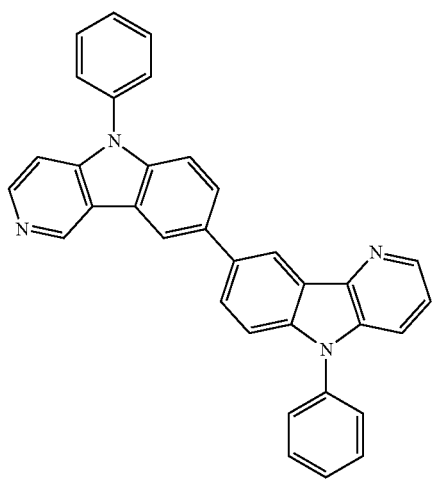
A-40
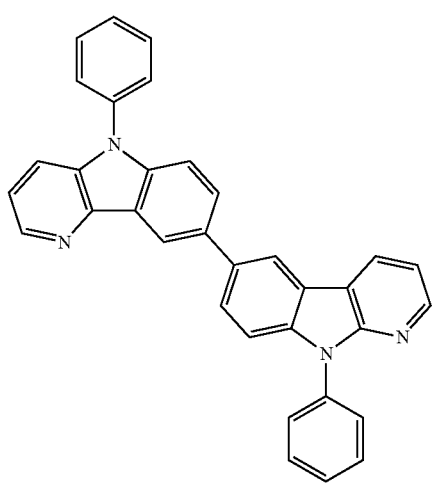
A-41
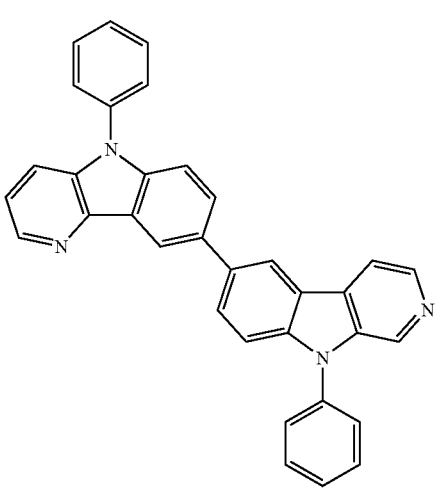

-continued
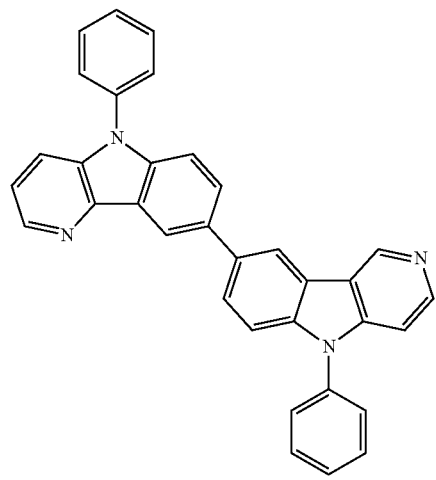
A-42
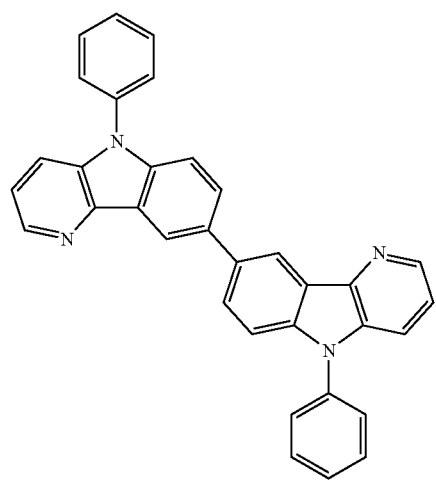
A-43
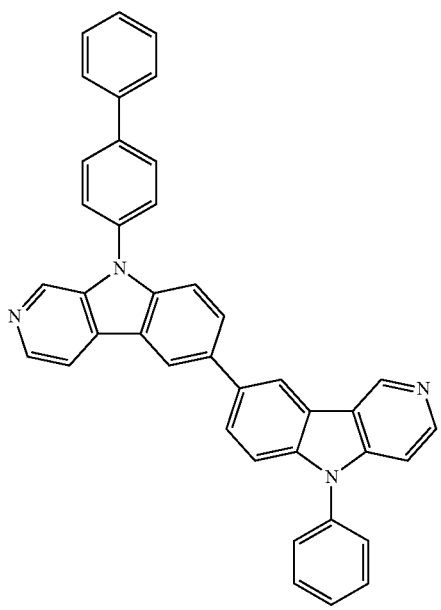
A-44
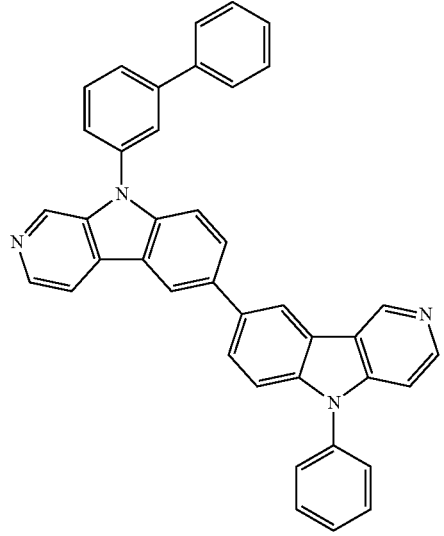
A-45
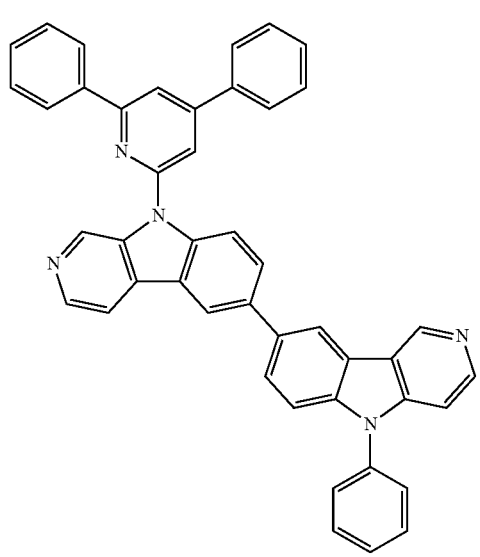
A-46
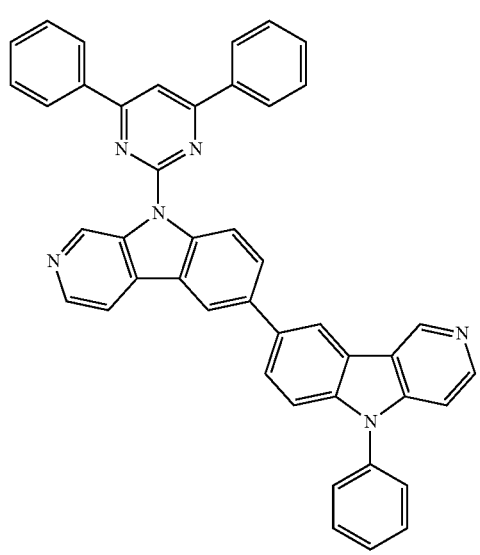
A-47

A-48
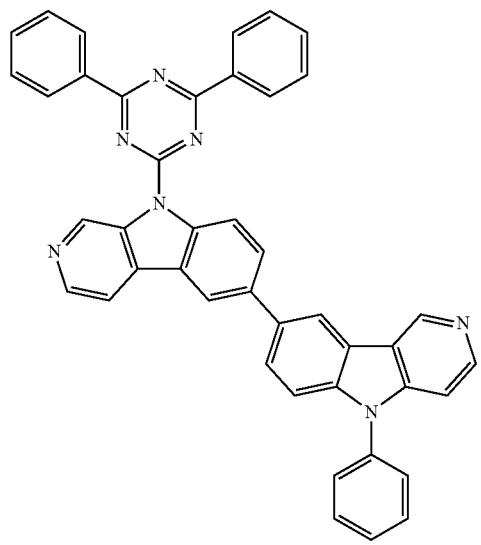
A-49
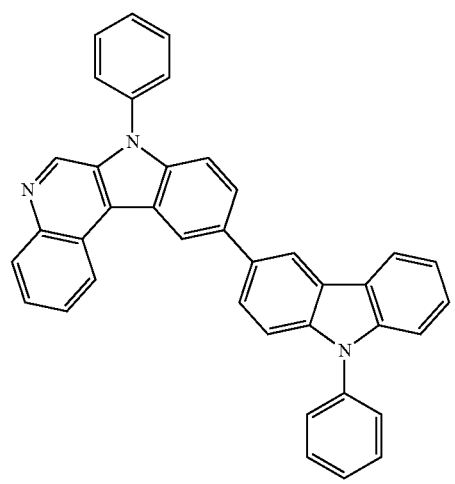
A-50
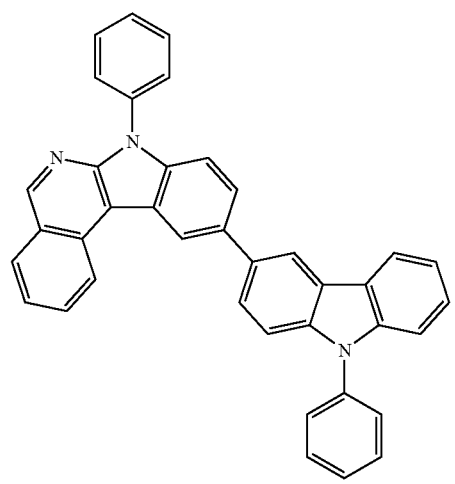
A-51
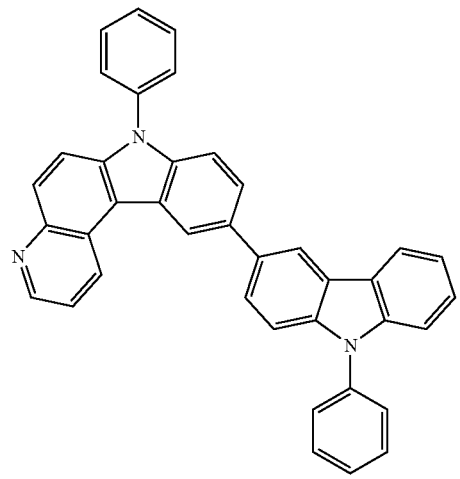
A-52
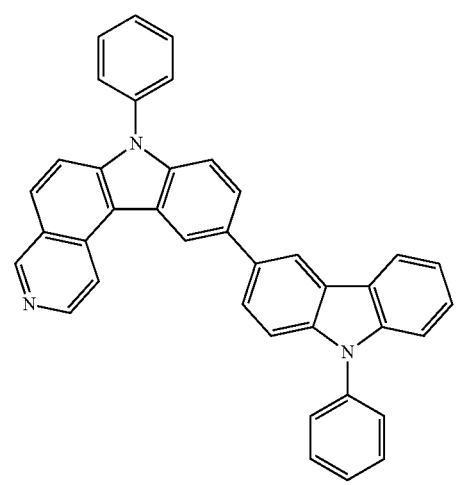
A-53
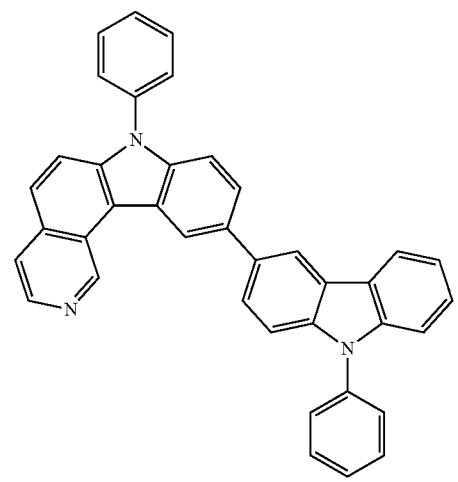

A-54
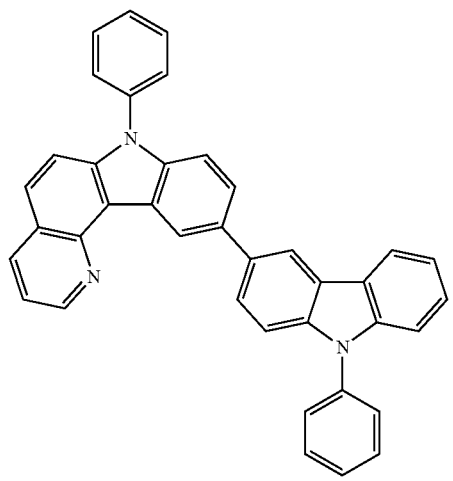
A-55
A-56
A-57
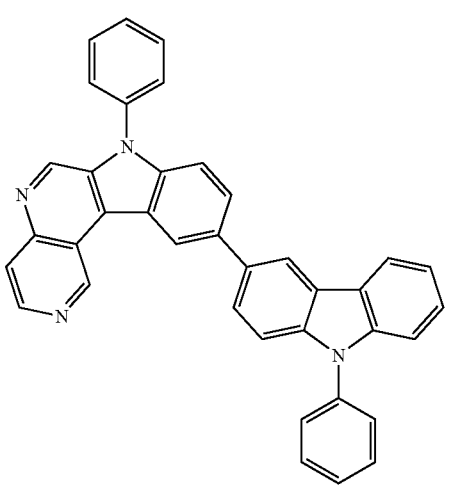
A-58
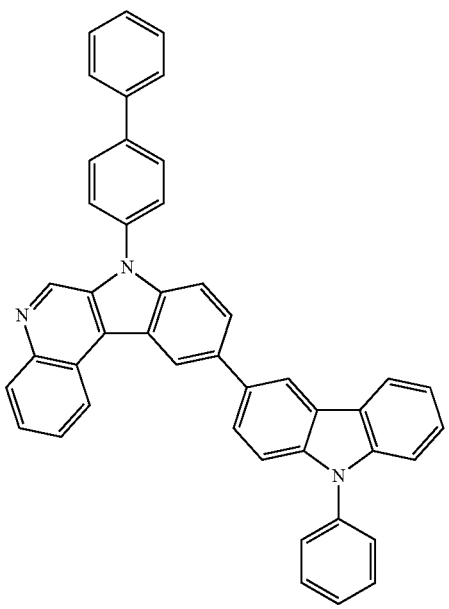

A-59
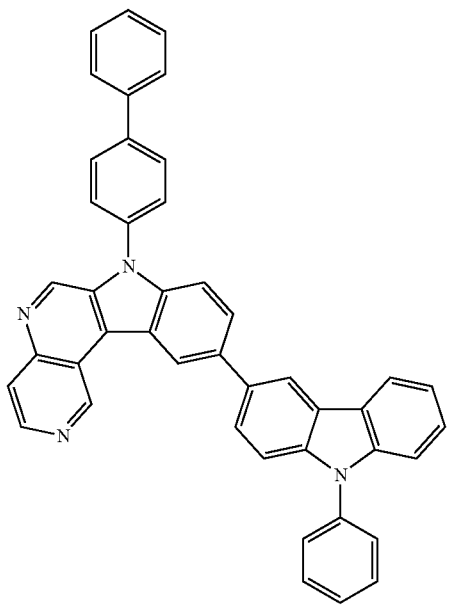
A-60
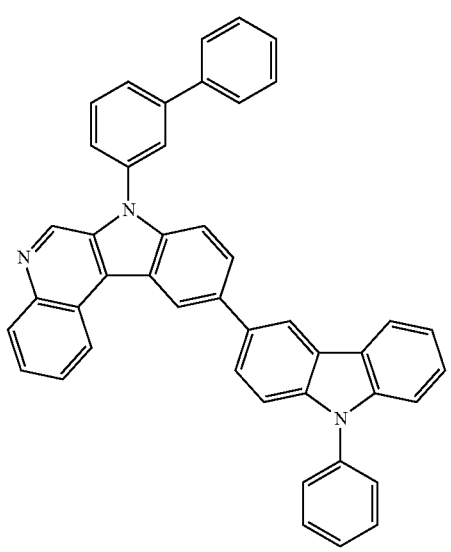
A-61
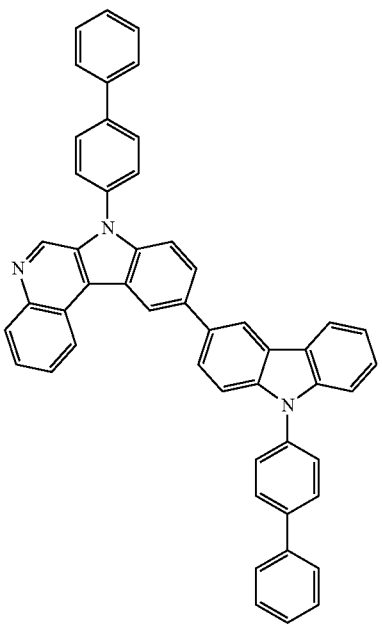
A-62
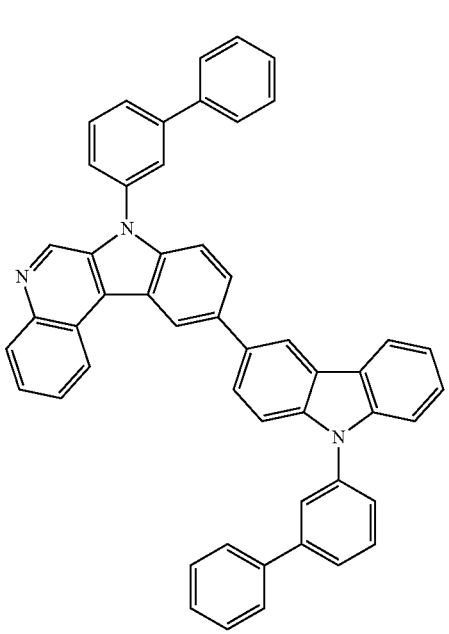

A-63
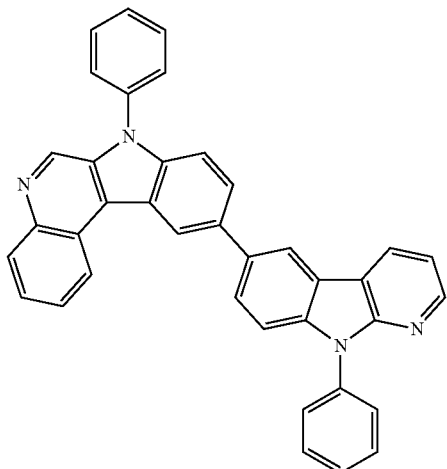
A-66
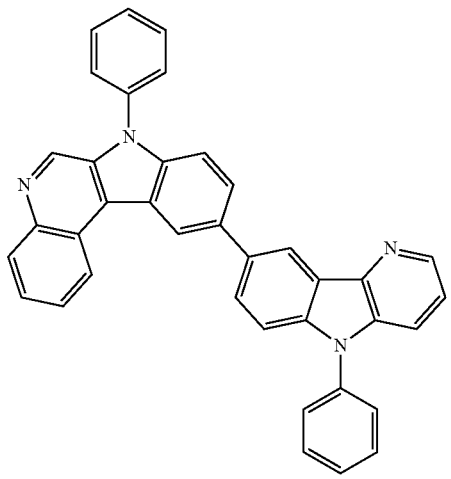
A-64
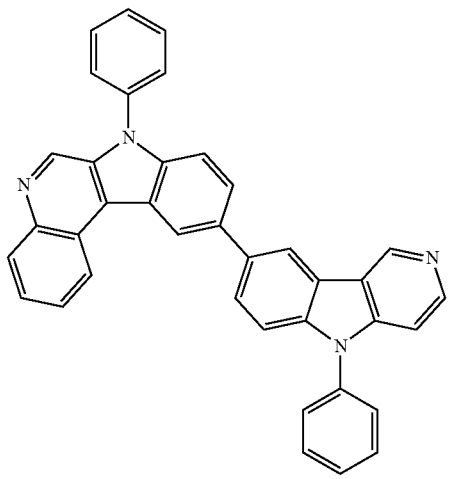
A-67
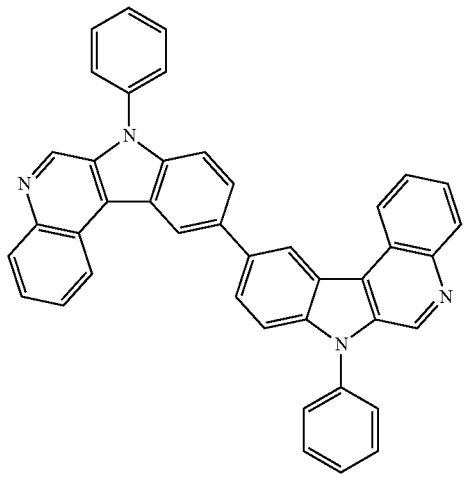
A-65
A-68
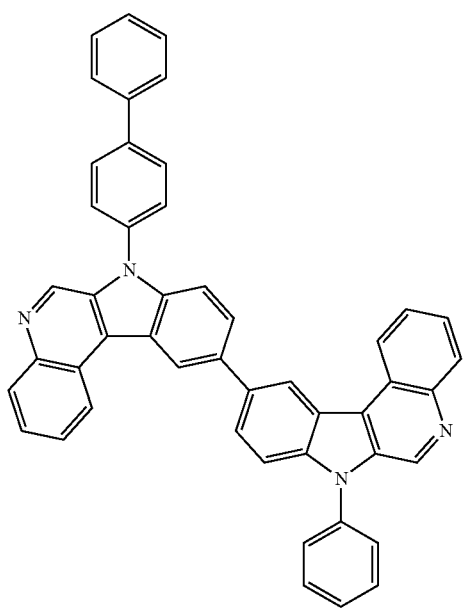

A-69
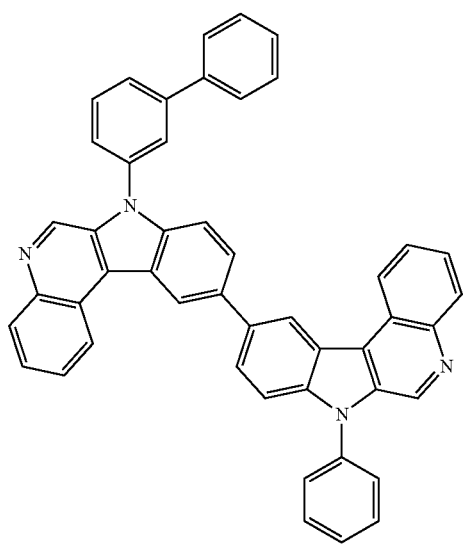
A-70
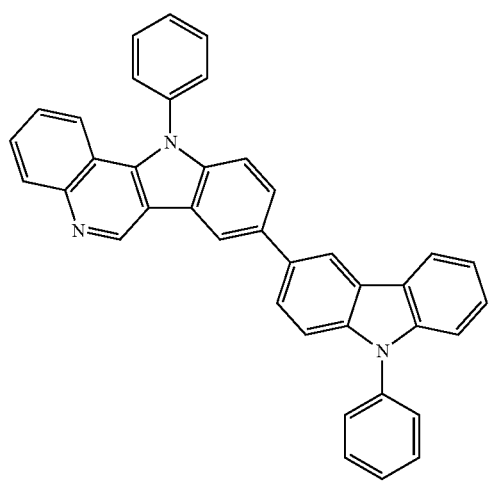
A-71
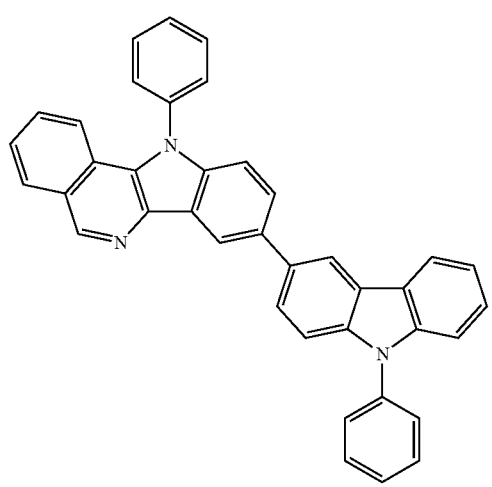
A-72
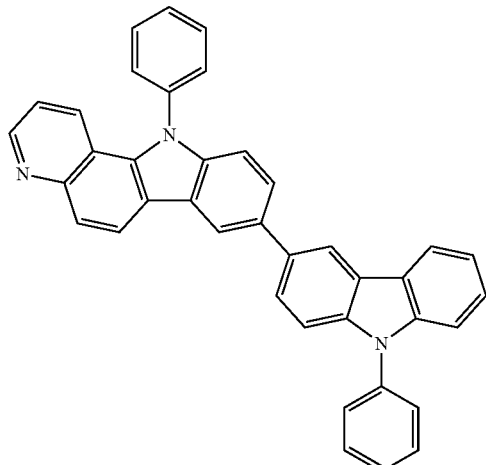
A-73
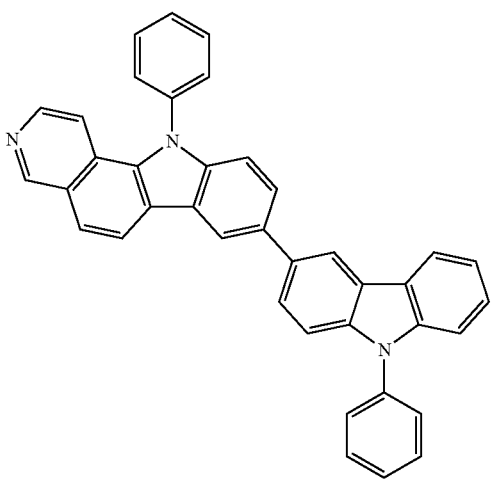
A-74
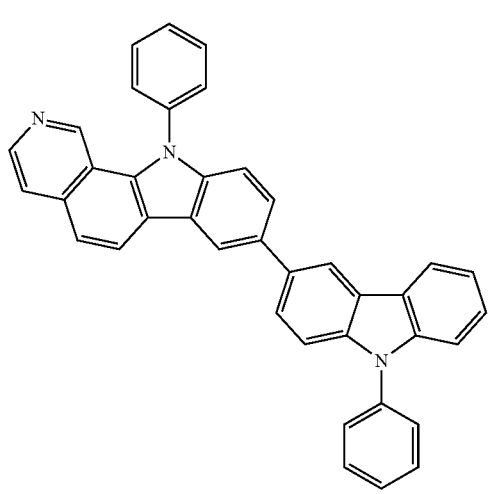

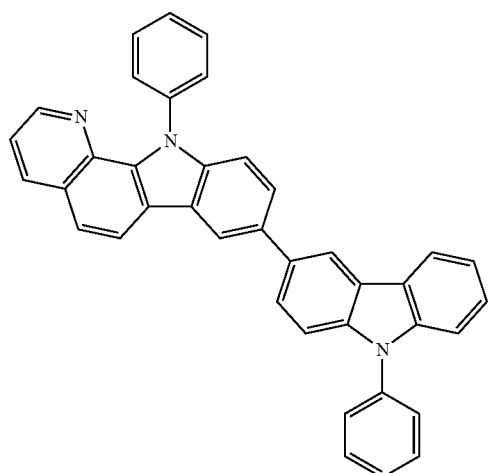
A-75
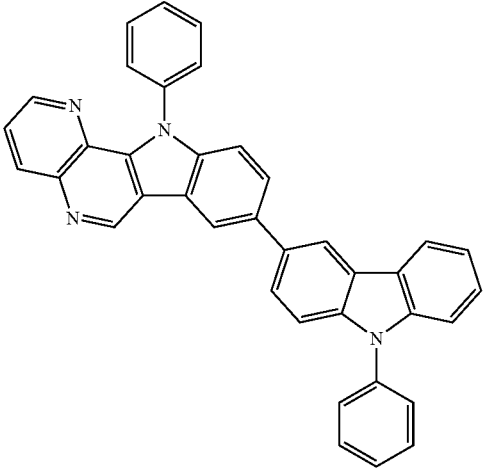
A-78
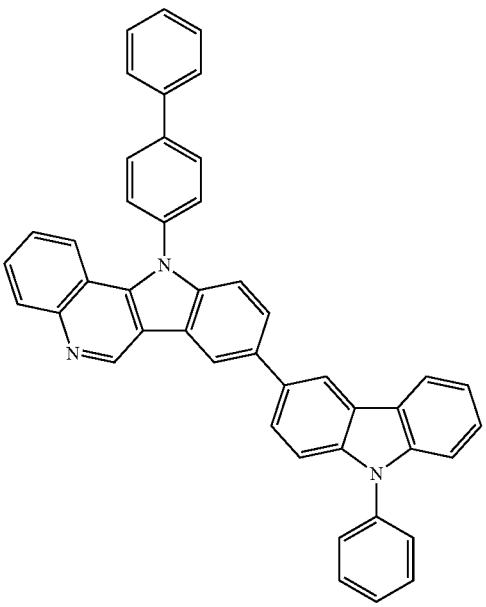
A-79
A-76
A-77

-continued
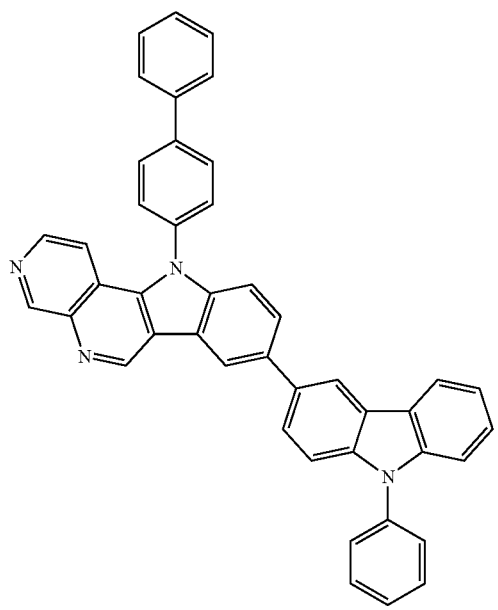
A-80
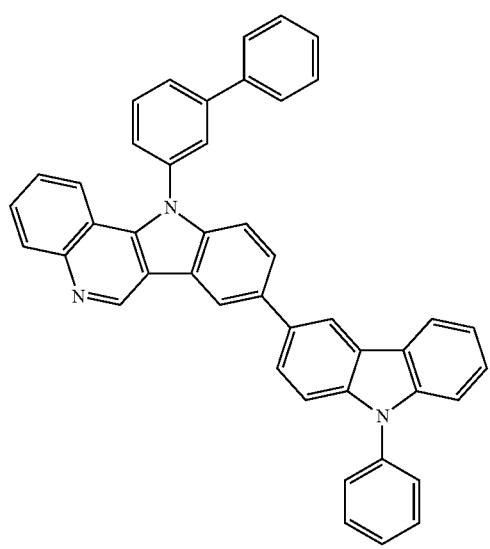
A-81
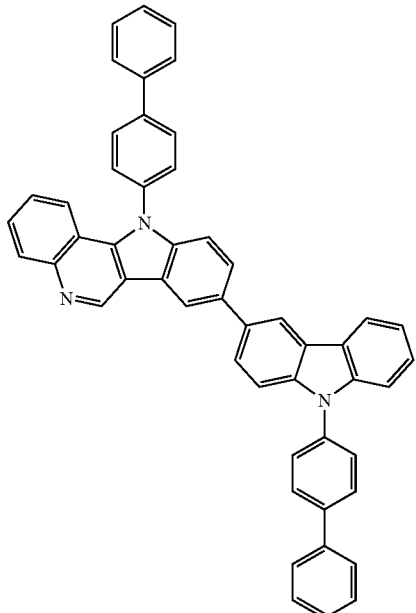
A-82
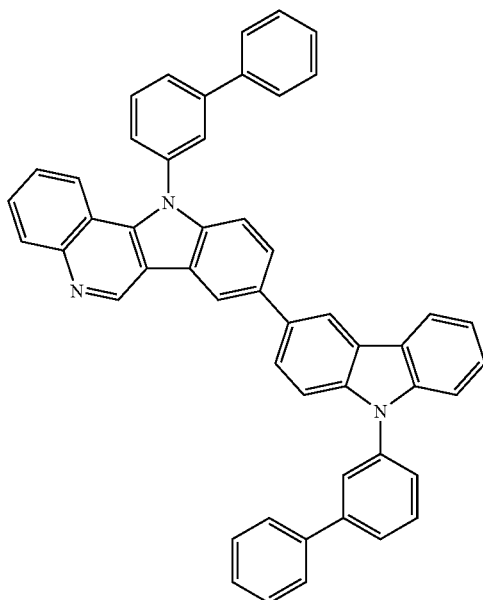
A-83

A-84
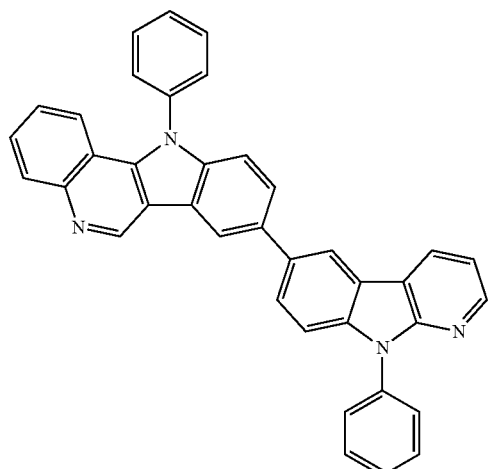
A-85
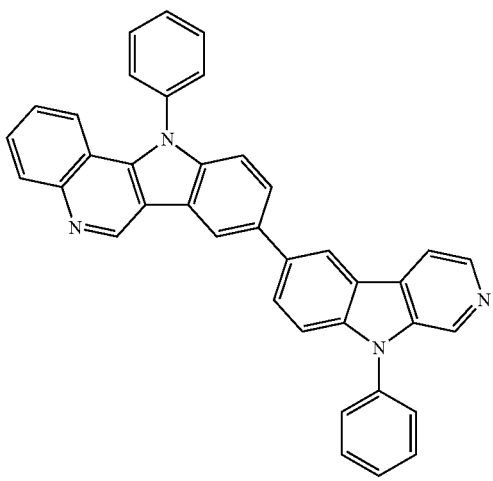
A-86
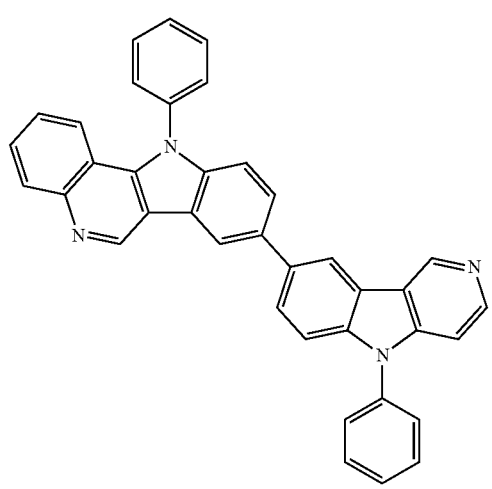
A-87
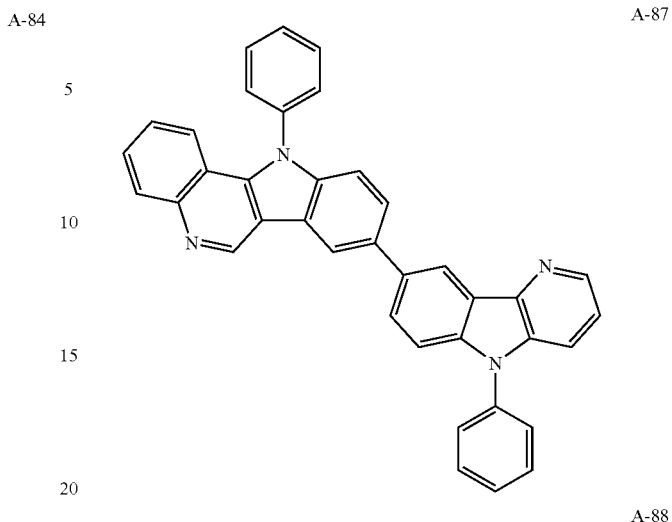
A-88
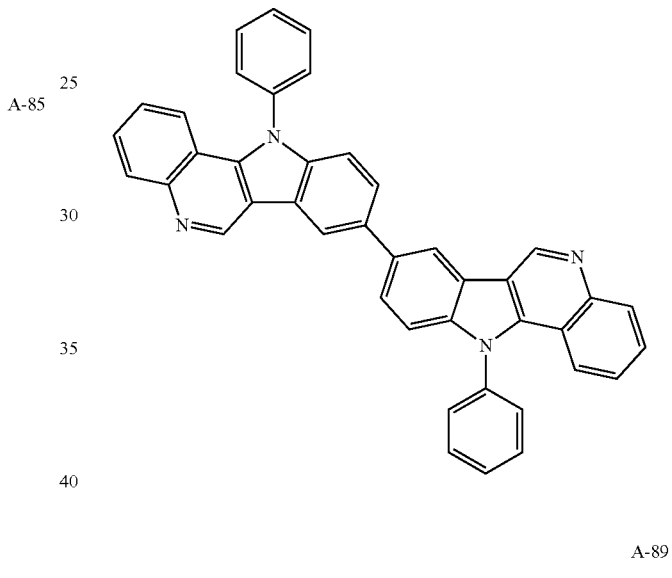
A-89
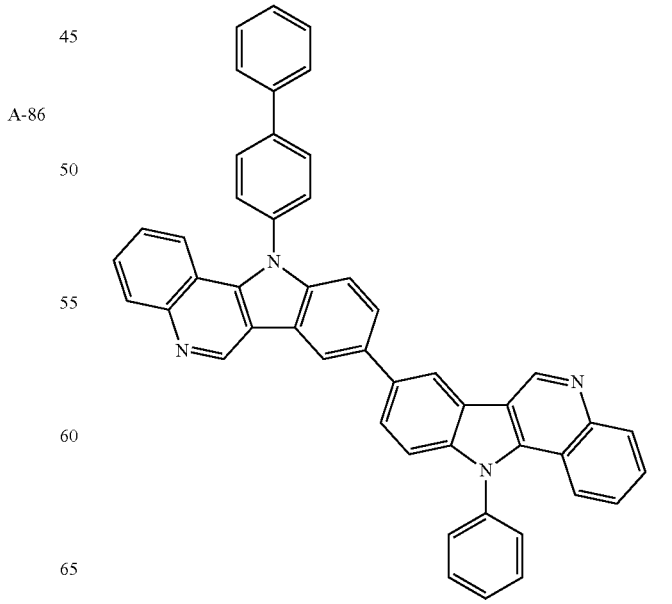

A-90
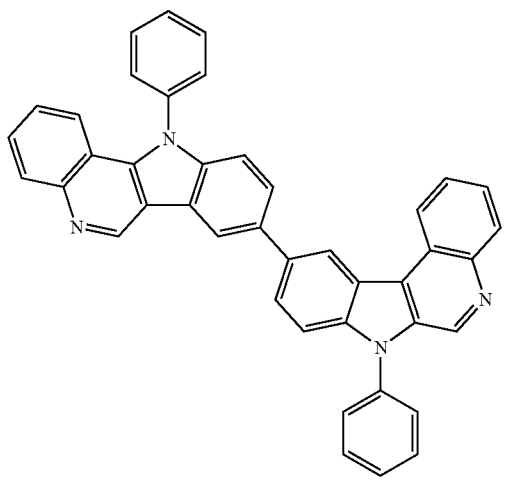
A-91
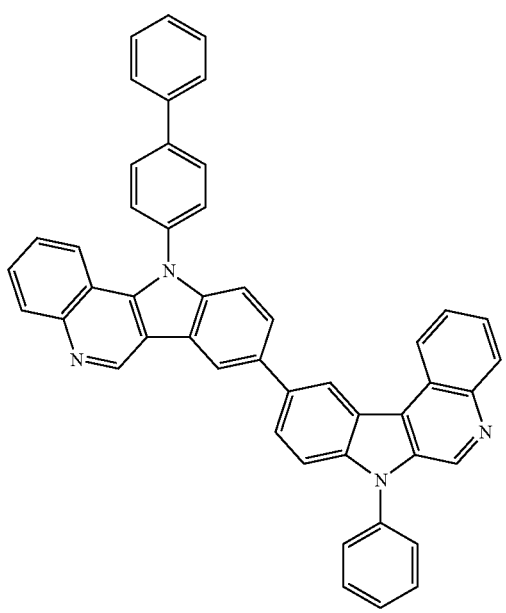
A-92
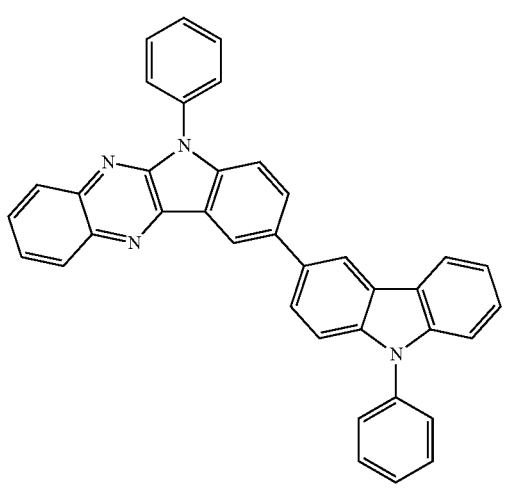
A-93
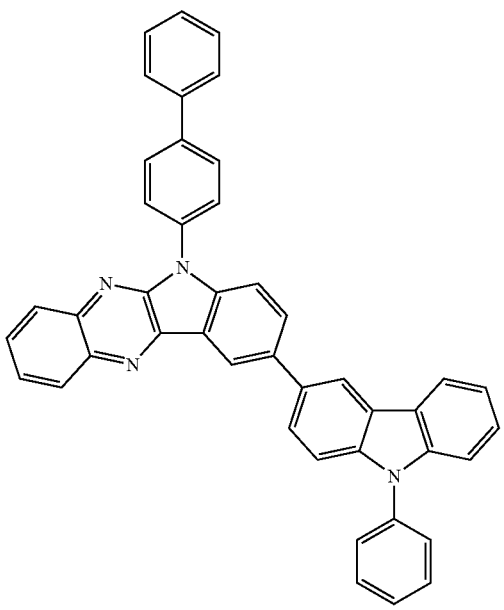
A-94
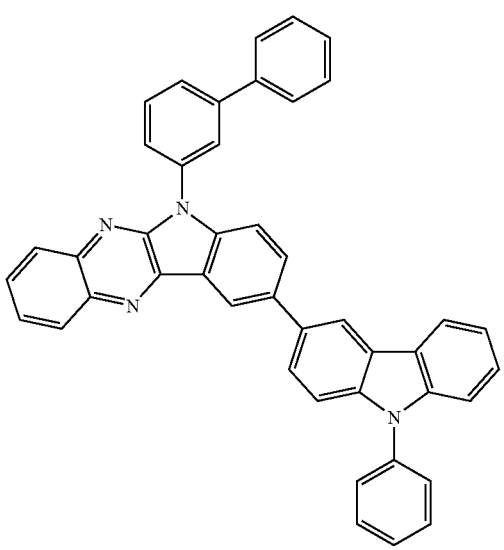
A-95
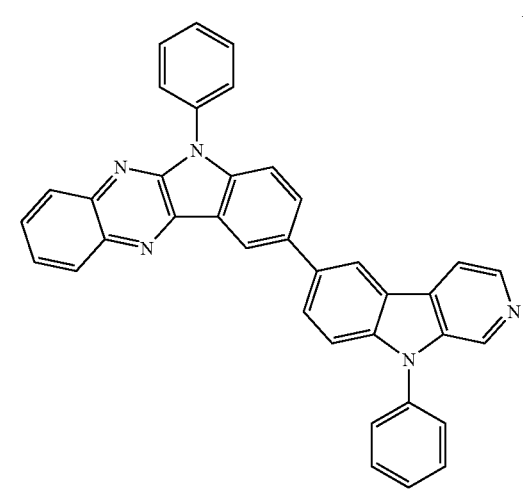

A-96
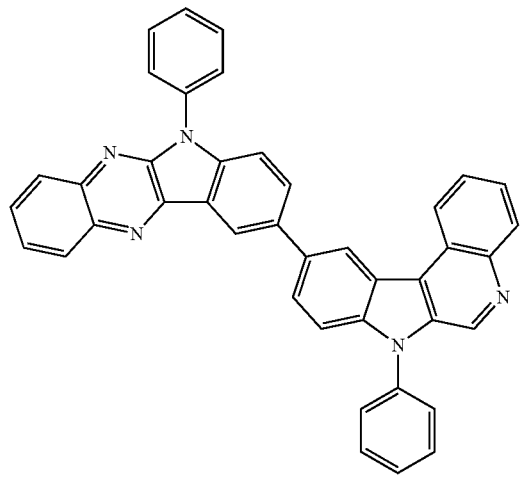
A-97
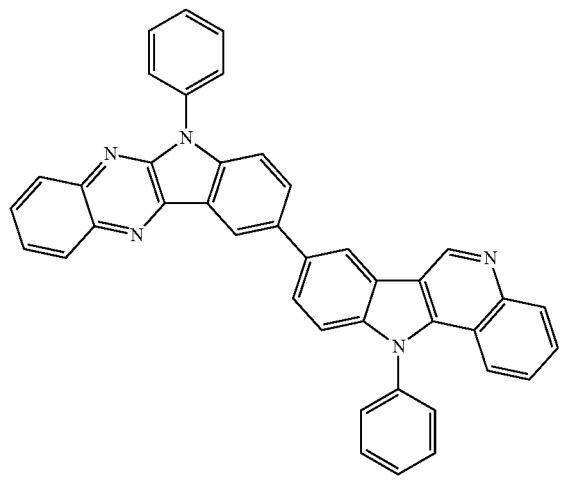
A-98
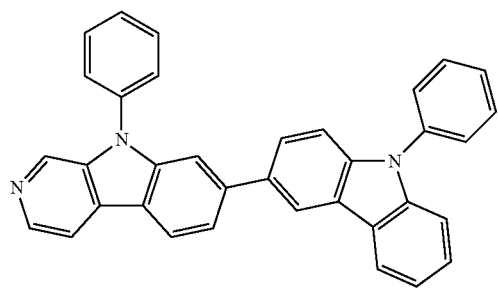
A-99
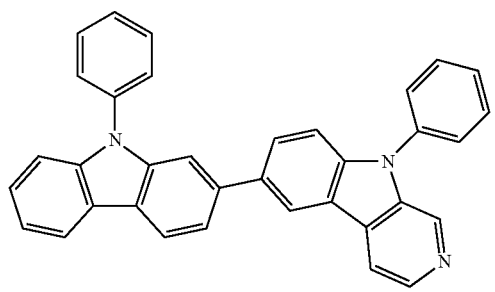
A-100
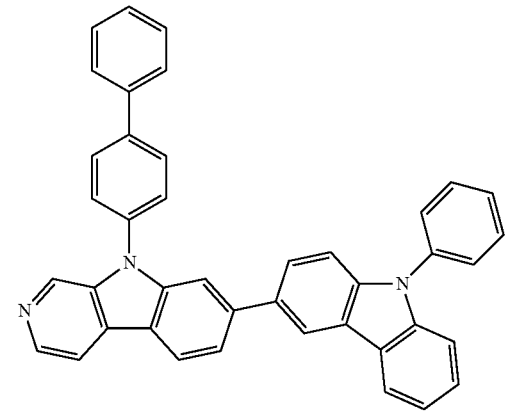
A-101
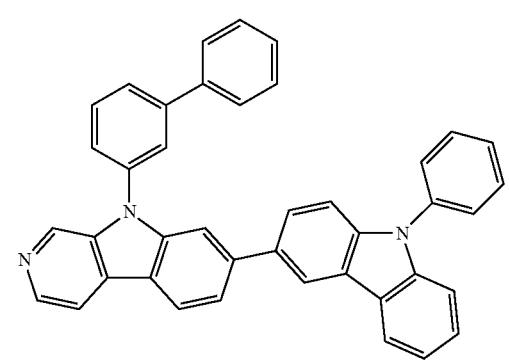
A-102
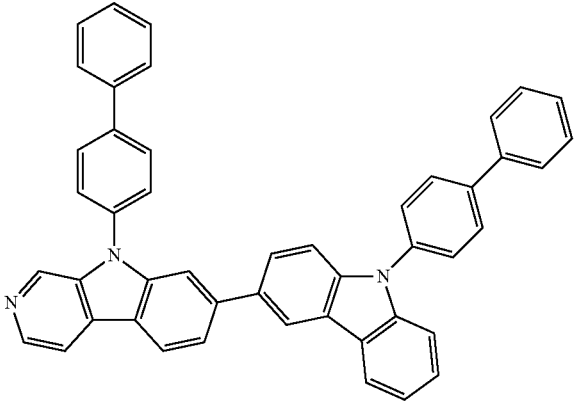
A-103
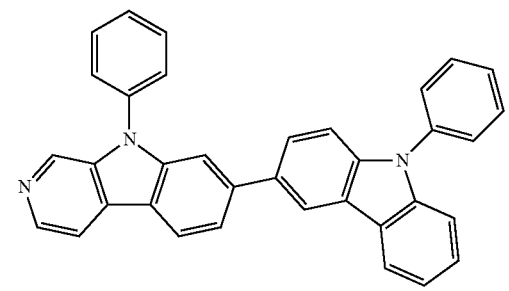

-continued
A-104
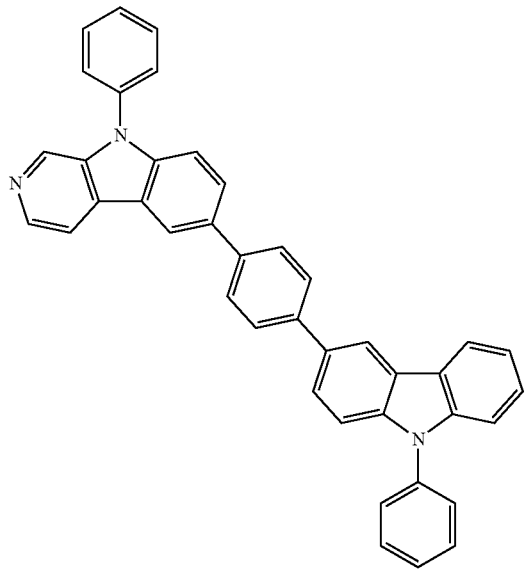
A-105
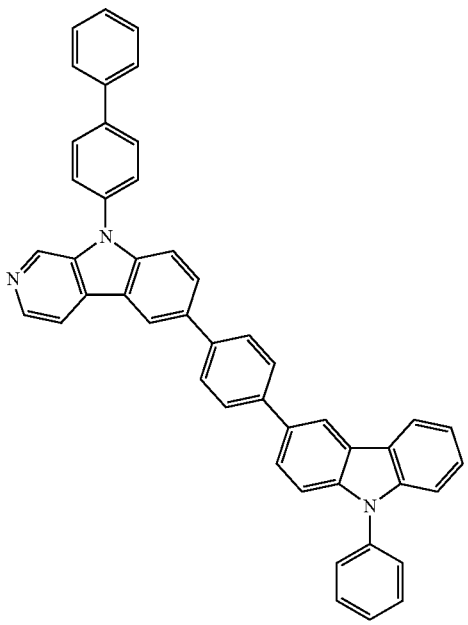
A-106
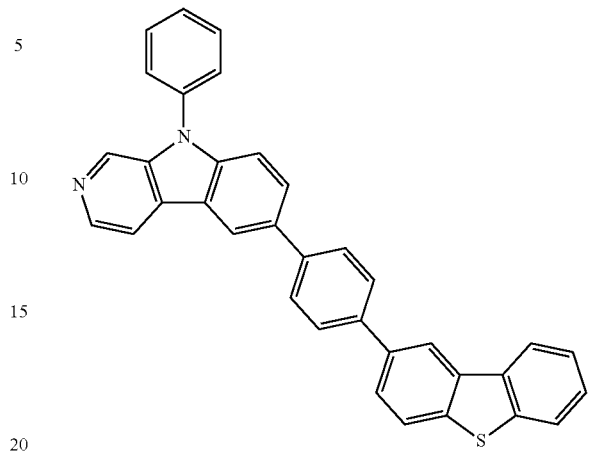
A-107
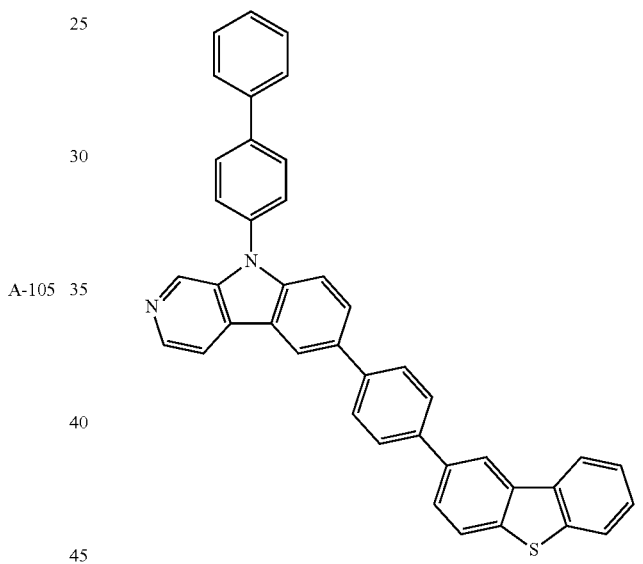
A-108
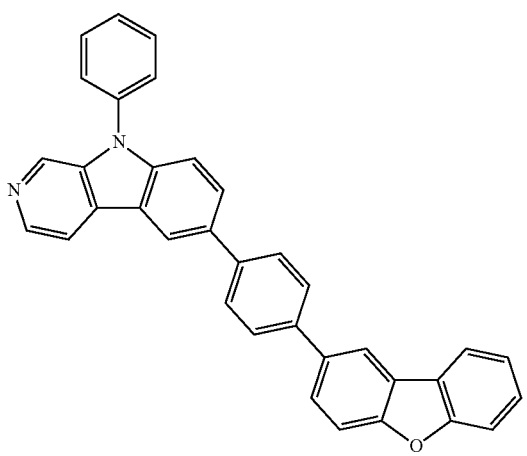

A-109
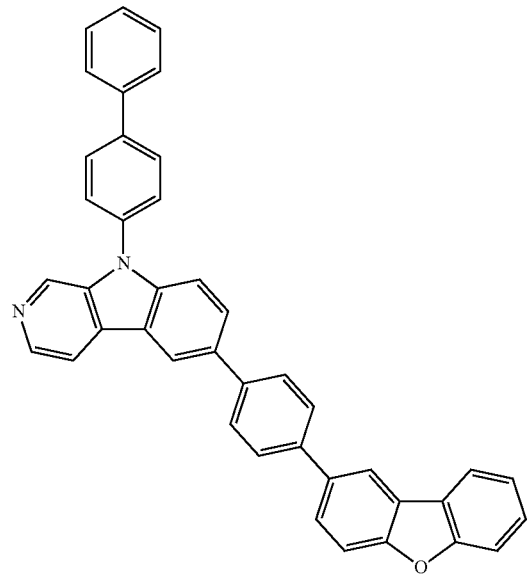
A-110
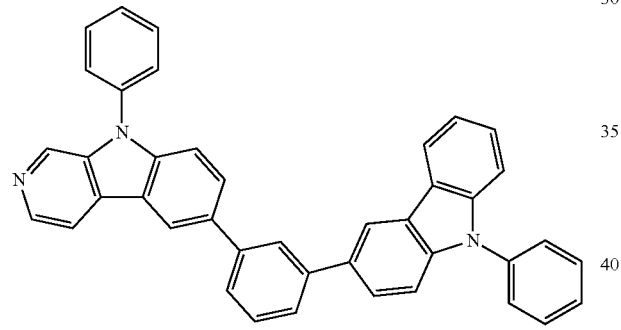
A-111
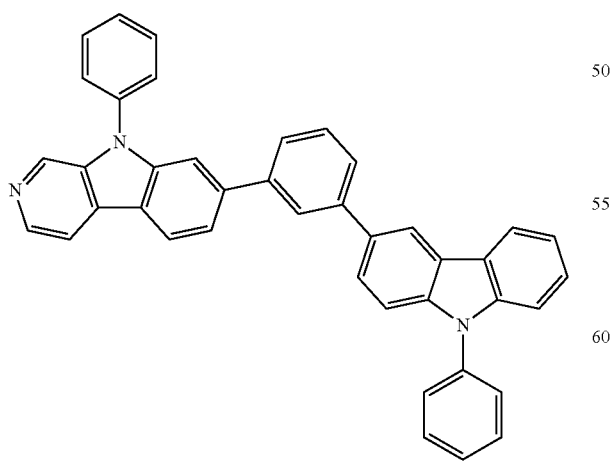
A-112
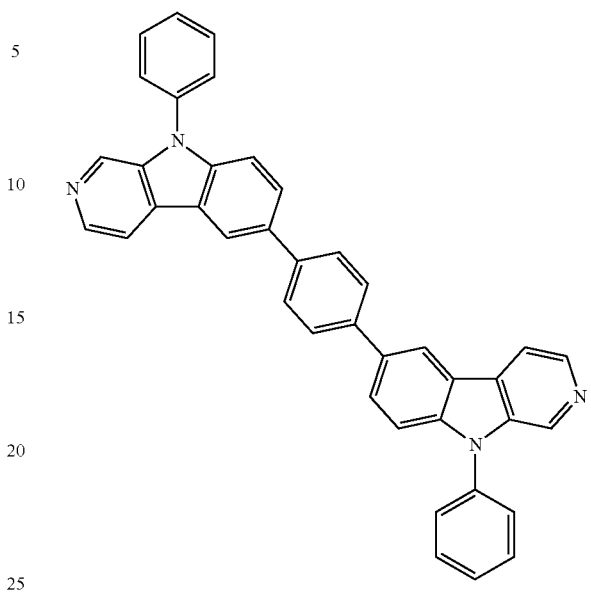
A-113

-continued
A-114
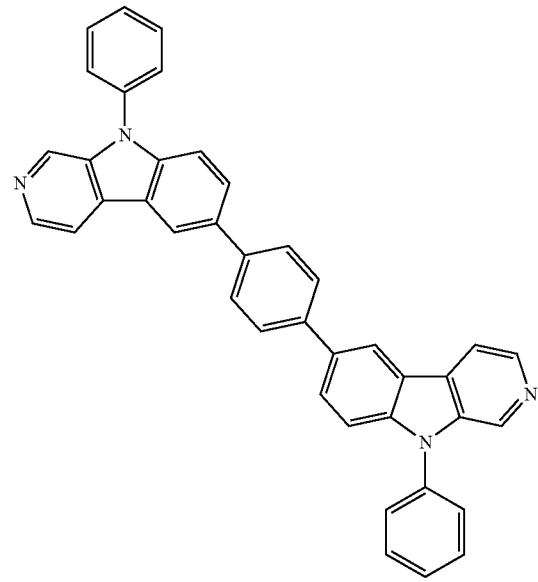
A-115
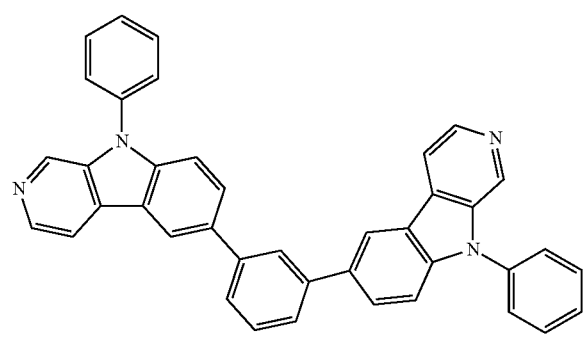
A-116
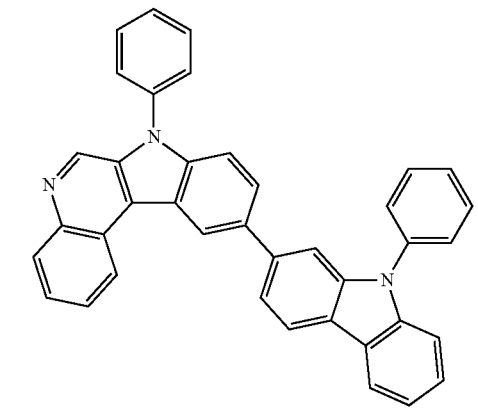
-continued
A-117
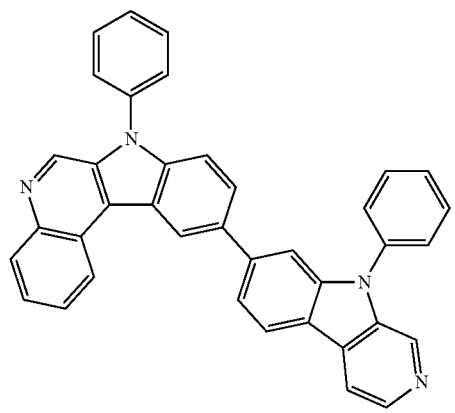
A-118
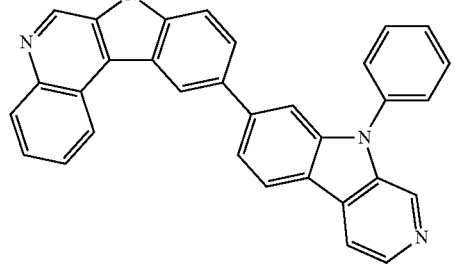
A-119
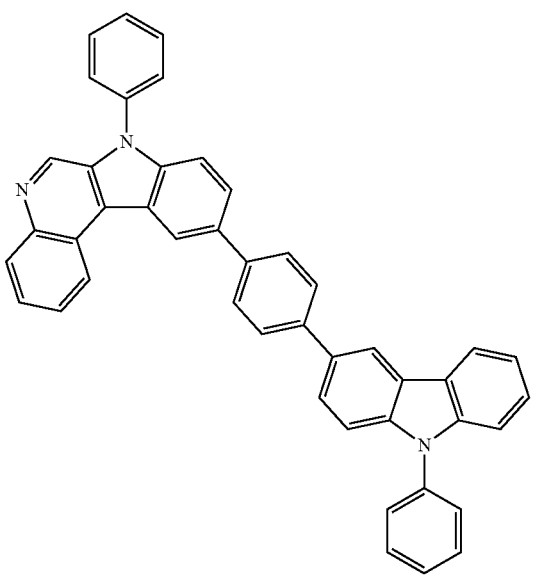

A-120
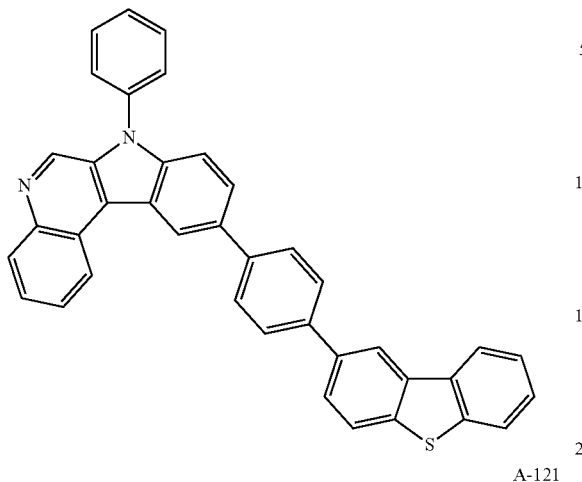
A-121
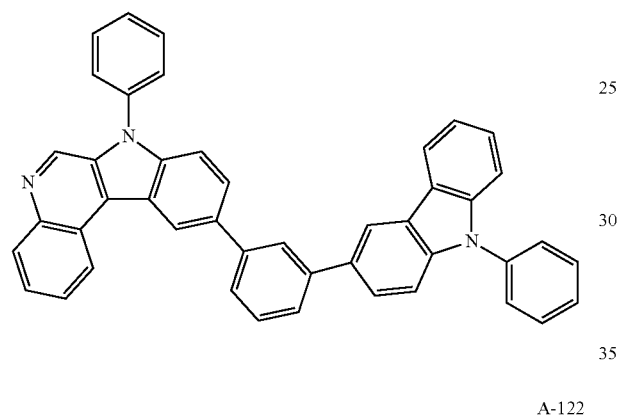
A-122
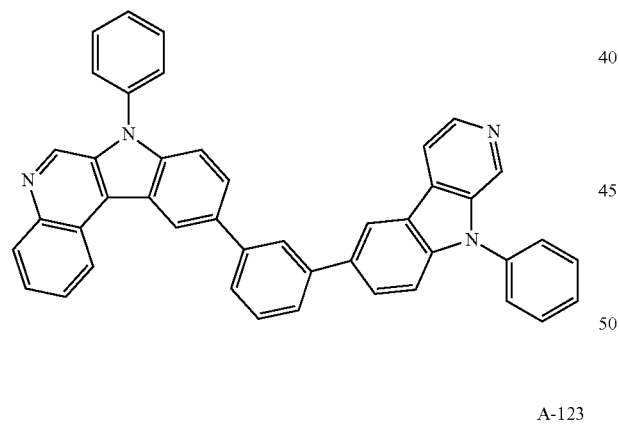
A-123
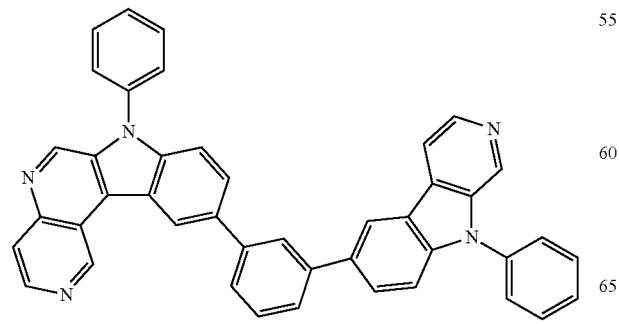
A-124
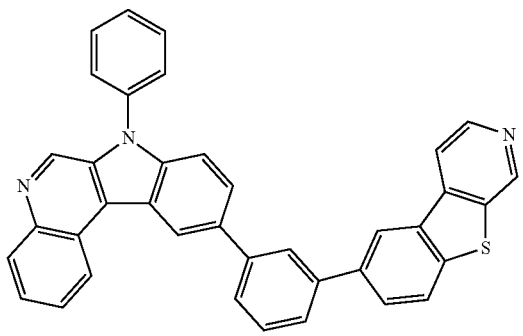
A-125
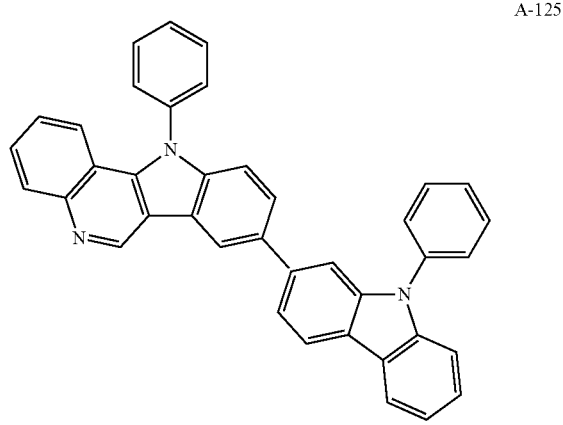
A-126
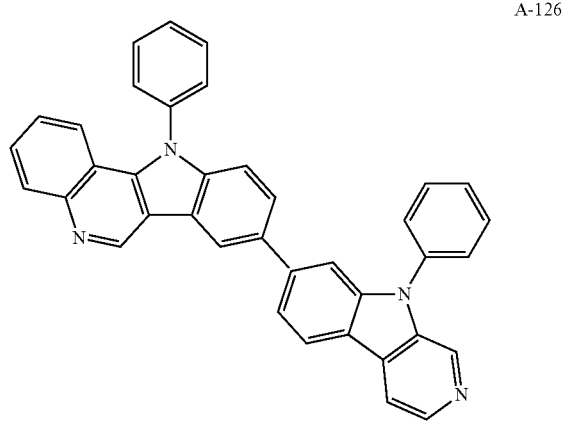

A-127
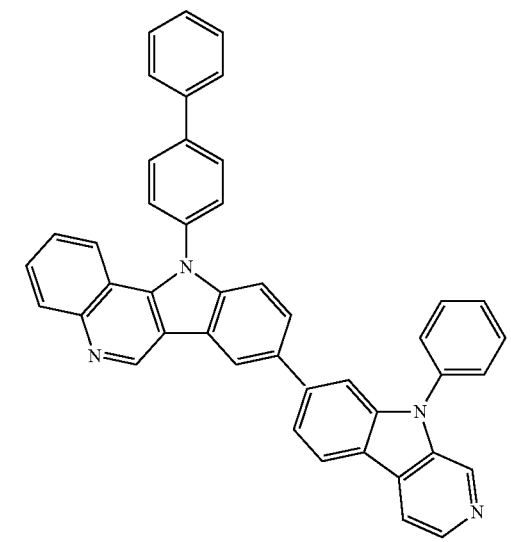
A-128
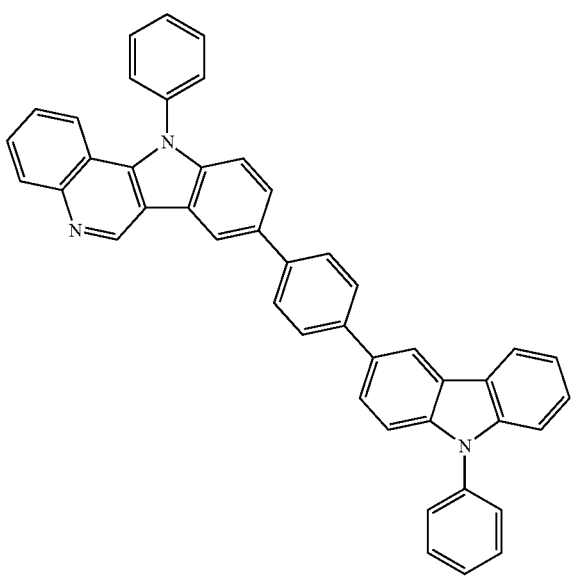
A-129
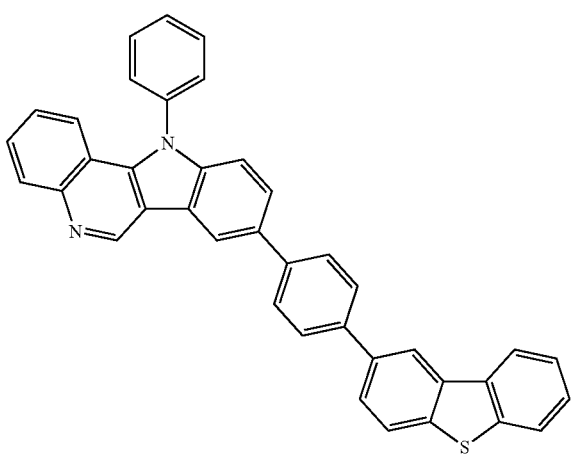
A-130
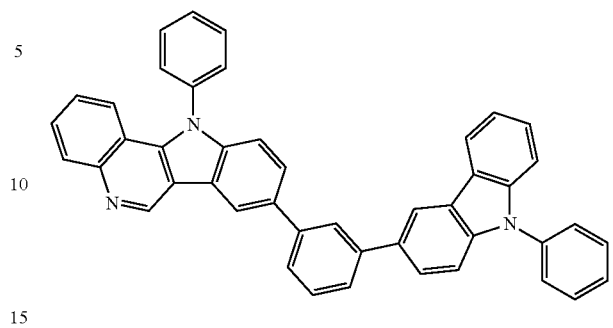
A-131
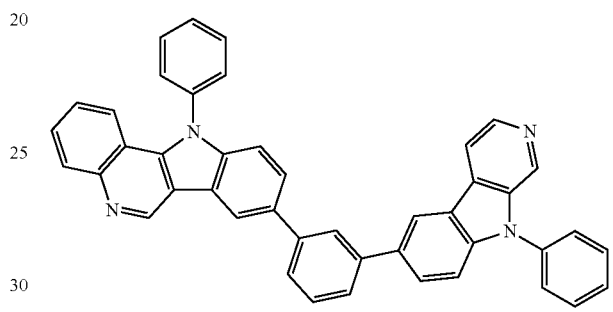
A-132
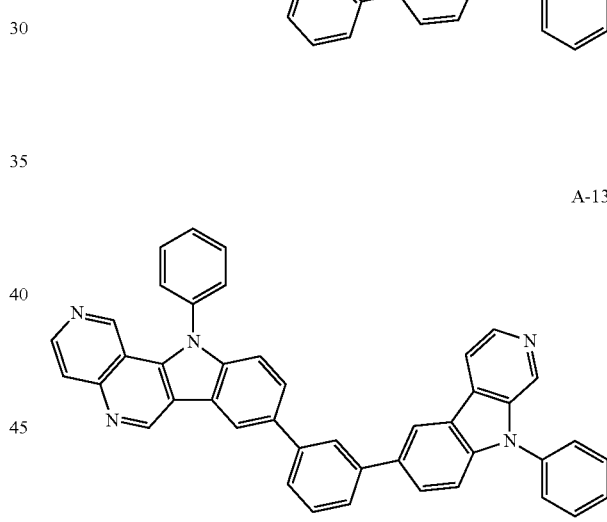
A-133
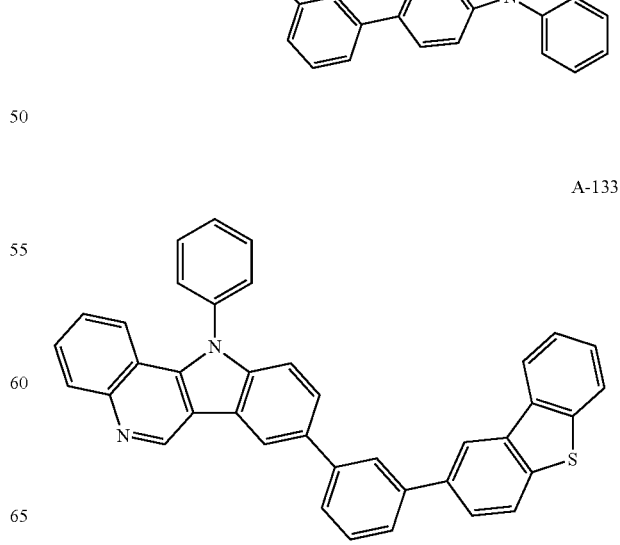

A-134
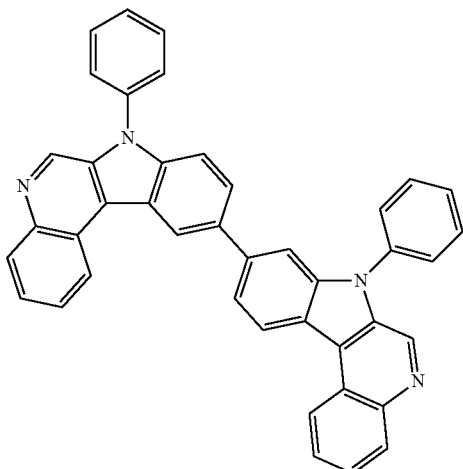
A-137
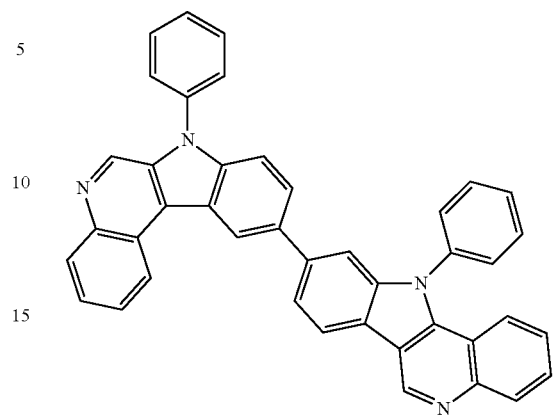
A-135
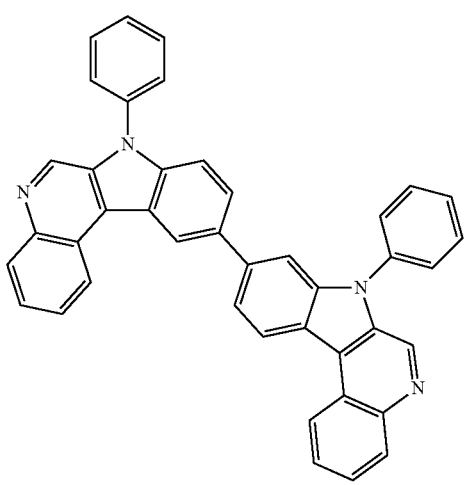
A-138
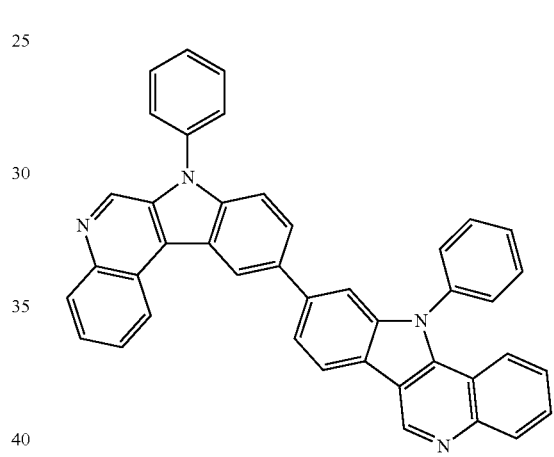
A-136
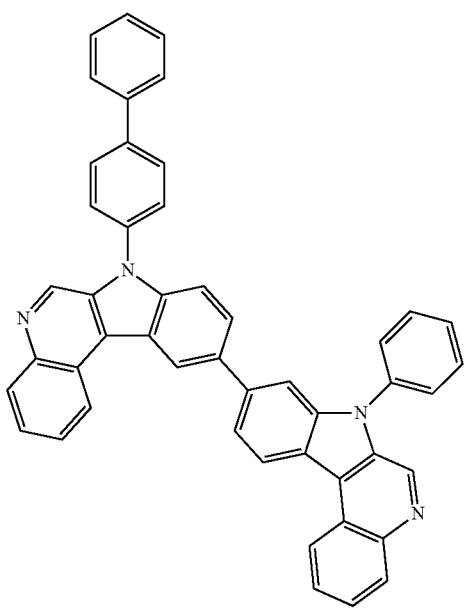
A-139
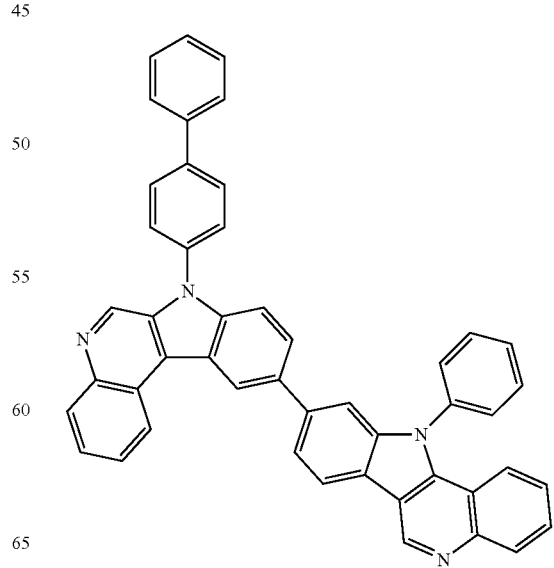

-continued
A-140
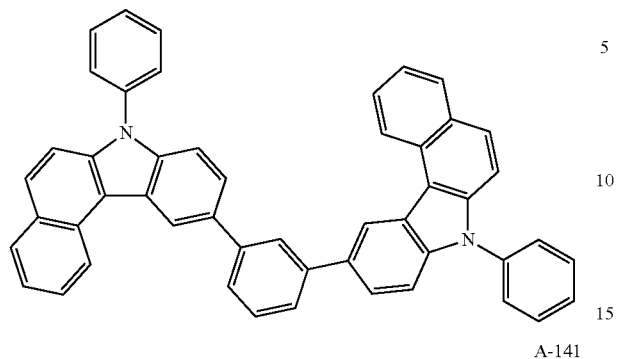
A-141
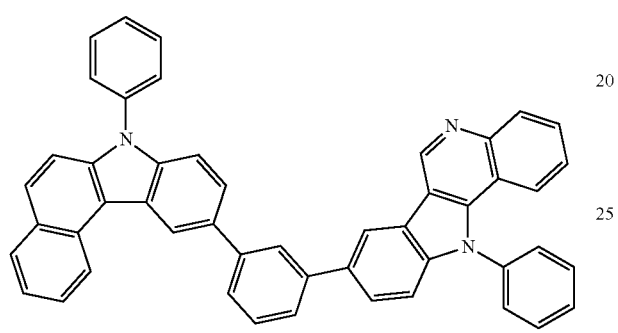
A-142
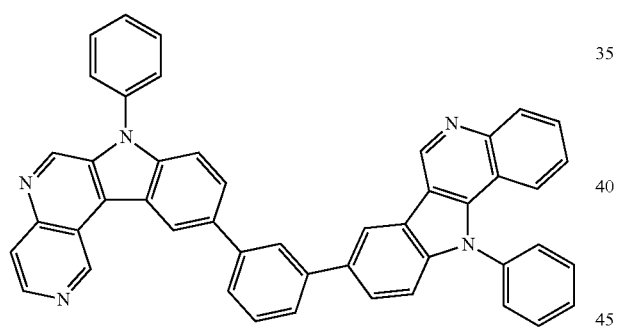
-continued
A-144
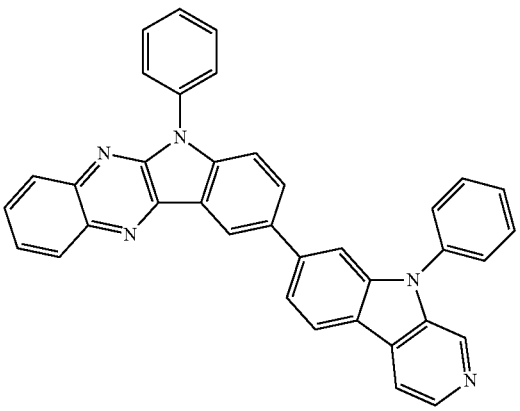
A-145
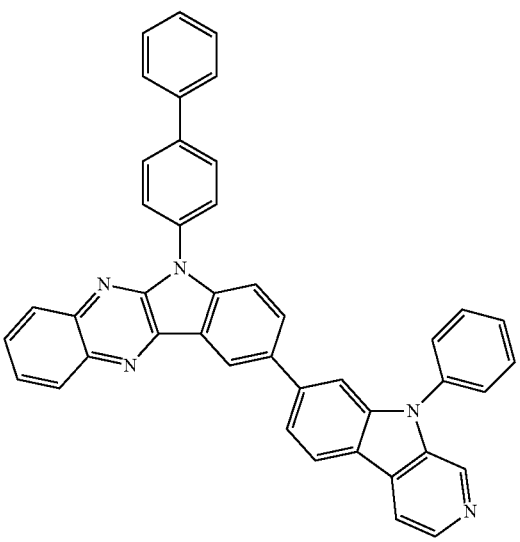
A-146
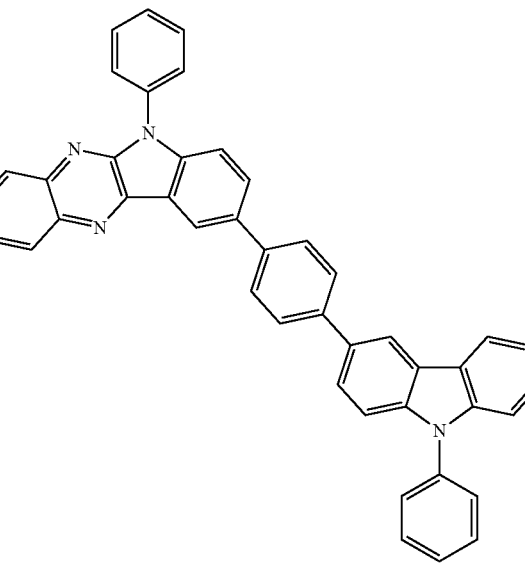

-continued
A-147
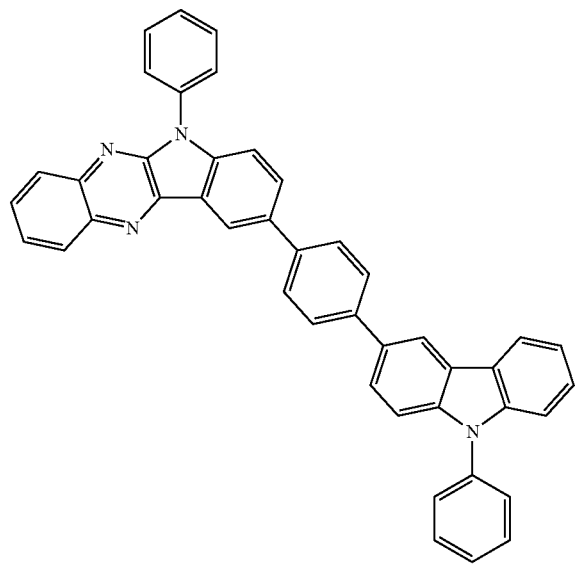
A-148
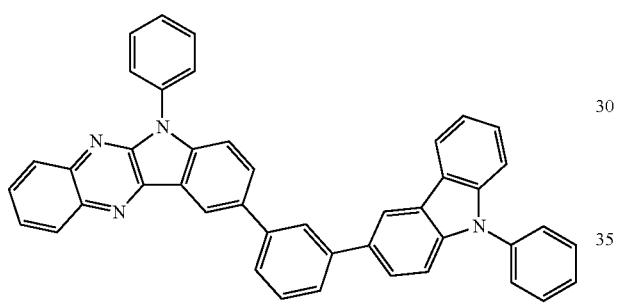
A-149
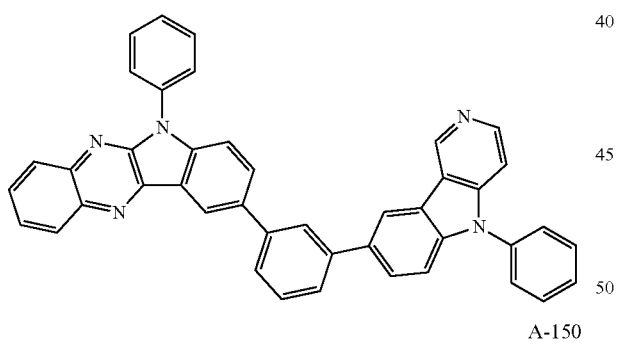
A-150
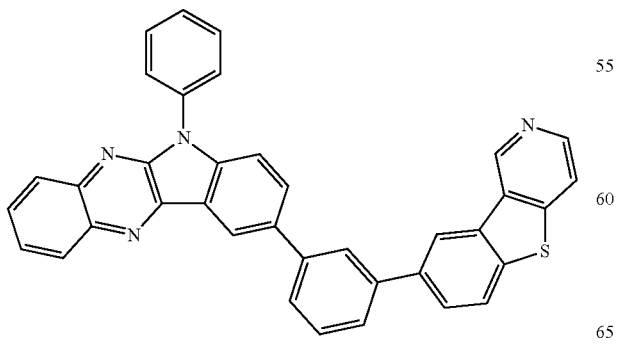
-continued
A-151
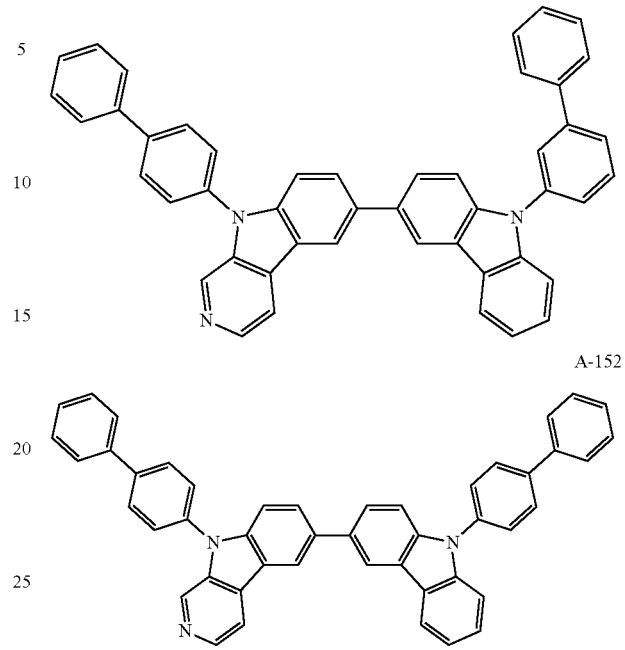
A-152
A-153
A-154
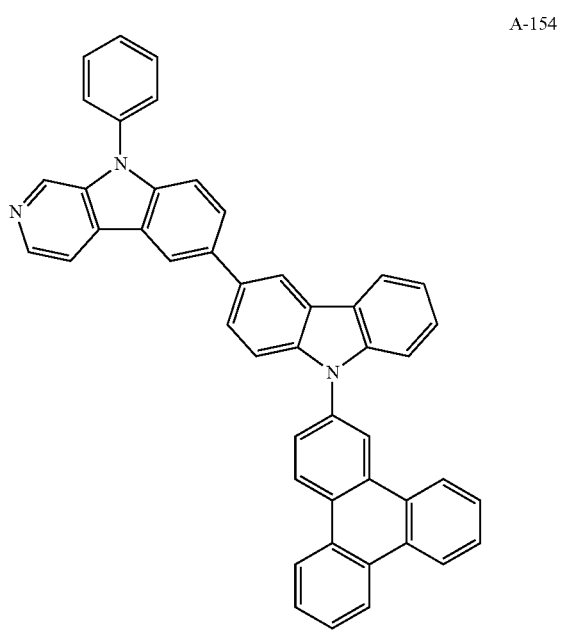

A-155
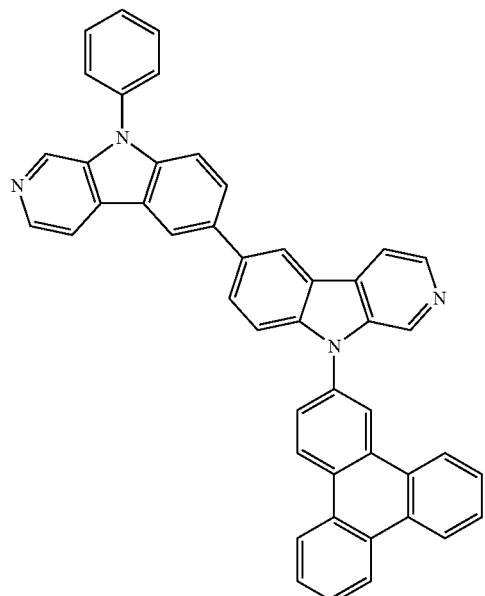
A-156
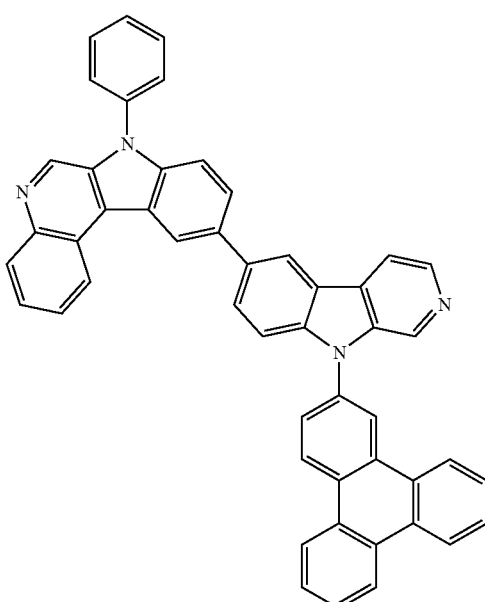
A-157
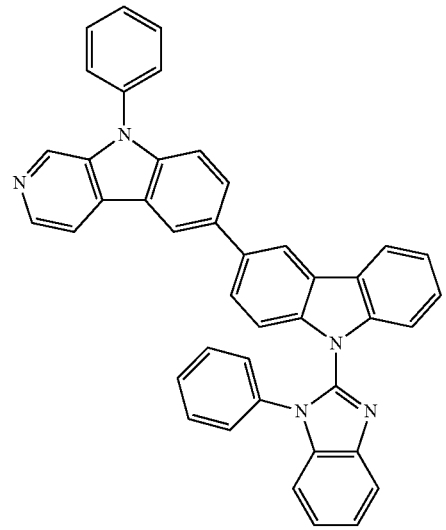
A-158
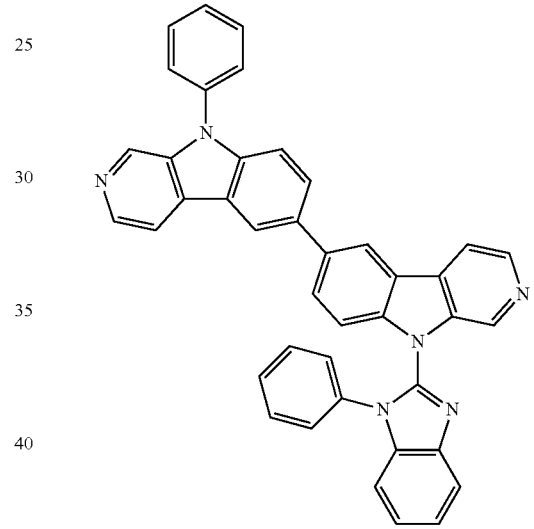
A-159
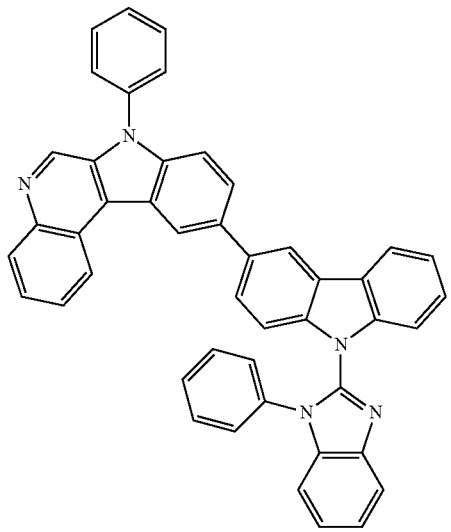

A-160
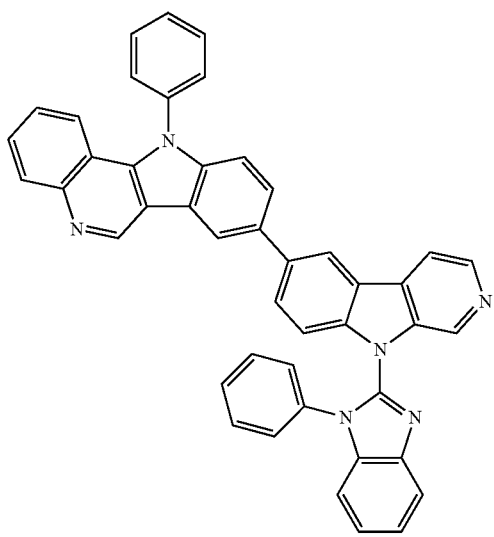
A-161
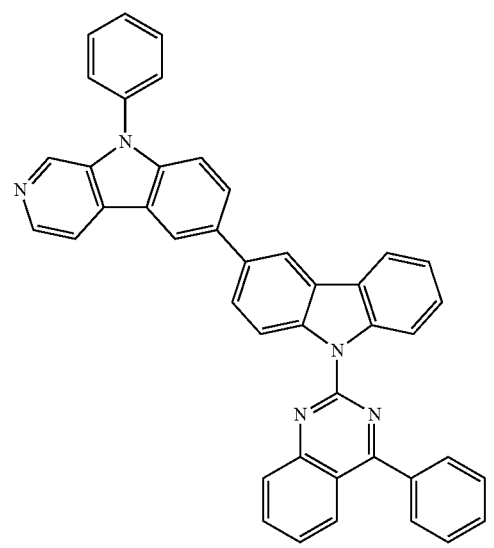
A-162
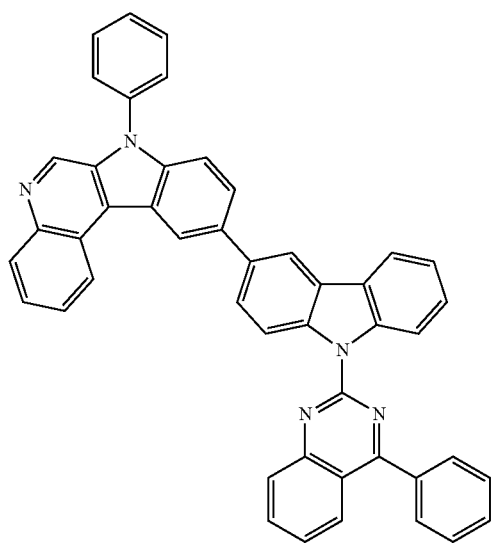
A-163
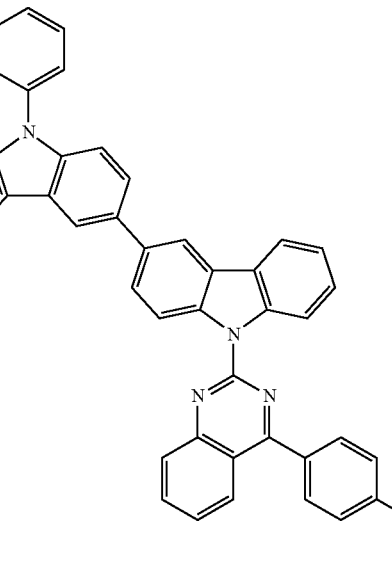
A-164
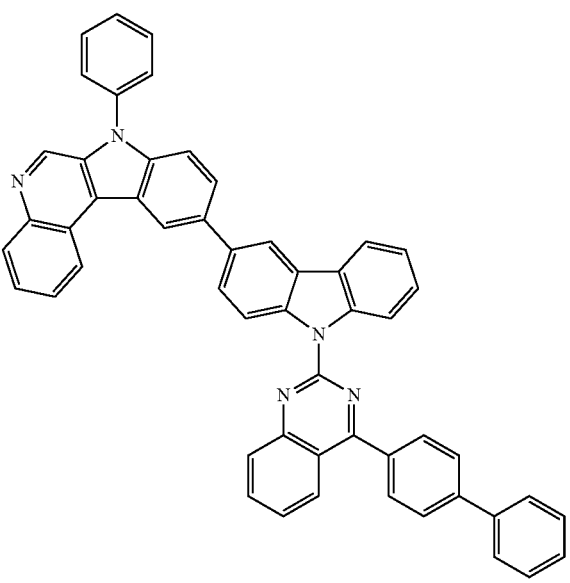

A-165

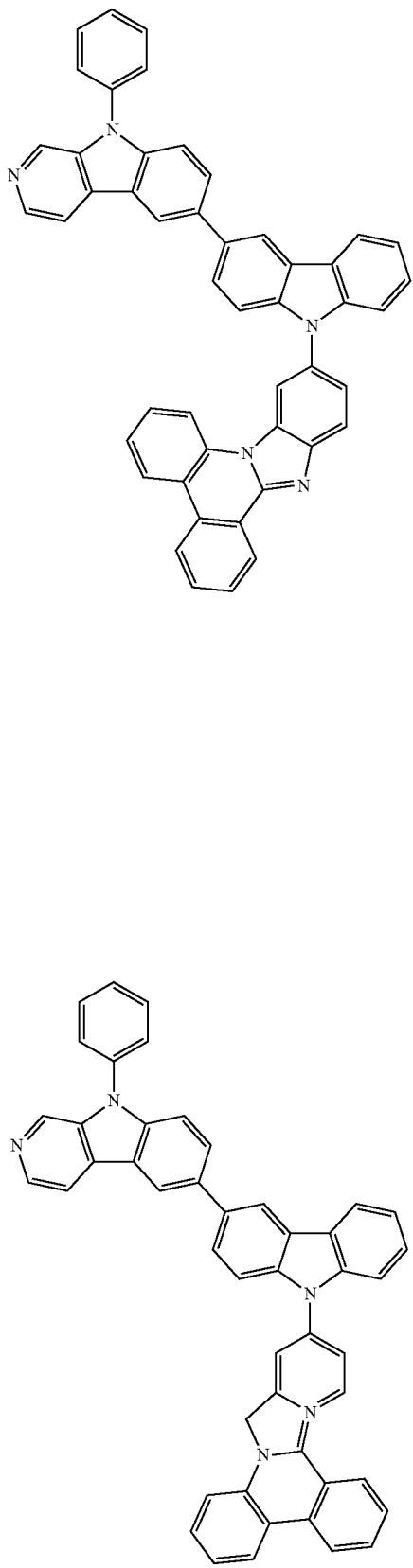

A-166

A-167

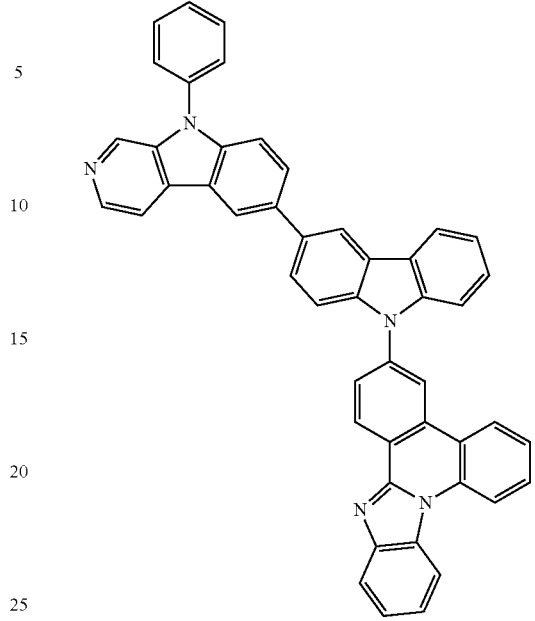

A-168

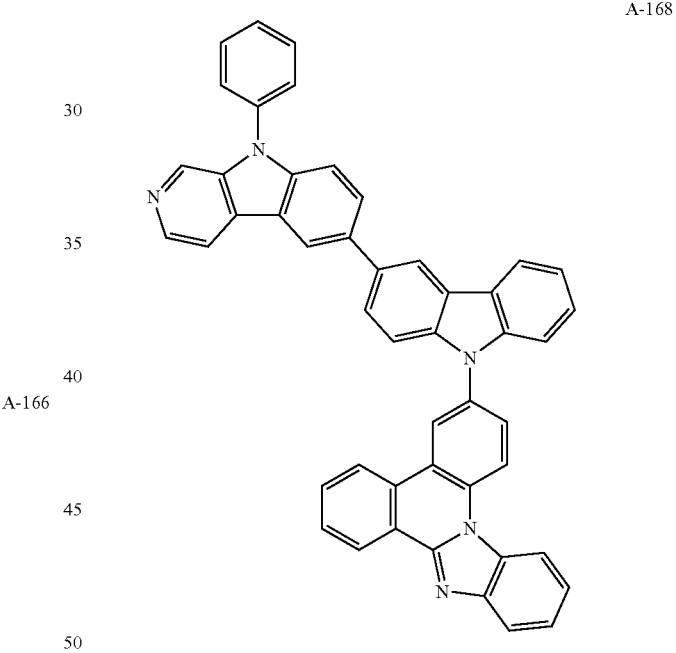

According to the embodiment, the compound includes a functional group having the electron characteristics when both electron and hole characteristics are required. Such a compound thus may effectively improve the life-span of an organic light emitting diode and decrease a driving voltage thereof.

The compound for an organic optoelectronic device has a maximum light emitting wavelength in a range of about 320 to about 520 nanometers (nm) and a triplet excited energy (T1) ranging from greater than or equal to about 2.0 electron Volts (eV), and for example, from about 2.0 to about 4.0 eV. Such a compound thus may well transport a host charge having high triplet excited energy to a dopant and increase luminous efficiency of the dopant. Such a compound is also freely adjusted regarding HOMO and LUMO energy levels and may decrease a driving voltage. Accordingly, the compound may be usefully applied as a host material or a charge transport material.

In addition, the compound for an organic optoelectronic device has photoactive and electrical activities, and thus may be usefully applied for a nonlinear optic material, an electrode material, a discolored material, a light switch, a sensor, a module, a wave guide, an organic transistor, a laser, a light absorbent, a dielectric material, a separating membrane, and the like.

The compound for an organic optoelectronic device including the above compounds has a glass transition temperature of greater than or equal to about 90° C. and a thermal decomposition temperature of greater than or equal to about 400° C., indicating improved thermal stability. Thereby, it is possible to produce an organic optoelectronic device having high efficiency.

The compound for an organic optoelectronic device including the above compounds may play a role of emitting light or injecting and/or transporting electrons, and may also act as a light emitting host with an appropriate dopant. In other words, the compound for an organic optoelectronic device may be used as a phosphorescent or fluorescent host material, a blue light emitting dopant material, or an electron transport material.

Since the compound for an organic optoelectronic device according to an embodiment is used for an organic thin layer, and it may improve the life-span characteristic, efficiency characteristic, electrochemical stability, and thermal stability of an organic photoelectric device, and decrease the driving voltage.

Further, according to another embodiment, an organic optoelectronic device that includes the compound for an organic optoelectronic device is provided. The organic optoelectronic device may include an organic photoelectric device, an organic light emitting diode, an organic solar cell, an organic transistor, an organic photoconductor drum, an organic memory device, and the like. For example, the compound for an organic optoelectronic device according to an embodiment may be included in an electrode or an electrode buffer layer in an organic solar cell to improve the quantum efficiency. It also may be used as an electrode material for a gate, a source-drain electrode, or the like in the organic transistor.

Hereinafter, an organic light emitting diode is described.

According to another embodiment, an organic light emitting diode includes an anode, a cathode, and at least one organic thin layer disposed between the anode and the cathode, wherein the at least one organic thin layer may include the compound for an organic optoelectronic device according to an embodiment.

The organic thin layer that may include the compound for an organic optoelectronic device may include a layer selected from the group consisting of an emission layer, a hole transport layer (HTL), a hole injection layer (HIL), an electron transport layer (ETL), an electron injection layer (EIL), a hole blocking layer, and a combination thereof. The at least one layer includes the compound for an organic optoelectronic device according to an embodiment. Particularly, the compound for an organic optoelectronic device according to an embodiment may be included in a hole transport layer (HTL) or a hole injection layer (HIL). In addition, when the compound for an organic optoelectronic device is included in the emission layer, the compound for an organic optoelectronic device may be included as a phosphorescent or fluorescent host, and particularly, as a fluorescent blue dopant material.

FIGS. 1 to 5 are cross-sectional views showing organic light emitting diodes including the compound for an organic optoelectronic device according to an embodiment.

Referring to FIGS. 1 to 5, organic light emitting diodes 100, 200, 300, 400, and 500 according to an embodiment include at least one organic thin layer 105 interposed between an anode 120 and a cathode 110.

The anode 120 includes an anode material playing a large work function to help hole injection into an organic thin layer. The anode material includes: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combination of a metal and an oxide such as ZnO:Al and SnO$_2$:Sb; or a conductive polymer such as poly(3-methylthiophene), poly[3,4-(ethylene-1,2-dioxy)thiophene] (PEDT), polypyrrole, and polyaniline, but is not limited thereto. In an embodiment, it is preferable to include a transparent electrode including indium tin oxide (ITO) as an anode.

The cathode 110 includes a cathode material having a small work function to help electron injection into an organic thin layer. The cathode material includes: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, LiO$_2$/Al, LiF/Ca, and BaF$_2$/Ca, but is not limited thereto. In an embodiment, it is preferable to include a metal electrode including aluminum as a cathode.

Referring to FIG. 1, the organic photoelectric device 100 includes an organic thin layer 105 including only an emission layer 130.

Figure 2:
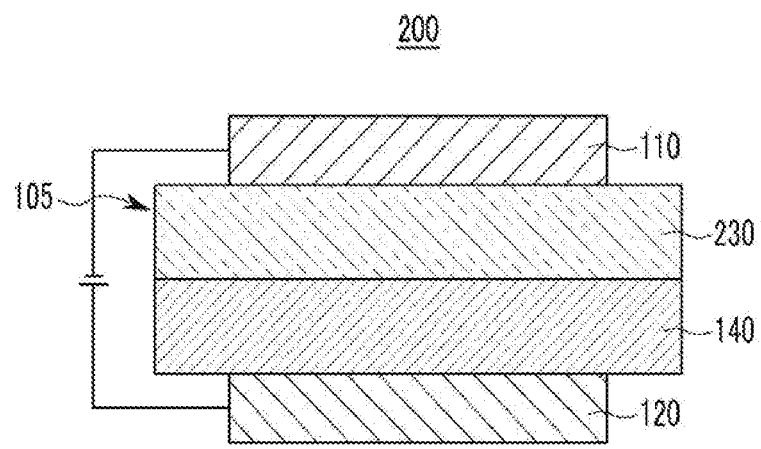

Referring to FIG. 2, a double-layered organic photoelectric device 200 includes an organic thin layer 105 including an emission layer 230 including an electron transport layer (ETL), and a hole transport layer (HTL) 140. As shown in FIG. 2, the organic thin layer 105 includes a double layer of the emission layer 230 and the hole transport layer (HTL) 140. The emission layer 130 also functions as an electron transport layer (ETL), and the hole transport layer (HTL) 140 layer has an improved binding property with a transparent electrode such as ITO or an improved hole transport capability.

Figure 3:
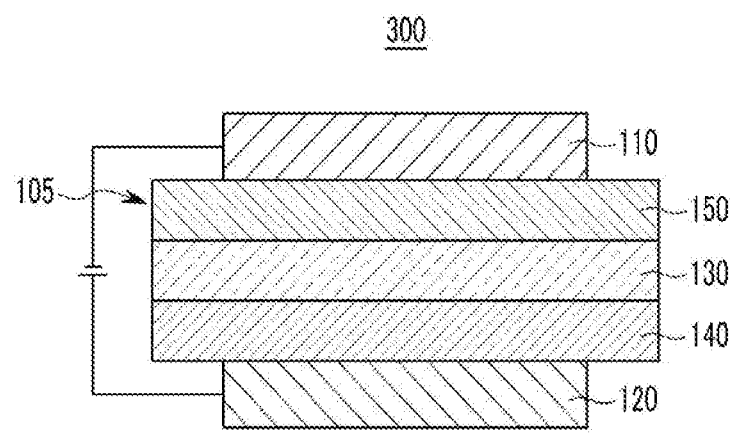

Referring to FIG. 3, a three-layered organic photoelectric device 300 includes an organic thin layer 105 including an electron transport layer (ETL) 150, an emission layer 130, and a hole transport layer (HTL) 140. The emission layer 130 is independently installed, and layers having an improved electron transport capability or an improved hole transport capability are separately stacked.

Figure 4:
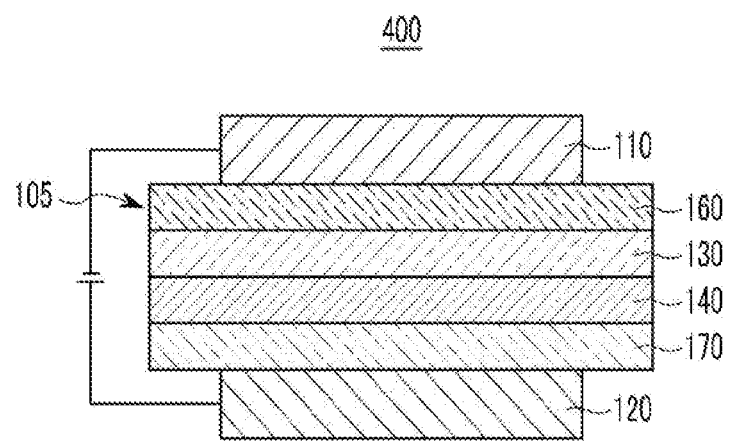

As shown in FIG. 4, a four-layered organic photoelectric device 400 includes an organic thin layer 105 including an electron injection layer (EIL) 160, an emission layer 130, a hole transport layer (HTL) 140, and a hole injection layer (HIL) 170 for adherence with the cathode made of ITO.

Figure 5:
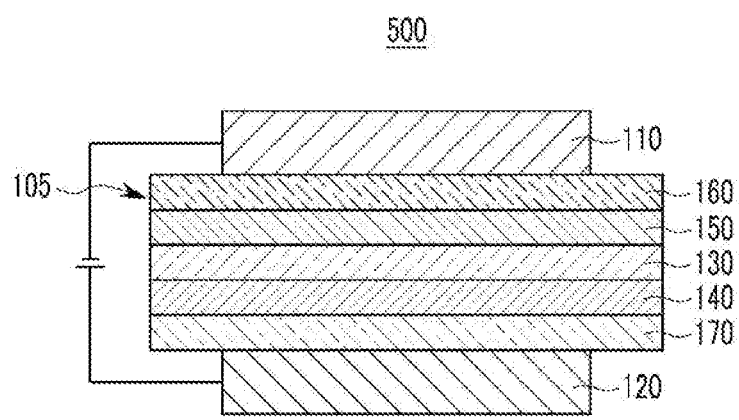

As shown in FIG. 5, a five-layered organic photoelectric device 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

In FIGS. 1 to 5, the organic thin layer 105 including at least one selected from an electron transport layer (ETL) 150, an electron injection layer (EIL) 160, emission layers 130 and 230, a hole transport layer (HTL) 140, a hole injection layer (HIL) 170, and combinations thereof includes a compound for an organic optoelectronic device. The compound for an organic optoelectronic device may be used for an electron transport layer (ETL) 150 including the electron transport layer (ETL) 150 or electron injection layer (EIL) 160. When it is used for the electron transport layer (ETL), it is possible to provide an organic photoelectric device having a more simple structure because it does not require an additional hole blocking layer (not shown).

Furthermore, when the compound for an organic photoelectric device is included in the emission layers 130 and 230, the material for the organic photoelectric device may be included as a phosphorescent or fluorescent host or a fluorescent blue dopant.

The organic light emitting diode may be fabricated by: forming an anode on a substrate; forming an organic thin layer in accordance with a dry coating method such as evaporation, sputtering, plasma plating, and ion plating, or a wet coating method such as spin coating, dipping, and flow coating; and providing a cathode thereon.

Another embodiment provides a display device including the organic photoelectric device according to the above embodiment.

Hereinafter, the embodiments are illustrated in more detail with reference to examples. These examples, however, are not in any sense to be interpreted as limiting the scope of the invention.

Preparation of Compound for Organic Optoelectronic Device

Example 1

Synthesis of Compound A-5

The compound A-5 as an example of a compound for an organic optoelectronic device according to the present disclosure is synthesized according to the following Reaction Scheme 1.

Reaction Scheme 1

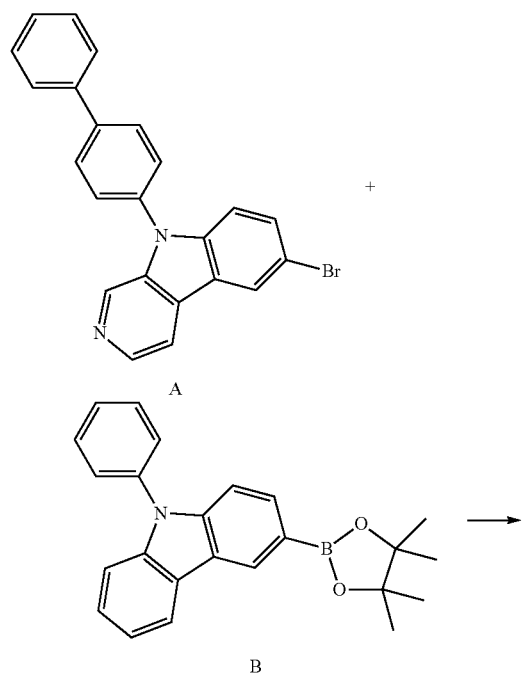

-continued

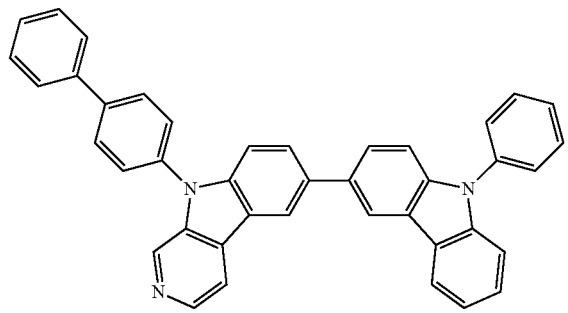

Synthesis of Chemical Formula A-5 Compound 20 g (50.090 mmol) of a compound A, 20.346 g (55.099 mmol) of a compound B, 5.788 g (5.009 mmol) of tetrakis(triphenylphosphine)palladium (0), and 19.8 g (143.258 mmol) of potassium carbonate are suspended in THF/toluene/distilled water mixed in a ratio of 150/150/150 mL, and then refluxed and agitated for 18 hours. When the reaction is complete, the obtained mixture is slowly poured into 2 L of methanol to produce a precipitate. The precipitate is filtered and washed with methanol and distilled water. Next, the precipitate is dried and then dissolved in dichloromethane ($CH_2Cl_2$) and separated through silica gel chromatography. Accordingly, 15.47 g of a compound A-5 is obtained (a yield of 55%).

$^1$H-NMR (600 MHz, $CDCl_3$): 8.97 (s, 2H); 8.59 (d, 2H); 8.53 (s, 2H); 8.47 (s, 2H); 8.27 (d, 2H); 8.14 (d, 2H); 7.97 (d, 2H); 7.90 (m, 4H); 7.79 (d, 2H); 7.75 (d, 8H); 7.67 (m, 10H); 7.54 (m, 8H); 7.46 (m, 6H); 7.35 (m, 2H)

Example 2

Synthesis of Compound A-18

Reaction Scheme 2

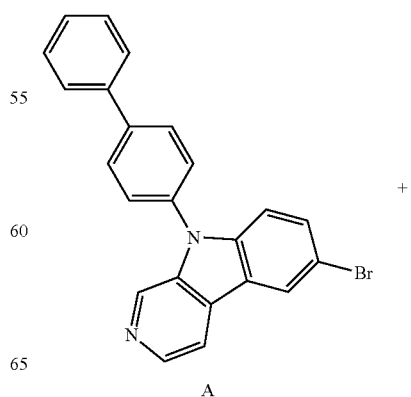

155 -continued

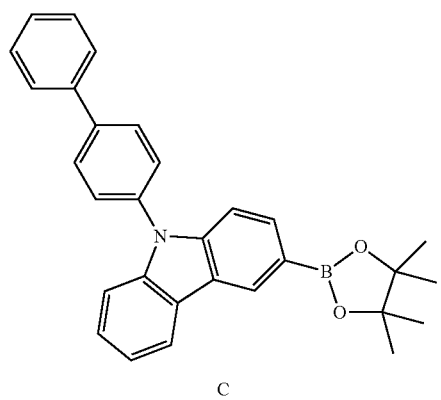

C

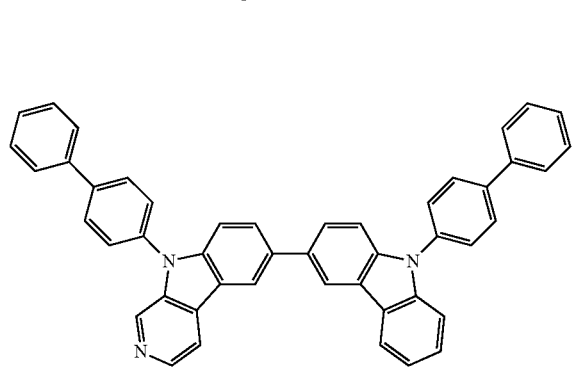

Synthesis of Chemical Formula A-18 Compound

The same reaction as aforementioned except for using 24.539 g (50.090 mmol) of a compound C instead on the compound B in Example 1 is performed. Then, 19.81 g of a compound A-18 (a yield of 62%) is obtained through recrystallization using dichloromethane instead of the silica gel chromatography.

Example 3

Synthesis of Compound A-151

Reaction Scheme 3

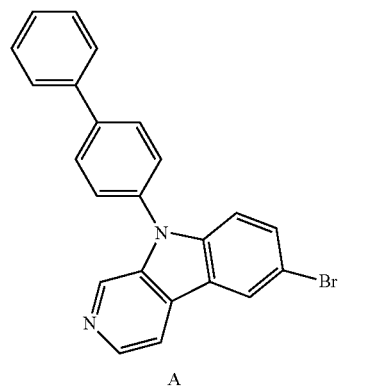

A

156 -continued

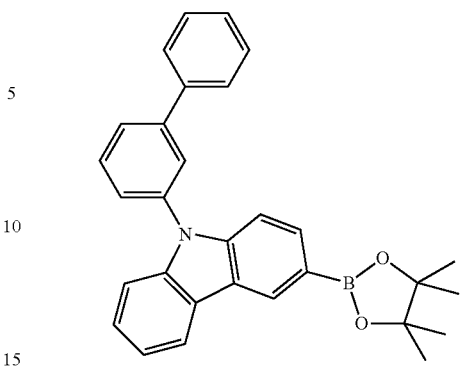

D

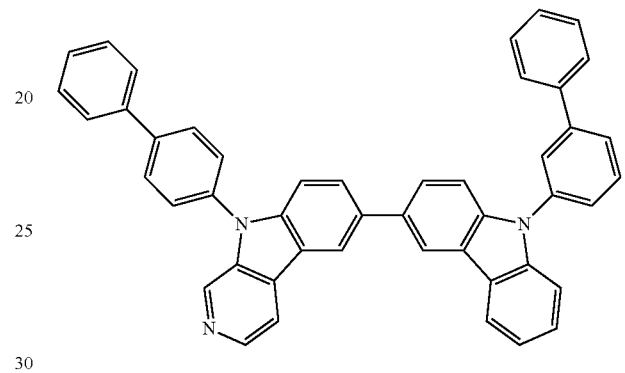

Synthesis of Chemical Formula A-151 Compound

The same reaction as aforementioned in Example 1 is performed except for using 24.539 g (50.090 mmol) of a compound D instead of the compound B. Then, 16.61 g of a compound A-151 (a yield of 52%) is obtained through recrystallization using dichloromethane instead of silica gel chromatography.

Example 4

Synthesis of Compound A-152

Reaction Scheme 4

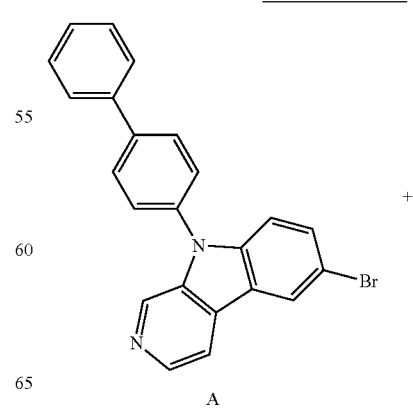

A

+

+

-continued

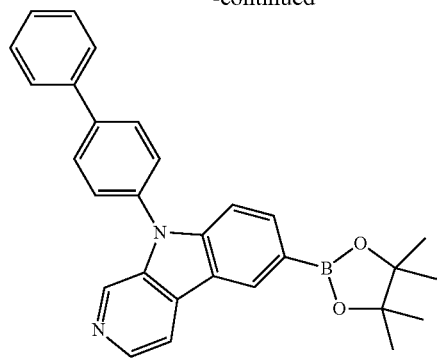

E

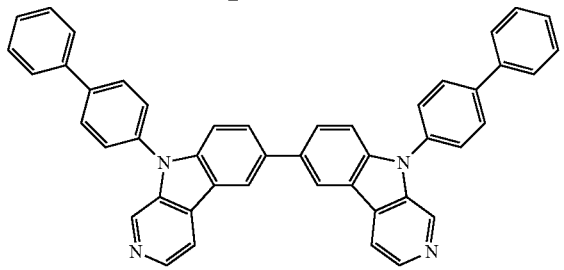

Synthesis of Chemical Formula A-152 Compound 20 g (50.090 mmol) of a compound A, 20.594 g (55.099 mmol) of a compound E, 5.788 g (5.009 mmol) of tetrakis (triphenylphosphine)palladium(0), and 19.8 g (143.258 mmol) of potassium carbonate are suspended in THF/toluene/distilled water mixed in a ratio of 150/150/150 mL, and then refluxed and agitated for 18 hours. When the reaction is complete, the resulting product is slowly poured into 2 L of methanol to produce a precipitate. The precipitate is filtered and washed with methanol and distilled water. Next, the precipitate is dried and dissolved in dichloromethane (CH$_2$Cl$_2$) for recrystallization. Then, 21.08 g of a compound A-152 is obtained (a yield of 66%).

$^1$H-NMR (300 MHz, CDCl$_3$): 8.97 (s, 2H); 8.59 (d, 2H); 8.51 (s, 2H); 8.13 (d, 2H); 7.95 (d, 2H); 7.90 (m, 4H); 7.74 (m, 8H); 7.69 (d, 2H); 7.56 (t, 4H); 7.45 (m, 2H)

Example 5

Synthesis of Compound A-153

Reaction Scheme 5

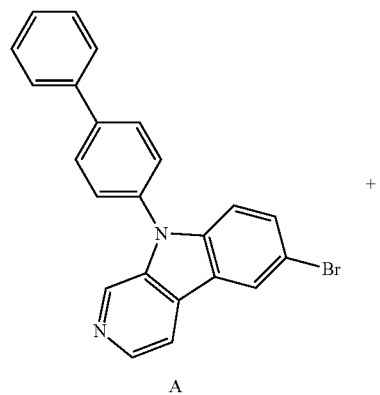

A

-continued

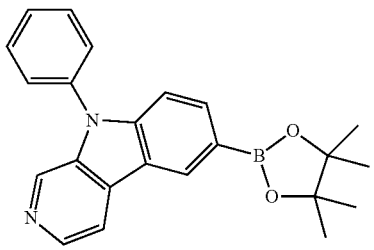

F

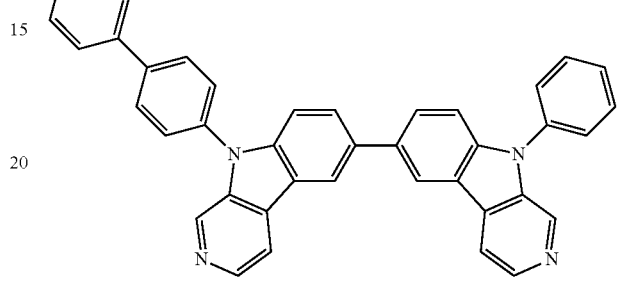

The same reaction as aforementioned in Example 4 is performed except for using 20.4 g (50.090 mmol) of a compound F instead of the compound E. Next, a precipitate produced therein is separated through recrystallization using dichloromethane instead of the silica gel chromatography. Then, 16.35 g of a compound A-153 is obtained (a yield of 58%).

Example 6

Synthesis of Compound A-33

Reaction Scheme 6

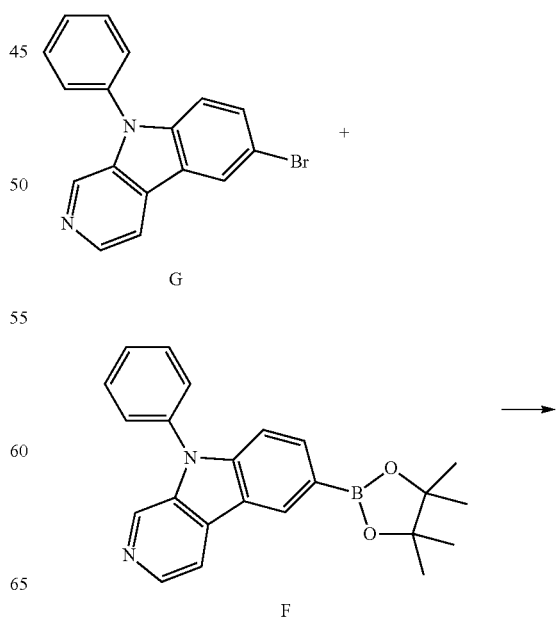

-continued

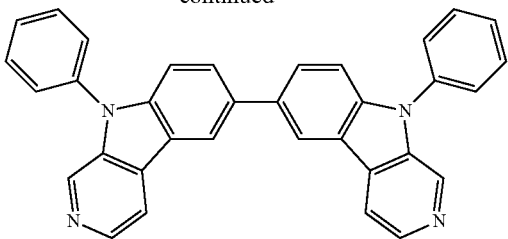

The same reaction as aforementioned in Example 4 is performed except for using 20 g (61.883 mmol) of a compound G instead of the compound A and 25.203 g (68.071 mmol) of a compound F instead of the compound E. Next, a precipitate produced therein is separated through recrystallization using dichloromethane instead of the silica gel chromatography. Then, 16.85 g of a compound A-33 is obtained (a yield of 56%).

Example 7

Synthesis of Compound A-49

Reaction Scheme 7

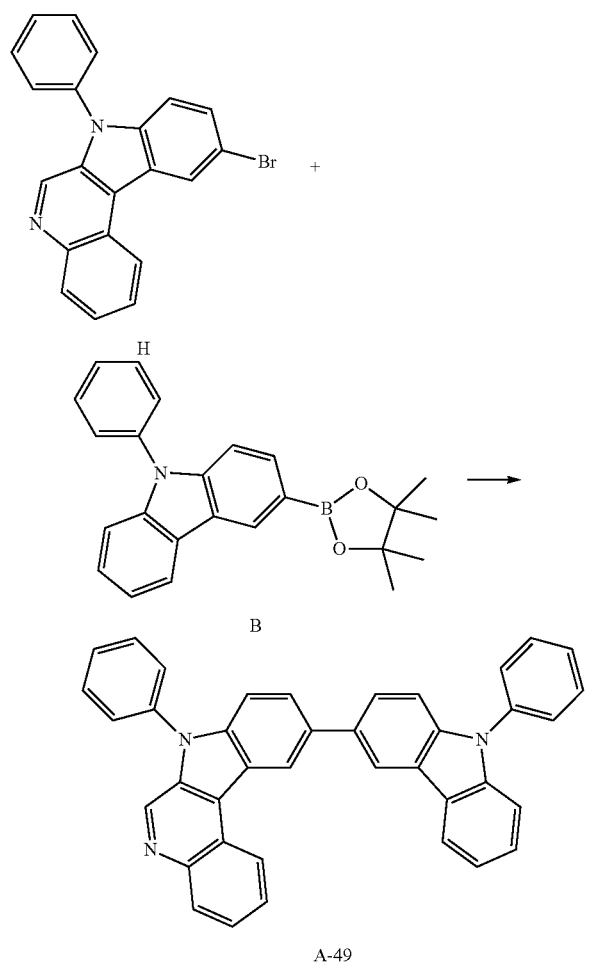

19 g (50.904 mmol) of a compound H, 20.677 g (55.995 mmol) of the compound E, 2.545 g (2.545 mmol) of tetrakis(triphenylphosphine)palladium(0), and 20.121 g (145.586 mmol) of potassium carbonate are suspended in THF/toluene/distilled water mixed in a ratio of 150/150/150 mL, and then refluxed and agitated for 18 hours. When the reaction is complete, the resulting produce is slowly poured into 2 L of methanol to produce a precipitate. The precipitate is filtered and washed with methanol and distilled water. Next, the precipitate is dried and separated through silica gel chromatography under a condition of dichloromethane ($CH_2Cl_2$). As a result, 15.00 g of a compound A-49 (a yield of 55%) is obtained.

$^1$H-NMR (300 MHz, $CDCl_3$): 9.17 (s, 1H); 8.91 (s, 1H); 8.89 (s, 1H); 8.50 (d, 1H); 8.32 (d, 1H); 8.28 (d, 1H); 7.94 (d, 1H), 7.81 (t, 2H); 7.71 (m, 5H); 7.64 (m, 5H); 7.57 (m, 2H); 7.55 (m, 1H); 7.46 (d, 2H); 7.35 (m, 1H)

Example 8

Synthesis of Compound A-64

Reaction Scheme 8

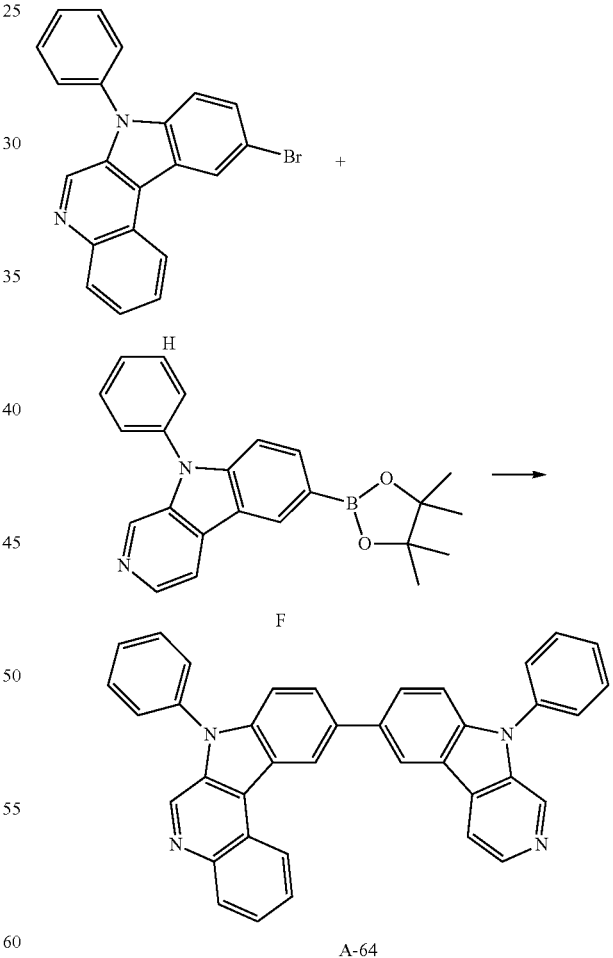

The same reaction as aforementioned in Example 7 is performed except for using 20 g (53.583 mmol) of a compound H and 21.823 g (58.942 mmol) of a compound F instead of the compound B. Next, a precipitate is dried and separated through silica gel chromatography under a condition of dichloromethane ($CH_2Cl_2$). As a result, 17.26 g of a compound A-64 (a yield of 60%) is obtained.

Example 9

Synthesis of Compound A-70

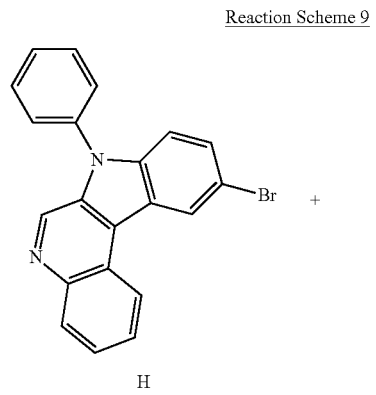

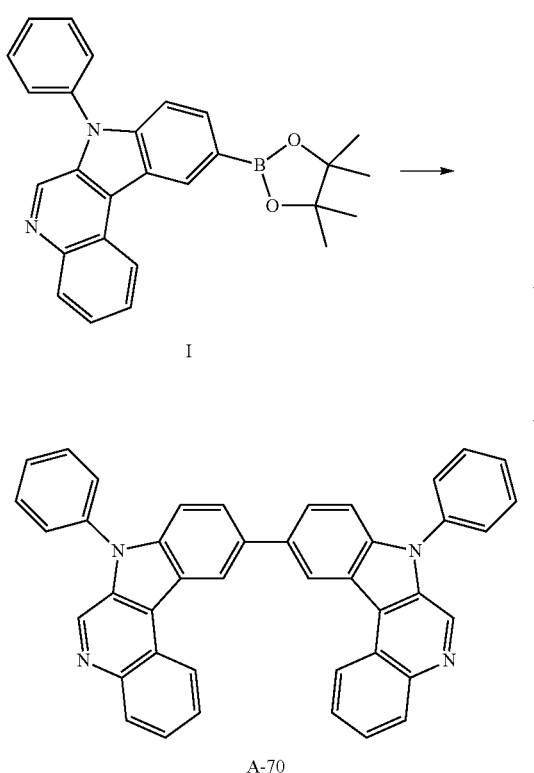

The same reaction as aforementioned in Example 7 is performed except for using 12.387 g (29.471 mmol) of a compound I instead of the compound B, and 10 g (26.792 mmol) of a compound H. Next, a precipitate is dried and separated through silica gel chromatography under a condition of dichloromethane ($CH_2Cl_2$). As a result, 11.20 g of a compound A-70 (a yield of 71%) is obtained.

Example 10

Synthesis of Compound A-74

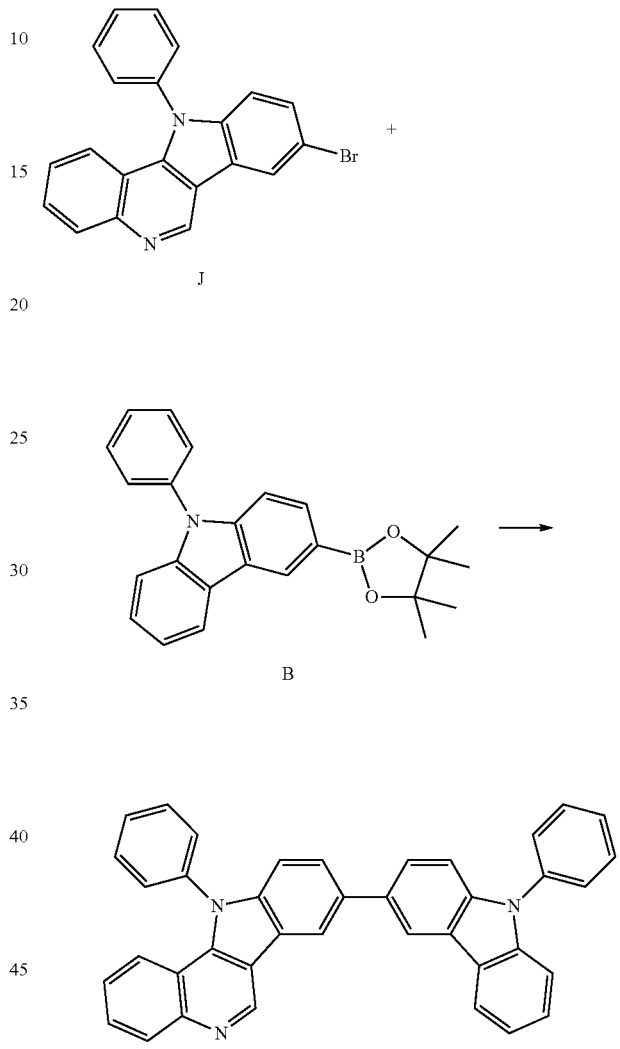

20 g (53.583 mmol) of a compound J, 21.765 g (58.942 mmol) of the compound B, 3.096 g (2.679 mmol) of tetrakis(triphenylphosphine)palladium(0), and 21.180 g (153.248 mmol) of potassium carbonate are suspended in THF/toluene/distilled water mixed in a ratio of 150/150/150 mL, and then refluxed and agitated for 18 hours. When the reaction is complete, the resulting produce is slowly poured into 2 L of methanol to produce a precipitate. The precipitate is filtered and washed with methanol and distilled water. Next, the precipitate is dried and separated through silica gel chromatography under a condition of dichloromethane ($CH_2Cl_2$). As a result, 18.00 g of a compound A-74 (a yield of 74%) is obtained.

Example 11

Synthesis of Compound A-85

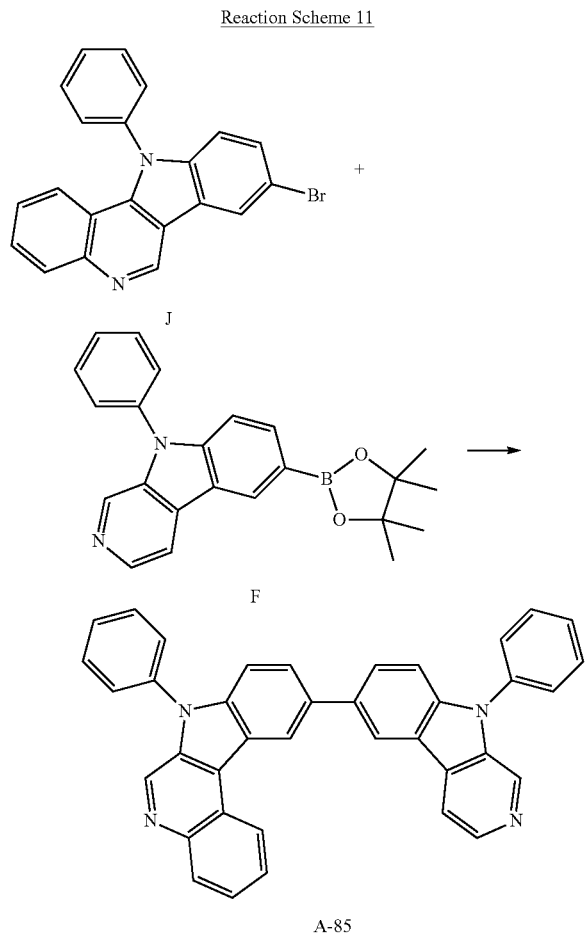

Reaction Scheme 11

The same reaction as aforementioned in Example 8 is performed except for using 20 g (53.583 mmol) of a compound J instead of the compound H and 21.823 g (58.942 mmol) of a compound F. Next, a precipitate produced therein is dried and separated through silica gel chromatography under a condition of dichloromethane ($CH_2Cl_2$). As a result, 18.50 g of a compound A-85 (a yield of 64%) is obtained.

Manufacture of Organic Light Emitting Diode

In general, an organic light emitting diode has a stack structure of anode/organic emission layer/cathode, for example, various structures of anode/hole injection layer (HIL)/hole transport layer (HTL)/emission layer/electron transport layer (ETL)/electron injection layer (EIL)/cathode, anode/hole injection layer (HIL)/hole transport layer (HTL)/emission layer/hole-blocking layer/electron transport layer (ETL)/electron injection layer (EIL)/cathode, anode/hole injection layer (HIL)/hole-producing layer/hole transport layer (HTL)/emission layer/hole-blocking layer/electron transport layer (ETL)/electron injection layer (EIL)/cathode, or these structures having no electron injection layer (EIL), may be used. Herein, the compound represented by Chemical Formula 1 may be used as an emission layer material.

Preparation Example 1

An ITO glass substrate is cut into a size of 50 mm×50 mm×0.5 mm and then washed in acetone isopropyl alcohol and pure water for 15 minutes and washed in UV-ozone for 30 minutes. Next, a 600 Angstrom-thick (Å-thick) hole injection layer (HIL) is formed on the ITO glass substrate by vacuum-depositing m-MTDATA at a speed of 1 Angstrom per second (Å/sec), and a 300 Å-thick hole transport layer (HTL) is formed thereon by vacuum-depositing a-NPD at a speed of 1 Å/sec. Then, a 400 Å-thick emission layer is formed on the hole transport layer (HTL) by respectively vacuum-depositing Ir(ppy)3 as a dopant material and the compound A-152 at each speed of 0.1 Å/sec and 1 Å/sec. Then, a 50 Å-thick hole-blocking layer is formed on the emission layer by vacuum-depositing (BAlq) at a speed of 1 Å/sec. Then, a 300 Å-thick electron transport layer (ETL) is formed on hole-blocking layer by vacuum-depositing an Alq3 compound. Then, LiF (an electron injection layer (EIL)) at 10 Å and Al (a cathode) at 2,000 Å are sequentially vacuum-deposited on the electron transport layer (ETL), fabricating an organic light emitting diode. This organic light emitting diode is called Sample 1.

Preparation Example 2

An organic light emitting diode having a structure of ITO/m-MTDATA at 600 Å/a-NPD at 300 Å/compound 6+10% (Ir(ppy)3) at 400 Å/Balq at 50 Å/Alq3 at 300 Å/LiF at 10 Å/Al at 2,000 Å is fabricated according to the same method as Preparation Example 1, except for using the compound A-33 instead of the compound A-152 as a host. This organic light emitting diode is called Sample 2.

Preparation Example 3

An organic light emitting diode having a structure of ITO/m-MTDATA at 600 Å/a-NPD at 300 Å/compound 10+10% (Ir(ppy)3) at 400 Å/Balq at 50 Å/Alq3 at 300 Å/LiF at 10 Å/Al at 2,000 Å is fabricated according to the same method as Preparation Example 1, except for using the compound A-64 instead of the compound A-152 as a host. This organic light emitting diode is called Sample 3.

Comparative Preparation Example 1

An organic light emitting diode having a structure of ITO/m-MTDATA at 600 Å/a-NPD at 300 Å/A+10% (Ir(ppy)3) at 400 Å/Balq at 50 Å/Alq3 at 300 Å/LiF at 10 Å/Al at 2,000 Å is fabricated according to the same method as Preparation Example 1, except for using a compound represented by the following Chemical Formula A (CBP) instead of the compound A-152 as a host.

The organic light emitting diodes according to Preparation Examples 1 to 3 and Comparative Example 1 are evaluated regarding characteristics. The evaluation is performed according to the following reference. The results are provided in the following Table 1.

(1) Measurement of Current Density Change Depending on Voltage Change

The obtained organic light emitting diodes are measured regarding current value flowing in a unit device using a current-voltage meter (Keithley 2400), while their voltages are increased from −5 Volts (V) to 10 V. The measured current value is divided by area to calculate current density.

(2) Measurement of Luminance Change Depending on Voltage Change

The organic light emitting diodes are measured regarding luminance using a luminance meter (Minolta Cs-1000A) while their voltages are increased from −5 V to 10 V.

(3) Measurement of Luminous Efficiency

Current efficiency (candelas per ampere, cd/A) and electrical power efficiency (lumens per watt, lm/W) at the same luminance (1,000 candelas per square meter, cd/m²) are calculated by using luminance and current density from (1) and (2) and a voltage.

TABLE 1

|  | Luminance (cd/m²) | Current efficiency (cd/A) | Driving voltage (V) |
|---|---|---|---|
| Preparation Example 1 | 3,500 | 43 | 6.0 |
| Preparation Example 2 | 3,500 | 41 | 5.9 |
| Preparation Example 3 | 3,500 | 47 | 6.1 |
| Comparative Example 1 | 3,500 | 33 | 8.1 |

Referring to the results in Table 1, the organic light emitting diodes according to Preparation Examples 1 to 3 show more improved current efficiency and driving voltage compared with that according to Comparative Preparation Example 1.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present inventive concept in any way.

What is claimed is:

1. A compound for an organic optoelectronic device represented by Chemical Formula 1:

Chemical Formula 1

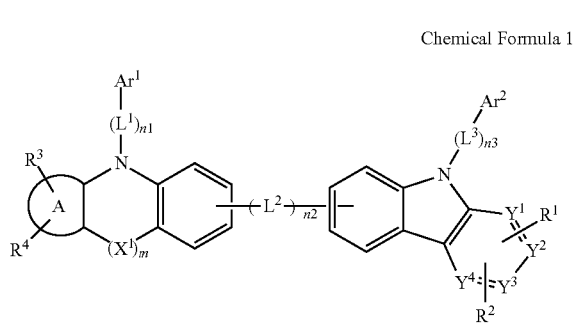

wherein, in Chemical Formula 1,

A is a C6 to C40 aryl group comprising 1 to 4 aromatic rings, wherein the 1 to 4 aromatic rings include at least one nitrogen, $Y^1$ to $Y^4$ are each independently CR' or N, $X^1$ is —CR'R''—, —SiR'R''—, —O—, —NR'—, —S—, —SO$_2$—, —C(O)—, or —P(O)—, m is an integer ranging from 0 to 2, $R^1$ to $R^4$, R', and R'' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

2. The compound for an organic optoelectronic device of claim 1, wherein the compound for an organic optoelectronic device is represented by Chemical Formula 2:

Chemical Formula 2

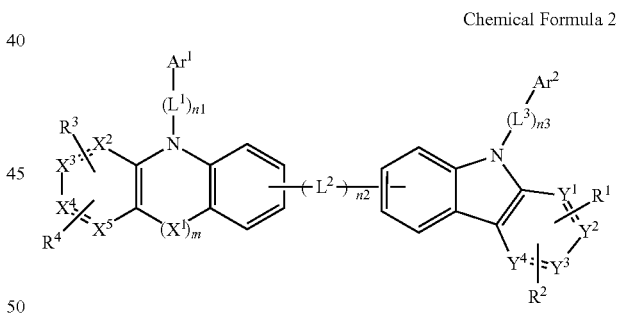

wherein, in Chemical Formula 2, $X^1$ is —CR'R''—, —SiR'R''—, —O—, —NR'—, —S—, —SO$_2$—, —C(O)—, or —P(O)—, m is an integer ranging from 0 to 2, $Y^1$ to $Y^4$ are each independently CR' or N, $X^2$ to $X^5$ are each independently CR' or N, provided that at least one of $X^2$ to $X^5$ is N, $R^1$ to $R^4$, R', and R'' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

3. The compound for an organic optoelectronic device of claim 2, wherein $X^2$ is N, and $X^3$ to $X^5$ are CR'.

4. The compound for an organic optoelectronic device of claim 2, wherein $X^3$ is N, and $X^2$, $X^4$, and $X^5$ are CR'.

5. The compound for an organic optoelectronic device of claim 2, wherein $X^4$ is N, and $X^2$, $X^3$, and $X^5$ are CR'.

6. The compound for an organic optoelectronic device of claim 2, wherein $X^5$ is N, and $X^2$, $X^3$, and $X^4$ are CR'.

7. The compound for an organic optoelectronic device of claim 2, wherein $X^2$ and $X^4$ are N, and $X^3$ and $X^5$ are CR'.

8. The compound for an organic optoelectronic device of claim 1, wherein the compound for an organic optoelectronic device is represented by Chemical Formula 3:

Chemical Formula 3

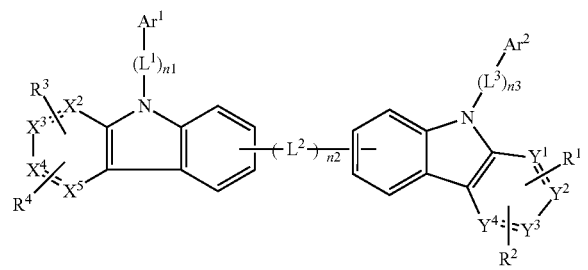

wherein, in Chemical Formula 3, $X^2$ to $X^5$ are each independently CR' or N, provided that at least one of $X^2$ to $X^5$ is N, $Y^1$ to $Y^4$ are each independently CR' or N, $R^1$ to $R^4$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

9. The compound for an organic optoelectronic device of claim 1, wherein the compound for an organic optoelectronic device is represented by Chemical Formula 4:

Chemical Formula 4

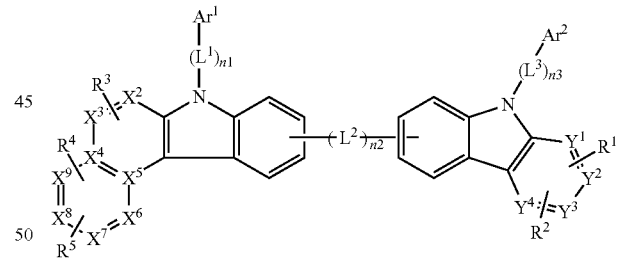

wherein, in Chemical Formula 4, $X^2$, $X^3$, and $X^6$ to $X^9$ are each independently CR', or N, and $X^4$ and $X^5$ are C, provided that at least one of $X^2$, $X^3$, and $X^6$ to $X^9$ is N, $Y^1$ to $Y^4$ are each independently CR' or N, $R^1$ to $R^5$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

10. The compound for an organic optoelectronic device of claim 1, wherein the compound for an organic optoelectronic device is represented by Chemical Formula 5:

Chemical Formula 5

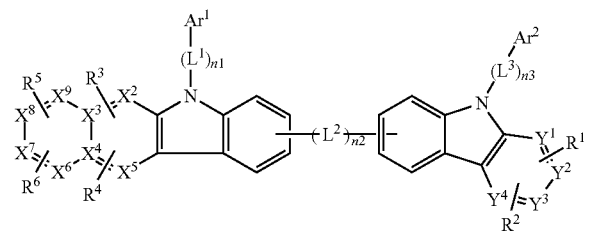

wherein, in Chemical Formula 5, $X^2$ and $X^5$ to $X^9$ are each independently CR', or N, $X^3$ and $X^4$ are C, provided that at least one of $X^2$, $X^5$, and $X^6$ to $X^9$ is N, $Y^1$ to $Y^4$ are each independently CR' or N, $R^1$ to $R^6$ and R' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the $R^1$ and $R^2$ are linked to each other to form a fused ring, $L^1$ to $L^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, $Ar^1$ is a substituted or unsubstituted C6 to C30 aryl group, or a substituted or unsubstituted C2 to C30 heteroaryl group having electron characteristics, and $Ar^2$ is a substituted or unsubstituted C6 to C30 aryl group.

11. The compound for an organic optoelectronic device of claim 1, wherein the compound for an organic optoelectronic device is represented by Chemical Formula 6:

Chemical Formula 6

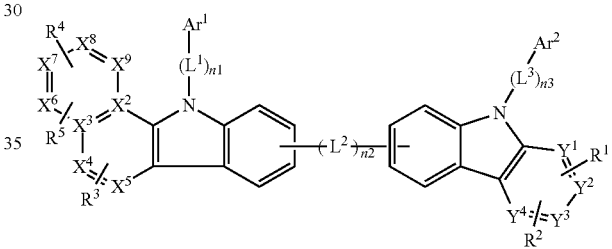

wherein, in Chemical Formula 6, $X^4$ to $X^9$ are each independently CR', or N, $X^2$ and $X^3$ are C, provided that at least one of $X^4$, $X^5$, and $X^6$ to $X^9$ is N, $Y^1$ to $Y^4$ are each independently, CR' or N, $R^1$ to $R^5$ and R' are each independently, hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, or the R$^1$ and R$^2$ are linked to each other to form a fused ring, L$^1$ to L$^3$ are each independently a single bond, a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, n1 to n3 are each independently integers ranging from 0 to 3, Ar$^1$ is a substituted or unsubstituted C6 to C30 aryl group, or a substituted or unsubstituted C2 to C30 heteroaryl group having electron characteristics, and Ar$^2$ is a substituted or unsubstituted C6 to C30 aryl group.

12. The compound for an organic optoelectronic device of claim 1, wherein Ar$^1$ is a substituted or unsubstituted C6 to C30 aryl group.

13. The compound for an organic optoelectronic device of claim 1, wherein n2 is 0.

14. The compound for an organic optoelectronic device of claim 1, wherein the Ar$^1$ and Ar$^2$ are independently selected from Chemical Formulae W-1 to W-8:

W-1

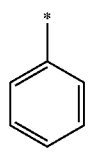

W-2

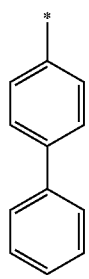

W-3

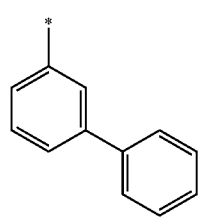

W-4

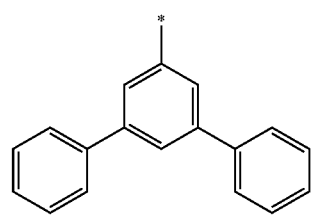

W-5

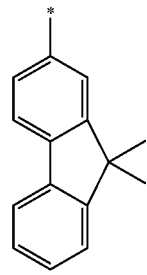

W-6

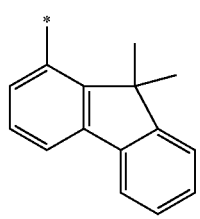

W-7

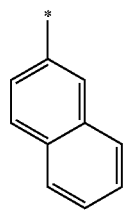

W-8

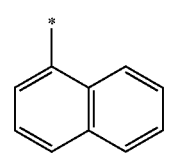

15. The compound for an organic optoelectronic device of claim 1, wherein the substituted or unsubstituted C2 to C30 heteroaryl group having electron characteristics is one of Chemical Formulae X-1 to X-22:

X-1

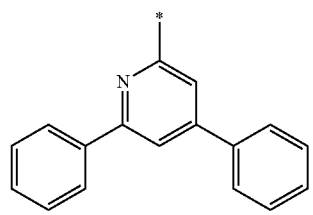

X-2

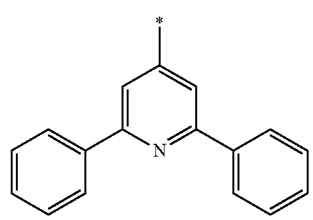

X-3
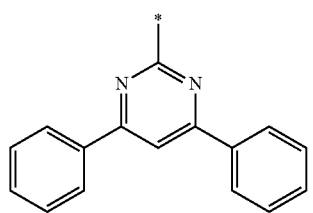
X-4
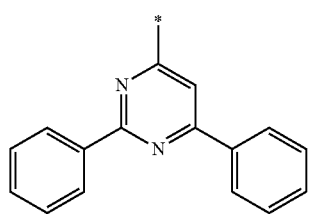
X-5
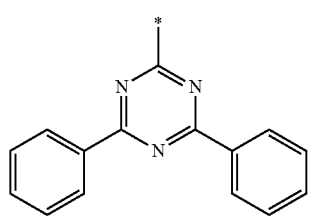
X-6
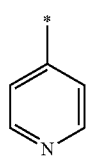
X-7
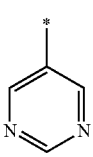
X-8
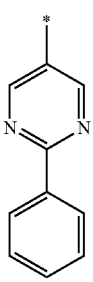
X-9
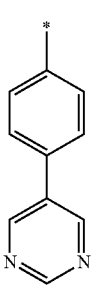
X-10
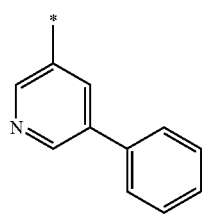
X-11
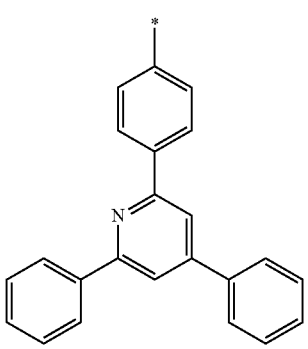
X-12
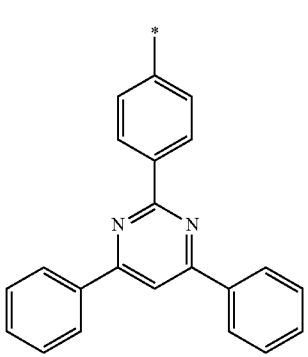
X-13
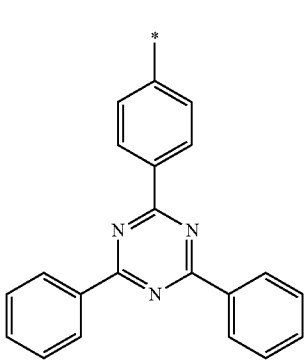
X-14
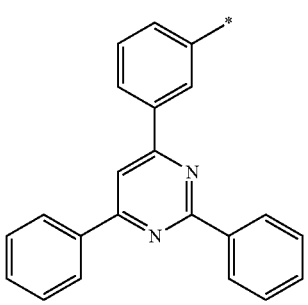

X-15
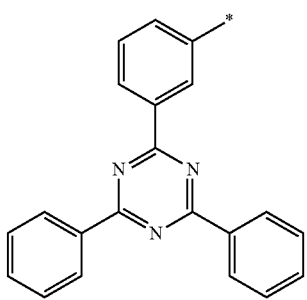
X-16
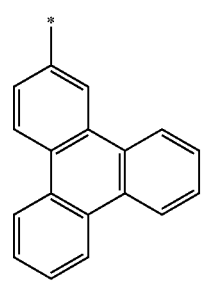
X-17
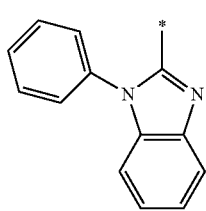
X-18
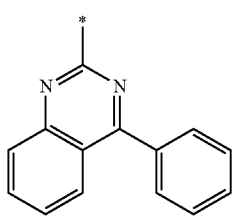
X-19
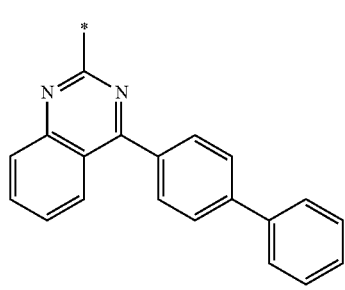
X-20
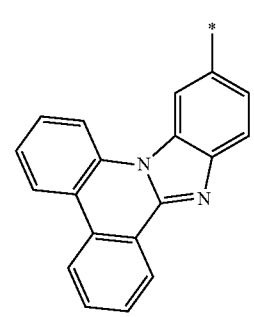
X-21
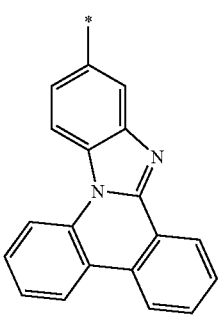
X-22
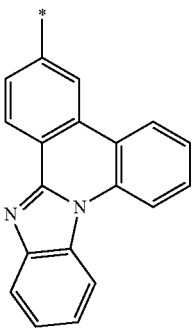
16. The compound for an organic optoelectronic device of claim 1, wherein the compound for an organic optoelectronic device is one of Chemical Formulae A-1 to A-168:
A-1
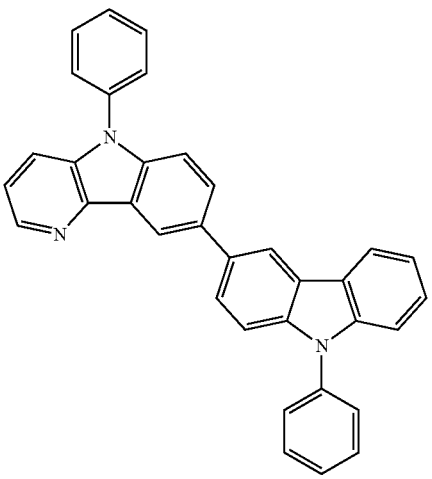

A-2
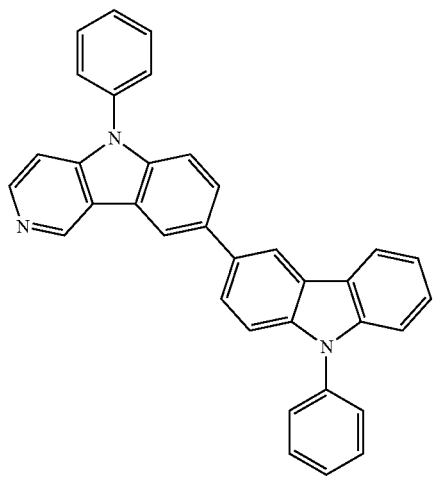
A-3
A-4
A-5
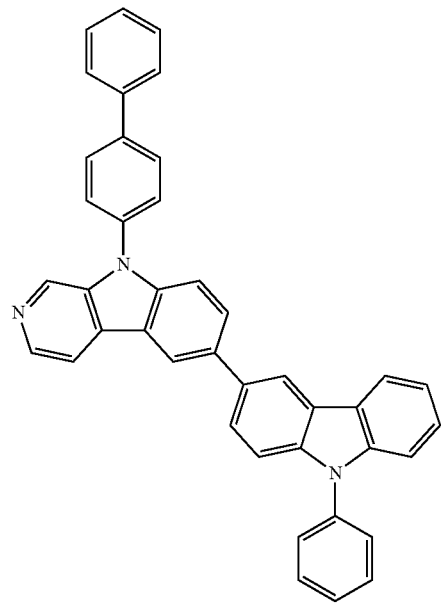
A-6

A-7
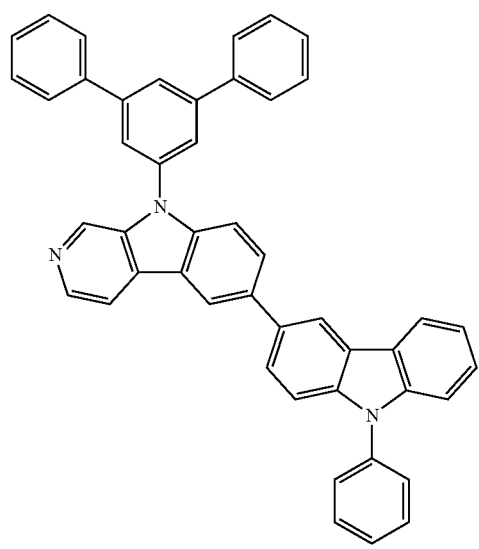
A-8
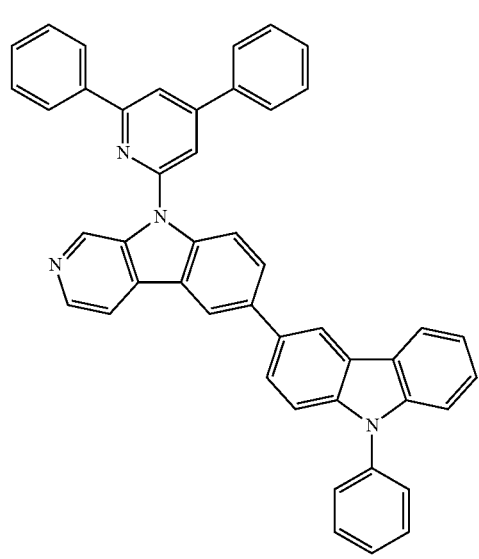
A-9
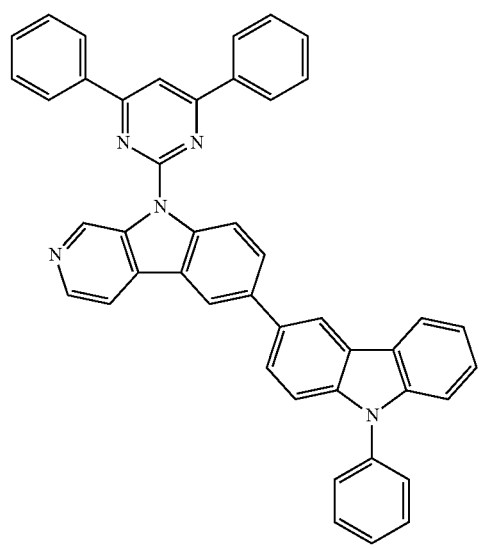
A-10
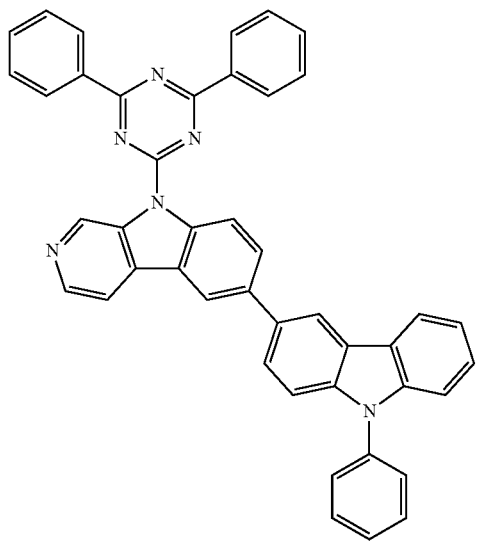
A-11

A-12
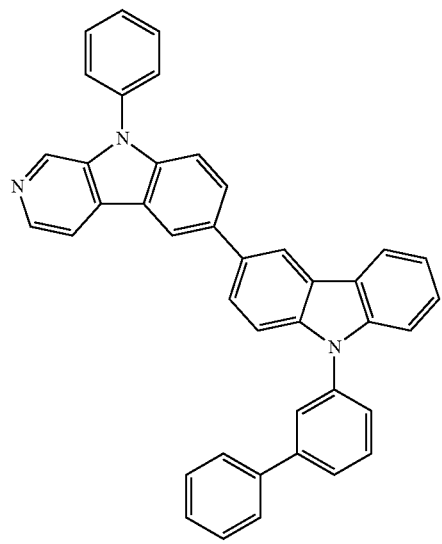
A-13
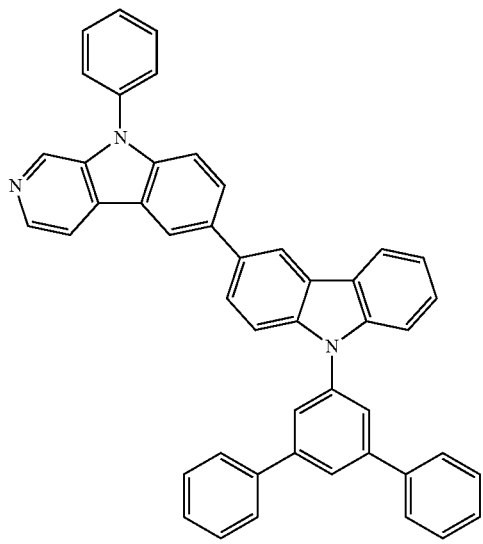
A-18
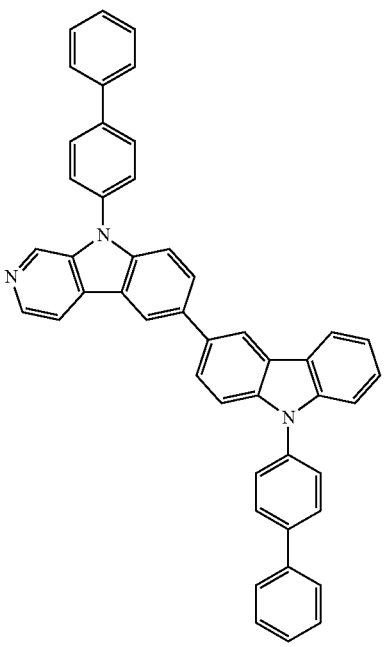
A-19
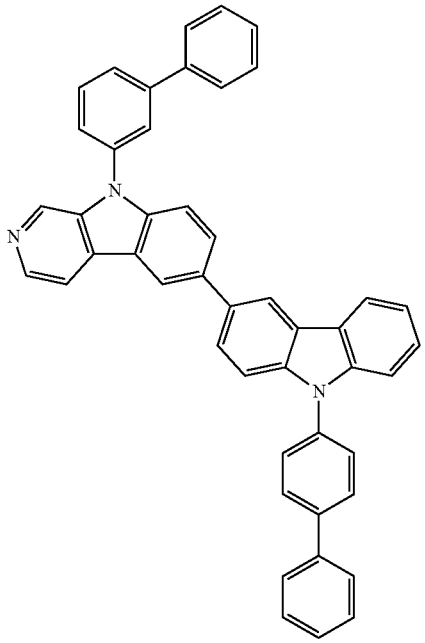

-continued
A-20
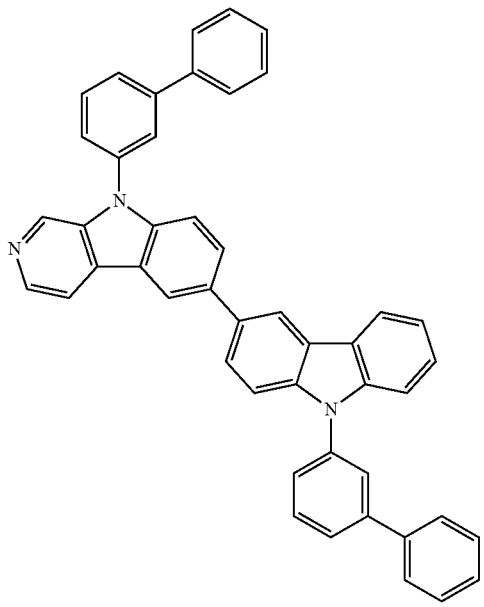
A-22
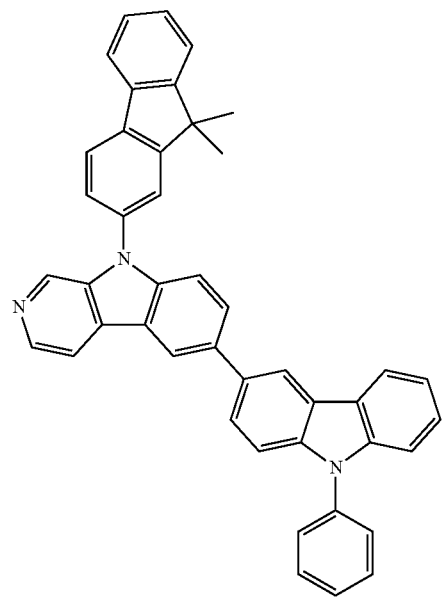
A-21
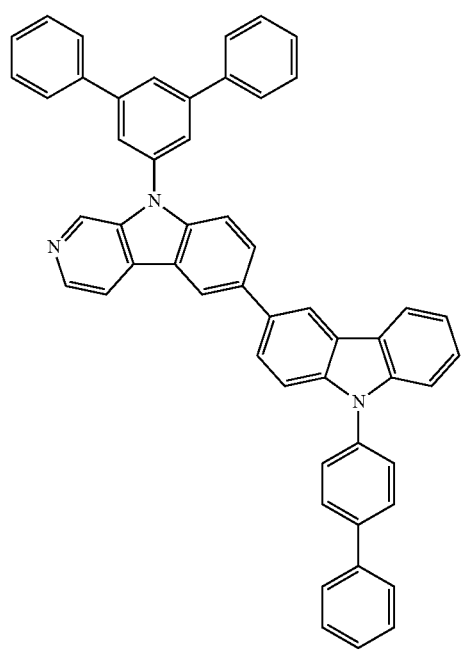
A-23
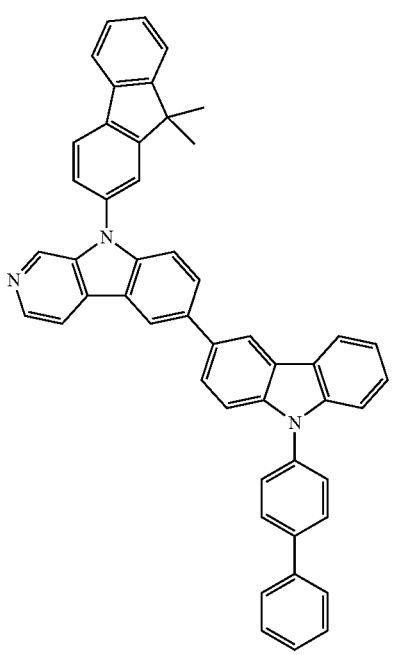

-continued
A-24
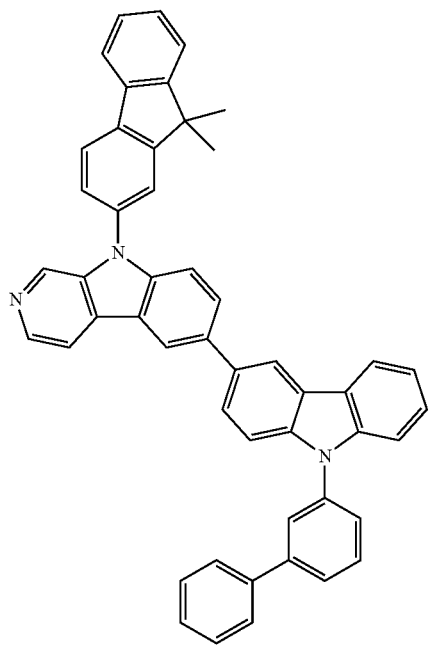
A-25
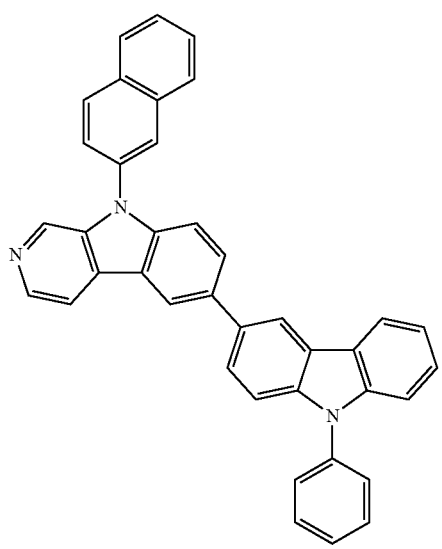
A-26
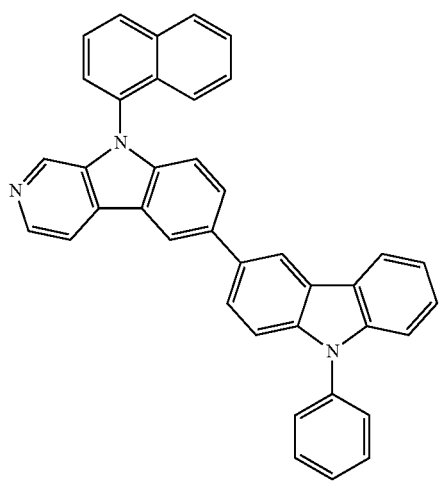
A-27
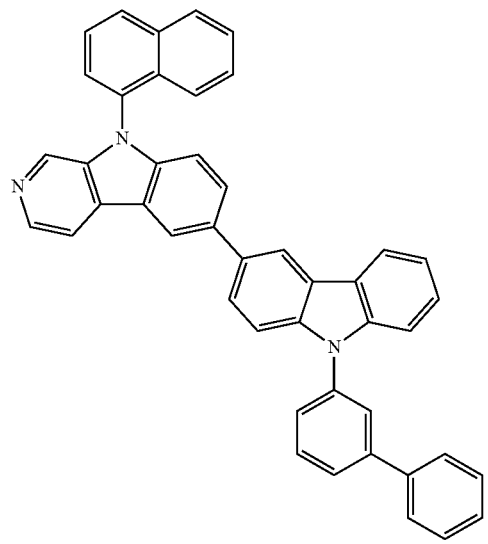
A-28
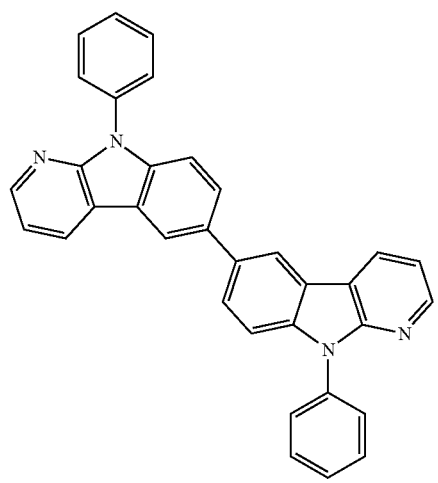
A-29
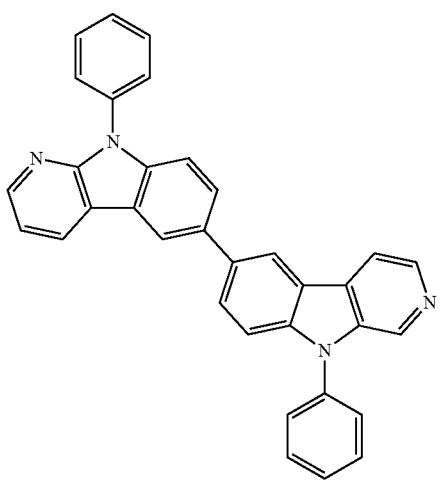

-continued
A-30
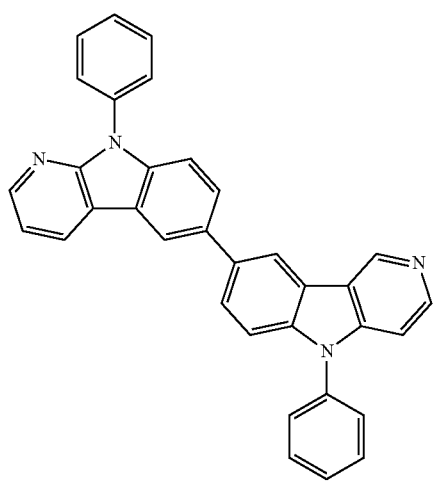
A-31
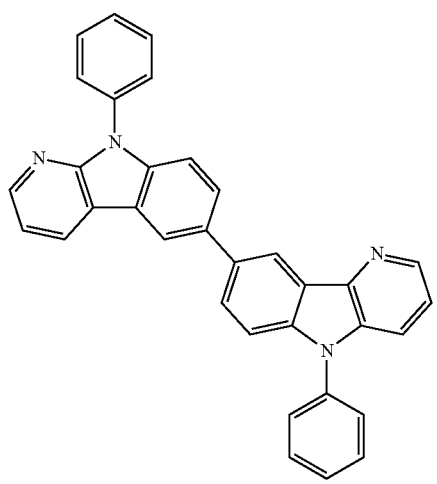
A-32
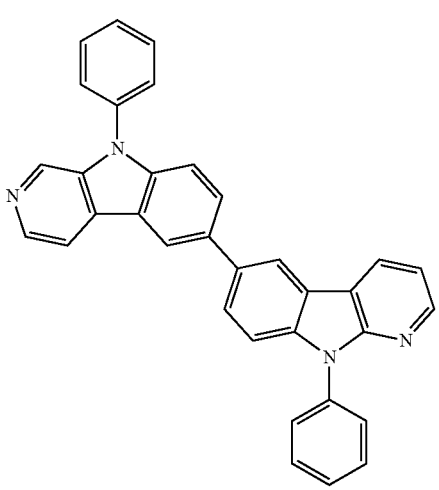
-continued
A-33
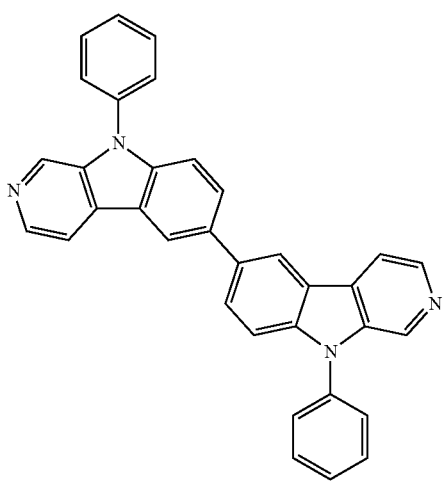
A-34
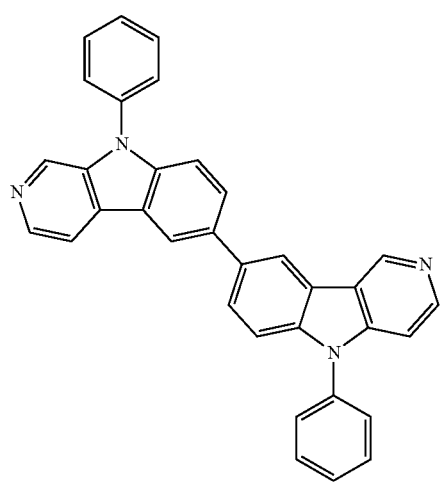
A-35
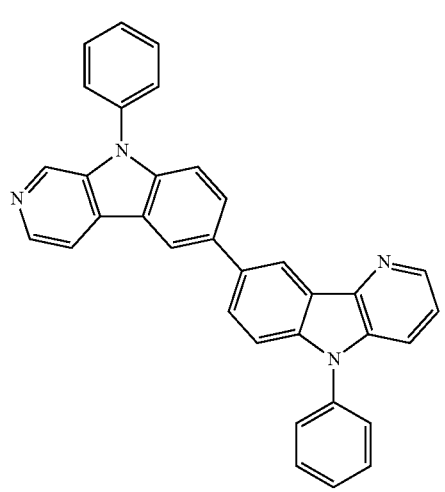

-continued
A-36
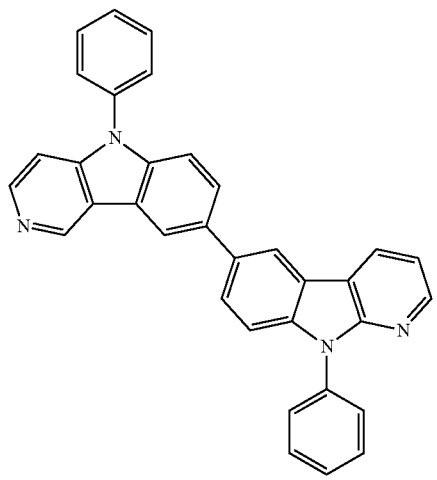
A-37
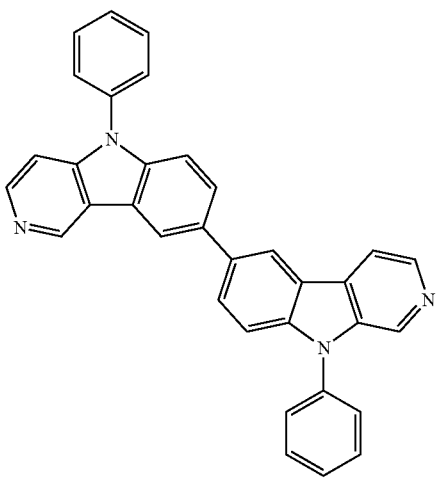
A-38
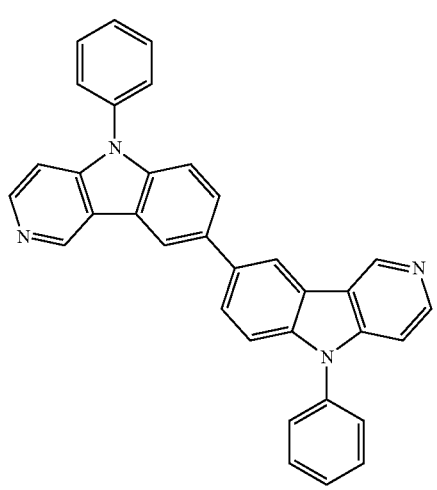
-continued
A-39
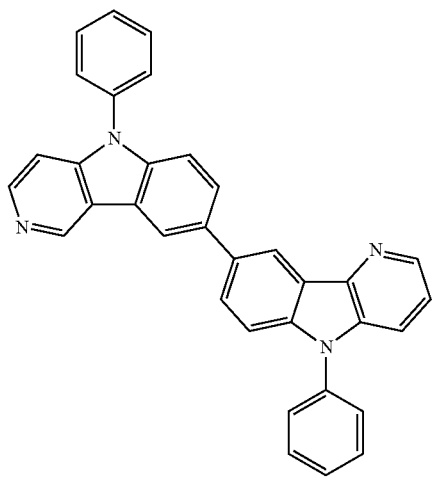
A-40
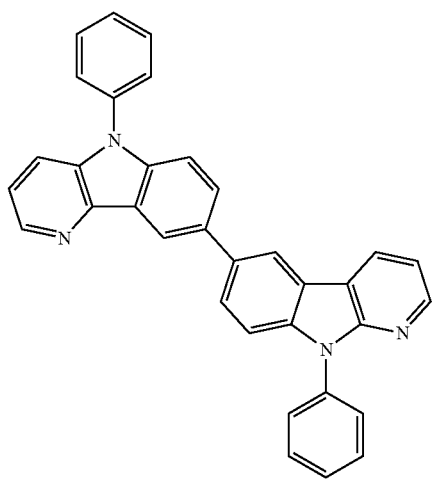
A-41
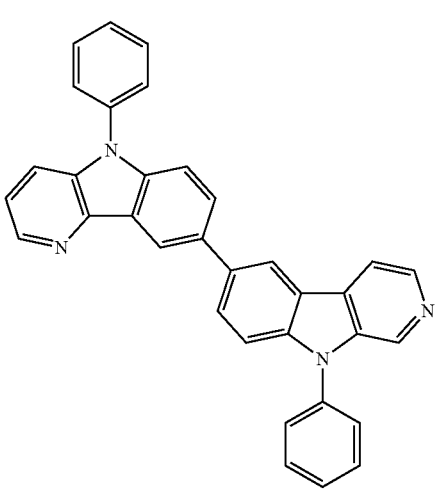

A-42
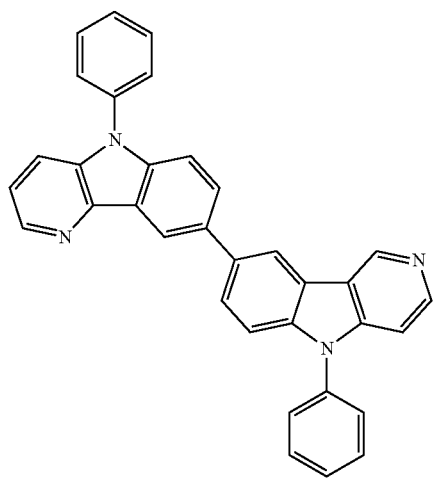
A-43
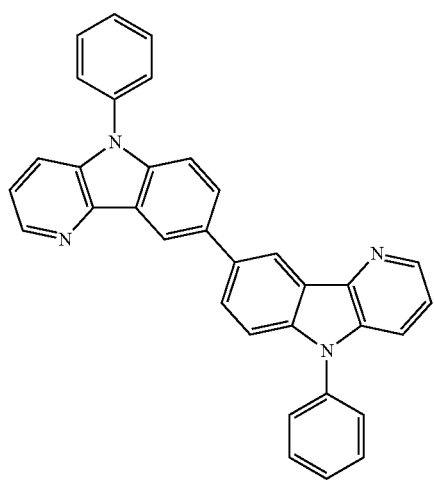
A-44
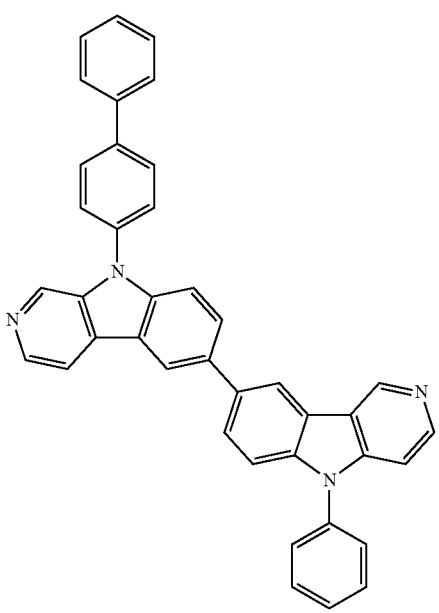
A-45
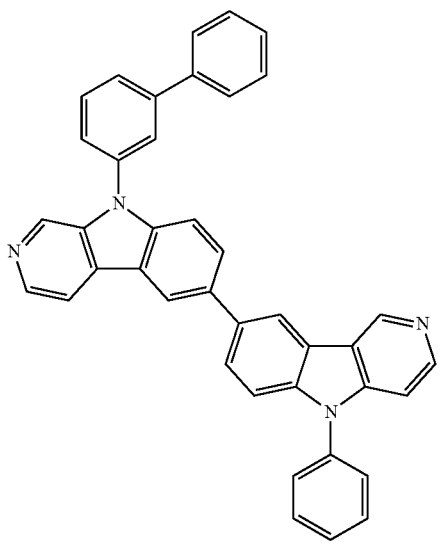
A-46
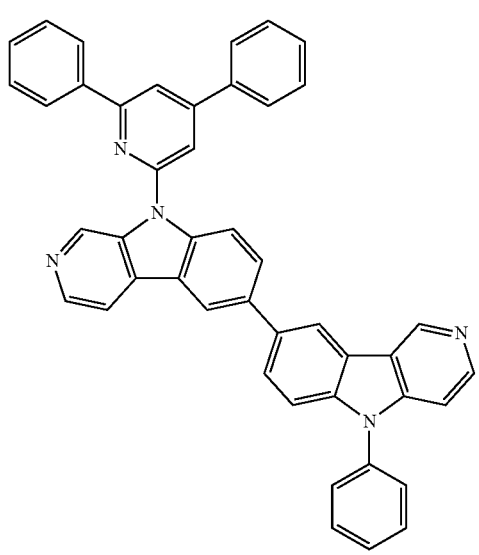
A-47
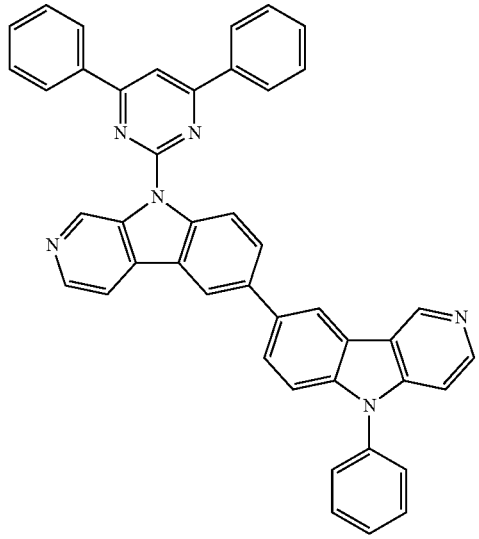

A-48
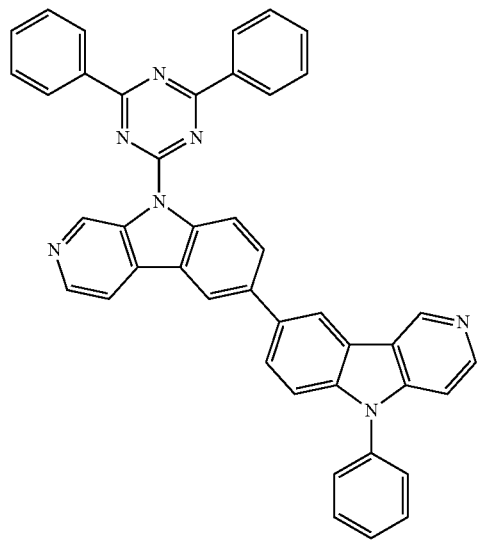
A-49
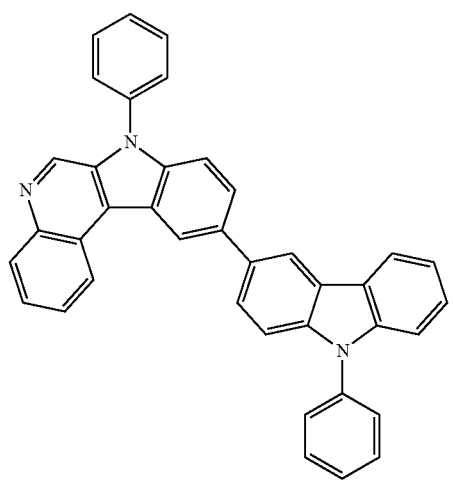
A-50
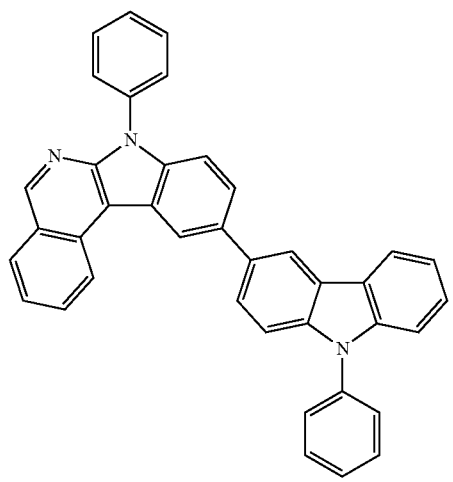
A-51
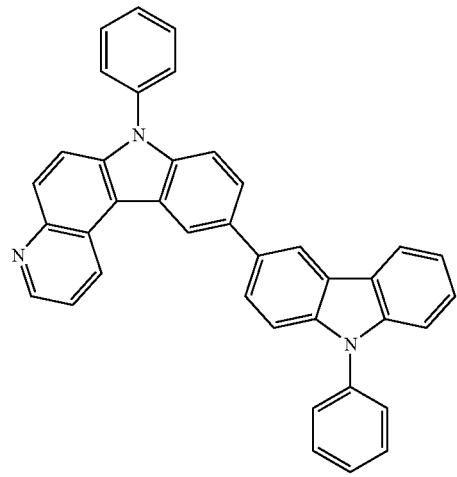
A-52
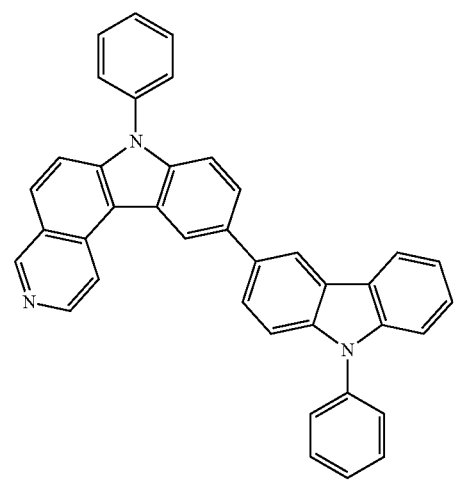
A-53
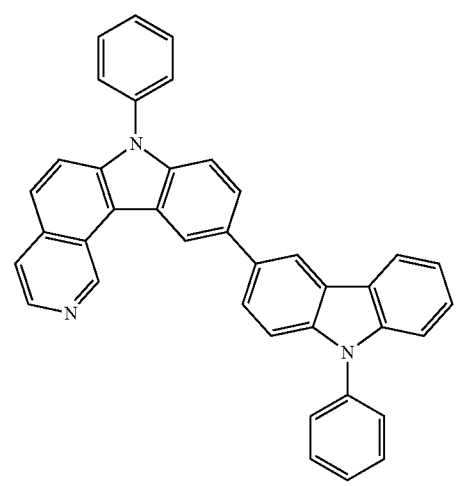

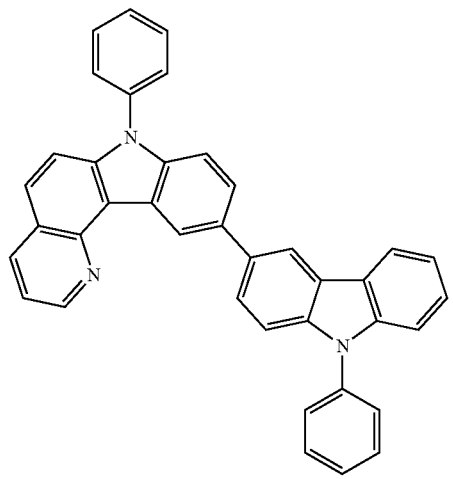
A-54
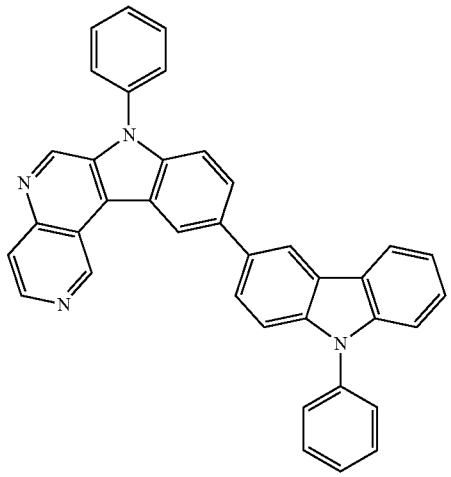
A-57
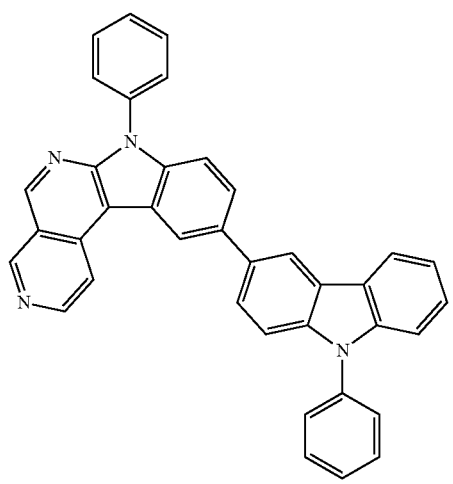
A-55
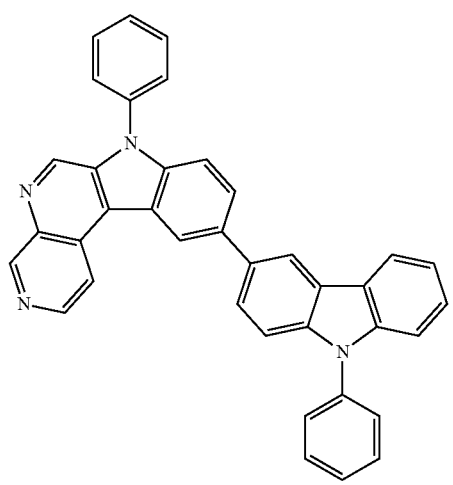
A-56
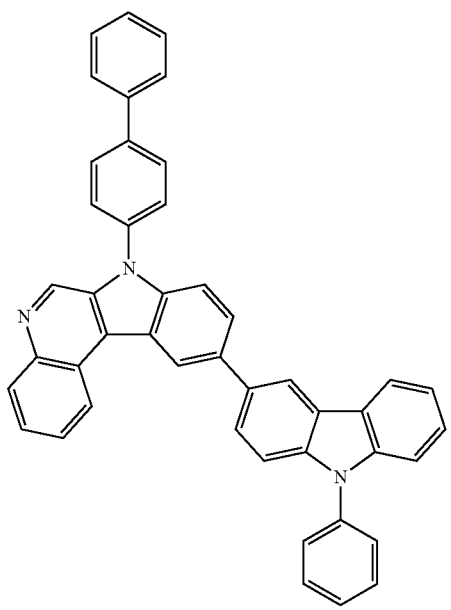
A-58

A-59
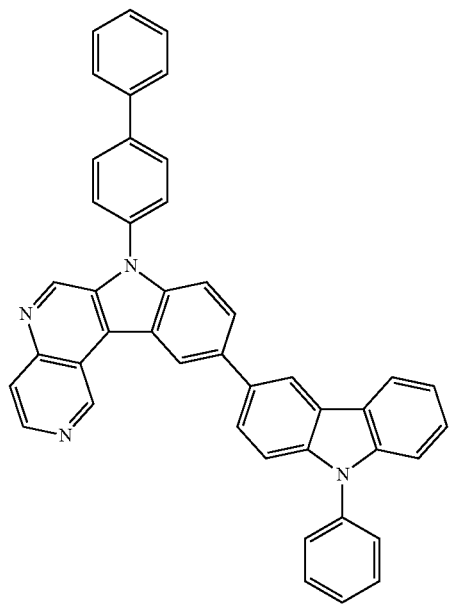
A-60
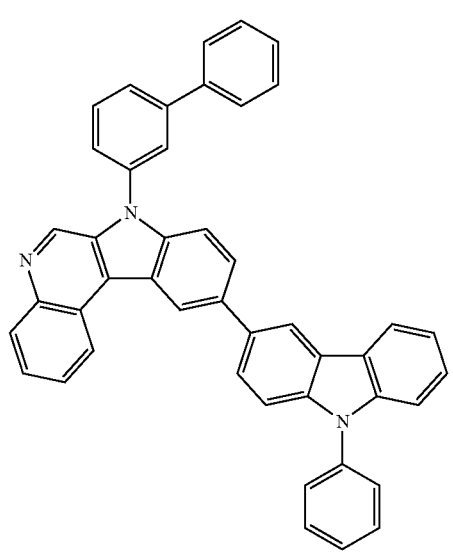
A-61
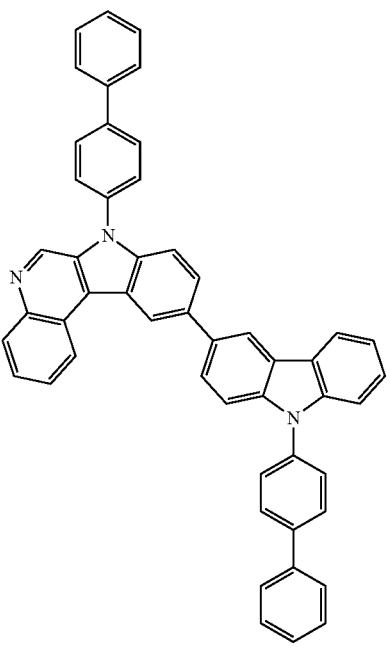
A-62
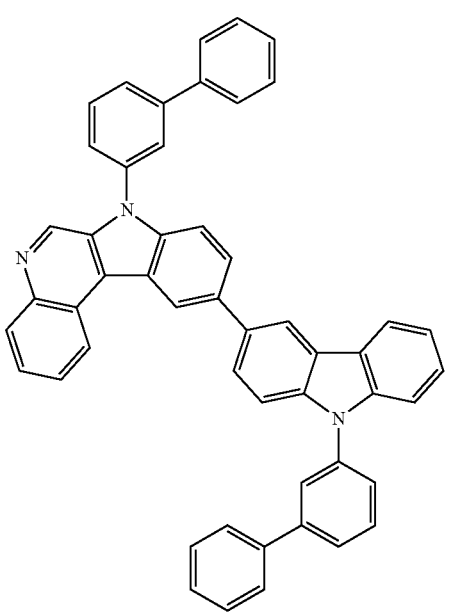

-continued
A-63
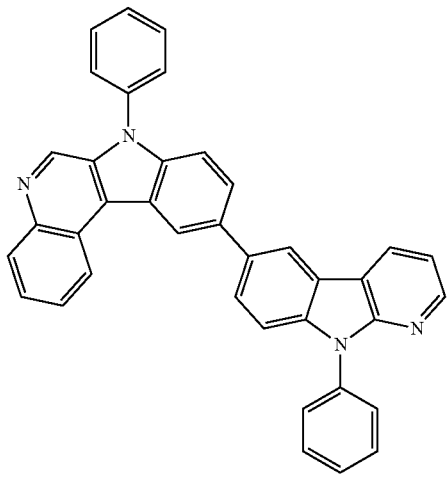
A-64
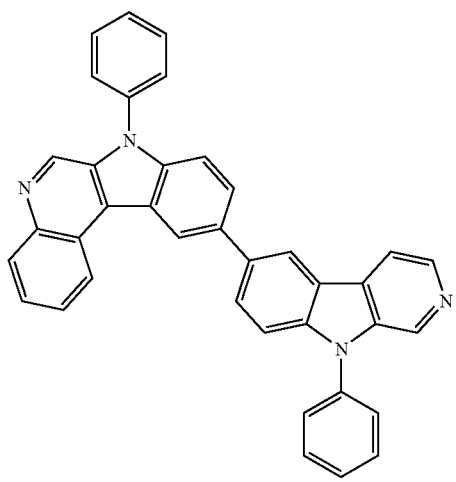
A-65
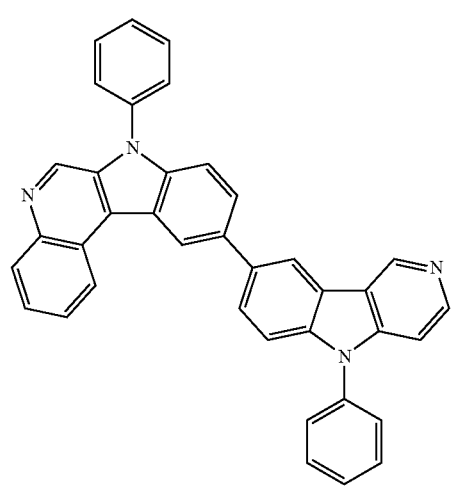
-continued
A-66
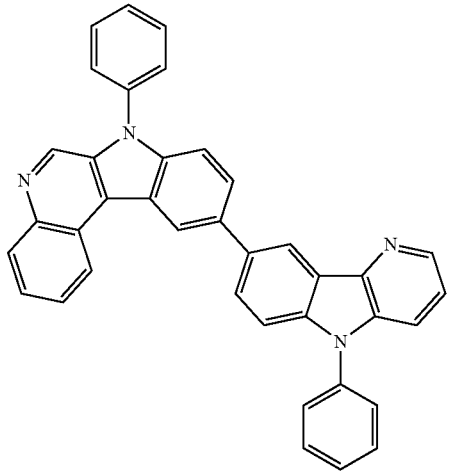
A-67
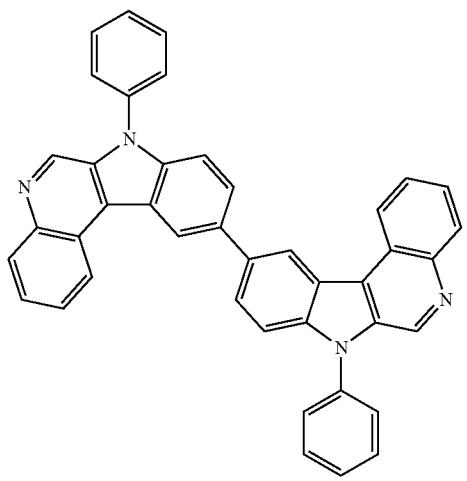
A-68
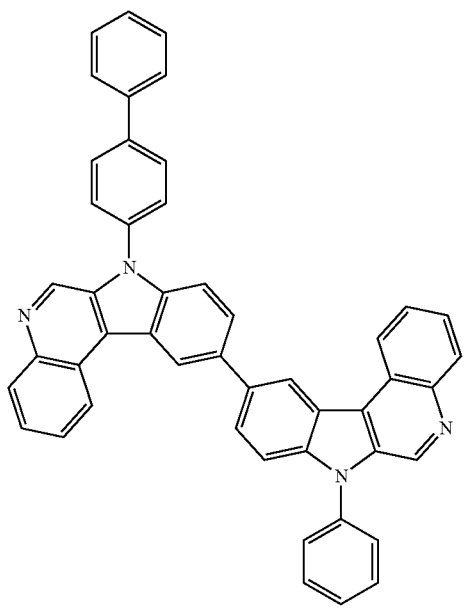

A-69
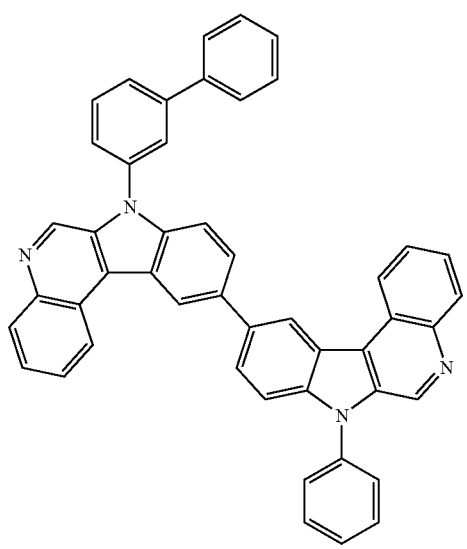
A-70
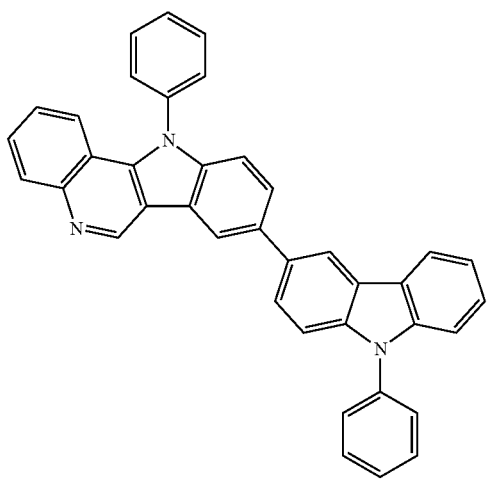
A-71
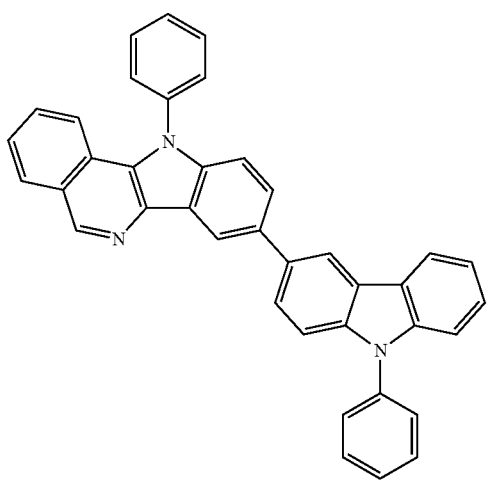
A-72
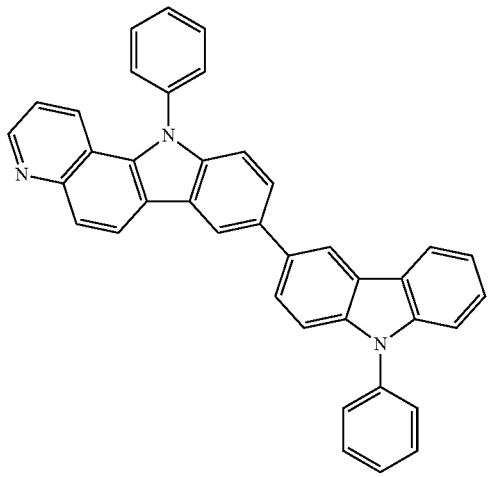
A-73
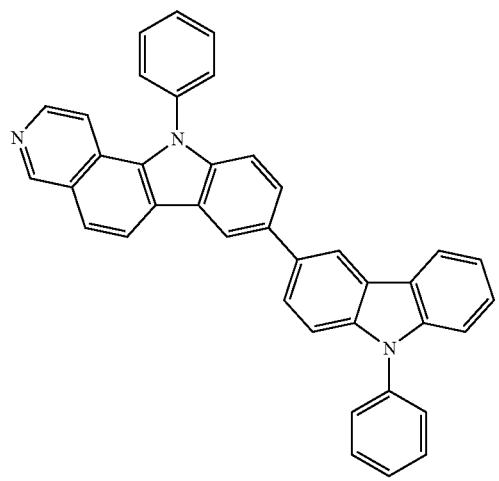
A-74
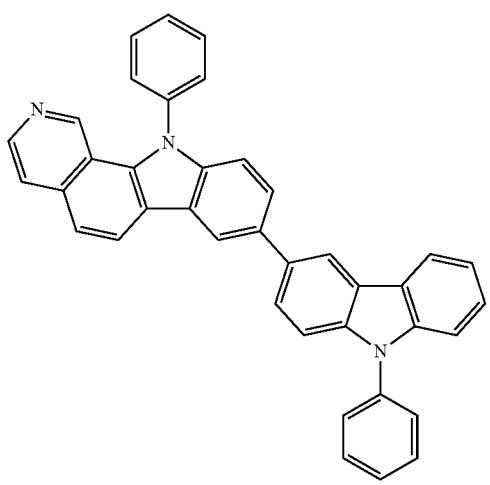

A-75
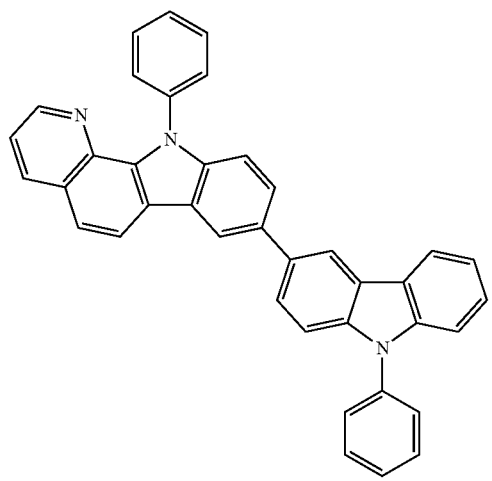
A-78
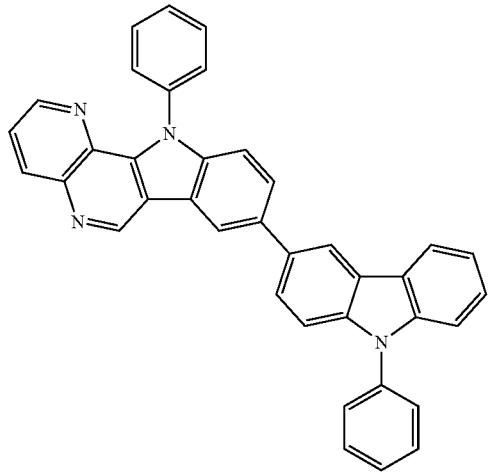
A-76
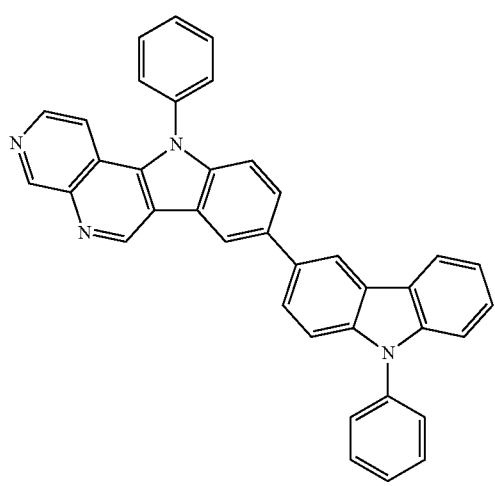
A-79
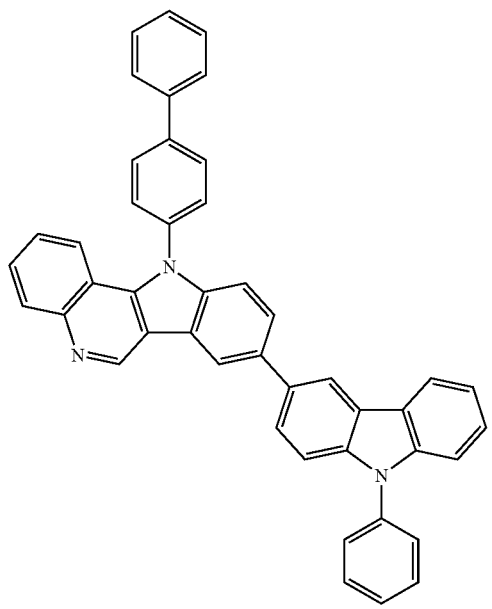
A-77
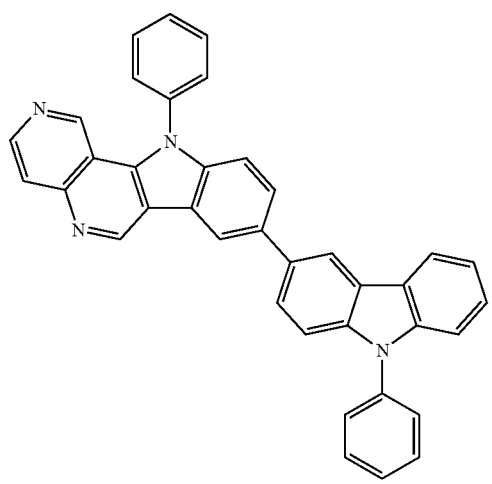

A-80
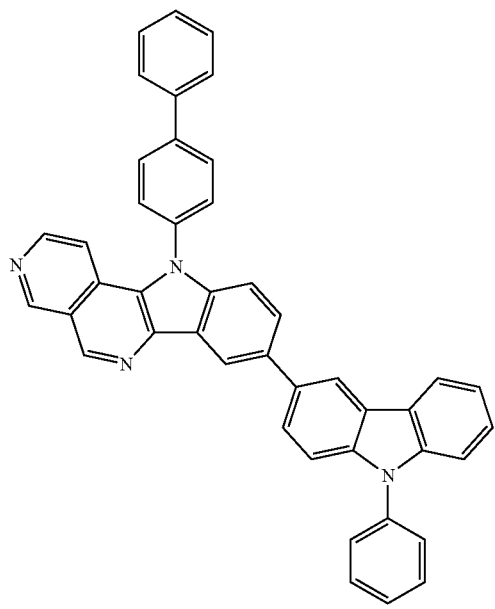
A-81
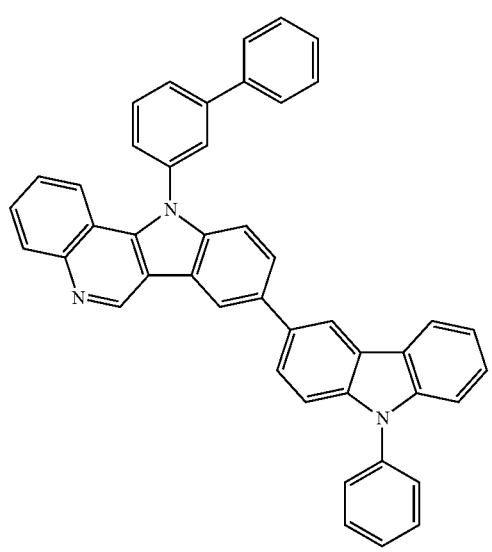
A-82
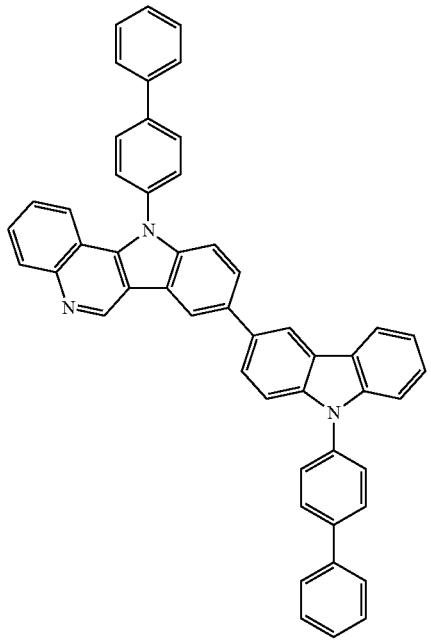
A-83
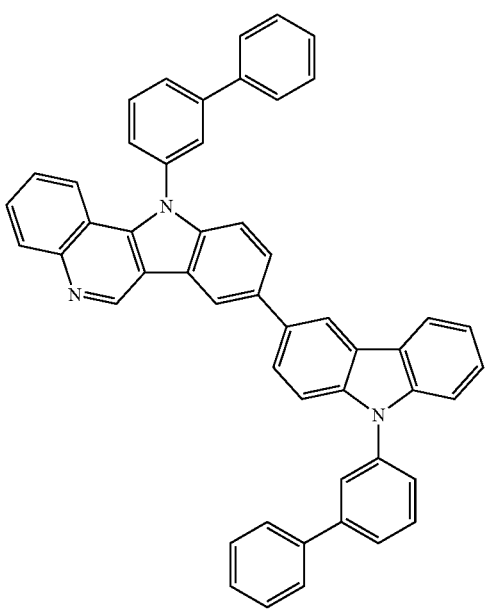

A-84
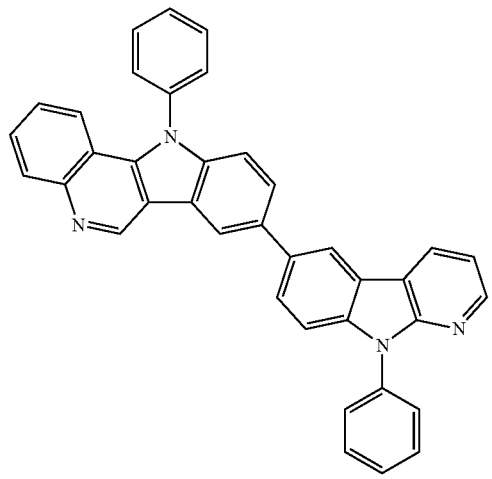
A-85
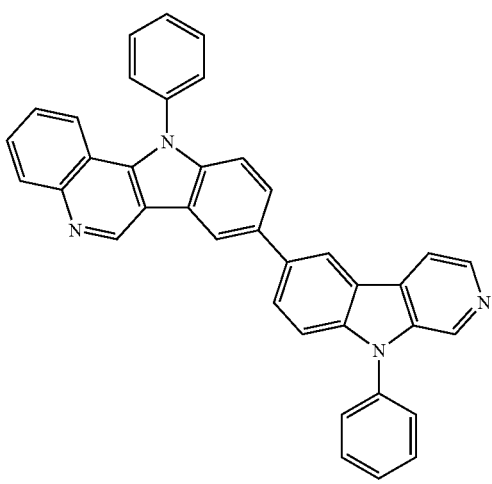
A-86
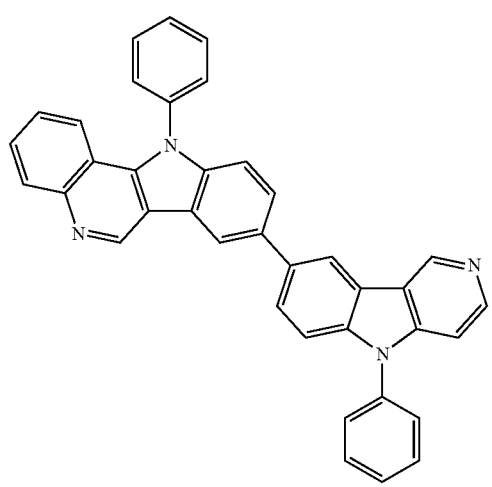
A-87
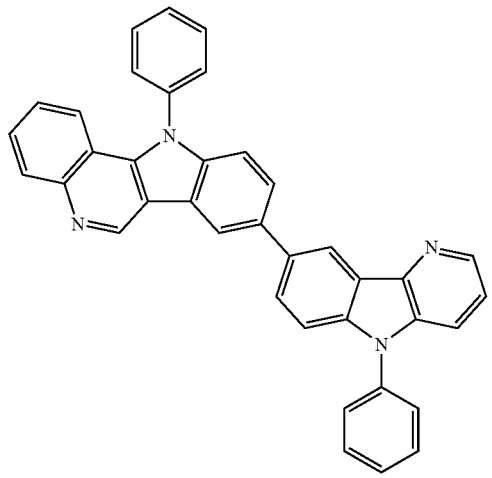
A-88
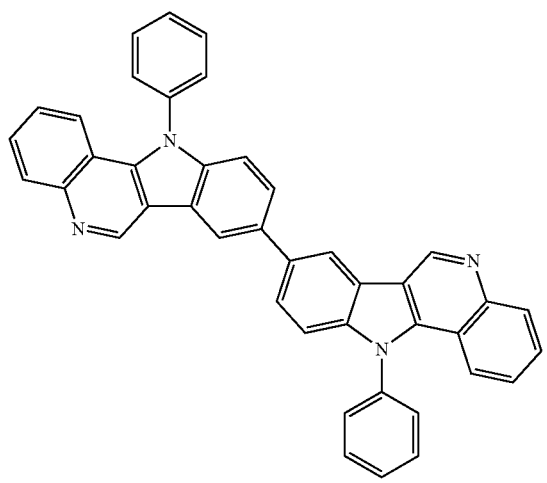
A-89
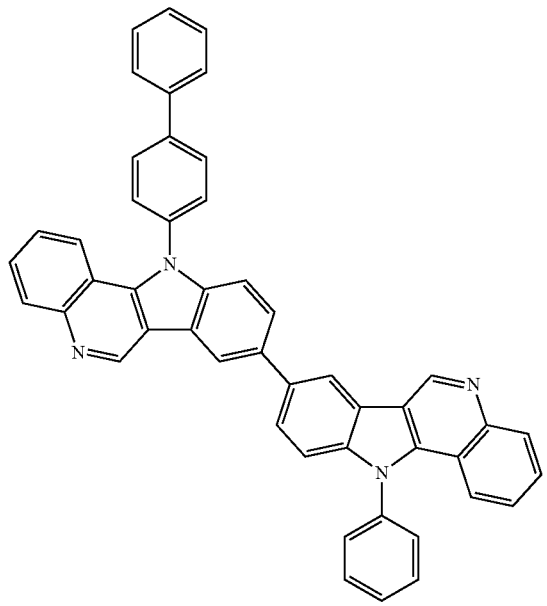

A-90
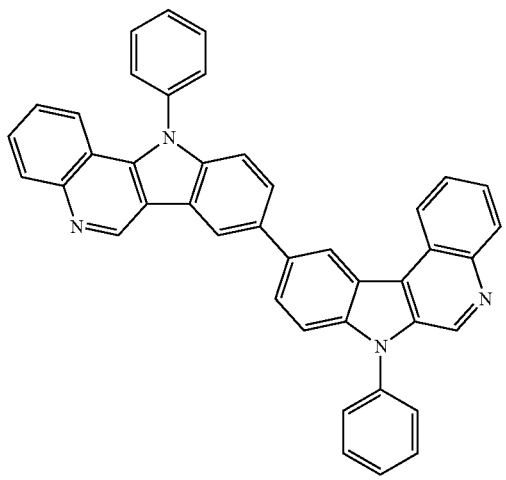
A-91
A-92
A-93
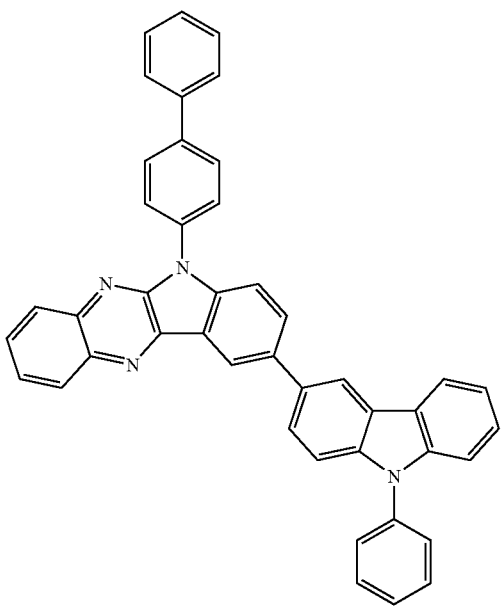
A-94
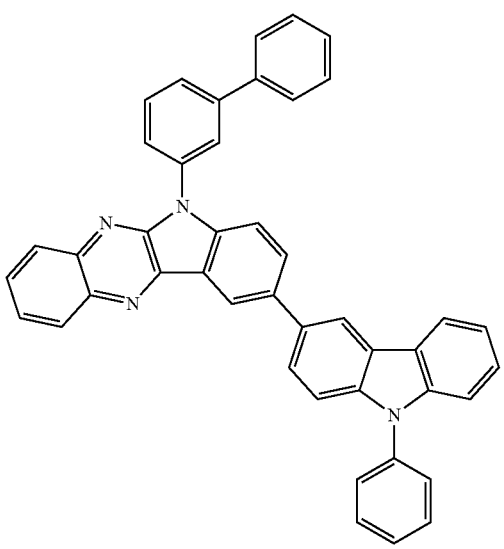

-continued
A-95
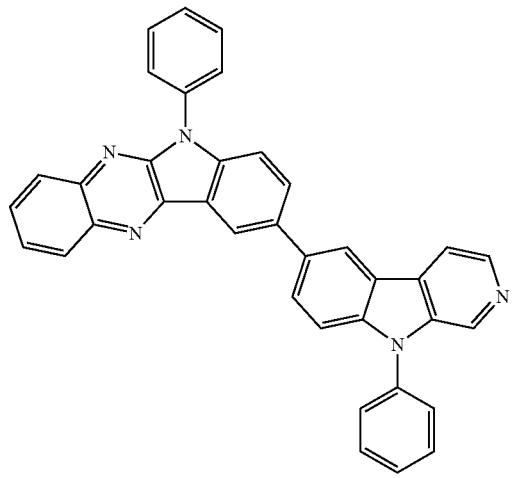
A-96
A-97
-continued
A-98
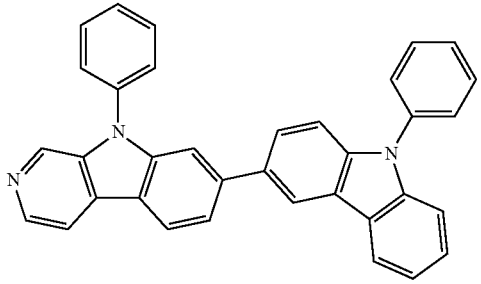
A-99
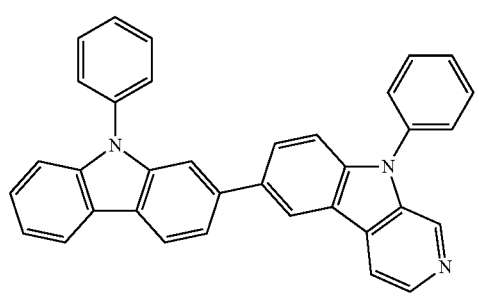
A-100
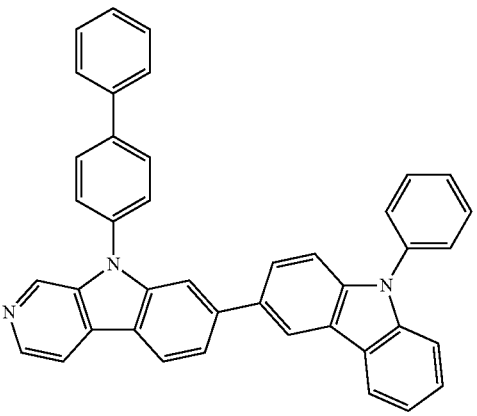
A-101
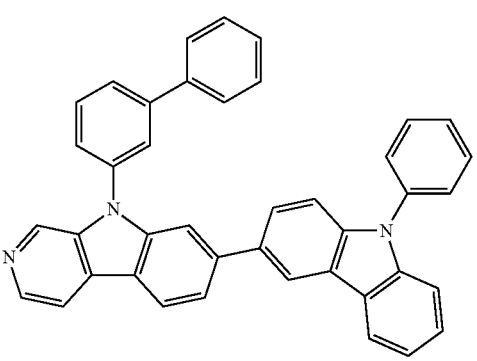

-continued
A-102
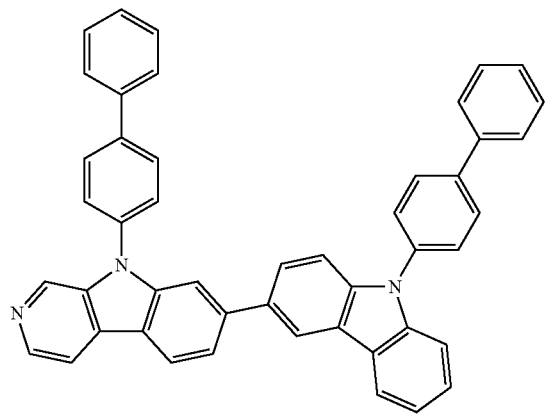
A-103
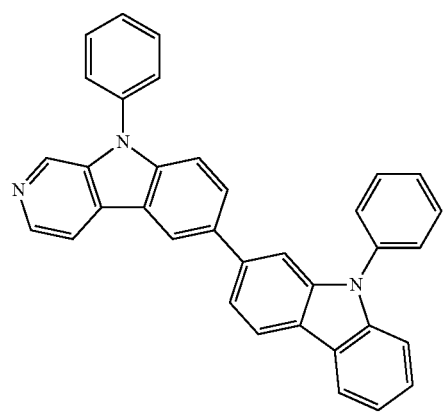
A-104
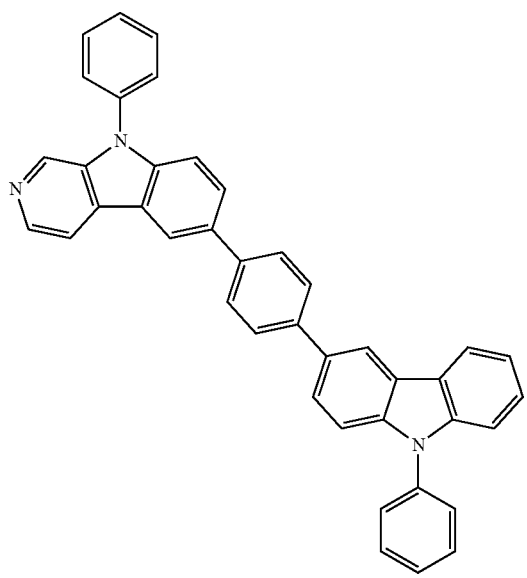
-continued
A-105
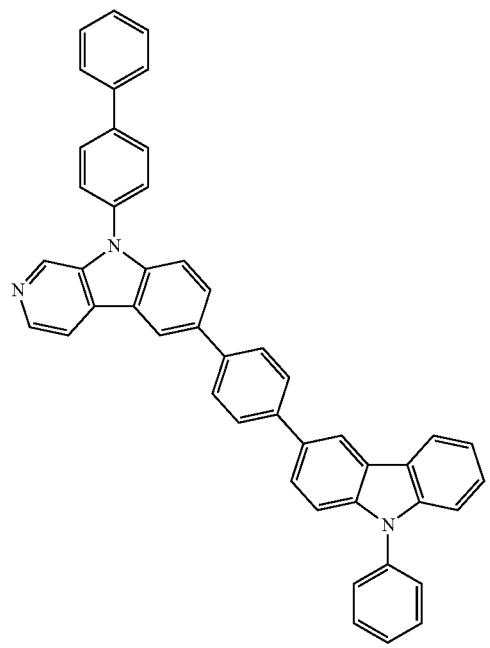
A-106
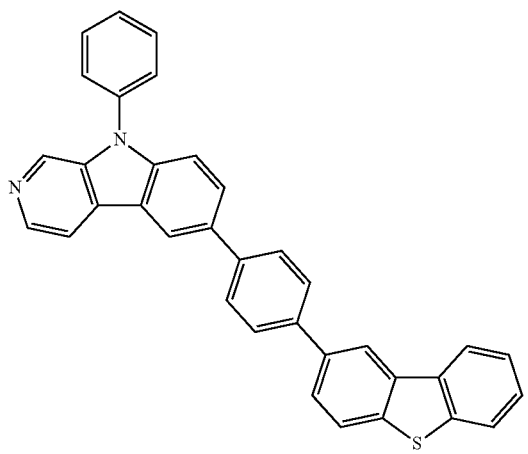

A-107
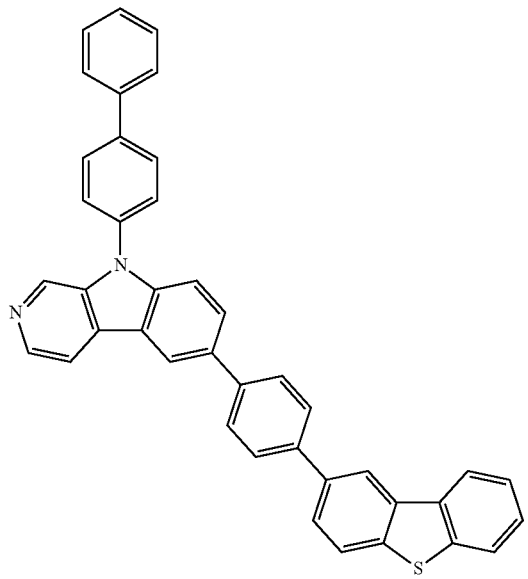
A-108
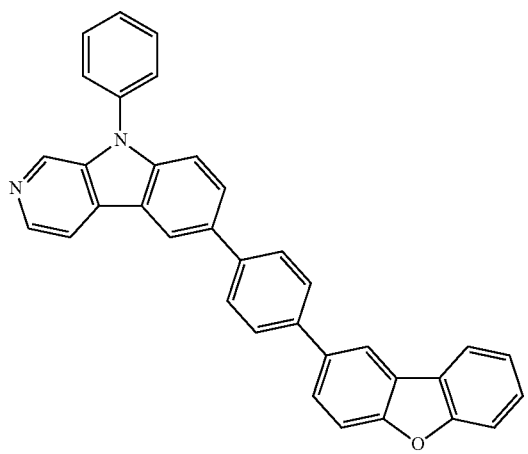
A-109
A-110
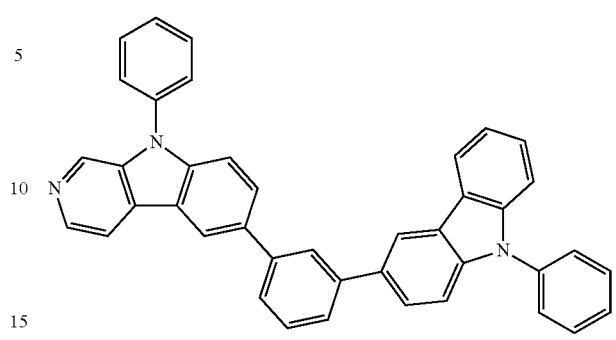
A-111
A-112
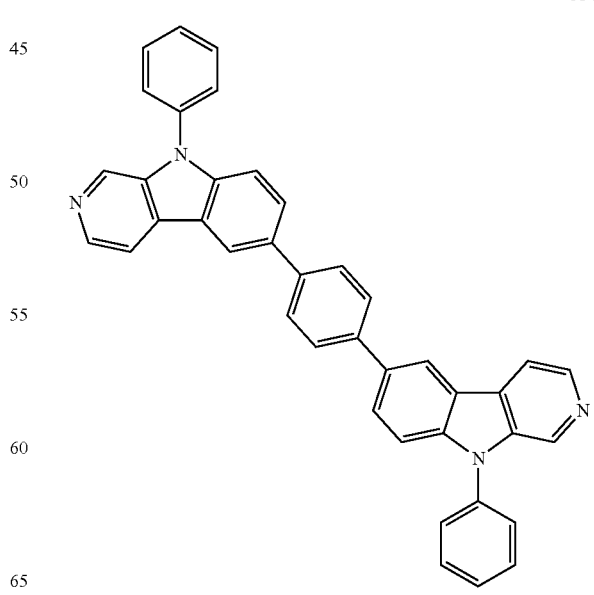

-continued
A-113
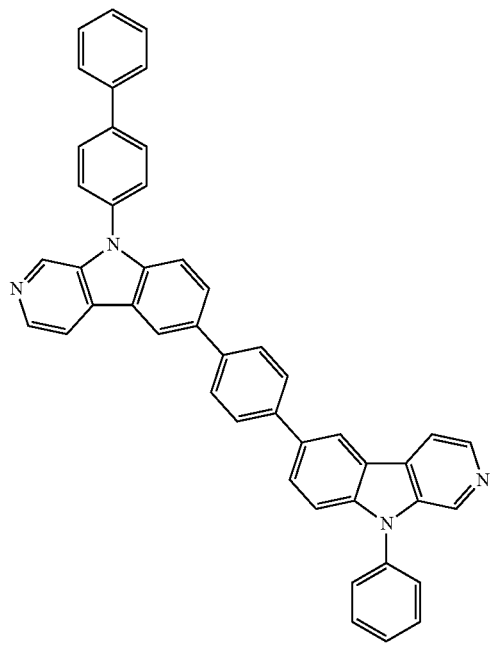
A-114
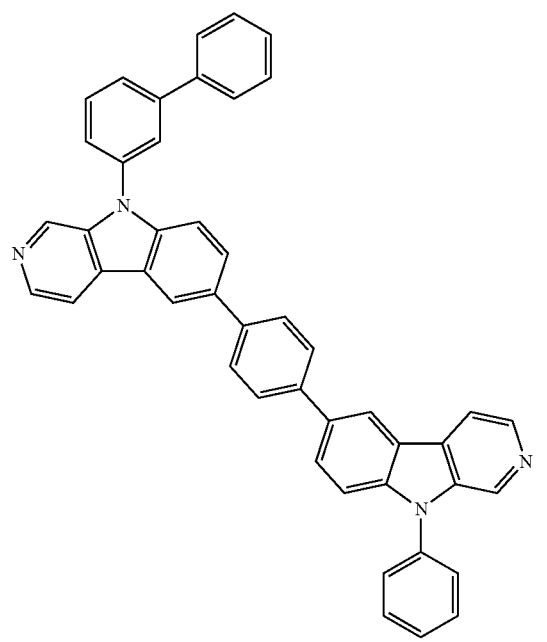
A-115
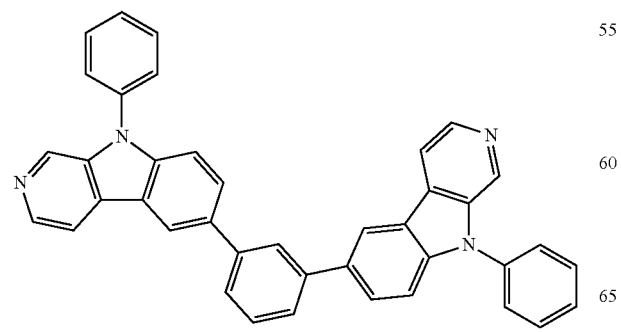
-continued
A-116
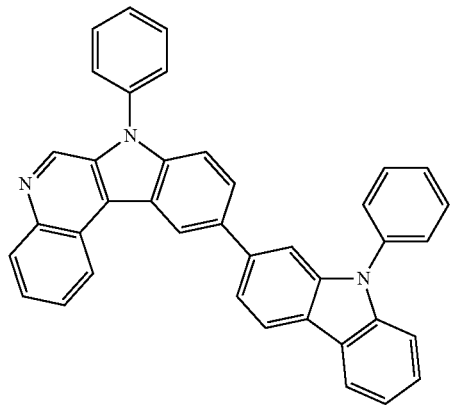
A-117
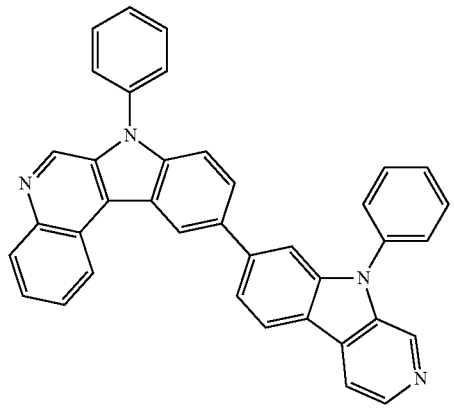
A-118
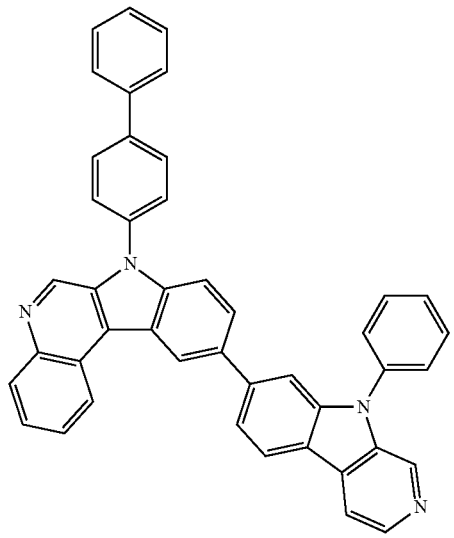

A-119
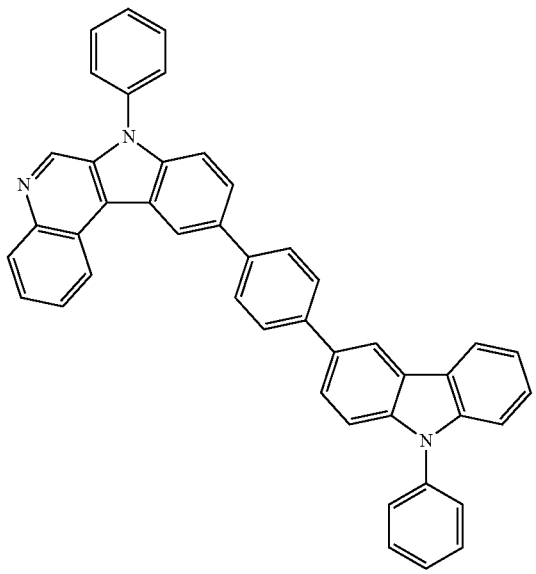
A-120
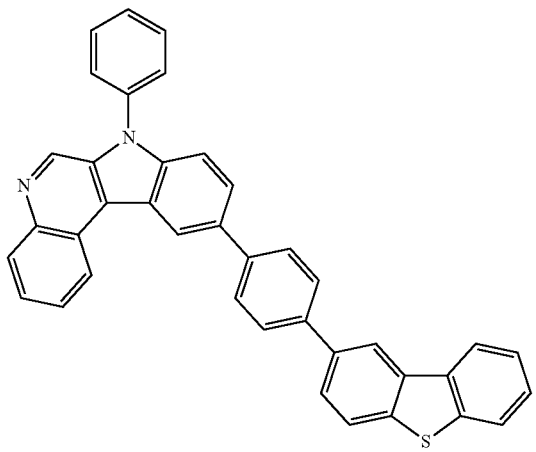
A-121
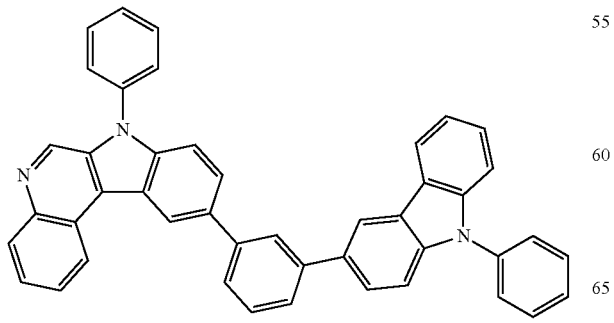
A-122
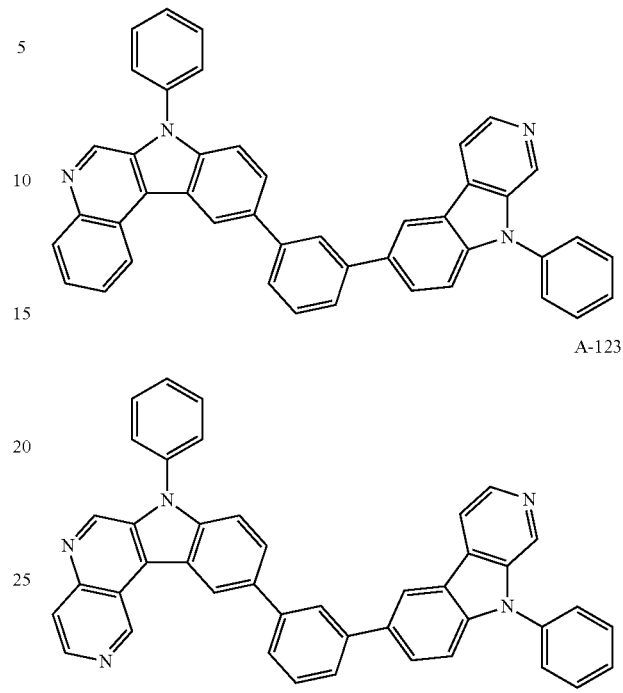
A-123
A-124
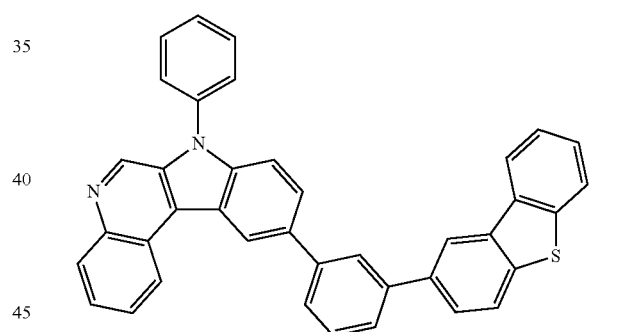
A-125
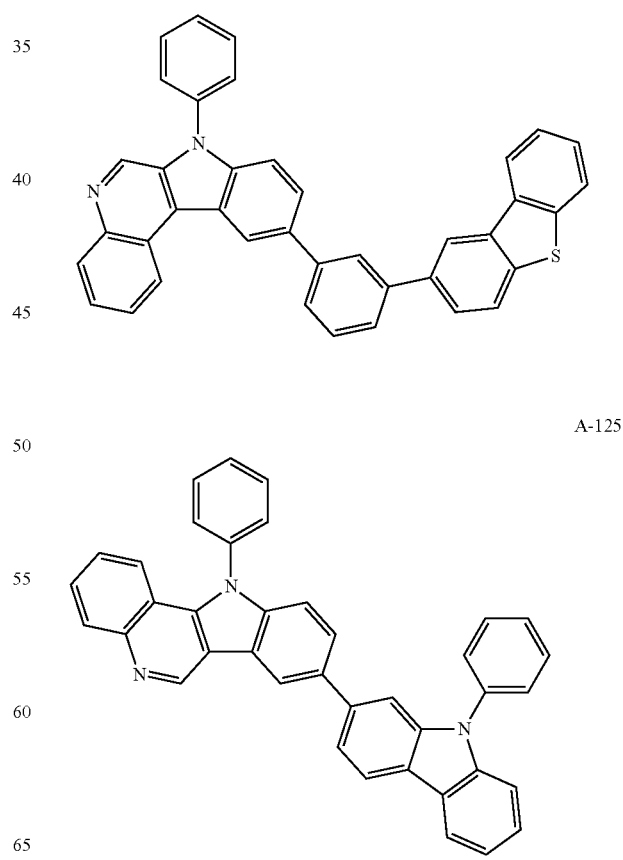

-continued
A-126
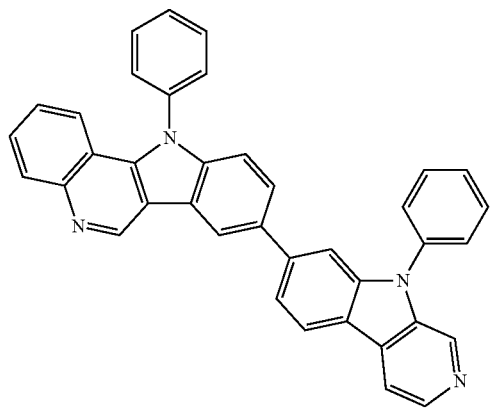
A-127
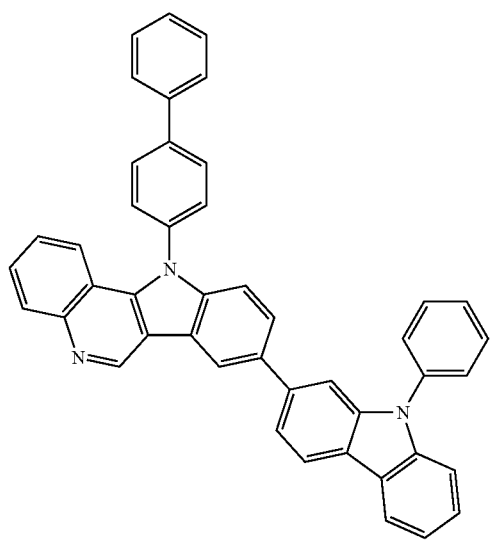
A-128
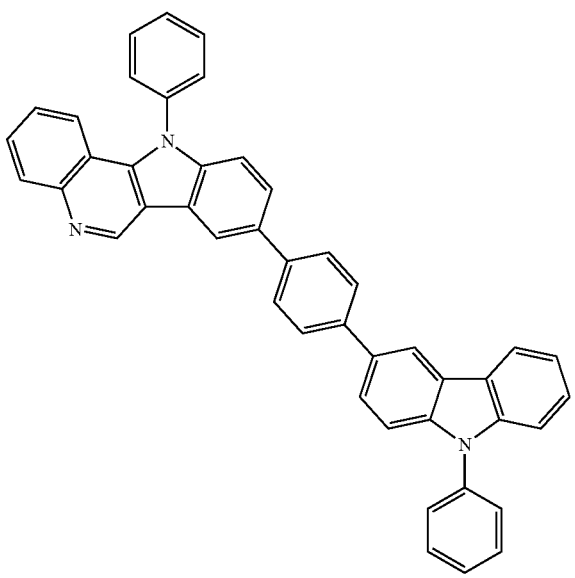
-continued
A-129
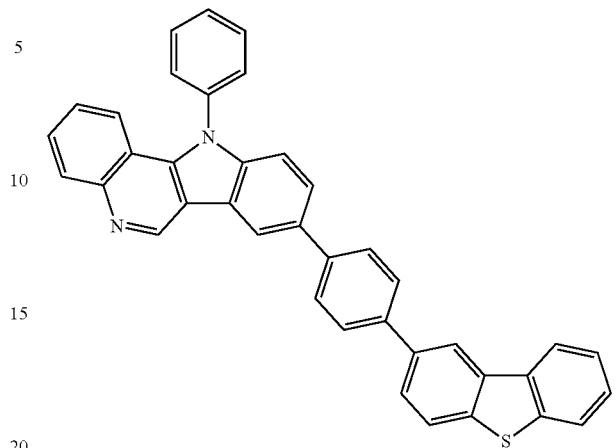
A-130
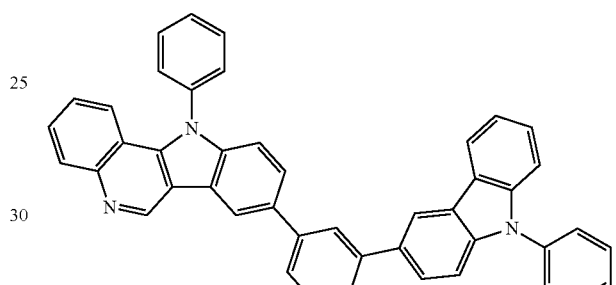
A-131
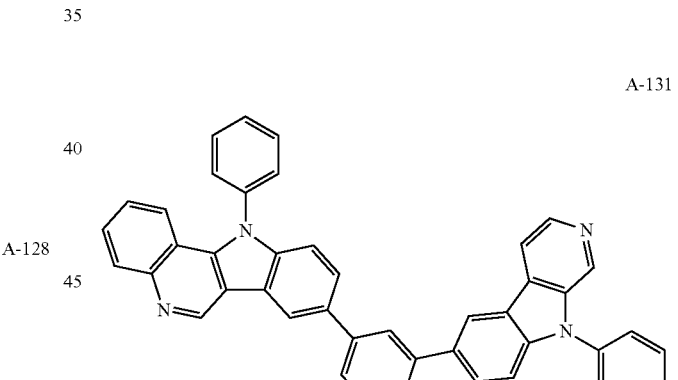
A-132
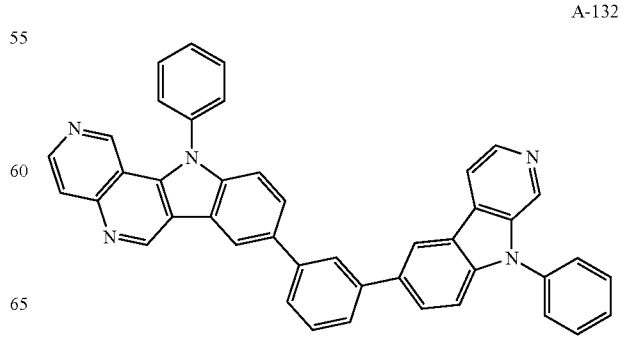

-continued
A-133
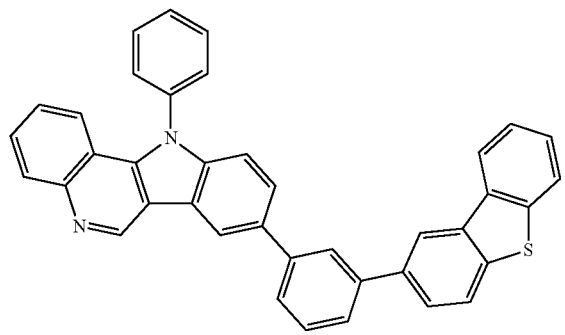
A-134
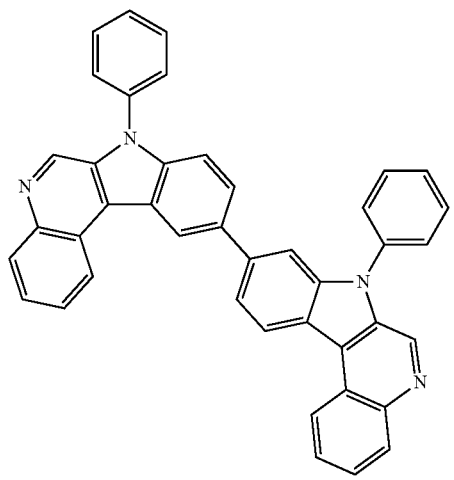
A-135
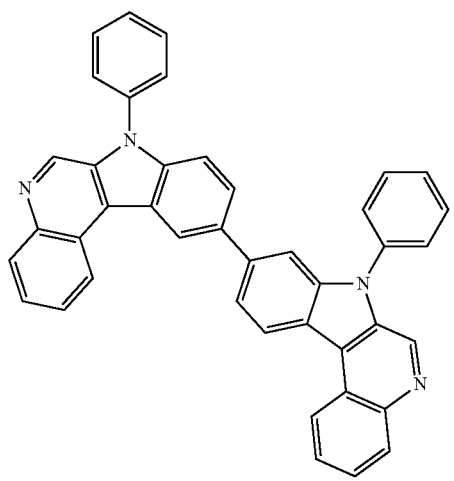
-continued
A-136
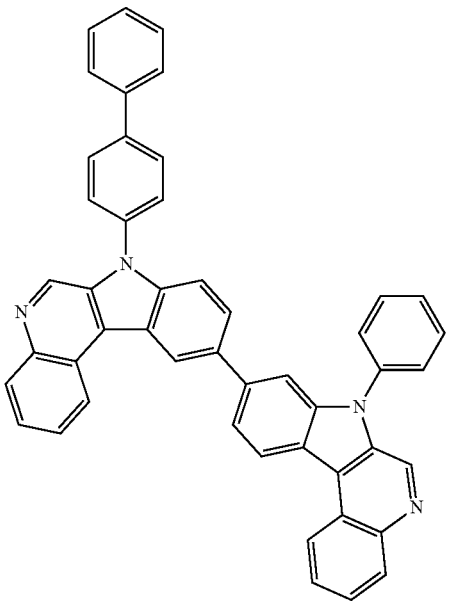
A-137
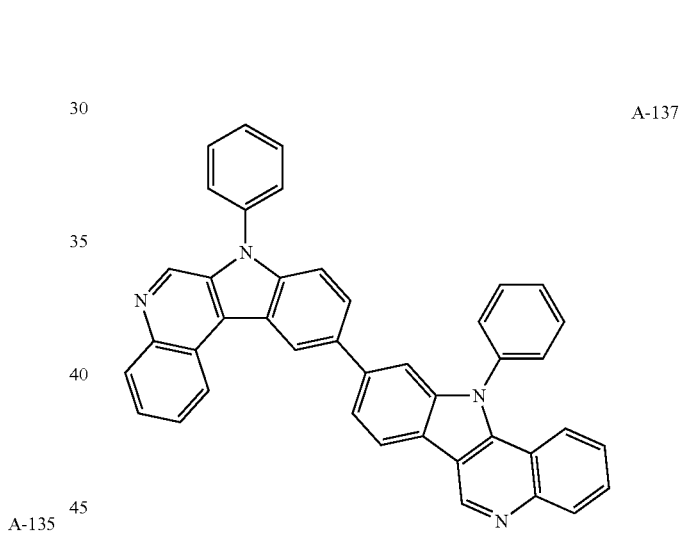
A-138
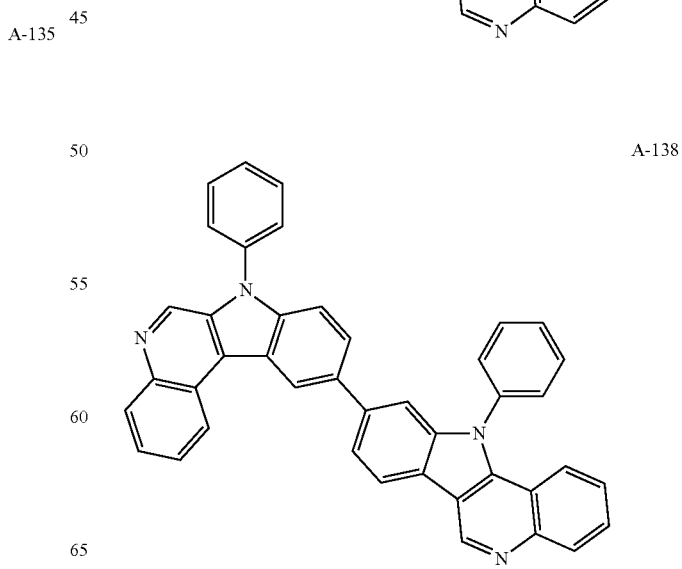

A-139
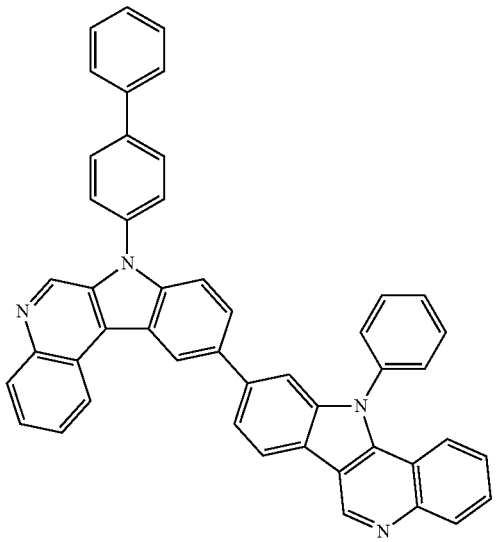
A-143
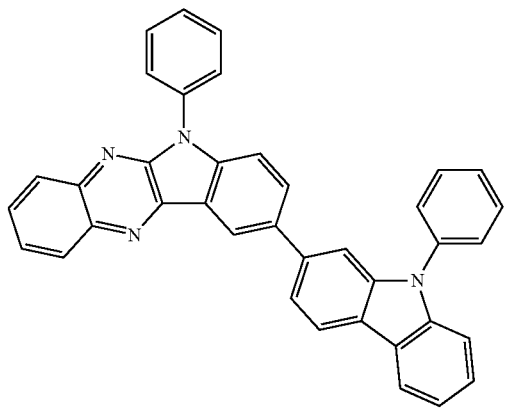
A-140
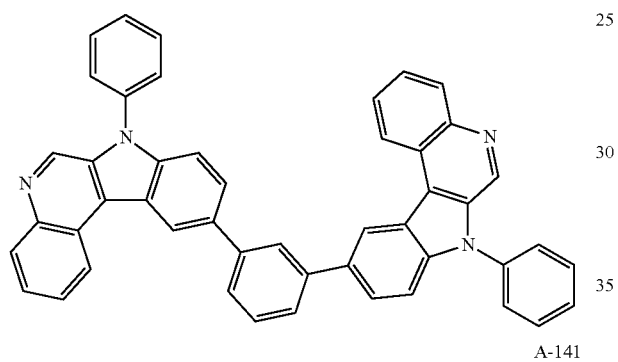
A-144
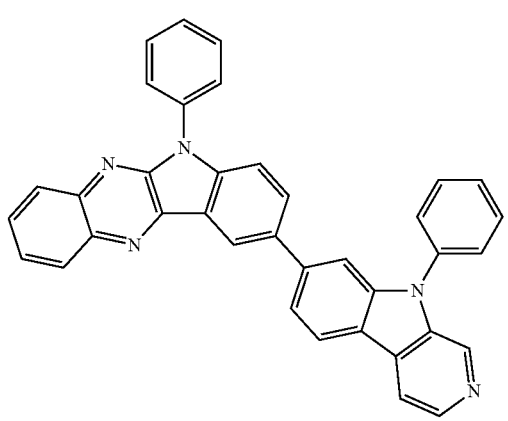
A-141
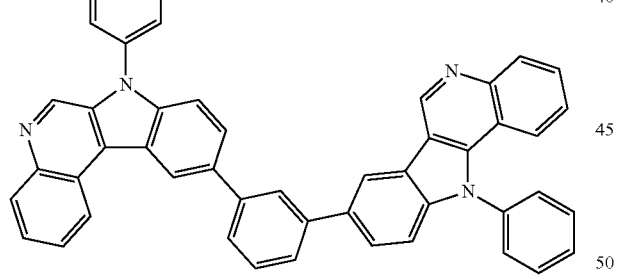
A-142
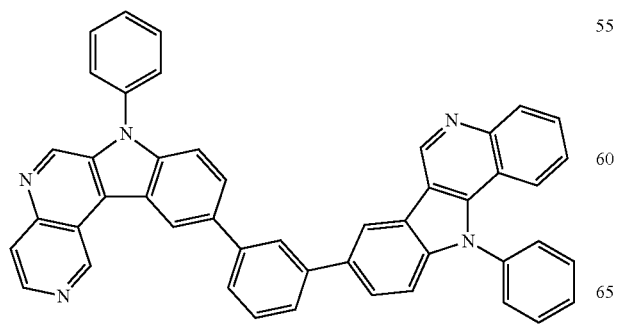
A-145
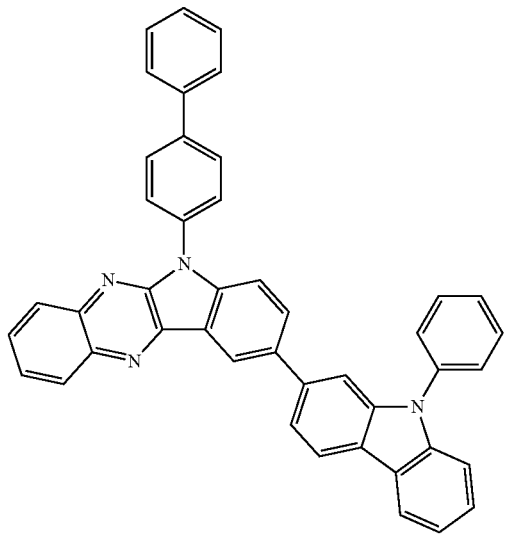

-continued
A-146
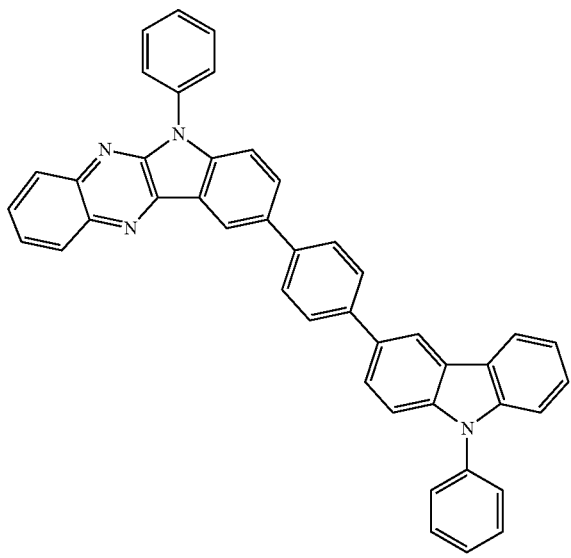
A-147
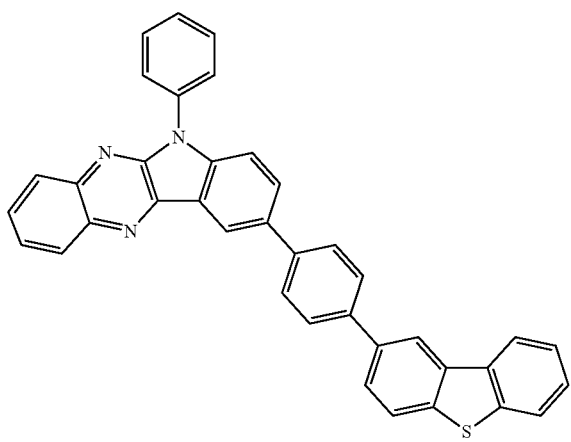
A-148
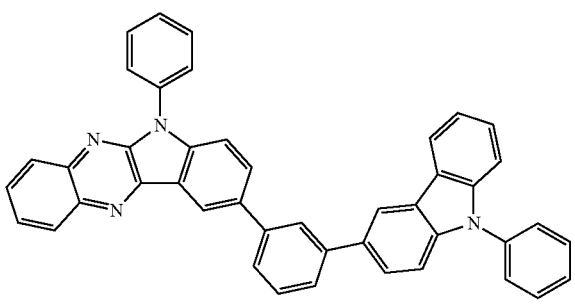
-continued
A-149
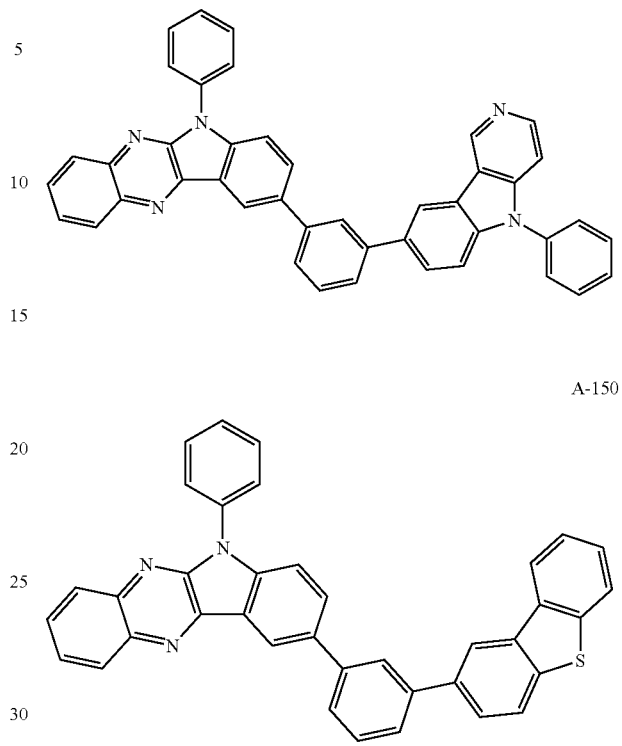
A-150
A-151
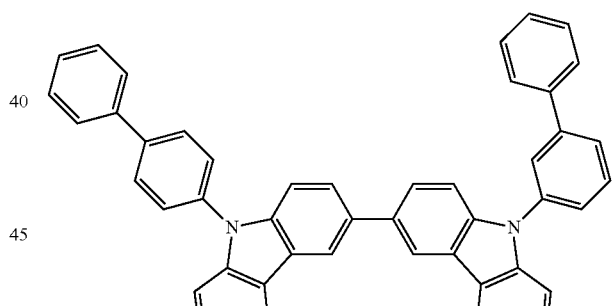
A-152
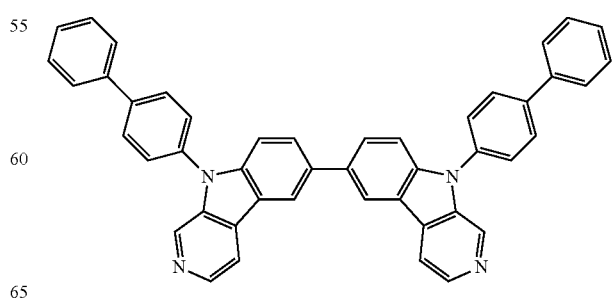

A-153

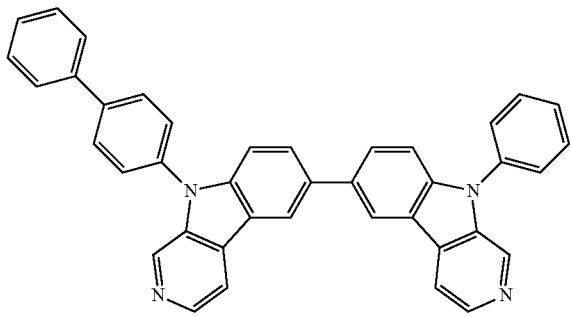

A-154

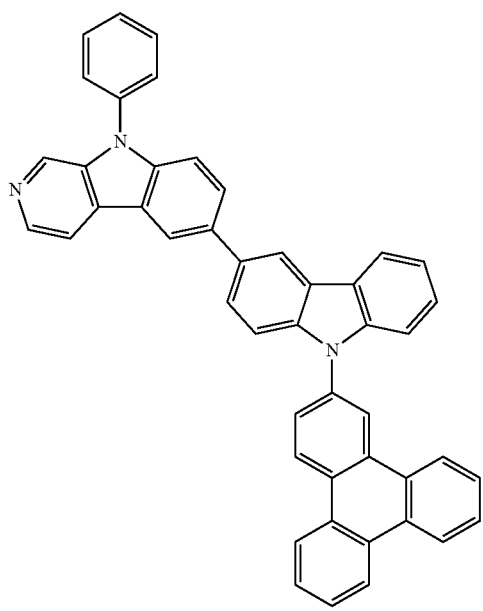

A-155

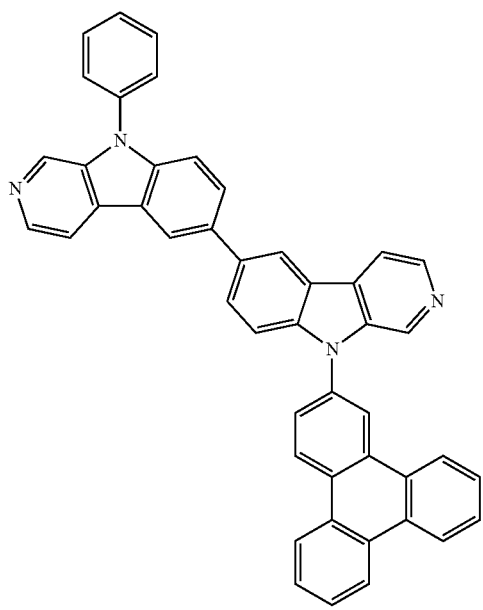

A-156

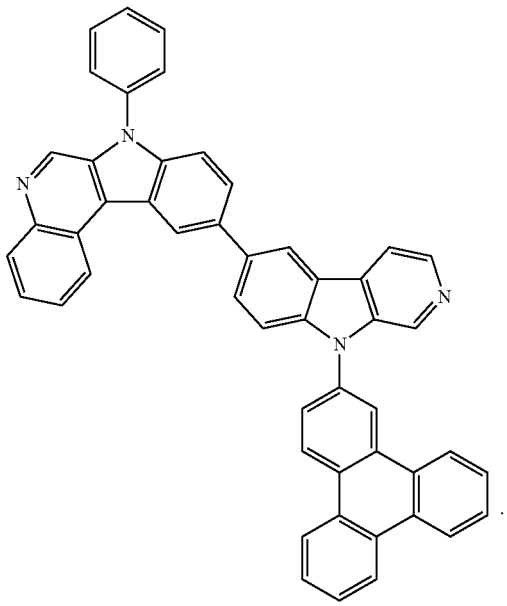

17. The compound for an organic optoelectronic device of claim 1, wherein the organic optoelectronic device is selected from an organic photoelectric device, an organic light emitting diode, an organic solar cell, an organic transistor, an organic photoconductor drum, and an organic memory device.

18. An organic light emitting diode, comprising
an anode,
a cathode, and
at least one organic thin layer disposed between the anode and the cathode,
wherein the at least one organic thin layer comprises the compound for an organic optoelectronic device according to claim 1.

19. The organic light emitting diode of claim 18, wherein the organic thin layer is selected from an emission layer, a hole transport layer, a hole injection layer, an electron transport layer, an electron injection layer, a hole blocking layer, and a combination thereof.

20. The organic light emitting diode of claim 18, wherein the compound for an organic optoelectronic device is included in an emission layer.

21. The organic light emitting diode of claim 18, wherein the compound for an organic optoelectronic device is a phosphorescent or fluorescent host material in an emission layer.

22. A display device comprising the organic light emitting diode according to claim 18.

* * * * *

UNITED STATES PATENT AND TRADEMARK OFFICE
CERTIFICATE OF CORRECTION

PATENT NO. : 9,627,629 B2  
APPLICATION NO. : 14/176287  
DATED : April 18, 2017  
INVENTOR(S) : Kyu Young Hwang et al.

Page 1 of 1

It is certified that error appears in the above-identified patent and that said Letters Patent is hereby corrected as shown below:

On the Title Page

The applicant CHEIL INDUSTRIES INC. has been omitted from the list of the assignees. The Assignee section of the patent should be listed as follows:

(73) Assignee: SAMSUNG ELECTRONICS CO., LTD., Suwon-Si,
Gyeonggi-Do (KR)
CHEIL INDUSTRIES INC., Gumi-Si,
Gyeongsangbuk-Do (KR)

Signed and Sealed this
Third Day of October, 2017

Joseph Matal
*Performing the Functions and Duties of the*
*Under Secretary of Commerce for Intellectual Property and*
*Director of the United States Patent and Trademark Office*